(12) United States Patent
Combs et al.

(10) Patent No.: US 8,530,174 B2
(45) Date of Patent: Sep. 10, 2013

(54) SOGA POLYNUCLEOTIDES AND POLYPEPTIDES AND USES THEREOF

(75) Inventors: Terry P. Combs, Chapel Hill, NC (US); James A. Swenberg, Pittsboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/376,239

(22) PCT Filed: Jun. 4, 2010

(86) PCT No.: PCT/US2010/037472
§ 371 (c)(1), (2), (4) Date: Feb. 15, 2012

(87) PCT Pub. No.: WO2010/141866
PCT Pub. Date: Dec. 9, 2010

(65) Prior Publication Data
US 2012/0174243 A1 Jul. 5, 2012

Related U.S. Application Data

(60) Provisional application No. 61/184,392, filed on Jun. 5, 2009.

(51) Int. Cl.
*G01N 33/53* (2006.01)
*C12Q 1/54* (2006.01)
*C07K 14/00* (2006.01)
*C12N 5/02* (2006.01)

(52) U.S. Cl.
USPC .............. 435/7.1; 435/14; 435/7.8; 435/325; 530/399; 530/380

(58) Field of Classification Search
None
See application file for complete search history.

(56) References Cited

U.S. PATENT DOCUMENTS

| 6,982,362 B1 | 1/2006 | Inoue et al. |
| 7,442,513 B2 | 10/2008 | Worley |
| 2005/0204410 A1 | 9/2005 | Karow et al. |

FOREIGN PATENT DOCUMENTS

| WO | WO 2008/016356 A2 | 2/2008 |
| WO | WO 2008/093464 A1 | 8/2008 |

OTHER PUBLICATIONS

Brajenovic et al. (2004) J. Biol. Chem. 279 (13), 12804-12811.*
"Human brain cerrebellum-specific protein SEO:5967", retrieved from EBI accession No. GSP:AUN04626, Feb. 3, 2011.
"Novel human cDNA sequence #2466", retrieved from EBI accession No. GSN:ADQ67493, Oct. 7, 2004.
"Psoriasis associated human gene SEQ ID No. 5247", retrieved from EBI accession No. GSN:ARY64380, Aug. 21, 2008.
"Psoriasis associated human protein SEQ ID No. 5248", retrieved from EBI accession No. GSP:ARY64381, Aug. 21, 2008.
"RecName: Full=Uncharacterized protein C20orf117", retrieved from EBI accession No. UNIPORT:094964, May 26, 2009.
European Search Report Corresponding to European Application No. 10 78 4183,5; Dated: Nov. 28, 2012; 7 Pages.
Genbank Accession No. NP542194.1, hypothetical protein LOC140710 isoform 1 [*Homo sapiens*] (2 pages) May 7, 2006.
International Application No. PCT/US2010/037472, filed Jun. 4, 2010, international preliminary report on patentability mailed Dec. 15, 2011.

* cited by examiner

*Primary Examiner* — Doug Schultz
(74) *Attorney, Agent, or Firm* — Myers Bigel Sibley & Sajovec, P.A.

(57) ABSTRACT

The present invention relates to the identification of polynucleotides and polypeptides involved in insulin and adiponectin signaling and regulation of glucose production. The invention further relates to the use of the identified polynucleotides and polypeptides, and inhibitors of the polynucleotides and polypeptides, in the regulation of glucose production and the monitoring and treatment of metabolic disorders such as diabetes.

10 Claims, 19 Drawing Sheets

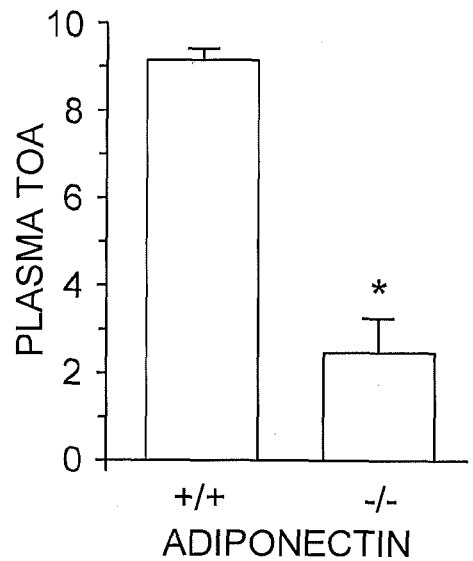
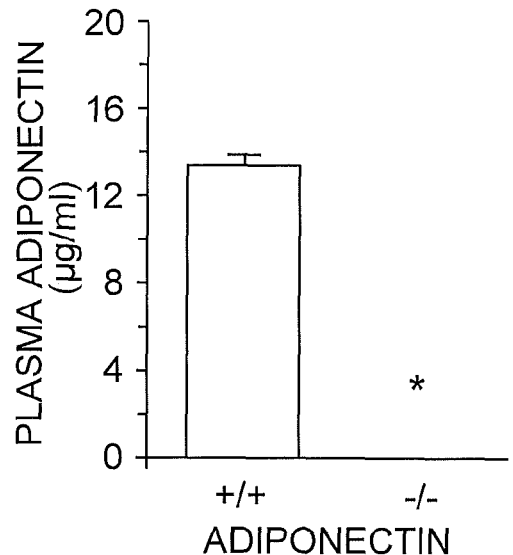
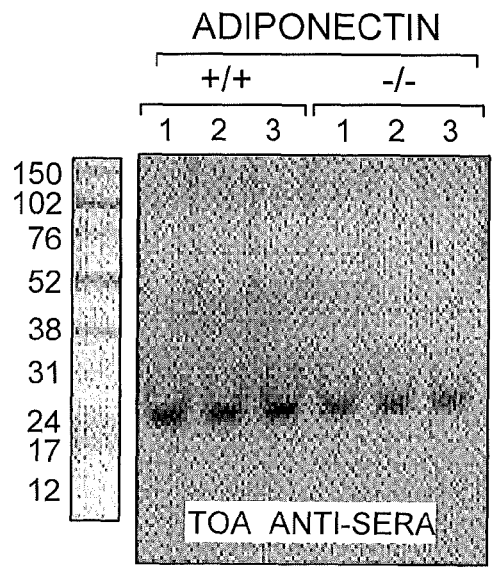
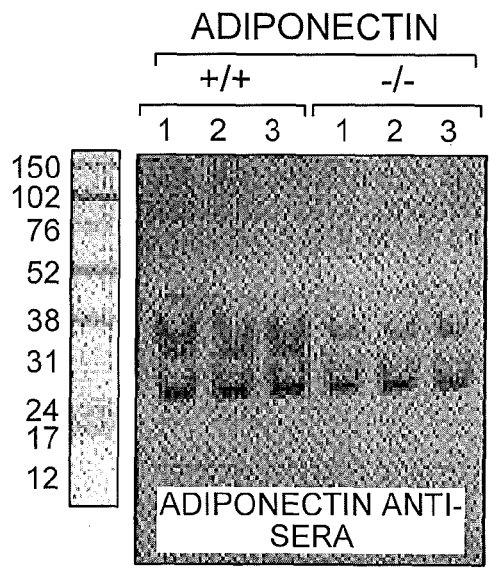
FIG. 5

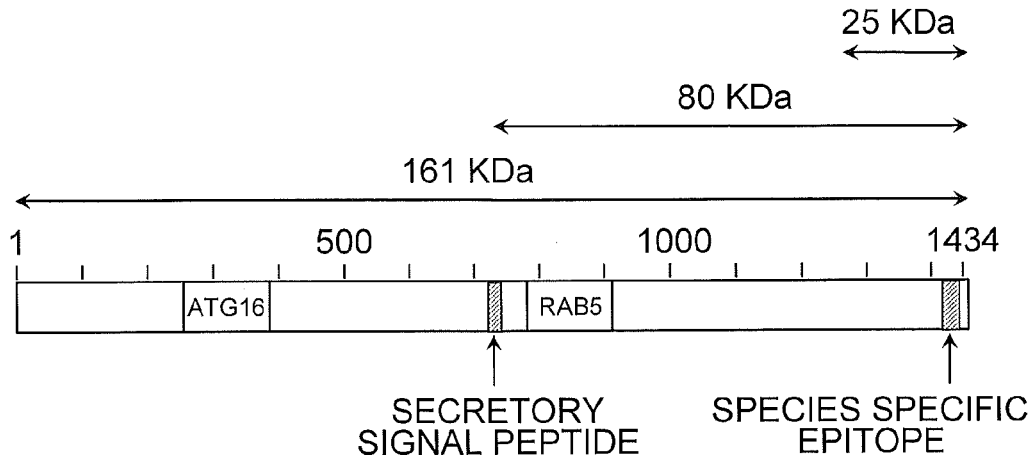

```
   1 MLDCGPGGLVRELEELRSENDYLKDEIEELRAEMLEMRDVYMEEDVYQLQYRLR
  55 KAERRSLRAAQTGQVDGELIRGLEQDVKVSKDISMRLHKELEVVEKKRMRLEEE
 109 NEGLRQRLIETELAKQVLQTELDRPREHSLKKRGTRSLGKTDKKPTAQEDSADL
 163 KCQLHFAKEESALMCKKLTKLAKENDSMKEELLKYRSLYGDLDAALSAEELADA
 217 PHSRETELKVHLKLVEEEANLLSRRIVELEVENRGLRAEMDDMKDHGGGGGPEA
 271 RLAFSSLGGECGESLAELRRHLQFVEEEAELLRRSSAELEDQNKLLLNELAKYR
 325 SEHELDVTLSEDSCSVLSEPSQEELAAAKLQIGELSGKVKKLQYENRVLLSNLQ
 379 RCDLASCQSTRPMLETDAEAGDSAQCVPAPLGETLEPHAARLCRAREAEALPGL
 433 REQAALVSKAIDVLVADANGFSVGLRLCLDNECADLRLHEAPDNSEGPRDAKLI
 487 HAILVRLSVLQQELNAFTRKADVALGSSGKEQPEPFPALPALGSQGPAKEIMLS
 541 KDLGSDFQPPDFRDLLEWEPRIREAFRTGDLESKPDPSRNFRPYRAEDNDSYAS
 595 EIKDLQLVLAEAHDSLRGLQEQLSQERQLRKEEADSFNQKMVQLKEDQQRALLR
 649 REFELQSLSLQRRLEQKFWSQEKNILVQESQQFKHNFLLLFMKLRWFLKRWRQG
 703 KVLPSEEDDFLEVNSMKELYLLMEEEEMNAQHSDNKACTGESWTQNTPNECIKT
 757 LADMKVTLKELCWLLQDERRGLTELQQQFAKAKATWETERAELKGHASQMELKA
 811 GKGASERPGPDWKAALQREREEQQHLLAESYSAVMELTRQLQLSERHWSQEKLQ
 865 LVERLQGEKQQVEQQVKELQNRLSQLQKAAEPWVLKHSDMEKQDNSWKEARSEK
 919 THDKEGVSEAELGGTGLKRTKSVSSMSEFESLLDCSPYLAGGDARNKKLPNGPA
 973 FAFVSTEPVEPEKDAKEKAGLSTRDCSHIGSLACQEPAGRQMQRSYTAPDKTGI
1027 RVYYSPPVARRLGVPVVHDKEGKILIEPGFLFTTAKPKESAEADGLAESSYSRW
1081 LCNFSRQRLDGGSGASTSGSGPAFPALHDFEMSGNMSDDMKEITNCVRQAMRSG
1135 SLERKVKNTSSQTVGVATVGTQTIRTVSVGLQTDPPRSSLHSKSWSPRSSSLVS
1189 VRSKQISSSLDKVHSRIERPCCSPKYGSPKLQRRSVSKLDSTKDRSLWNLHQGK
1243 QNGSAWARSTTTRDSPVLRNINDGLSSLFSVVEHSGSTESVWKLGMSEARTKPE
1297 PPKYGIVQEFFRNVCGRAPSPTTAAGEESCKKPEPLSPASYHQPEGVSRILNKK
1351 AAKAGGSEEVRPTMLSQVGKDGILRDGDGSLILPSEDAVCDCSAQSLASCFIRP
1405 SRNTIRHSPSKCRLHPSESGWGGEERAAPQ
```

FIG. 10

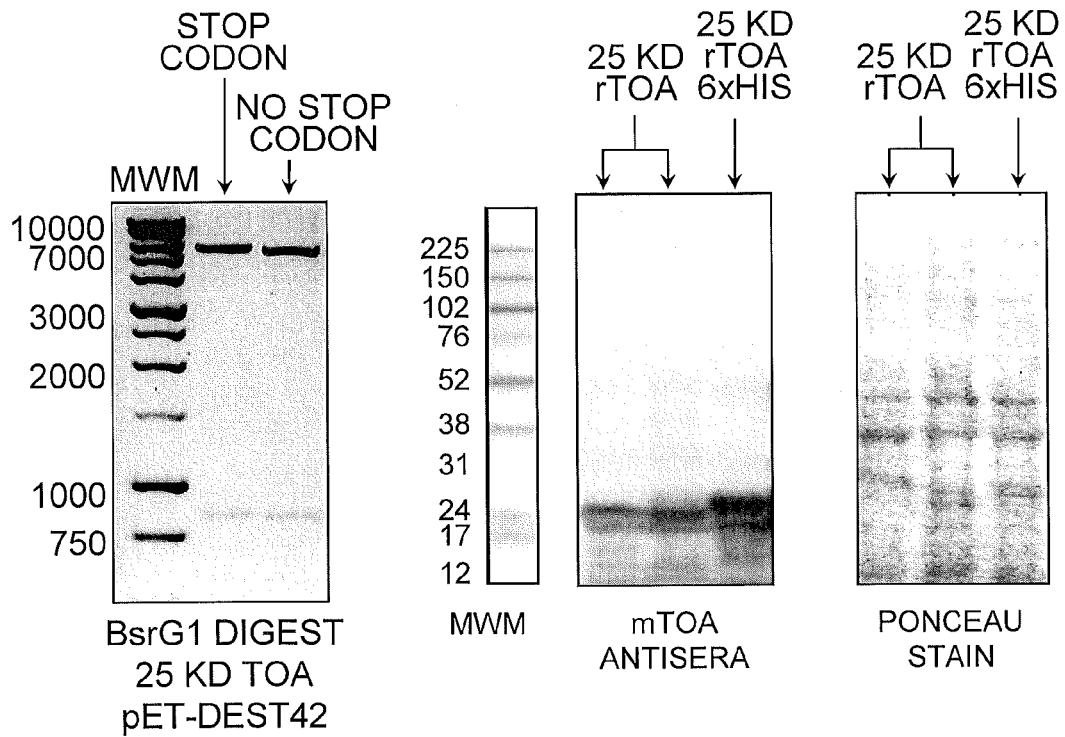
FIG. 13A
FIG. 13B
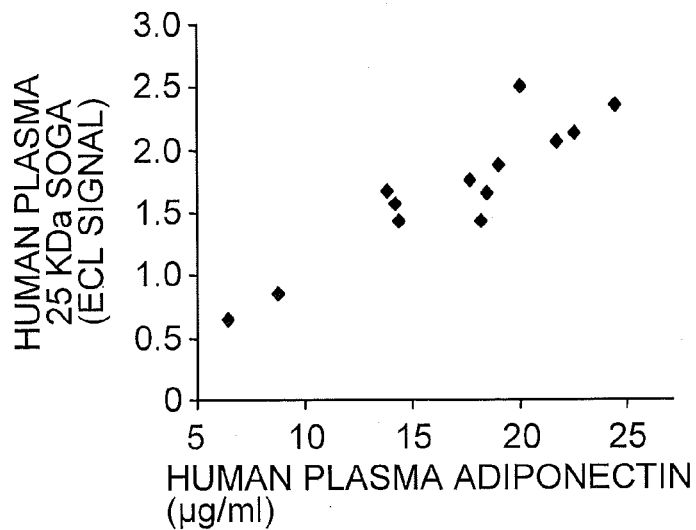
FIG. 14A

SEQUENCE LISTING

```
<160> NUMBER OF SEQ ID NOS: 11

<210> SEQ ID NO 1
<211> LENGTH: 4716
<212> TYPE: DNA
<213> ORGANISM: Mus musculus

<400> SEQUENCE: 1
agttgggcct ggagctggcg ctgagcagcg acgccgagtc tgcggcgggc ggcccggcgg      60
ggacccgcac cgggcagccg ccccagccag cgcagtcggg gcagcagcct ccgcggcctc     120
ccgcctcccc ggatgagccg tcggtggccg catcgtcggt gggcagcagc cgcttgccat     180
tcagcgcctc gctagccttc tccgacctca ccgaggagat gctggactgt gggcccggag     240
gcttggtgcg ggagctggaa gagctgcgtt ccgagaacga ctatctcaag gatgagattg     300
aggagctacg ggctgagatg ctggagatgc gggatgtcta catggaggaa gacgtgtatc     360
```

```
agctgcagta ccgactgcgt aaggctgagc gccgcagcct ccgcgctgcc cagacaggcc    420
aggttgatgg ggaactcatc cgaggtctgg aacaggacgt caaggtctct aaggacatct    480
ccatgcggct tcacaaggag ctggaggtgg tggagaagaa gcggatgagg ctggaggagg    540
agaacgaggg gcttcgacag aggctcattg agacagagct ggccaagcag gtgctacaga    600
cggagctgga tcgtcccaga gagcattcct tgaagaaaag aggaacccgg tctctgggga    660
agacagataa gaagcctact gcacaggagg atagtgcaga cctgaagtgc agctgcatt    720 ttgcaaagga ggagtcggcc ctcatgtgca agaagctcac caagttggct aaggagaacg    780
acagcatgaa ggaggagctg ctcaagtaca gatcgctcta tggggacctg gatgcagccc    840
tgtcggcaga ggagctggcg gatgctccgc actcccgtga gactgagctg aaggtgcacc    900
tgaagctggt ggaggaggag gccaacctgc tgagccggcg catagtggag ctggaggtgg    960
agaaccgtgg cctgcgagcc gagatggacg acatgaagga ccacgggggt ggcggggtc   1020 ccgaggccag gctggccttc tcttctctgg gtggtgagtg cggggagagc ctagccgagt   1080
tgcggcgcca cctgcagttc gtggaagagg aggctgagct gctgaggcgc tcctcagctg   1140
agctggagga ccagaacaag ttgctgctga acgagctggc caaataccgc tcggagcacg   1200
agctggacgt gacgctgtcg gaggacagct gctccgtgct cagcgagccc tcgcaggagg   1260
agctggcagc cgccaagctg cagatcggcg agctcagcgg caaggtcaag aagctgcagt   1320
atgagaaccg cgtgctcctc tccaatctgc agcgctgtga cctggcctcc tgccagagca   1380
cacgccccat gctggagacg gacgctgagg ctggggactc tgcgcagtgc gtgcctgccc   1440
ctctgggtga gacgctggag ccccacgccg cccggctgtg cagggcccgt gaagccgagg   1500
cgctgcccgg cctacgggag caggccgctt tggtcagcaa ggccatcgac gtcctggtgg   1560
ctgatgccaa tggcttctca gtcggcctcc gcctgtgcct ggacaatgag tgtgctgact   1620
tgcgactgca cgaggcgcct gacaacagcg agggccccag ggatgccaag ctcatccacg   1680
ccatcctggt gcggctgagt gtgttgcaac aggagctgaa cgccttcacc cgcaaggcag   1740
atgtggcctt ggggagctct ggcaaggagc agcctgagcc cttccctgct ctgcctgcct   1800
tgggctccca gggccctgct aaggagatca tgctgtccaa agaccttggc tctgacttcc   1860
agccacctga cttcagagac ctgcttgagt gggagcccag gatccgagag gccttccgta   1920
ccggggactt ggagtccaag cctgacccta gtcggaactt caggccctac cgagctgaag   1980
ataacgattc ttatgcctct gagatcaagg atcttcagct ggtcctggcc gaggcccacg   2040
acagcctccg gggcttgcaa gagcagctgt cccaggagcg gcagctccgg aaggaggagg   2100
ctgacagctt caaccagaaa atggtccagc tgaaggaaga ccagcagagg gcgctgctga   2160
gacgggagtt tgagctgcag agtctgagcc tccagcggcg actggagcag aagttctgga   2220
gccaagagaa gaacatcctg gtgcaggagt cccagcagtt caagcacaac tttctgctgc   2280
tcttcatgaa gctccggtgg ttcctgaagc gctggcggca gggcaaggtt ctgcccagcg   2340
aagaggatga cttcctggag gtgaacagca tgaaggaact gtacctgctg atggaggaag   2400
aggagatgaa cgcccagcac tcggataaca aggcctgcac aggggagagc tggacccaga   2460
acacgcctaa tgagtgcatc aagaccctgg ccgacatgaa ggtcaccctg aaggagctgt   2520
gctggctgct ccaggacgag cgtcgggtc tgactgaact tcagcagcag ttcgcaaagg   2580
ccaaggccac ctgggagaca gagcgtgcag agctcaaggg ccacgcctcg cagatggagc   2640
tgaaggctgg gaagggtgcc agtgagaggc ccgggcctga ctggaaggct gcactgcaga   2700
gagagcggga ggagcagcaa cacctcctgg cagagtccta cagcgccgtc atggagctga   2760
```

```
cgaggcagct gcagctgagc gagcgccact ggagccagga gaagctgcag ctggtggagc    2820
ggctgcaggg agaaaagcag caggtggagc agcaggtgaa ggagctgcag aaccgcctca    2880
gtcagttgca gaaggctgcc gagccctggg tcctgaagca ctcagacatg gagaagcaag    2940
acaacagctg gaaagaggca cgaagtgaga agacccatga caaggagggt gtctctgaag    3000
ctgagctcgg gggaactggc ttaaagagga ccaaatcagt ctcctccatg tctgagtttg    3060
aaagtttgct cgactgctcc ccgtaccttg ctggcgggga tgcccggaac aagaagctgc    3120
ccaacggccc tgcttttgcc tttgtgagta ctgagccagt ggagcctgag aaagacgcca    3180
aggagaaggc ggggctttcc acccgggact gtagccacat tggtagcttg gcctgtcagg    3240
aacctgcagg gagacagatg cagcgcagct acacggctcc agacaagacg ggaatccgag    3300
tctactatag tccgccagtg gctcggcgcc tgggtgtccc tgtggtccat gacaaggagg    3360
gcaagatcct cattgagcca ggcttcctct tcactaccgc caagcccaag gagtcagccg    3420
aggctgacgg gctggccgag agctcctaca gccggtggct ttgcaatttc tcccggcagc    3480
ggctggatgg aggatccggg gccagcacct cgggttccgg acctgctttc cccgccttgc    3540
atgactttga gatgtcgggc aacatgagtg acgacatgaa ggagatcacc aactgcgtgc    3600
ggcaggccat gcgctccggc tctctggaga ggaaggtaaa gaacacatcc agccagacgg    3660
taggcgtggc caccgtgggc acccagacca ttcggacggt cagtgtaggt cttcagaccg    3720 acccacccg cagcagcctc cacagcaaga gctggtcacc ccgcagctcc tcgcttgtgt    3780
ctgtgcgcag caagcagatc tcttcctccc tggacaaggt ccattctcgc attgagcggc    3840
catgttgctc gcccaagtac ggctcaccca agctccagag acgatcggtg tccaagctgg    3900
atagcaccaa ggaccgcagc ctgtggaacc tgcaccaggg caagcaaaat ggctccgcct    3960
gggctcgctc caccaccaca cgggatagcc ctgtactgag gaacatcaat gatgggcttt    4020
ctagcctctt tagtgtggtg gagcactctg ggagcaccga gtctgtgtgg aaactgggca    4080
tgtctgaggc ccgaaccaaa cctgagcctc ccaagtatgg cattgttcag gagttcttcc    4140
ggaacgtgtg tggccgggca ccgagcccca ctactgcagc aggcgaggaa agctgcaaga    4200
aaccagagcc cctttcgcca gccagctacc atcaacccga gggtgtatcc aggatcctga    4260
acaagaaggc ggccaaggca ggtggtagcg aagaggtcag acccaccatg ctgtcccagg    4320
tggggaagga tggcatcctt cgggatggag atggatcctt gatccttccc agtgaggatg    4380
ccgtatgtga ctgtagcgcc cagtcacttg cctcctgctt catccggcca tcccgcaaca    4440
ccatccggca ctctccttcc aagtgcaggc tgcacccttc agagtcaggc tggggcgggg    4500
aggagagggc agctccccag tgagtccctg agcaaccaag cacccacctc aagcagccca    4560
gaccctggag atgaggcaag ggctcgtgtc ctcagcctca gtccatccag gaggaatggc    4620
agctgtgcca ctgccacaga gagctttca cattaaggta aagcaaggtg tcttgctgac    4680
tgctgggcag tgacctctga tttccagggg aagaca                             4716
```

<210> SEQ ID NO 2
<211> LENGTH: 1434
<212> TYPE: PRT
<213> ORGANISM: Mus musculus

<400> SEQUENCE: 2

```
Met Leu Asp Cys Gly Pro Gly Gly Leu Val Arg Glu Leu Glu Glu Leu
1               5                   10                  15

Arg Ser Glu Asn Asp Tyr Leu Lys Asp Glu Ile Glu Glu Leu Arg Ala
            20                  25                  30
```

```
Glu Met Leu Glu Met Arg Asp Val Tyr Met Glu Glu Asp Val Tyr Gln
             35                  40                  45
Leu Gln Tyr Arg Leu Arg Lys Ala Glu Arg Arg Ser Leu Arg Ala Ala
 50                  55                  60
Gln Thr Gly Gln Val Asp Gly Glu Leu Ile Arg Gly Leu Glu Gln Asp
 65                  70                  75                  80
Val Lys Val Ser Lys Asp Ile Ser Met Arg Leu His Lys Glu Leu Glu
                 85                  90                  95
Val Val Glu Lys Lys Arg Met Arg Leu Glu Glu Asn Glu Gly Leu
                100                 105                 110
Arg Gln Arg Leu Ile Glu Thr Glu Leu Ala Lys Gln Val Leu Gln Thr
                115                 120                 125
Glu Leu Asp Arg Pro Arg Glu His Ser Leu Lys Lys Arg Gly Thr Arg
    130                 135                 140
Ser Leu Gly Lys Thr Asp Lys Lys Pro Thr Ala Gln Glu Asp Ser Ala
145                 150                 155                 160
Asp Leu Lys Cys Gln Leu His Phe Ala Lys Glu Ser Ala Leu Met
                165                 170                 175
Cys Lys Lys Leu Thr Lys Leu Ala Lys Glu Asn Asp Ser Met Lys Glu
                180                 185                 190
Glu Leu Leu Lys Tyr Arg Ser Leu Tyr Gly Asp Leu Asp Ala Ala Leu
                195                 200                 205
Ser Ala Glu Glu Leu Ala Asp Ala Pro His Ser Arg Glu Thr Glu Leu
210                 215                 220
Lys Val His Leu Lys Leu Val Glu Glu Ala Asn Leu Leu Ser Arg
225                 230                 235                 240
Arg Ile Val Glu Leu Glu Val Glu Asn Arg Gly Leu Arg Ala Glu Met
                245                 250                 255
Asp Asp Met Lys Asp His Gly Gly Gly Gly Pro Glu Ala Arg Leu
                260                 265                 270
Ala Phe Ser Ser Leu Gly Gly Glu Cys Gly Glu Ser Leu Ala Glu Leu
    275                 280                 285
Arg Arg His Leu Gln Phe Val Glu Glu Ala Glu Leu Leu Arg Arg
    290                 295                 300
Ser Ser Ala Glu Leu Glu Asp Gln Asn Lys Leu Leu Leu Asn Glu Leu
305                 310                 315                 320
Ala Lys Tyr Arg Ser Glu His Glu Leu Asp Val Thr Leu Ser Glu Asp
                325                 330                 335
Ser Cys Ser Val Leu Ser Glu Pro Ser Gln Glu Glu Leu Ala Ala Ala
                340                 345                 350
Lys Leu Gln Ile Gly Glu Leu Ser Gly Lys Val Lys Lys Leu Gln Tyr
                355                 360                 365
Glu Asn Arg Val Leu Leu Ser Asn Leu Gln Arg Cys Asp Leu Ala Ser
    370                 375                 380
Cys Gln Ser Thr Arg Pro Met Leu Glu Thr Asp Ala Glu Ala Gly Asp
385                 390                 395                 400
Ser Ala Gln Cys Val Pro Ala Pro Leu Gly Glu Thr Leu Glu Pro His
                405                 410                 415
Ala Ala Arg Leu Cys Arg Ala Arg Glu Ala Glu Ala Leu Pro Gly Leu
                420                 425                 430
Arg Glu Gln Ala Ala Leu Val Ser Lys Ala Ile Asp Val Leu Val Ala
                435                 440                 445
Asp Ala Asn Gly Phe Ser Val Gly Leu Arg Leu Cys Leu Asp Asn Glu
                450                 455                 460
```

-continued

```
Cys Ala Asp Leu Arg Leu His Glu Ala Pro Asp Asn Ser Glu Gly Pro
465                 470                 475                 480

Arg Asp Ala Lys Leu Ile His Ala Ile Leu Val Arg Leu Ser Val Leu
            485                 490                 495

Gln Gln Glu Leu Asn Ala Phe Thr Arg Lys Ala Asp Val Ala Leu Gly
        500                 505                 510

Ser Ser Gly Lys Glu Gln Pro Glu Pro Phe Pro Ala Leu Pro Ala Leu
    515                 520                 525

Gly Ser Gln Gly Pro Ala Lys Glu Ile Met Leu Ser Lys Asp Leu Gly
530                 535                 540

Ser Asp Phe Gln Pro Pro Asp Phe Arg Asp Leu Leu Glu Trp Glu Pro
545                 550                 555                 560

Arg Ile Arg Glu Ala Phe Arg Thr Gly Asp Leu Glu Ser Lys Pro Asp
                565                 570                 575

Pro Ser Arg Asn Phe Arg Pro Tyr Arg Ala Glu Asp Asn Asp Ser Tyr
            580                 585                 590

Ala Ser Glu Ile Lys Asp Leu Gln Leu Val Leu Ala Glu Ala His Asp
        595                 600                 605

Ser Leu Arg Gly Leu Gln Glu Gln Leu Ser Gln Glu Arg Gln Leu Arg
    610                 615                 620

Lys Glu Glu Ala Asp Ser Phe Asn Gln Lys Met Val Gln Leu Lys Glu
625                 630                 635                 640

Asp Gln Gln Arg Ala Leu Leu Arg Arg Glu Phe Glu Leu Gln Ser Leu
                645                 650                 655

Ser Leu Gln Arg Arg Leu Glu Gln Lys Phe Trp Ser Gln Glu Lys Asn
            660                 665                 670

Ile Leu Val Gln Glu Ser Gln Gln Phe Lys His Asn Phe Leu Leu Leu
        675                 680                 685

Phe Met Lys Leu Arg Trp Phe Leu Lys Arg Trp Arg Gln Gly Lys Val
    690                 695                 700

Leu Pro Ser Glu Glu Asp Asp Phe Leu Glu Val Asn Ser Met Lys Glu
705                 710                 715                 720

Leu Tyr Leu Leu Met Glu Glu Glu Met Asn Ala Gln His Ser Asp
                725                 730                 735

Asn Lys Ala Cys Thr Gly Glu Ser Trp Thr Gln Asn Thr Pro Asn Glu
            740                 745                 750

Cys Ile Lys Thr Leu Ala Asp Met Lys Val Thr Leu Lys Glu Leu Cys
        755                 760                 765

Trp Leu Leu Gln Asp Glu Arg Arg Gly Leu Thr Glu Leu Gln Gln Gln
    770                 775                 780

Phe Ala Lys Ala Lys Ala Thr Trp Glu Thr Glu Arg Ala Glu Leu Lys
785                 790                 795                 800

Gly His Ala Ser Gln Met Glu Leu Lys Ala Gly Lys Gly Ala Ser Glu
                805                 810                 815

Arg Pro Gly Pro Asp Trp Lys Ala Ala Leu Gln Arg Glu Arg Glu Glu
            820                 825                 830

Gln Gln His Leu Leu Ala Glu Ser Tyr Ser Ala Val Met Glu Leu Thr
        835                 840                 845

Arg Gln Leu Gln Leu Ser Glu Arg His Trp Ser Gln Glu Lys Leu Gln
    850                 855                 860

Leu Val Glu Arg Leu Gln Gly Glu Lys Gln Gln Val Glu Gln Gln Val
865                 870                 875                 880

Lys Glu Leu Gln Asn Arg Leu Ser Gln Leu Gln Lys Ala Ala Glu Pro
```

-continued

```
                885                 890                 895
Trp Val Leu Lys His Ser Asp Met Glu Lys Gln Asp Asn Ser Trp Lys
            900                 905                 910
Glu Ala Arg Ser Glu Lys Thr His Asp Lys Glu Gly Val Ser Glu Ala
            915                 920                 925
Glu Leu Gly Gly Thr Gly Leu Lys Arg Thr Lys Ser Val Ser Ser Met
            930                 935                 940
Ser Glu Phe Glu Ser Leu Leu Asp Cys Ser Pro Tyr Leu Ala Gly Gly
945                 950                 955                 960
Asp Ala Arg Asn Lys Lys Leu Pro Asn Gly Pro Ala Phe Ala Phe Val
            965                 970                 975
Ser Thr Glu Pro Val Glu Pro Glu Lys Asp Ala Lys Glu Lys Ala Gly
            980                 985                 990
Leu Ser Thr Arg Asp Cys Ser His Ile Gly Ser Leu Ala Cys Gln Glu
            995                1000                1005
Pro Ala Gly Arg Gln Met Gln Arg Ser Tyr Thr Ala Pro Asp Lys
        1010                1015                1020
Thr Gly Ile Arg Val Tyr Tyr Ser Pro Pro Val Ala Arg Arg Leu
        1025                1030                1035
Gly Val Pro Val Val His Asp Lys Glu Gly Lys Ile Leu Ile Glu
        1040                1045                1050
Pro Gly Phe Leu Phe Thr Thr Ala Lys Pro Lys Glu Ser Ala Glu
        1055                1060                1065
Ala Asp Gly Leu Ala Glu Ser Ser Tyr Ser Arg Trp Leu Cys Asn
        1070                1075                1080
Phe Ser Arg Gln Arg Leu Asp Gly Gly Ser Gly Ala Ser Thr Ser
        1085                1090                1095
Gly Ser Gly Pro Ala Phe Pro Ala Leu His Asp Phe Glu Met Ser
        1100                1105                1110
Gly Asn Met Ser Asp Asp Met Lys Glu Ile Thr Asn Cys Val Arg
        1115                1120                1125
Gln Ala Met Arg Ser Gly Ser Leu Glu Arg Lys Val Lys Asn Thr
        1130                1135                1140
Ser Ser Gln Thr Val Gly Val Ala Thr Val Gly Thr Gln Thr Ile
        1145                1150                1155
Arg Thr Val Ser Val Gly Leu Gln Thr Asp Pro Pro Arg Ser Ser
        1160                1165                1170
Leu His Ser Lys Ser Trp Ser Pro Arg Ser Ser Leu Val Ser
        1175                1180                1185
Val Arg Ser Lys Gln Ile Ser Ser Ser Leu Asp Lys Val His Ser
        1190                1195                1200
Arg Ile Glu Arg Pro Cys Cys Ser Pro Lys Tyr Gly Ser Pro Lys
        1205                1210                1215
Leu Gln Arg Arg Ser Val Ser Lys Leu Asp Ser Thr Lys Asp Arg
        1220                1225                1230
Ser Leu Trp Asn Leu His Gln Gly Lys Gln Asn Gly Ser Ala Trp
        1235                1240                1245
Ala Arg Ser Thr Thr Thr Arg Asp Ser Pro Val Leu Arg Asn Ile
        1250                1255                1260
Asn Asp Gly Leu Ser Ser Leu Phe Ser Val Val Glu His Ser Gly
        1265                1270                1275
Ser Thr Glu Ser Val Trp Lys Leu Gly Met Ser Glu Ala Arg Thr
        1280                1285                1290
```

| | | | | | | | | | | |
|---|---|---|---|---|---|---|---|---|---|---|
|Lys|Pro|Glu|Pro|Pro|Lys|Tyr|Gly|Ile|Val|Gln|Glu|Phe|Phe|Arg|
| |1295| | | |1300| | | |1305| |
|Asn|Val|Cys|Gly|Arg|Ala|Pro|Ser|Pro|Thr|Thr|Ala|Ala|Gly|Glu|
| |1310| | | |1315| | | |1320| |
|Glu|Ser|Cys|Lys|Lys|Pro|Glu|Pro|Leu|Ser|Pro|Ala|Ser|Tyr|His|
| |1325| | | |1330| | | |1335| |
|Gln|Pro|Glu|Gly|Val|Ser|Arg|Ile|Leu|Asn|Lys|Lys|Ala|Ala|Lys|
| |1340| | | |1345| | | |1350| |
|Ala|Gly|Gly|Ser|Glu|Glu|Val|Arg|Pro|Thr|Met|Leu|Ser|Gln|Val|
| |1355| | | |1360| | | |1365| |
|Gly|Lys|Asp|Gly|Ile|Leu|Arg|Asp|Gly|Asp|Gly|Ser|Leu|Ile|Leu|
| |1370| | | |1375| | | |1380| |
|Pro|Ser|Glu|Asp|Ala|Val|Cys|Asp|Cys|Ser|Ala|Gln|Ser|Leu|Ala|
| |1385| | | |1390| | | |1395| |
|Ser|Cys|Phe|Ile|Arg|Pro|Ser|Arg|Asn|Thr|Ile|Arg|His|Ser|Pro|
| |1400| | | |1405| | | |1410| |
|Ser|Lys|Cys|Arg|Leu|His|Pro|Ser|Glu|Ser|Gly|Trp|Gly|Gly|Glu|
| |1415| | | |1420| | | |1425| |
|Glu|Arg|Ala|Ala|Pro|Gln| | | | | | | | | |
| |1430| | | | | | | | | |

<210> SEQ ID NO 3
<211> LENGTH: 4862
<212> TYPE: DNA
<213> ORGANISM: Homo sapiens

<400> SEQUENCE: 3

```
cgctgagcag cgacgccgag tccgcggccg ggggcccggc gggggtccgt acggggcagc      60
cggcccagcc cgcgccctcc gcgcagcagc ccccgcggcc gccgcctcc ccggacgagc     120
cgtcggtggc cgcgtcgtcg gtgggcagca gccgcttgcc gctcagcgcc tcgcttgcct     180
tctccgacct caccgaggag atgctggact gcgggcccag cggcttggtg cgggagctgg     240
aggagctgcg ctcggagaac gactatctca aggacgagat tgaggagctg cgggccgaga     300
tgctggagat gcgggacgtc tatatggagg aggacgtgta tcagctgcag taccggctgc     360
gcaaagccga gcgccgcagt ctccgtgccg cccagaccgg ccaggtggac ggcgagctta     420
tccgtggtct ggagcaggat gtcaaggtct ctaaggacac ctccatgcgg ctgcataagg     480
agctcgaggt ggtggagaag aaacgggcgc ggctggagga ggagaacgaa gagcttcgtc     540
agcggctcat cgagactgag ctggctaagc aggtgctgca gacggagctg agcgaccga     600
gagagcattc cttgaagaaa gaggaaccc gctccctggg gaaggccgat aagaagactt     660
tggtgcagga ggacagtgca gacctgaagt gccagttgca cttttgcaaag gaggagtcag     720
ccctcatgtg caagaagctc actaagcttg ccaaggagaa tgacagcatg aaggaggagc     780
tgctgaagta ccgctcgctc tatggggacc tggacagcgc gctgtcagcc gaggagctgg     840
ccgatgcccc ccactcgcgg gagaccgagc tgaaggtgca cctgaagctg gtggaggagg     900
aagccaacct gctgagccgc cgcatcgtgg agctggaggt ggagaaccga ggcctgcggg     960
ctgagatgga cgacatgaag gatcatggag gtggctgtgg gggtcctgag gcacgcctgg    1020
ccttctccgc gctgggtggc ggagagtgcg gggagagctt ggcagagctg cggcgacacc    1080
tgcagtttgt cgaagaggag gccgagctgc tgcggcgctc ctctgccgag ctcgaggacc    1140
agaacaagct gctgctgaac gagctggcca agttccgctc ggagcacgag ctggacgtgg    1200
cgctgtcgga ggacagttgt tctgtgctca gcgaaccttc acaggaggag ctggcggccg    1260
```

```
ccaagctgca gatcggcgag ctcagcggca aggtcaagaa gctgcagtac gagaaccgcg    1320
tgctcctctc caacctccag cgctgtgacc tcgcctcctg ccagagtacg cggcccatgc    1380
tggagacgga cgccgaggcc ggggactctg cccagtgtgt gcctgctccc ctgggcgaga    1440
cacacgagtc ccatgcggtc cgactctgca gagccaggga ggccgaggtg ctgcctgggc    1500
tgagagagca ggccgccctg gtcagtaagg ccatcgatgt cctggtggct gatgccaatg    1560
gcttcacggc tggcctccgg ctgtgtctgg acaacgagtg tgctgacttc cggctgcatg    1620
aggcccccga caacagcgag ggccccaggg acaccaagct catccatgcc atcctggtgc    1680
gcctgagcgt gctgcagcag gagctgaatg ccttcacgcg gaaggcagat gcagtcctcg    1740
ggtgctctgt caaggaacag caggagtcct tctcatcact gccccccttg ggctcccagg    1800
ggctctctaa ggagattctt ctggcaaaag accttggctc agactttcag ccacctgact    1860
tcagggacct gccggaatgg gagcccagga tccgagaggc tttccgcact ggtgacttgg    1920
actctaagcc cgaccccagc cggagcttca ggccttaccg agctgaagac aatgattcct    1980
atgcctctga gatcaaggag ctgcagctgg tgctggctga gcccacgac agcctccggg    2040 gcttgcaaga gcagctctcc caggagcggc agctacgaaa ggaggaggcc gacaatttca    2100
accagaaaat ggtccagctg aaggaggacc agcagagggc gctcctgagg cgggagtttg    2160
agctgcagag tctgagcctc cagcggaggc tggagcagaa attctggagc caggagaaga    2220
acatgctggt gcaggagtcc cagcaattca agcacaactt cctgctgctc ttcatgaagc    2280
tcaggtggtt cctcaagcgc tggcggcagg gcaaggtttt gcccagcgaa ggggatgact    2340
tcctcgaggt gaacagcatg aaggagctgt acttgctgat ggaggaagag gagataaacg    2400
ctcagcattc tgataacaag gcctgcacgg gggacagctg gacccagaac acgcccaatg    2460
agtacatcaa gacactggcc gacatgaagg tgacgctgaa ggagctgtgc tggctgctcc    2520
gggatgaacg ccgtggtctg acggagcttc agcaacagtt tgccaaggcc aaggctacct    2580
gggagacaga gcgggcagag ctcaagggcc atacctccca gatggagctg aagacaggga    2640 aggggggccgg ggagcgggca gggcccgact ggaaggcagc cctacagcgg gagcgtgagg    2700
agcagcagca cctcctagct gagtcctaca gcgctgtcat ggagctgact cggcagctgc    2760
agatcagtga gcgcaactgg agccaggaaa agctgcagct ggtggagcgg ctgcagggtg    2820
agaagcagca ggtggagcag caggtgaagg agctgcagaa ccgcctaagc cagctgcaga    2880
aggctgccga cccctgggtc ctgaagcact cggagctgga aagcaggac aacagctgga    2940 aggagacacg cagtgagaag atccacgaca aggaggctgt ttccgaagtt gagcttggag    3000
gaaatggttt aaagagaacc aaatctgttt cttccatgtc tgagtttgaa agtttgctcg    3060
actgttcccc ttaccttgct ggcggagatg cccggggcaa gaagctgcct aacaaccctg    3120
cctttggctt tgtgagctcc gagccagggg atccagagaa agacaccaag gagaagcctg    3180
ggctctcgtc gagggactgc aaccacctgg gtgccctggc ctgccaggac cccccaggga    3240
ggcagatgca gcgcagctac acggctcctg acaagacggg catccgagtc tactatagtc    3300
ccccggtggc ccggcgcctc ggagtccctg tggttcatga caaagagggc aagatcatta    3360
tcgagcccgg cttcctcttc accacagcca agcccaaaga gtcggccgag gctgatgggc    3420
tggctgagag ctcctatggt cggtggctct gcaacttctc acggcagcgc ctggacggag    3480
gctcagcggg cagcccctcg gcggccgggc ctggcttccc agcggccctg catgactttg    3540
agatgtcagg caacatgagt gatgacatga aggagatcac caactgtgtg cgccaggcca    3600
tgcgctccgg ctcactggag aggaaagtga agagcacatc cagccagacg gtgggcctgg    3660
```

-continued

| | |
|---|---|
| ccagtgtggg cacacagacc atccgcacgg tcagcgtggg cctgcagacc gacccacccc | 3720 |
| gcagcagcct ccatggcaag gcctggtcac cccgcagctc ttcgctcgtg tctgtgcgca | 3780 |
| gcaagcagat ctcctcctcc ctggacaagg tccattcgcg catcgagcgg ccctgctgct | 3840 |
| cccccaagta tggctcacca aagctccaga ggcggtctgt gtccaagctg acagcagca | 3900 |
| aggaccgcag cctgtggaac ctgcaccagg gcaagcagaa cggctcggcc tgggcccgct | 3960 |
| ccaccaccac gcgggacagc cctgtattga gaaacatcaa cgatggactc tccagcctct | 4020 |
| tcagtgtggt ggagcactca gggagcacgg agtctgtctg gaaactaggc atgtctgaga | 4080 |
| cgcgggccaa gcccgagcct cccaagtacg gcattgtgca ggaattcttc cgtaatgtgt | 4140 |
| gtggccgggc accgagcccc acctcatcag caggagagga gggcaccaag aagccagagc | 4200 |
| ccctctcccc agccagctac catcagccag agggtgtggc caggatcctg aacaagaagg | 4260 |
| cagccaagtt gggcagcagt gaggaggtca gactcaccat gctcccccag gtggggaagg | 4320 |
| atggtgtcct ccgggacgga gatggagccg tggtccttcc caatgaggac gctgtttgtg | 4380 |
| actgtagtac ccagtctctc acctcctgct tcgcccgatc gtcccgctct gccatccgcc | 4440 |
| actctccttc caagtgcagg ctgcacccct cagagtccag ctggggtggg gaggagaggg | 4500 |
| cactccccc cagcgagtga cagagcagcc aagctccccg cctcaaccag cccagcccct | 4560 |
| ggatagcaga agggaaccag cagagacgag acgaggtgag gcgaggggct gtgtcctcag | 4620 |
| cattgcctgg ccctggaggg acagcagtga tgccactgcc agaatgcagc tttcacatca | 4680 |
| aggtaaagcc gggtctcctg ctggcccctg ggtggtgagc ttcgacttcc aggggaagg | 4740 |
| cagtgagtgg gagagagacc aaacctgggc ttcccaagca tccactgaga gatctgtcaa | 4800 |
| gagccgatcc ctgggtccta agagagagcc ttgcctggtt ctgcccatgc caccctcttg | 4860 |
| ga | 4862 |

<210> SEQ ID NO 4
<211> LENGTH: 1439
<212> TYPE: PRT
<213> ORGANISM: Homo sapiens

<400> SEQUENCE: 4

Met Leu Asp Cys Gly Pro Ser Gly Leu Val Arg Glu Leu Glu Glu Leu
1               5                   10                  15

Arg Ser Glu Asn Asp Tyr Leu Lys Asp Ile Glu Glu Leu Arg Ala
            20                  25                  30

Glu Met Leu Glu Met Arg Asp Val Tyr Met Glu Glu Val Tyr Gln
        35                  40                  45

Leu Gln Tyr Arg Leu Arg Lys Ala Glu Arg Ser Leu Arg Ala Ala
    50                  55                  60

Gln Thr Gly Gln Val Asp Gly Glu Leu Ile Arg Gly Leu Glu Gln Asp
65                  70                  75                  80

Val Lys Val Ser Lys Asp Ile Ser Met Arg Leu His Lys Glu Leu Glu
                85                  90                  95

Val Val Glu Lys Lys Arg Ala Arg Leu Glu Glu Glu Asn Glu Glu Leu
            100                 105                 110

Arg Gln Arg Leu Ile Glu Thr Glu Leu Ala Lys Gln Val Leu Gln Thr
        115                 120                 125

Glu Leu Glu Arg Pro Arg Glu His Ser Leu Lys Lys Arg Gly Thr Arg
    130                 135                 140

Ser Leu Gly Lys Ala Asp Lys Lys Thr Leu Val Gln Glu Asp Ser Ala
145                 150                 155                 160

-continued

Asp Leu Lys Cys Gln Leu His Phe Ala Lys Glu Glu Ser Ala Leu Met
                165                 170                 175

Cys Lys Lys Leu Thr Lys Leu Ala Lys Glu Asn Asp Ser Met Lys Glu
            180                 185                 190

Glu Leu Leu Lys Tyr Arg Ser Leu Tyr Gly Asp Leu Asp Ser Ala Leu
        195                 200                 205

Ser Ala Glu Glu Leu Ala Asp Ala Pro His Ser Arg Glu Thr Glu Leu
    210                 215                 220

Lys Val His Leu Lys Leu Val Glu Glu Ala Asn Leu Leu Ser Arg
225                 230                 235                 240

Arg Ile Val Glu Leu Glu Val Glu Asn Arg Gly Leu Arg Ala Glu Met
                245                 250                 255

Asp Asp Met Lys Asp His Gly Gly Cys Gly Gly Pro Glu Ala Arg
            260                 265                 270

Leu Ala Phe Ser Ala Leu Gly Gly Glu Cys Gly Glu Ser Leu Ala
        275                 280                 285

Glu Leu Arg Arg His Leu Gln Phe Val Glu Glu Ala Glu Leu Leu
    290                 295                 300

Arg Arg Ser Ser Ala Glu Leu Glu Asp Gln Asn Lys Leu Leu Leu Asn
305                 310                 315                 320

Glu Leu Ala Lys Phe Arg Ser Glu His Glu Leu Asp Val Ala Leu Ser
                325                 330                 335

Glu Asp Ser Cys Ser Val Leu Ser Glu Pro Ser Gln Glu Glu Leu Ala
            340                 345                 350

Ala Ala Lys Leu Gln Ile Gly Glu Leu Ser Gly Lys Val Lys Lys Leu
        355                 360                 365

Gln Tyr Glu Asn Arg Val Leu Leu Ser Asn Leu Gln Arg Cys Asp Leu
    370                 375                 380

Ala Ser Cys Gln Ser Thr Arg Pro Met Leu Glu Thr Asp Ala Glu Ala
385                 390                 395                 400

Gly Asp Ser Ala Gln Cys Val Pro Ala Pro Leu Gly Glu Thr His Glu
                405                 410                 415

Ser His Ala Val Arg Leu Cys Arg Ala Arg Glu Ala Glu Val Leu Pro
            420                 425                 430

Gly Leu Arg Glu Gln Ala Ala Leu Val Ser Lys Ala Ile Asp Val Leu
        435                 440                 445

Val Ala Asp Ala Asn Gly Phe Thr Ala Gly Leu Arg Leu Cys Leu Asp
    450                 455                 460

Asn Glu Cys Ala Asp Phe Arg Leu His Glu Ala Pro Asp Asn Ser Glu
465                 470                 475                 480

Gly Pro Arg Asp Thr Lys Leu Ile His Ala Ile Leu Val Arg Leu Ser
                485                 490                 495

Val Leu Gln Gln Glu Leu Asn Ala Phe Thr Arg Lys Ala Asp Ala Val
            500                 505                 510

Leu Gly Cys Ser Val Lys Glu Gln Gln Glu Ser Phe Ser Ser Leu Pro
        515                 520                 525

Pro Leu Gly Ser Gln Gly Leu Ser Lys Glu Ile Leu Leu Ala Lys Asp
    530                 535                 540

Leu Gly Ser Asp Phe Gln Pro Asp Phe Arg Asp Leu Pro Glu Trp
545                 550                 555                 560

Glu Pro Arg Ile Arg Glu Ala Phe Arg Thr Gly Asp Leu Asp Ser Lys
                565                 570                 575

Pro Asp Pro Ser Arg Ser Phe Arg Pro Tyr Arg Ala Glu Asp Asn Asp
            580                 585                 590

```
Ser Tyr Ala Ser Glu Ile Lys Glu Leu Gln Leu Val Leu Ala Glu Ala
        595                 600                 605

His Asp Ser Leu Arg Gly Leu Gln Glu Gln Leu Ser Gln Glu Arg Gln
    610                 615                 620

Leu Arg Lys Glu Glu Ala Asp Asn Phe Asn Lys Met Val Gln Leu
625                 630                 635                 640

Lys Glu Asp Gln Gln Arg Ala Leu Leu Arg Arg Glu Phe Glu Leu Gln
                645                 650                 655

Ser Leu Ser Leu Gln Arg Arg Leu Glu Gln Lys Phe Trp Ser Gln Glu
            660                 665                 670

Lys Asn Met Leu Val Gln Glu Ser Gln Gln Phe Lys His Asn Phe Leu
        675                 680                 685

Leu Leu Phe Met Lys Leu Arg Trp Phe Leu Lys Arg Trp Arg Gln Gly
    690                 695                 700

Lys Val Leu Pro Ser Glu Gly Asp Asp Phe Leu Glu Val Asn Ser Met
705                 710                 715                 720

Lys Glu Leu Tyr Leu Leu Met Glu Glu Glu Ile Asn Ala Gln His
                725                 730                 735

Ser Asp Asn Lys Ala Cys Thr Gly Asp Ser Trp Thr Gln Asn Thr Pro
            740                 745                 750

Asn Glu Tyr Ile Lys Thr Leu Ala Asp Met Lys Val Thr Leu Lys Glu
        755                 760                 765

Leu Cys Trp Leu Leu Arg Asp Glu Arg Arg Gly Leu Thr Glu Leu Gln
    770                 775                 780

Gln Gln Phe Ala Lys Ala Lys Ala Thr Trp Glu Thr Glu Arg Ala Glu
785                 790                 795                 800

Leu Lys Gly His Thr Ser Gln Met Glu Leu Lys Thr Gly Lys Gly Ala
                805                 810                 815

Gly Glu Arg Ala Gly Pro Asp Trp Lys Ala Ala Leu Gln Arg Glu Arg
            820                 825                 830

Glu Glu Gln Gln His Leu Leu Ala Glu Ser Tyr Ser Ala Val Met Glu
        835                 840                 845

Leu Thr Arg Gln Leu Gln Ile Ser Glu Arg Asn Trp Ser Gln Glu Lys
    850                 855                 860

Leu Gln Leu Val Glu Arg Leu Gln Gly Glu Lys Gln Gln Val Glu Gln
865                 870                 875                 880

Gln Val Lys Glu Leu Gln Asn Arg Leu Ser Gln Leu Gln Lys Ala Ala
                885                 890                 895

Asp Pro Trp Val Leu Lys His Ser Glu Leu Glu Lys Gln Asp Asn Ser
            900                 905                 910

Trp Lys Glu Thr Arg Ser Glu Lys Ile His Asp Lys Glu Ala Val Ser
        915                 920                 925

Glu Val Glu Leu Gly Gly Asn Gly Leu Lys Arg Thr Lys Ser Val Ser
    930                 935                 940

Ser Met Ser Glu Phe Glu Ser Leu Leu Asp Cys Ser Pro Tyr Leu Ala
945                 950                 955                 960

Gly Gly Asp Ala Arg Gly Lys Lys Leu Pro Asn Asn Pro Ala Phe Gly
                965                 970                 975

Phe Val Ser Ser Glu Pro Gly Asp Pro Glu Lys Asp Thr Lys Glu Lys
            980                 985                 990

Pro Gly Leu Ser Ser Arg Asp Cys  Asn His Leu Gly Ala  Leu Ala Cys
        995                 1000                1005

Gln Asp  Pro Pro Gly Arg Gln  Met Gln Arg Ser Tyr  Thr Ala Pro
```

-continued

```
            1010                1015               1020
Asp Lys Thr Gly Ile Arg Val Tyr Tyr Ser Pro Val Ala Arg
    1025                1030               1035

Arg Leu Gly Val Pro Val Val His Asp Lys Glu Gly Lys Ile Ile
    1040                1045               1050

Ile Glu Pro Gly Phe Leu Phe Thr Thr Ala Lys Pro Lys Glu Ser
    1055                1060               1065

Ala Glu Ala Asp Gly Leu Ala Glu Ser Ser Tyr Gly Arg Trp Leu
    1070                1075               1080

Cys Asn Phe Ser Arg Gln Arg Leu Asp Gly Gly Ser Ala Gly Ser
    1085                1090               1095

Pro Ser Ala Ala Gly Pro Gly Phe Pro Ala Ala Leu His Asp Phe
    1100                1105               1110

Glu Met Ser Gly Asn Met Ser Asp Met Lys Glu Ile Thr Asn
    1115                1120               1125

Cys Val Arg Gln Ala Met Arg Ser Gly Ser Leu Glu Arg Lys Val
    1130                1135               1140

Lys Ser Thr Ser Ser Gln Thr Val Gly Leu Ala Ser Val Gly Thr
    1145                1150               1155

Gln Thr Ile Arg Thr Val Ser Val Gly Leu Gln Thr Asp Pro Pro
    1160                1165               1170

Arg Ser Ser Leu His Gly Lys Ala Trp Ser Pro Arg Ser Ser Ser
    1175                1180               1185

Leu Val Ser Val Arg Ser Lys Gln Ile Ser Ser Ser Leu Asp Lys
    1190                1195               1200

Val His Ser Arg Ile Glu Arg Pro Cys Cys Ser Pro Lys Tyr Gly
    1205                1210               1215

Ser Pro Lys Leu Gln Arg Arg Ser Val Ser Lys Leu Asp Ser Ser
    1220                1225               1230

Lys Asp Arg Ser Leu Trp Asn Leu His Gln Gly Lys Gln Asn Gly
    1235                1240               1245

Ser Ala Trp Ala Arg Ser Thr Thr Thr Arg Asp Ser Pro Val Leu
    1250                1255               1260

Arg Asn Ile Asn Asp Gly Leu Ser Ser Leu Phe Ser Val Val Glu
    1265                1270               1275

His Ser Gly Ser Thr Glu Ser Val Trp Lys Leu Gly Met Ser Glu
    1280                1285               1290

Thr Arg Ala Lys Pro Glu Pro Pro Lys Tyr Gly Ile Val Gln Glu
    1295                1300               1305

Phe Phe Arg Asn Val Cys Gly Arg Ala Pro Ser Pro Thr Ser Ser
    1310                1315               1320

Ala Gly Glu Glu Gly Thr Lys Lys Pro Glu Pro Leu Ser Pro Ala
    1325                1330               1335

Ser Tyr His Gln Pro Glu Gly Val Ala Arg Ile Leu Asn Lys Lys
    1340                1345               1350

Ala Ala Lys Leu Gly Ser Ser Glu Glu Val Arg Leu Thr Met Leu
    1355                1360               1365

Pro Gln Val Gly Lys Asp Gly Val Leu Arg Asp Gly Asp Gly Ala
    1370                1375               1380

Val Val Leu Pro Asn Glu Asp Ala Val Cys Asp Cys Ser Thr Gln
    1385                1390               1395

Ser Leu Thr Ser Cys Phe Ala Arg Ser Ser Arg Ser Ala Ile Arg
    1400                1405               1410
```

```
His Ser Pro Ser Lys Cys Arg Leu His Pro Ser Glu Ser Ser Trp
    1415                1420                1425

Gly Gly Glu Glu Arg Ala Leu Pro Pro Ser Glu
    1430                1435
```

<210> SEQ ID NO 5
<211> LENGTH: 23
<212> TYPE: PRT
<213> ORGANISM: Artificial
<220> FEATURE:
<223> OTHER INFORMATION: Synthetic human-specific peptide antigen

<400> SEQUENCE: 5

```
Ser Thr Gln Ser Leu Thr Ser Phe Ala Arg Ser Ser Arg Ser Ala Ile
1               5                   10                  15

Arg His Ser Pro Ser Lys Cys
            20
```

<210> SEQ ID NO 6
<211> LENGTH: 16
<212> TYPE: PRT
<213> ORGANISM: Artificial
<220> FEATURE:
<223> OTHER INFORMATION: Synthetic murine-specific peptide antigen

<400> SEQUENCE: 6

```
Cys Ser Ala Gln Ser Leu Ala Ser Cys Phe Ile Arg Pro Ser Arg Asn
1               5                   10                  15
```

<210> SEQ ID NO 7
<211> LENGTH: 24
<212> TYPE: PRT
<213> ORGANISM: Artificial
<220> FEATURE:
<223> OTHER INFORMATION: Synthetic overlapping murine-specific peptide
      antigens
<220> FEATURE:
<221> NAME/KEY: MISC_FEATURE
<222> LOCATION: (8)..(8)
<223> OTHER INFORMATION: Xaa is acemidomethyl cysteine

<400> SEQUENCE: 7

```
Ser Ala Gln Ser Leu Ala Ser Xaa Phe Ile Arg Pro Ser Arg Asn Pro
1               5                   10                  15

Ile Arg His Ser Pro Ser Lys Cys
            20
```

<210> SEQ ID NO 8
<211> LENGTH: 16
<212> TYPE: PRT
<213> ORGANISM: Artificial
<220> FEATURE:
<223> OTHER INFORMATION: SOGA peptide fragment sequence

<400> SEQUENCE: 8

```
Lys Val Leu Pro Ser Glu Glu Asp Asp Phe Leu Glu Val Asn Ser Met
1               5                   10                  15
```

<210> SEQ ID NO 9
<211> LENGTH: 22
<212> TYPE: PRT
<213> ORGANISM: Mus musculus

<400> SEQUENCE: 9

```
Phe Lys His Asn Phe Leu Leu Leu Phe Met Lys Leu Arg Trp Phe Leu
1               5                   10                  15
```

Lys Arg Trp Arg Gln Gly
                 20

<210> SEQ ID NO 10
<211> LENGTH: 60359
<212> TYPE: DNA
<213> ORGANISM: Mus musculus

<400> SEQUENCE: 10

| | | | | | |
|---|---|---|---|---|---|
| agttgggcct | ggagctggcg | ctgagcagcg | acgccgagtc | tgcggcgggc | ggcccggcgg | 60 |
| ggacccgcac | cgggcagccg | ccccagccag | cgcagtcggg | gcagcagcct | ccgcggcctc | 120 |
| ccgcctcccc | ggatgagccg | tcggtggccg | catcgtcggt | gggcagcagc | cgcttgccac | 180 |
| tcagcgcctc | gctagccttc | tccgacctca | ccgaggagat | gctggactgt | gggcccggag | 240 |
| gcttggtgcg | ggagctggaa | gagctgcgtt | ccgagaacga | ctatctcaag | gtggggacct | 300 |
| gggggggatg | ggggaggcgc | aggggcggga | gaggactggt | catccgggct | caagagtcca | 360 |
| gggcgctgac | caagcaggga | gagtgcccca | ccttctcttc | ccacttttcc | ggtgaggagg | 420 |
| attatggata | agacaccgag | taaaggaccc | caatgtgcac | tttcccaccc | gcggtaaaac | 480 |
| tgttttagag | gacacgttct | gatgggtgag | tggggatagt | cagccaaggc | tgaccttccc | 540 |
| cccctctaac | ctgcccagga | ccccggtccc | agatcagcag | gctttctcgg | ctctctgttc | 600 |
| tggaaccaat | gtccgtgtgt | taggctgcca | gggaaaccgt | gctatcccct | ggcaaggaga | 660 |
| ggcagaacac | catcctaagt | ccttacccag | ggcttccccg | gcaggcctgt | cctcgcctgc | 720 |
| cttttggggc | ggatccagtt | tgaaagcgtg | acatctggga | acatcccctt | ggctcgagtc | 780 |
| cacttccgcc | cagtctaacg | gtcccacagc | ctgggaggat | gatgtcgtgg | gagaactggt | 840 |
| tcagaggcca | cttcctcaat | cccaggatat | tgtcttctgt | cccctctgag | agaggtttgg | 900 |
| gcagacttgg | cccgtgctcc | ctgtgggaag | agggaaactg | tcctgctggt | tagggtatt | 960 |
| ccctctgtgt | gtgggcctgg | agagctgtct | gggagaagca | atcgtcggtg | actgggcacc | 1020 |
| taggtgcagc | ccatgctctg | gctgcctctt | ctttgacatg | gtggcagcta | tggggacagt | 1080 |
| cctgccctgg | cttcttgacc | ttggtgtggg | aagctgggat | cttcacgggc | tgcactgccg | 1140 |
| ctgctggaag | aggctacagt | attgtctgca | cttgacagtt | gatggcctgg | cacaacaccc | 1200 |
| agagtgccct | ggccaggagc | cattgagttg | acagcactct | aatgacatgt | ctgccctgtg | 1260 |
| gcacttaact | gcctcttgct | tctactgtcg | ggggagtctt | ccttaggatg | ttggggtgtc | 1320 |
| cctcttgctt | tcctttgggt | cctctatcca | gcatgttctc | aggaaactcc | tgtacactag | 1380 |
| aggacacagg | tctatctgac | aaaggattat | ttaccacctg | tttgtagcct | gggccttccc | 1440 |
| caaaccaggc | ctccattttt | ttttttttc | agttaaatgg | gagtgtaagt | cttcacaaag | 1500 |
| gtgttactca | ctgttgacat | tgggagctg | gggttcagtt | agagggcgaa | gtcttctgaa | 1560 |
| gtcagtggtt | agagtgcagg | ccctgaggat | ggagtcagtc | ttccgagatg | ctcctcgtgg | 1620 |
| cttcctgaat | tcccagcctg | agctactcca | gacctggacc | cgagcaccag | atgagcacaa | 1680 |
| ctcacagttc | ttggtttggt | ttcttcctgc | ccagatcccg | ggcccttttcc | tgtgctccca | 1740 |
| ggaagtggtc | agacagagtc | cctaactcca | tctgaagcta | cccatgagta | tgtagatggg | 1800 |
| aaagtggtcc | caggaggctg | ggggtcgagt | ccaggttctc | ctagagacca | agactgggtt | 1860 |
| gagttccagt | tccaggccca | gactgagcct | cactttctgc | caaccattca | gttgagtttt | 1920 |
| tgggcgaaag | cttcaggccc | ctgttggatc | tgtagcttcc | tggctgtgta | atcttgggca | 1980 |
| cattacttac | catgtttgga | cctgagtttt | ctcatcttaa | gacttgaata | agtacacaca | 2040 |
| gatcatcctt | aaagattaaa | tgtgcacgta | gctagagcat | ttggcacggt | aggaaacttc | 2100 |

```
agatgcggtg gctgagatct cctgctgctc tcaggatgga gagcatggtg ccttgtgcat   2160
ctgtcacatt cttttgtgga ttctatggga tcaggctggg gtcttcctcc ttacctcgag   2220
gccatccatc catccatcca tccagtcagt cactgtttgc ttagagcaga ttttggagta   2280
tgagtgaact agggagagcc tctgtgacac caagagttaa acaatagtca caacaaaaca   2340
caatgcgcct ggtgataagg gtgagctttg tggaggtggg gcagaggact catggaggcc   2400
aggagttggg agatgatgta gacagccaaa tgaggagctg caagaaaaac attctagact   2460
gaagaaagtt gggcgagtga ggaagggagc catgccaact cttgctgcat gcattcaggc   2520
agtacccaca ctgctctgca gggctgtttt ccacagtgtc tgccctcacg gagatacagt   2580
aaaagccctg ggagtgtgga ctgtacacct acagggcagc ttcttactgg aggtgttatg   2640
ttgtcacagt gccagggct ggcttagcca gagcaggaag gcgacctgct ccaggcagcc    2700
agggctggga gtcagggaga agcagtctcc tgagtgtttc ctgtttctct aaactacttt   2760
acatctgagg tacagaaact gggttagaag gaaaatgact ccaaatcccc agggtgtgca   2820
ctgcagactg accttctgag tccagggaat gccctggact ctagctggct ctctcgtcag   2880
gttcacctcc ctgtgtgtgt gtgtgtgtgt gtgtgtgtgt gtgtgtgcgc tagggggtggc  2940 acggtgtggg taaactgtca accaggaagg acccttgggt aactgcatat ctcctgtctt   3000
aagaacccct gctctaggac ctaagttaga gaggtagcag aacctctagc ctctgccagt   3060
gaaaagacag aaagcacttc tgcagggaag gtggtgagct tggtgtcact tgaactatgc   3120
agagaggcct ggatacaggc atagggttgg tgggagcatc atgtaaatgg ttcttagtgt   3180
tggttgtgat ccctggggtg caactgggga ggtatgtgtg gtggctacag tctgacatga   3240
ggtcccttct agtcaaggtg tctgcggggg gtgggggggt gggggggtca tccgatgtgg   3300
tttttaggac ccagaaatac aactttagct gtagagcagc caggttaact gggtctgact   3360
ttgacccagt ggcctgaggt ccctatgacc actaaccgtt ccccttgtcc ccctgggcca   3420
tgttgtatct cagagtactg gagctcaaag atctggcttg gagccctgat tctacctttg   3480
ctgtgtggtc atggtcaagg gctggacctc tccgcgatgc tcttgttttt gttttgtttt   3540
gttttgtttg tttcatttgt ataatggaga tgacggatgg ggtgtgcctg gacactctcc   3600
aaggattttc tcagtaatca gggtagatgt aaatagtgaa gaaagcatct gaaagtgaga   3660
tccttgtatt gtgaggaact gttaggattt caagccaatg agcagacagg atgtctgttt   3720
gttcattttc ggaggaactg ggaggagtcg ggagggtggg catcctcagc ccttgagggt   3780
taataaaccc tcccgcttca ggcaggatag acaggcaaga tcacattccc ccctgcacag   3840
gctggcagtg gggagactag gcccctgcct gggggttcca gctgggagtc acaggtccca   3900
gagaaaagcc cttactgact ggcgattgcc attatataga tgggcaagtg gagactccag   3960
gattctgtca tacagcccat attccaacct tgctgttcac tcttggtcca tatccttctg   4020
ccatgtggcc ggcgagactg tgcttttgat cgctactggc gtgtctggtc ttggatagag   4080
gttggtgaga ggagtcctgt gggccaggtg ccaggccaag attgtaggc agccatggtg    4140 agtaagctca gttggggcag tgtctgctca gcatgcacaa agccctggct ccatccctag   4200
atccgaataa gcctgaatg ctggcacacg cccgtctgta atcctgccat ttgggaggca    4260
gaggaaggct atcctcggca gtgtagtgag ttcaaggcca gctgggcta agactgagtc    4320 tcaaaaaaca aaacctaaa aggctgattg atatctatct aagcctgtag gtgggggtgt    4380
gcctctgggg catttatac atgtctgtaa aatgggatt gaattgtcat ggacctctta     4440
attgtgagga tgcagtgtcc attgctcagt aaatgtgcca acccaatcac catcctttcc   4500
```

```
ctctcttcct ccctcccttc tctgatgta gcccagagtc ttgtgagtgg catgcctgag    4560
gcagttcctt caaagctcct gggagatagg agaggaggga cccagcctgt caccatgtca    4620
gcgatgtccc ctggttcctg ccctgagttg tagcttctgg ggagggggg tgcagcaggg     4680
cttggaggtt gggggagcag ctccagcagg atggaaaatg tgggcggcag ctgctgtggc    4740
cagaggatac cacagagctc ggcgcactct gcaaggggct gggcctgtgt ccctggacac    4800
agccctgtac acataaacac atgcacactt cttcagagct caagcctaga gacccacagt    4860
tactcatgcc tggctgatgt atacattcag tgactcactt atgctatatg cttccagaaa    4920
ccagcctcca gacacgttca ctgtggatcc acatggaaag tgacagacag acccttcatg    4980
ccacacacta ccaaacacaa cacttagcag caggagacgc caggctggga agtacacact    5040
ccctcacaca gcctgaagac actctcagac acaggaagtc catatacacg ggaaagtgtg    5100
cacatacgtg cacacagaca ttatctatac gcaccagcat ccataggatc ccagagactt    5160
gtcaggggac acagacacca tccactccag tacccagtgc cacctcttcc tcagagagca    5220
agcaacctt gcacaagtac ctggggttca acagatgtca catgaatacc cacaaagagg     5280
ttcgcaggca ggatggaccc aacctccgca cacattagca ccaacacaag ggttgatcat    5340
gcagatgtca gacatggtgt ttgcttaacc agggcaccca gacatacatg ctcatgcaca    5400
cgcacgtcta tttacactga cggtgacatt tcacctacgc acataaacac aggaactctt    5460
ggtcagtgtt ccccggagct actgtgtatg actcttctgt ttccagctgt ttcataaggc    5520
ttcttgtctt gctgccggga ccataagtgg cgtcaggact gggtttgtaa ctgtctggat    5580
ctggggtccc aggggcccag ctgaggaggg ctgcaggtgg agtctggagg tctccataac    5640
tggagaaact gcatctaagt tgcccaggct ccagagccac gccctgtggg actaagggaa    5700
atagacacat gtcaagcctg ccacagaagg aacggtgcct cagggtaact cttctaatcc    5760
cttttggaatt tcctgcatac cctgcctccc tctgctgcaa gtcacagagg ccgcaatgcc    5820
ctgatctgta gagggtgccc atgcctagtc tagaactagt ctagaagtga aagaggtat    5880
acgcacctaa gagcagctga gcaggcttcc tggaggagga ggtgtcacag ctggggattt    5940
gcctgattgg ctgcctcagt gctcagcttc tggataaggg cctgccgcct tgcaggggct    6000
cactaagtag atgtgtatgc ttaattgatc agctatggtt ctggcctaga aatgatagt     6060
aggtttggaa aggagggctg gagccaggtg tggaggtatg tacgctcagt ccttgtactc    6120
aggaggctgg ggcaggagtt caaggccagc tggttactac atagtgagac ctgtcaggaa    6180
aggacagagc gagagggagg aaagaatagt tgagtcatgg gtgtgagagt catggaacta    6240
ggggttgggg ttgaggagta gtagaaggtc aggaggactt aggaaggaca ctaggtacct    6300
gagcagtaga cccttggctg gaagatagtt ttgttggttt gtagcagggc tggggccagg    6360
tggccctagc actaggcaca aaattgctgc tatctcaggg tgccaatgaa ggcaaaagca    6420
aggaagactg tgaggtccca caggcacact ccgtctttag aatcaggtcc gaggccaagc    6480
cacaccttgt tatgtccctt cctgtgcatg ttgcctcttg gaacctcagt cttccagtct    6540
gtatagaggg aattcaatcc ctttcttgca gatactctgg gagataagag ttcagacaca    6600
tgagagccca tttctgtcct gtatacagaa gatgggaggg actccaggct ctaggtagcc    6660
tctgtggcag agggacactc cagaaaaggg cttggttaag ttcaaggcaa agggctggct    6720
gtcagccagg gttctaactg tggccagccc ctagcctcca acatatgaca tcatctgtag    6780
tctatacaca cccctctggt gcaggaaggt ggggcccctg cggtcagcac tgtggctgcc    6840
tttgctggct ttccaagctg gggcaggagt cggaggaggt agaagctact gttcatccct    6900
```

```
cccttgtctc agtctaaagg tctgaaagct tgggatctgg accaagcctg ggctgcatct    6960
gggcctgtgc tttgctccct gttcccctc  caggaaatgt tctgcagtgt caccatgatc    7020
attcaacagg agggagccgg tgtgtgagga gttggtcccc tctgtgtttc actcatcctg    7080
gttgtcagcc cttacccttc aacagctcca gaaatgtgta gacacatttc tccttggcag    7140
ctcacttacc ctaagtcact cctcccctga tggccaaaac ctgtgtctca tttgcaacct    7200
ggtgatgctc gcttagtggt gaaggaccac ccttgggggc ccattccaag atagtggtaa    7260
aacatctcct gcctgggcta cagatgaaaa taaaggtgac tggtgtgtgt gtgtgtgtgt    7320
gtgtgtgtgt gtgtgtgtgt atgtgtgtgt gtgtgtatgt gtgtgtgctg tgattcccca    7380
actgctggtg tgtatgtgtg tgtgtgtgtg tgtgtgtgtg tgtgtgtgtg tgtgtgtgta    7440
tgtgtgtgta tgtgtttgtg ctgtgattcc ccaactgcct gagcctccgt ggctctttgg    7500
gactcttcag tagcaccaga ctttgttttgg tcacccctcc ctggtctgcc ttgcctaggc    7560
accatcctcc tgtcccagcc catggctaag tgcgcggctg agctgccttt aagtcttgct    7620
tccccagcct tttcacccag acgcccccag tgtcctcttt gcccttttcat tatggatcca    7680 tcccctgtc  ccctttccat gatctcctgg ggactgctcc aggcctggtt tcctgtgtta    7740
ggtactagga gctgtgggga ctcctcggtg ggacatttag ctcacagtga ctagacttgt    7800
taacaggaca tttctggctt cgcagcagcc actcctgctt ctgcatgcag tgtggcgctt    7860
ccagggtgct tagccccttc cttctaacca ggcttaaact gcagcccgag cattacgtca    7920
ccttgcttgc tagtcacatt agctgtaaag gacaagaggg attcaggccg tgtggttctc    7980
ggtgattctg caagcctcga ctccctgccc ttttctgtta cagacttggc tgaagcccag    8040
aggttggggg atgttgtcaa caaaccctga tccaaagctg ccttccttcc tgggcaggac    8100
aggagagaca gtgtctgtgc ttccttgagt gtgcccagca gcccagggcc tcggggcgct    8160
gcccctaggc tacacacaca cacacacaca cacacacaca cacacacaga gagagagaga    8220
gagagagaga gagagagaga gagagagacc tggagacaac ctcacttccc tccctcagcc    8280
tcagttggtt cccctgggaa gtgggcaggg taagaataga gcttgccaca aagtatcacc    8340
aatgagaaag agagaatagc ttctcacctc tgctggtgtc tggcacatgc catcccttg     8400 gaagtgccca gctgttgtta cttctgttgt cccatttatg agcctcaaaa tgagcctaag    8460
tcctgactcc tgacgcctct gctttcaggc ttcttgccta ctggggaggg agggactaac    8520
tgtgtgctgt tggcatgagc ctgccgtggt cagtctgtct gctctctctg gtgttggaga    8580
ggcagggccc agagaagtgg gacctcatag atctctaggg tcagatatcc ccagtgccaa    8640
tggaacagga gcattgagat cctgtaactc ggtgatgcat ggctggatgt gacttcctct    8700
gtgacactta accctgattc ccccaaacct ctgcccacag aggctaagct gggttgagct    8760
tgaacaggag gcaggaaccc agagtccttc ttggcctcac tgcgcgttct gtaaaggaca    8820
aggagtcttt gagttcccct tctcctggag tgtttgcatt caaactggga gggaagtgaa    8880
gctctttgca gccttctcct ggggtctgac tgtgatgatc tcatctggag ccctgtcaga    8940
gtcccgggga ggaggaggga cagcagatgg ctttttctggc cttttgggtg gggctggcct    9000
gctgtccctg tggccactgc tggtcagctc ttccatagct ggggtaggtt gccagggcca    9060
gagtgggtga caagtggtct ggagccaggg tggcagatgg gtaggcagcc tgggccttgg    9120
cccaggggag gaccatggta gccaagtggt gtgggaggag gagggcaaag cggagcccct    9180 ggtccttgt  agagtggttg attagagtga agtccctggc cccatataga gcatagcttt    9240
tcctgtccat ccctaagtct gcttttgagc tgggcaggaa atgatccatt tgggtaagat    9300
```

```
ttggaatatg tcacggctgc ggtcgggtgt catggtgctg ggagttgaag cctccgtgga   9360
gattggcctc ggagtctaaa cagttgctgc agctgctcag tgggatggtg gtcctccctt   9420
cagcctggct gttctgttcc ctcatggcta tttcttgagc ccctctatat gtgcccgttc   9480
tctggtgact gaagtgggtc ttccacaacc aagcagacaa atgagtaaaa tacccgtcac   9540
taatagaact gtgtcgtgca gtgtgaggga aggagaaggg taggctgcac ggcttggcag   9600
gaggcctgac aggaggtgcc ataggccacc cacacaggaa tggcagaggc tgaaggctgt   9660
gacaggccag gtgatttctg ctggtgcagg aagactcggg tggctgagtg tggcccacgt   9720
gagggtggt taagggacat ggaggtgaag ggagtcaggg ttgggcctgg tggagcctga    9780
gctcctagga taggtttgct ctgcgtgatg aacgagaccc cccggaggtt ctgtttctgc   9840
tttgctttat gtctatttga aaaaaaggtc tcactgtaaa ataagttttg ataaatgtac   9900
tataactgtt aaccccagtc aagataaggg ctaacgccta taaactaggt acattaggat   9960
tgtatttctt cttcaatcta tttatctatc tacttagtta attaattaat gtgagtgtgg  10020
gcgtgcatgt gggggtcctt gtggaacttg gttctcccct cccatcaagt gggttcttgg  10080
aattaaagtc aaatcgtcaa gcttggtggt aagggtcttt gctccctgaa ccagctcaca  10140
ggcccctaat tggatacatt aattttttt aaatttaatt ttatttttac tgtatataag   10200
ttatacctga gagctaggga tgtagtagct cagggccaga gcctggactt cacatgtgag  10260
agatgctggg tttaatcctt agcaatcaaa aagaaaggg agtgggggat tagaagtgtt   10320
cattgttcag ccaaacttcc tctacaacca gagccctccc tcgactactg atctgttctc  10380
tgtcccttag cctcacccat tcacagtgtc acatgcatgg caccctcagc atctcctgtg  10440
gctggcttcc ttcgaggagt caaagcccgg ctgctccagg cttccagagc accccacccc  10500
caccccccacc cctcgctgct gctggtgtta catggtgggg tcacagctta gccatttgtg  10560
agtcaggagt cacgtgggct gtccccacgt tttgattatc attggagggc ttaaagcagg  10620
gaacatttaa acagttttaa tcacatttta agtattaaaa aaaaaatcac aggctggaga  10680
gatggcttag gggttaagag cactgactgc tcttccagag gtcctgagtt caattcccag  10740
cgaccacatg gtggctcaca accatctgta acggaatctg acgccctctt ctggtccgta  10800
ctcacataca taaataaat aaatagttca ttaaaaaaaa atcactcttt gggagctggg   10860
gtacagagca agcactaata tgcaaggtgc tgagttcaat ccccggagct ggagaagcga  10920
tgggggtggg gggagaaaga gagggaggga gaattactgt gtcttgtact aagttgggag  10980
cagcttactg aggtcaagga agggtcacca tgacaagaat ctgggcccgg ccaccaggcc  11040
tgctgtaggc actcactaag tattcaaaca cctggatgtg cccaaggaag tctgtgtttc  11100
tgaggtaaag agttaggagg cagtgacaga gcaggaggcc caggtgtgct gtctgtgggc  11160
tcactgcgat aggctgtcag ttcccagctt ctgaccctgc ctgggcacaa ctgggatctc  11220
agatgtggtc attaggcttc cagggtggca ctgggagtta ttctccagtg ggagggagtt  11280
gagggtctcc acatatcatc ctcttgtctt caggaacttt atgtcccctt ggctccttct  11340
tggttgggac tgtctctggg gtcagactac ccactgccac ttgctgtgtg tctgcaaagg  11400
gatgtcgtgt ccagtcctca tttcccacag gccagatcca tcatgcacac agtctgcact  11460
cctgtacaag gaaggacttc accaaagcca ttccctctg tgttctcagg acagtcaat    11520
catcttacat ccatgtaggc ggcacagaat caatccttgg atctgaagtc agggctggcc  11580
aggaagttca gggatctgcc tgtctccacg cctggcttta ccatgggtg ccggatgacc   11640
tcagatctgt gtgcttgcac agcgagtact ttgcccgccc agccatctcc ccagtgttgt  11700
```

```
ttctcccttt tgatgctctg agctatcagg ggctggggta ataacccagg ctttgcagat    11760
catggtgctc ccaagagaat agaggctctg gcattgtatt ctatgcatgg accctattac    11820
tgttataagt tatactgtta taggaccccta ttataggtta taacctctgc tgagaccctc    11880
aggataatgt ctttcagtgt taacctccaa atccaaggag attcaagcta gattgaaaca    11940
attactaaag tatgctacaa ctatgatata gttatgtgct tgttaactct tggattctga    12000
tagctgcttt aactactgta attacaaggt actgatgagt ataaacaata ttttgacatt    12060
tttgcaacaa ccgttatagg atatgaagat attagcaatt tctttggtgt ccaagtcttg    12120
agtgcttctg atacaacctc actttgttct tgagtccaca atggaaggag atgcaaattt    12180
caagaggttg ttgcaaataa agatgcaact ttgttgagta gccaacagag aggaggggac    12240
ctgagggaag catcccttca gggctctgcc tgttggggta ggctcagcag gcccggtccc    12300
ttgatgcaca cagctctctc tgtacaacgg attcctggct tgccttgctt tctgcaggac    12360
tcatgaggtg attcaccagg aatgtctgta taaactgtgg agtcccttgc aaccctgcaa    12420
gcctattatt agcaatattg tgagttcatg ttgggtcctc gagcccagcc tgaacttaga    12480
gactcttccg ggccagtttc ccaggagtcc tgggaactgg ccatctctga gaggttgctt    12540
cctgccggca gccctcacgg aggtacttga catgtaggag atgtgtggga agcttgcggt    12600
tccctgggca ggcagacctt gctatcctcc tgaggtggca ctggagtcag cctgggctct    12660
ccctgccctt tcacacaagc cctagatctg gggtcaaaag acagaaggc tccaggctat    12720 ggaaagagac caggcaggcc aatagccttt ctcttttgtt cacacctgcc catggtgcct    12780
gttgcattcc acatcctagg gatgttgggg agcagaagtg ggtgagaccc agcctcactc    12840
tgccctgccc ttcctcaggc agttagaggt agaacgacga ggagcaagcc gatgtaaccg    12900
taagtcgtta ccaccaggga cctgcagttc agggtgtagg ttctgaacag ggaagagaga    12960
gaggaatgtt ctggaaagcc gagagagctg ggagttctcg tggtgaaggt cagtagagca    13020
tagcacacgg cctgcgtaaa gctggaagaa tgcagttcgc atgccctggc ccagggccac    13080
tgccttgtat gtaatccagc ttcaccccctc cctagcttga acagtctctgg gaaacttctg    13140 agcctcagat gcccctctg caaaatggga gcattttcga tgcctctcac agggttagca    13200
agagatttaa cactcagaag tgcgtggatg agcctgtgtt tgtgagcctc cctgtagggc    13260
cagggtcagc cattcagtcc tagtatagct gggtgcaggt gcaagataga atagggaaca    13320
gattggcaag gggtcagagg ttaggggctt ggacctgagg tggaagccag gggaatgagc    13380
ctgaaagcca cctgctttta ttcagactag tcaacagaca ctgccttccg aacagagcca    13440
aggagccttg caaagggacg atcatggcag gctgcactgt ccctagaccc tgccctcct    13500 tctactccct gtctgcaacc tggacttaga tgttgtctaa gggacagagg gcagcaggga    13560
gtcagagcct ggcggggctg cttgactcct ttcttcagct tccttaggct tgataacagt    13620 ctagggtct aatttatttc agggtgtagg gttgagaact gggggcccct cagactccag    13680
ggtgggcact gcacagtgtg gccttttaca tctgaggtag agggtgagat ttggagtgcc    13740
cccatgctgg aaggggggaa cctcagaacc ttgttctatg agattgatcc ctctttcttg    13800
atgtcctata gaagagttca agaggtggca tctctgtggg gcctctggac tgtctgtgaa    13860
gaaaccagga ggcctgtgtc tcagctctct ccaactggac ctgtcacccc agagcctcca    13920
aaggcaaaac tctgactgta gggcccaggt gcccagaaga tctctgggct gggtgtggac    13980
accgagcctc tgtcttttcc ctgccccctc ctcagaccca gatacccaga gtctctgcct    14040
aagcactaca gtgtccagcc catgtgggct acaagcctgc ttttgtcaac tcaagccgtg    14100
```

```
ccaggagggg ctggtgggtg ttttgcccgc agctggggca agcccccaga ggcttcagcg   14160
ccccaacccc ctcagataca gaactggcat gcccacaaca gcctgcactg tggtgagggc   14220
agttcccccg agagacagct gttggggata gccattcagt cacttcttcc ctagacgcct   14280
gtgtcaggct cagagccagg gacttgtgcc gtgagatggg gctcttgtct tctgtgggga   14340
agaaagtggg aaggaagttc cttgcctcgg aatcacttgg ggaacccacc cctgaagttt   14400
ctgcttagta ggtgtggatt gggaatatgt gtggggtggg ggttgcatag ccctgggggta  14460 gaaccacacc cctgagcatg tttggcagac actgccagtg agctatacca tcctggggaa   14520
cacttgtcat tcagaaccag atagagaaat tgtgattgat gttttctgta tttttcaaaa   14580
ctttctgttt gaccgtggtg gactaccttc acaaaagccc gttacttaaa atatagaggg   14640
atgtcacctc ctgtgatctg tatggagcga catctccacc tgtgatccca tcagcctgag   14700
cttgagtatg tctgtgttcc ccttgactca ttctgaccta gagtcacttg gaccctcaca   14760
tcctcccagt taccgtgttg tcaggataac agggtaacat gtgagctgct cgtggttggc   14820
aaggccctgc agcctgggcc atggatgtag ctgtctgcct tcacttcctg cccttccctt   14880 cctgcccct tccctgccag ctgagctggt tcatgggctc ctcacttccc catttctccc    14940
accgactgtc tcacttcctc cctgtccacg ctggtctgcc cagttggcat ggtgtggggt   15000
ggtgactctg ggtactttga gatgactgct cctctgcagc cagtaggcag ggtcacccac   15060
tccggttgct ggtgaacaca ccctctggac acagtctggt gctgcacagg gatacttgga   15120
tcagttgtga gttgagagag acagcatgtg gtggggtgga gccgccaatt tgtcacttct   15180
gtcttccttt cctgggttct gagaaatagt tccagaagtt aggcagatgg atgggagggc   15240
ccctggagtg tgctgtggcc tggatagttt ggcttcttac ctgtccatca atccagcaag   15300 ccacacccctt tccccctcaca gggagccatt gcagccagga catattctgg tcccactgca  15360
gtgtggaccc acagcctgtg ctcggcccag tggaggctgg caggcaggtg tgaggagagg   15420
tctccgtgtt tccttttcca gactatcaga tccctggggc gagcacaggg tgtggggagc   15480 agagggatc ccacccctac accctcccct ttattcccat cttctttagg ggactccagc    15540
cctccagagt agcctttctg ttctggttgt ctccctgctt ccatcagtac caaccttgtg   15600
agcttctcct gggagcagag ccttcgtcag ggcctggtcc ctggtgactc agtttccctt   15660
ctgtgtgtaa tctcgttaaa gctaacagca aatattattc atgtttgtga ctcagtttcc   15720
acatttctta tgagacataa ttatgtgttt cctctgggag cgtccacat cccccctctg    15780 tgtagtgtct gggagtcacg tcccatcttt cacagtgaga agtctctctt attctctctt   15840
ccttagctag gcatgttttc gttcgttctg ttagtacctg ttgagagtgt gcaggaggct   15900
aagcaggtgc tgggtgtgtg tgtgggggggg gtaggggcag gcaggtaggg cgacctgaag   15960
attcccacag tcactgggag agcaactgcc aaacagcttc agatgagctg aggtgggtga   16020
ggcaccgata ggagctgtga cagaggtggc agtagctggg cttcctgagc gaggtcacct   16080
gaagatcccc cactcaaaac tccaaccaga ccttccaggc ctgcaaggct gatccctcca   16140 tatcccagc cttgtgggtt ttggacagtc tcacatagat gaggctggtt ttgaaatcat    16200
gatcttctta attccatatc cccgtgcctg accttgctc gatctttaaa acaaacaaac    16260
aaaagctttt ttagacaata gtcccactat gtataagact tggctggcct gcagctttct   16320
ctatagacca gactggcctg gtctgaaatc aagtcactct gctctgagat cctgcctttt   16380
tgtctctgcc ttttttcaga tgctgagatt aaaggtatgc accattatta aataaatatg   16440
tttttgatta aaaaaatttt ttttcaagac agggttctct ctgggtagtc ctgtctgtcc   16500
```

```
tggaactcac tctgtagacc aggctggcct tgaactcaga gatccttctg cctctgtctg   16560
tctcttgagt gctgggatca aaggcgtgca gcacactacc tgaccaatat acttttaaaa   16620
tgacatttct ttgtacatgt atgtgccaca gaatacatga ggagatcaga ggacagctta   16680
cagaagtggg ttctctcctc tcttctacca cgtgggtccc aaggaccaaa ctcaagccac   16740
taggcttggt gggcagcacc ctgacccatc ttacctgtcc cattgatgtg tctttgtttt   16800
ctcagctgag acagggcctt actgtgtagc cctggctatc tcagaactta ctctgtagac   16860
caggctgccc ttgacatctg cttgcctctg cctcccaagt gctgggcttc aaggcatgca   16920
ccactacact caacgtcttg cagtgtctgg atacattgag ttctacttct aagcctttgt   16980
acacactgtt ccctcttcct ggaactcctc tggatgttgc ttcttgcctt ggcttagatg   17040
tcccttcttt agagatggcc cccttcctcg ctcactgcca tgtaacccac attgttactt   17100 tgttatttt gcctccatga tacttactta acagtatctg aatttgcttt ttgtttactt    17160
tgttttccaa acaaggctgc gctaacatcc ttccctggtt ttgtgtgcta cacagtgtcg   17220
gttatgtagc agacactcat gaatgtttgt ggagtggatc cctggtgtat gtttcccatt   17280
gcttctgtct gcgacaagcc tctactgttc cctctgtcgc tatgacaaga gaaggaaggc   17340
tgtgtttccc atgctttgg aggcctccgt tcaagatcat tttgttcctc ctgtgacaca    17400
gagccatcaa gcagggaga gcgtgacgca ggaggctgtc acctcatggt gaccaggaag    17460
caaggcacag ggtatcaata gcctttcaag ggccctttcc aaagatgtct ctcccttgcc   17520
tcctgaaaat ggtccactgc ttcacagtag aaccatgagg aatactcagc ccatagcaag   17580
tgactttggg gggggggggc gctttaagat ccaaatcgta agagtggtgt ggctgtaaat   17640
tatcttccag gtctttgaga ctcgagtcct ggtggctcac atgtctgctg agtgttctga   17700
gacaaacagc atcctctcct gggccttttg gcccttgtgg atggttcaca ctgtggaggc   17760
cacctgtact ccctggctgg tggccctttc tctacctgca caacctgtca gtatttcccc   17820
tatttctccc tcacattgct cgctcccact aacttccctc tcatggccca cccagatggt   17880
caagaataat actcccatct agagacccct ctcttagtct cgtttgcaaa gccccctttg   17940
ctgtggaagg catatattta ggatccctg aatttagctg tggctgtctt tgggtggtgg    18000
tattcagcct gtaaccccag ctggctttct gagtgtggcc agcattcagg caccctggct   18060
actgccatga catctgtagg tctgacccct tcttttcacc cctcaggatg agattgagga   18120
gctacgggct gagatgctgg agatgcggga tgtctacatg gaggaagacg tgtatcagct   18180
gcaggagttg cggcagcagc tggaccaagc cagcaaaacc tgtcgcatcc tgcagtaccg   18240
actgcgtaag gctgagcgcc gcagcctccg cgctgcccag acaggccagg ttgatgggga   18300
actcatccga ggtctggaac aggacgtcaa ggtcagtctg gggtcactgc caaccttcac   18360
aggtgccctc gttgggtggt tggatcataa accccattgg ggatccaggt taggcctgtg   18420
gcttactgct tgccttgagc aaattatcct gcctctctgg gcctcagttt ttccatcttc   18480
aaagtgggga cccctggtgg atcaacacat cctccaaaca ggatagccag gaaatggtat   18540
gacaagaacc cttctgaagc agcaagaggc cgtttcttgt atgtctgctt tgtatgtggc   18600
tttggcctct gagtaggccc tactatggt ccctgctcag caccacaggc ttcttatggg    18660
aagactgcag ctgaaccagg atggttcaga gctgggctcc aggatacttg gctttgagg    18720 tttaatcaa gtcttctata tttcaatgtc ctcatctgca aaatgggtat aagaacctac    18780
aatccagaat attaaaaccc tggctaagac accagaggga ctgacagtga gtagctatta   18840
ttactgcatc cgttttctgg aggaggggc tgggcctcag aggagagaag cacctatcca    18900
```

```
gggtcaagac gtcaggccca tccacctctc agacctcact gctggaacct gctgcttctc   18960
tgcctaagga gaaagcctga atggcgccac ttaggtcggg gatggaggag agaagtcccc   19020
attgccagtc tgtcttatgt aagcccccaa aatgtgggga ccctgagcca gcctccgctc   19080
tcagaactca gtccagtgtg aacaaggaac tcagggtgct gcgaccggta cagaactggg   19140
aggagcctag gagttctgca ggtagcccaa gggggaagag ggcgtgagcc tgggaaagat   19200
ccaggacttc cttggggaaa gatcccaagg gccccggagg gcaggcaggt gctgagcaag   19260
ccacacacct gctgctggaa agccctgaga atccagccct gcagggcatt cagaaaggac   19320
actgttcatt ctgtgaccag cgttgagact ctatgcaagc ctgtgaacct gtgtggagcc   19380
agtttccttg actgcacact aagatcttgt tatccaaaaa atcataaaca aaacacgatt   19440
taaaaaaaaa acaacctaac aactccccgg ttccctcatc ggtaggagac agagcaggga   19500
gggaaagagc ggagcgagcc gttcaggcga atctgcggtt gggccctggt ctttgaatct   19560
gggagggacc ctagacaagc aagaccgaga agagaggtgg ggagcaggct ggtgggcggg   19620
gccagagcag ctgggatggg ggtggggctc agccctccag gaggagggga agggcccctt   19680
ctgttaggat ttgaacgagc caatctgcat gcccgcgctg ctcctgccca cccccgcagc   19740
tgcaacgctg agctcatgtt ctggctctgt cttagcgggc cgcacagttt gccatcacc    19800 cttcctccca gtgtgctggg gatgttagag gcaattatgg aggtcctcag aatgctgact   19860
tccctgtctt cccctaggca cctctcaacc aggtggagag ggactggggg cggggacgga   19920 ggtgggggt atgcctaggg attcctctcc tgctcagcag gctccttggc cctgtgccct    19980
gcagggcttt tgagctccgg tggttttatt gagctggtat gttattagtg agattcccca   20040
gccgccaccc cagaacaacc ctcccaggct ccttttgctg gtccacacag ttaacaagat   20100
ctccgaccct caacagggag acccgctagc atgaggatgg tctggccact ttatggccgt   20160
gtgggcttgg gtaagctgct tcaatctctg atcctgtttc cactgtggaa catggagata   20220
agtttagtat cctatagaga cttaaaaaa aaaacacaca aacaaacctt tatttactat    20280
gtctgtagct ttctgcttac atatatgcct caacaccaga agaggcacca gatttcagta   20340
cagatggttg tgagccacca tgtggttgct gggaattgaa ctcaggacct ctggtagagc   20400
agccagtgct cttaaccgct gagccatctc tccagccccc tatagagact ttcatgacta   20460
taaaatgaaa ttcaaaaata gagtcctgtg tggtaggcat ggcaccaatc ataggagcac   20520
gtgatgggag gagcctcggc tgggggactc tgggatccac tgcttttcct gtagagagcc   20580
ccagaacatg tcagtaacat gtaccccatc cttctataag gatgctctgg ccttggctct   20640
gtgtcctggg tgacctgcat cacttcctcc ttggagcctc agtttccctc tgtcaaatgg   20700
cgtgacaaca cccatcatgt gattttttgag tttggtcaca catgcctcag gatgcttgcc   20760
tggcctgagg tactgcttat gatttccatc tctctccttg aagatcagag ccacagggtc   20820
gcactgcaat cccaggttca gagcccagag actgatctac caggagctg ggggccaccg    20880 ctgctgctgg cctttggcag ggaccagcac tgtgaatagt gacctcatgg atgagcacat   20940
ttgtttgtgc tttaggcatt tgctgtgtgt ccaaggctgc ctctcctctt tgtctccctg   21000
cttataactt cggggctcaa tgagacaggc acacaaggcc cttcaggctc tttggacata   21060
gaaagttgtg ttgggacttg ctgttgacag gccattgtta atcattgtag tccttcaagc   21120
ttgcccttct tcggcatcat cagcttcata gttgacccat gctaccttcc tagtcatgtg   21180
accttgggca actgcccttt cctttctggg attcaaagct gtcatgaaac atgtcctgag   21240
ggtgagaaga gcctatggtt atagcctgga gaggctataa gtgacccgtg agagcccagg   21300
```

```
gccctgggac cactggaaat ctgggcctgg atatgggcgg tggtacccett ttcttccgga   21360
ctctaatgga ggcttcaagg cactggatgc agggatctaa gcttgtaggc tcttctgttt   21420
agaatgctgc agcttcccag gggatgggtg cttctttct tttatttat tttattttt     21480
ttggttttc gagacagtgt tctctgtgt agtcctggct gtcctggaac tcactttgta    21540
gatcaggctg gccttgaact cagaaatccg cctgcctctg cctcctgagt gctgggatta   21600
aaggcgtgcg ccaccatgcc cggccttttt tttttttaa agaattattt atttattata   21660
tgtaagtaca ctgtagctgt cttcagacac accagaggag gtgtacttat gtcagatctc   21720
attacgggtg gttgtgagcc accatgtggt tgctgggatt tgaactcagg acctccagaa   21780
gaggagtcag tgctcttaac tgcccagccc gatgggtgct ttcttttttt tttttttt    21840
taaagattta tttatttatt tattatatgt aagtacactg tagctgtctt cagacacacc   21900
agaagagggc atcagatctc attacagatg gttgtgagcc accatgtggt tgctgggatt   21960
tgaactctgg acctctggaa gagcagtcgg gtgctcttac ccactgagcc atctcaccag   22020
cccggatggg tgcttcttta acatgtggcc ctggggacag ggaattcatg gagaaggaag   22080
aggatccagg aactctgatg gtgaccagat gggcttccca ggtaggccat ggtggagaca   22140
gagccccttcc tatcccaatg gaagcatgtt tgggagacga cccttggccc cagtgaccct   22200
ctttggacaa tggggtaggg gctgtggagg agagtgcctg acaccttgct agggcaggtt   22260
ccgctcccac atgtattcca ccagccactc ctccttttc ttgttctggg tcttgatttg   22320
tttgtccacc caacaagtat ttctaggcat tcagtgtgtg gtgagccctg gctgctgct   22380
ggaacacaaa tctaaatgaa tccagatagg cgtggccta ggtttaccac ttctaccca    22440
gtaccaaggc gagatgaatg aatgaatgaa tgagtgaatg gaatgttggt gaggacagag   22500
cttcctgagt gacctagtag cccaaaattg ggcctgggcc aaggtgaata aaaccaatac   22560
aaagaggcaa agcagtagga atgcattaaa caacaacaac aacaacaaca acaacaacgc   22620
ttttgtgact cagctggcag ggtgcttacc tagcaggcac gaagccctgg ggttggtctt   22680
gagtgctgca tagactaagc aagacggcat agactaagca agatggcata ggattagcac   22740
agcgcttggg agacagagac aggaagatca gaagttcaag gctatccctg actagtagca   22800
agctcaagtc cctcctggag aggaaaactt ttttgtgtcc ctggagatgt agttgagtgg   22860
gcgagtactt gcctagtgtg cacaaaagtc taaccattcc cagcacaggc taaaagtcaa   22920
aatccctgtg tggatggctc cttgacctcg tgcctttgag ctgcccagtg agcccttaaa   22980
tattttacac aatcaaaaac aggtcaagaa actatgaaat caatacaact tttgtaatac   23040
actaaataga ctgaattatt taaaaataat agtaaataag aagccttgtg ttttttgagc   23100
acctcctgga ttccagccac cactcaagca cccatgatgg catttgctcc ctcttgccac   23160
cacgggaaca gtgtatccat gtaatggtga ccagatgtag gctccagatg ttcagggctc   23220
tggcactggg tttgaatcga gttttcttct ctgcaaaatc ttttctttgc tattgaaggg   23280
tggggagagc tttgtggccc acagtggcca caggggaggc ttgtgggcct ctgcctggcg   23340
tcctcagaga gctccaggct agaggggca gtggccgag gagagagtag gctgtgccc     23400
agtttccttt caactattat ttttcctggc cttccctgca cattgccaaa ggggtctgtg   23460
ctaagttggg cttgggccca ggcagagggc agagccaggg agggcctctt cccttccaga   23520
gggaggagac acgtggtcat ttccgacatt ggcagccttg agtgctaggt tgtctgtgcc   23580
acacaggtct ggctgaccag gctttttggc tcctcagggg gctctgacta tgcaggctcc   23640
tccaaacccc agggagtcct agcccagccc aggcatgccc gatgtacagg accctgagaa   23700
```

```
agtcactcct gctctgacct tcagtaaagc ctagcatcta gtgggtagga gttagcagga    23760
cccagcctac gtggggagtg gcacctattt gcatatatct gctctgtagg gcttccttca    23820
ccccacctca gcccccttgc cctgctttcc cacgcccagc agcagggcca ggactgaggg    23880
gatcttccca attttggggt gcttttcctg ctgagcctgg acctgaaatt ggagactgct    23940
gttctgtgag ctgcatctaa gggatggctt ggacactagc ccagcctgtg tcattctagc    24000
atgttcttta tcccagaaca ggcctcaggg tcactgtgac ctccagcaaa tcatgcccgt    24060
ctctggacct cggttccggg gagcagcagc cacgagtcac cagacactca ctgtggcagg    24120
cactgggtga aggctttgta agcaatagcc gatgtgatcc tgctgtcggc cctgagagtg    24180
ttctgctact gctgtgccca ttttatacgt caggaacact gaggcacaag gccaggaaat    24240
gacttgccga gaagcacaca ctgcccgctt tgtgctggcc ttccaaacca gttctctttc    24300
ctttcaggct cttgtgaaga cagggctggg agtactgctt agtggaagag tgattgtcag    24360
agagaagcaa ggctgggttc agactccagc acagctctgg cggaacataa aggctacttt    24420
aagaactaaa ccagaggggt tggtgagatg gctcattggt taagagccac tgctattcca    24480
gaggtcctga gttcaatccc cagcaaccgc atggtggctc acaaccatct ctagggaagt    24540
ctgatgccct cttcaggcag gcgaatgtat atgcagctga gcactcatac aataaataaa    24600
attaaaaaga aaaaaaataa agatcatcac agctttgggg gggcaacata ttgggagctg    24660
gagtgcctgg gatcggatct gataatcctt agattcatgg ctcttggtga gactttagac    24720
ctctctgctg agtgagggtg aagaggtgac actgtaacca aggagagatg ctcactgaga    24780
ctcgaggtgt gtcctcctcc tgcttgacca tgccctctgt ctctctccca ccctggctca    24840
ggtctctaag gacatctcca tgcggcttca caaggagctg gaggtggtgg agaagaagcg    24900
gatgaggctg gaggaggaga acgaggggct tcgacagagg ctcattgaga cagagctggc    24960
caagcaggtg ctacagacgg agctggatcg tcccagagag gtgagggcgg cagcccagct    25020
ggggctggtg tgatgcatat ccctgcctgg ttgcttgtgg actgaagacg ggcacccttg    25080
tgccttgaca gcgctgtttc tccatccacc cttccagcat ttgctgagca cctaatctgt    25140
attcagccct ggttactctc tctgggacta actgaggcta tgttcagcaa tgcccagcat    25200
gggcctggcc ctgtgcctca gtttccttgt ctataagact tggcagttgt tccctggtca    25260
tcgacagggc cactgactgg cttgtgtgga gatgttttag ggactagtgt gctgtggcca    25320
cttggtttaa gaaggatgct agggccgggc agtagtggct catgccttta atcccagcac    25380
ttgggaggca gaggcaggtg ggtttctgag ttcgaggaca gcctgctaca cagagaaacc    25440
aaggctatac agagaaaccc catcttgaaa aaccaaaaaa aaaaaaaaaa aaaaggatgc    25500
taggcttggg tctcccactt ttgtctctga atgtgacttt cagatccatg tccccagtca    25560
tggtgatgtc agcccttcct cctactgtaa ccttctccag ctgtgtgtta ggctcacata    25620
aagacagttt atctcagaaa cctccgcaaa ggcccaacaa agctgtggac attccatggc    25680
cgagtgagca gcagccggcc aggaagagtg aggcagattc tcaaggtcat gcagggtgca    25740
ggggacttca cagtggaaag ccatcagccc gggtgatgct taaagcctgg gtaactcctg    25800
attcctggtg gggtcagcag ttcaaacact aggtggcctc tggccccaga ggcatagctg    25860
gccctcagct ggttggttgc tcatgaggcg aaccgggctg cattcttctg gggcacccac    25920
ctgcttccca agaggcccgg catgccagac gttcaggact gagacatcag tgtccccggg    25980
gcagagcagt cctttggctg ttcttcctac tgggcatgtt ggtgctatgg ccagtgcca     26040 tgtagggtgg agaggggagg acctgccctg tgggcttctg tggagggcac catgctgtgg    26100
```

```
agctgggtgg gaggcttcct gctggcttcg ggctgcctat gcactgcgaa ctgtcgcaca   26160
caaccttgtc gctttcatct ctgatggtga aaaggagggg cattacaaag cctgttcttg   26220
cacagctagg gagactgagg cactcggctg cagcttgttg agtttgcccc agcctttcct   26280
cagcagagac atgtctgcag ccacttcccc ctccaagtcc cggcttcttc ctctgtgatg   26340
tcagccaata gtagcagctt aagaggatgt tttggatcac taagaagttt gtggaacgca   26400
gcccagaggt agagcatgtg cttggcacat gggaggccct gggttcaagc cttagggccg   26460
gaaagcaaag gatcaatatt gtaaagttcc ctttatctga gattccccag agtagtgaat   26520
gagattcata agacagggag cagagctact gggcggggga ggagggagcg aggctcactg   26580
ggggtgggaa tagagtttca gtttgggctg atgaaagggt ttggaggcaa actgtgcctg   26640
tgatctaagc agggtgtgtt gttgctacca acacctggga ggcaaaagca aaagacttag   26700
gaattcaggc caccctgggg tctgtgagac cctgtcttta aaaaaaaaaa ggcctggttc   26760
aagccgggca gtgatggtgc atgcctttaa tcccagtact caggaggcag aggcaggcga   26820
atttctgagt tcgagaccag cctggtctac aaagtgagtt ccaggacagc cagagctaca   26880
cagagaaaca ctgtctcgaa aaaaacaac acaaaacaaa atagaatgtt taaaatgata   26940
catttatatc atctaacctt taccacatgt taaaagtag aaaatgtgt attgatatga   27000 caagctcccc aaggtgttct gtaaaccaga gaaggaaatt aagaaactag gcctggtggt   27060
tgaaggggga ggttctaggc ctgcttgagc tgcagtgtgt ctgtctgtct gtctgtctgc   27120
ctgcctctct gtatgtgtgt atatttgtgt gtgtatgtgt atgtatgtgt gtatggggg   27180 ggtatatgtg tgtgcctgct tgtctgactg tgcaccacat gtgtcccggt gcctgcagag   27240
gccagaagat ggcattggaa tccctggaac ttgagctatc gtgtttgtaa gctgctcagt   27300
gagggagctg ggacgagagc tagtcctctg caagagcagc aagtgttcct acctgccaag   27360
ccatctcttc aggtccctgg cggttaaata agaagaatgt acagtcccag tagttaggaa   27420
ccaactgggc tctgtgatgt gaggccagcc tgggctacaa cgtaagactt tctcaaaaca   27480
caaagaataa aataaaaatg gattggcact gtagctcaga tggtagagcg cttgcctagg   27540
atgagtgagc tcctggactc aatatgcagt tcccaataaa atgggcgtgg ctccacacat   27600
ctctacccca gcacccagga gatagagaca tgacctacag tagaagcttg gggtcatcct   27660
ttgtgtggaa atcctgggct acatgaggca gtgccccaag agaaagtcct taaacaggac   27720
atgatgagaa cgtctacagt cccgttacag ggaagcctga gggagaagat ggctgatgtc   27780
taggtatcta aaagctgctg ggatagcata gcaagaccct gtcttacaac aaacaaacaa   27840
acaaccccat gatttactta ggaattactt gtgagattaa aattttacaa catttgaaaa   27900
ctttatttca tgtctgtgtg tgtgtgtgtg tgtgtgtctg ttcgtctgtc tgtctgtctc   27960
tgtctgcata tgtgctccac tgtaggcatg tggcaatcag aggacaactt gaagcacttg   28020
gttctcttct tctacactct ggatcctagg gatccaactc aggtcatcag ggttggtagc   28080
aggcgccttt tgcccactga cttctcacca tgcctctttg tggaccctta aatgtagatt   28140
ttagggtttt aatgtaaaga tcccacaatg gaccctgaca ccgagtaggc gctgaagata   28200
ttggttctca ctcctgggaa gcctgatgga gcctcccagt gtttagtgct ggctccagag   28260
cctgtttatt tgctgtttgc cctctcctcc tccctctcct tcctgacatg gttgctatgg   28320
agacaagggt ccctcagcac ttctgccaga gctacagtct tatccttggg atctgccttt   28380
tccatcctga cagatgatga ggtgatgctg tcacccgact gggaatggga gctgatgctg   28440
ttgccgtgga gacagctcct ggcgagacag aagggaggtg gcatgtcctc actgctgtct   28500
```

```
gcagtggcac cgtggcccag ctgggttgcc gcttcagaat ctaacggcag ctgccccttc    28560
attcccacta tcatctccct tgtctgcagg cagagagcca gtgtgagagt gtgattcgtc    28620
ctaacacagc cgctgtgtct gagagcttac cctgtaccag gcaccactgc cagccttgcc    28680
catgtgccgt catgccgttt aaccccccgt tgtccctgct ttgtaggtac tactccttgg    28740
acattttaaa atcacagttt ttaattcagt gatcacagaa tgcaccattt tacagttcag    28800
ttgcatagat tggggtgctg ttatcagcat gaccgaattc cagaaagctc cctttactct    28860
tgtgagtaac cccacacctg ttagcagtca ctcctcactc cccgtagccc ctggcaactg    28920
ctggcctgtt ttctgtctct aatgatttct ccaatcagga gactgcatta aaatgggatc    28980
aagcaatgcg tgatcattgg tggtgggcgc tactacttag aacaaggctt tcagagtttg    29040
gacatccatg ttgaaggacc tcgttgtttt tttttgtttt ttgcttttttt tccccatagc    29100 tgggtaatgc tgcattgtgt gggcagagtg ccttatattt gatatttggg tggcttctgc    29160
ttttccgctg tcataaataa tgctgtggtg gacatgttca agttttttgtg attctgtatg    29220 tgttttctct gggtatgtac acaggagtag aattgtctgt gaatgagacc ggggggaaaga    29280 tacgtaaggg attcaaaccc cggggccctgg ctctcccaca ctcacactca ctcctaacag    29340
agttgccgat cggctccgga ctcatcaagg ggctttccag agcctgcatc tgtggttcct    29400
catctggctt tccttcttga tgggtggggc gagcacctcc agccacttgg ggttgagcct    29460
ggttctcctg ctgtgcagtg tgttctggcc ccagtgtgtg agctgcagag caaacccagc    29520
caaggagcca cgtagacctg ggcatggaat cttggctttg ctgtttcctt gagagtgact    29580
gccaccttgg gcagatggca cagcagctca atgctcactt gctctgttta cagaaaggga    29640
aaatcagccc ctacagcttg tgggtgtttg tgaagattaa atgaggctgg gaagtgctca    29700
gcatagaata ggcgcttgct aaacacagtg tgtaccatta tcgttaccat ctcaaccagc    29760
cactggctgt gggcctggag aagcctttgc tgcctccctc gcacaggggt tcccccaca    29820 gagctggcag ctgtacgtgg aaggaacagc tacgctgaaa actgttgggt ctaaacttat    29880
tttttgctgg ctttggggtg actgtaatgc tcagagacct tgctgactca gcatgatgat    29940
ctgagttcag atctccgcag cccacataaa aagctgggca tgatcccaag cagacctata    30000
actccagcac tttgcttgcc tccaggctca gtggaaaacc ttgtctcaaa ggagcaagga    30060
gacaaagcag gacacccgac atcctggctt ccatgtgtgt acaagtgtgt gcgcatacac    30120
cacatctgca tacatacaca cactataaa tttaaaatta aaataaaaa aattaaaaat    30180 ttttttctcc acccaagtgg tggtctctcc aggggactat atggcttgtc tgcatggcat    30240
tttggccatg gtgcaaagag catacctcac tctagagatg ctcccccaac ccaggtccca    30300
ttcatggtca gttctgtgca catagcaatc tggtttcagt aagacttaca tggacaccct    30360
ccacatttgc tgagtcggca gccaggaagc tcaggagata ttggggacag aggggacaga    30420
gtttagacag ctctctcctg aacttagggc actgcctgga ggcttctggg gaagacagac    30480
cccaggctca tgctgggaag ggttgggcca gggattctca gagctatcac ccaggctgct    30540
aatagtggct tgaggagtgg ggaatctgcc ttggggctgg gtcctcctgg accttagacc    30600
tggagaatcc ttttgaggtt cttgcaattt accactctag gattcctact tgagaggtga    30660
acacacactt cccataggat tttctgtgta ttcacacaca ttattttcta tgtatatgtg    30720
tgtgtaatgc ttccttaaat ttaaaaatgc agtataaact taatgaggca aaaatcctgc    30780
cacaaaagcc cataaacgca tacctgacat gaccctgagg aaagttccag caaattccga    30840
ggcaggaatc cgggacctgc tccatctctc tgttcctctt gtgtactctc tgaatcttca    30900
```

```
ccacgtgact gaggaatctt attcaaaatg acagatctag cttaaacata tacaaaataa    30960
tgaaagcctt cccaggccac ccccctgctc atctgcctaa cctgaggata acagtttgct    31020
ttgtgttttt ctggatcttt ctctgtgctt gacaatgtgc ttttctgtgt ctttaaaaaa    31080
taaagatggg cttcgtttgc acacagggtt tctgtaatgt gcaggatcat gttgcataga    31140
tatagtcctt taaaatgcca gatgctttgg gggttttctt cagtctgaag tgcttattat    31200
agaaacaaac aaacaaacaa aacaaaaacc acggaatcaa ataagcatag gaaggaaaga    31260
aagtcataaa tagcactctc tatttcaacc ttaaacaggg ggctgaaggt ttagagtcag    31320
ctcctgaagc atcagttggc aaagatccct cggggagggg aggaggatgg gacagcatga    31380
ggggcgtggc tttagctacc tgacttatgg ctttgctggg ttttttgttt gtttagttgg    31440
ttggttggtt ggcttgggga ggggagttgt tttaatttat gttttcgag acagggtttc     31500
actgtgtatc cctgactgcc cttgaactca ctctgtagag caggctgacc tcgatctcag    31560
agatctgcct gcctctgcct cttgagtgtc agtaccacca cccagcaaca tatgtgtttt    31620
ctgatgaggc ttccctggaa ctaactgcac accaggttgg actggacttt gcgatgcaca    31680
caagctggcc ttgaacttcc ggcatccttc cagtttctat ttccaggtgc tggaattaca    31740
gatgtgtgct gctgtgctca gcaatccagt tttggattga gatgtaattc acatactatg    31800
aagtctgcct tcgtcctttt tatttgcagt gctgagaact gaacccgtgc cagccagatg    31860
ctctactatt gagctacatt actggcccaa gtttgccctt ttaagctgca tagttagtgg    31920
gttgcacagt tgtatatcca tccctactgc ctaattccag aaccttttg tttcacccctt    31980
aaaaaaaacc ctcacacata ttagcagcct cttcccatct ccccaccaca ctccctcctc    32040
agctctgaga tatcagtaat atattttcca tctttgagaa tttgcatggt ctggacattt    32100
tgtagaaatg aaatctgatt ctatgtgcct gttgtgtgac aaaacttta ctggggagac     32160
aaaacacata catctgttca cctcagatag ggatcccatg ataagccaaa ggatggatac    32220
caccatagtc caacattgtg aaaaaacagg ttttatggga gttacttaca ggaacagaaa    32280
tgactcacag acagctgctt accccagcac aggtgacagc tcacaaaagc tgggaacctg    32340
gaacacacag cacagcctgt aggcagctca acaggttaga gcgtgttctt tcttagcaac    32400
tctggtctaa gcctcttcca ggcaggtgat cagctctcag agtcttctgt gcagctttcc    32460
tcctctaaga atccttggaa ttcagtttca tgtcacgtga aaggactct cagctcttaa     32520
tacttattct ggcagaaaag gagcctagtg aatctggtca gtttcaggaa cttcctgaat    32580
caatttgagt tgtcttcctg cgtaaggaac ttccaatagg gtggaatgtt ttaagctagg    32640
aggagattgt tacacaacat gtcaggatgt cctggctcac atggtgtctt cacggcgccc    32700
atgctgcctg ggcatcagga tcttgttcct ttcatgactg aataagtttt taccacgtgg    32760
ccacccata  gtttgttcct ctgttcctca tctggaggcc atattgggtt ggaggtttta     32820
tttgtaaatt acttccttct cttcacagag tgttccggct ttgtgtcagc cactatcatg    32880
accccccagtt gttcctactg cttttttata tcatctcatg ggtgcgtgtg atagcttgaa    32940
cctcttgagg tccttagata gcctaggctc ttcaatcctt ggtggagctg ggatcaccta    33000
agtcatggat tcttcaatgt gtgggttcac cagaactgat accacagcca aggcaccagt    33060
caacctgtga tggcaagccc agttctctta ggctgagtct gacccagagc accacatcac    33120
tctgtggtag tctccctctg agctccctc cagggccctt accctggtgt agcagctcct     33180
gtgaagggct tgttgtgtgg ccccctttcc aagatctctt taggtagcct ggtgtattca    33240
aactcatctc caccttcctg cctcatttgt gttcccaaag ttctcactta gagtaggccg    33300
```

```
agaagatgtg aagacaccag acacttcagg tgatggtggt gctcgcctct aatctcagca   33360
ctggcagaca aagacagttg aatttctgag ttcaaggcca gcctgatata tagagtgagt   33420
tccaggatgg ccagggctat acagagaaac cctgtgtcat gagaaatcaa ccaaccaacc   33480
aaaaatgaaa agcaaccacc accaacaaaa cagaaacaaa tcaacaacaa caacaacccc   33540
cagactcagt aaggaactcc ctggatcctt agcagttagc ctagcataat ccaggcaaat   33600
gaacaaccat gactcagaaa aacaggatga aatgatggag gtgttctgaa cacagaccta   33660
aggttgtcct ctagtctcca catacatgaa aacatatgca cacatgcaca catggatttg   33720
tgcatgacac ataaatgctc acacacatgt acacacacat gtgcacccat gcggacacac   33780
ttacacacat gataaagctg acctgctttc ctgggaagct actttaaatt tcagtggctg   33840
agacataacc caggccagtt attccagaat ctttgacgtg gtacctggtc attggtattt   33900
tcttaaatcc cccaggaaat tcttctctgc gtgcaggttg aaaaccacta caccactagg   33960
gtccatgctg gccctaatca tagatgcgtt ttctcctacc aagcctttgg aactcagtca   34020
agagctaggt caagaattgg tctcaggagc cgggtggtgg cggcgcacgc ctttctttaa   34080
tcccagcact cgggaggcag aggcaggtga atttctgagt tcaaggccag cctggtctac   34140
aaagtgaaaa aaaaaaaaaa ttggtctcag gttggctttg tatttgctat agaattctgg   34200
tcaagttcct tccctcctct gtttgagcaa acagggctc acagagatgg agagatgact   34260
cagcaattaa gagccctggc tgctcttcca gaggatccaa gttcaattcc cagtaccaca   34320
tggcagctca gagccaactc ttaactccag gtccaggaga tctagtgccc tcttctggct   34380
tccataggca ctgcacacac tgcacactat gtgatataca aagatatatg tgggcaaaac   34440
acccatacac ataaaataca aataaatttt aagcaaagtt tgtgttatgt cagtggtttg   34500
cctacaaggg tggggagtga gaggtgaggg ttggtggtga gcatgtattt aaagtcaact   34560
gggagcattt tcagaaatcc aagtgggcag ctcaactcag aaagttgaga gcaacctgtg   34620
gtttccaacg ctgccagcgt gaattatcct ctctcggtag gaagcgttca gtggaatctt   34680
gtgtcgaagt gaatgatttt tttttttaaa caagtaactg cagcactaat tattgtggca   34740
tttcctcaaa ttcccatctg tgcggcttac gctgttttgc actcatgcca gcaacaacta   34800
aaccttcttg tttagcaaga gcctcaccag taggatatac tgtgaggtgg ctcagggttt   34860
cgctagtctg atcagtgaga ggctcagccc agtagcattg ctctgggtgt ctccctcctg   34920
agaagggctg agtgtcttct cagggttaag atctgtttgt tttcctccca taaaccattt   34980
tgtttggttt tggttttttc cttctctgaa cctagagtcc catgcacact gggcaagctc   35040
taaaagtgaa ctgcgtccct tagtctttca tttgtctttt tattatgaga caaggtcaaa   35100
atctgtcagg tgggccttgg gttacgattc tcctgcctca ctgggcctga cttctatgct   35160
ctttcttgta ttcctaaccc gctttcctat tgcagatatt tcccccagct cattgcctat   35220
tttttaatgc acgcgcgcgt gtatgtgtgt gtgtgtgtct gtgtctgtct gtctctggga   35280
tgggaactgg ggcttgtgc tctgcccctg agctgcacag catggattgc tgtcctgttt   35340
tgtgttccat gcagtgttta cccgtgtaat caatgcattg attcccctcc ctccaacgct   35400
tctgggtttt tcaatcctcg tttgttgcta gtctctctca gtcattttca gaaatgatcg   35460
agtctcctgt gctgtttata gttttctacc cgtatttgt ttgttagtta gtcttcatcc   35520
tgtgttcagg gtcctacgaa atgtcacttc ccgtgaggcg gagacttgca tgcagttta   35580 gagacaagcc cctttggctg tgagggagtg agtcacatca catagatggc ctcagctgga   35640
gctagtgggg acctgggata gtctttagat gtgtattcca cacaagaaga gcatataaag   35700
```

```
cgacccccct  ggccagcaag  caccactaag  aatggtcctc  agcctggagg  gctttctgcc   35760
cacagcatcc  ttagcatctc  atctgtctag  ctcactgcta  tgtgctctac  cctctgagat   35820
ttgcccggga  aacctctgat  gagcggatga  aagcaagcg   tcagccatga  aaacatacat   35880
acatgtgaca  tctggagtga  gcaggatgta  tttatatatt  taggaacaca  catatatgta   35940
gcaacattta  aagaccataa  atttgcatga  gaacagggaa  ggggatacat  gagaagggtc   36000
agagggaaga  aagtgaaggg  agaagatgat  gtaattgtag  tataattggg  gggggataa    36060 aagccccaaa  catcaaagat  gaacaagagc  acaaattctg  atttccagcc  aacaggacca   36120
cagaggccag  atgggtgcag  tggggtactg  caccccttgtg  ccggtgtcta  atcatttctt   36180 tctttttcttt  tcttttcttt  tctttttcttt  tctttttcttt  tcttttttttt  tttttttgaga   36240 cagggtttac  ctgtgtagcc  ctggctgtcc  tggaactcat  tctgtagacc  aggctggcct   36300
cgaactcaga  aattcgcctg  cctctgcctc  ccaagtgctg  ggattaaagg  cgtgcgccac   36360
catacccggc  ctagtcattt  cttccagtac  ttgtggtcat  tctctcctgc  acaaggtgct   36420
cggtgatccc  tggttccgct  gtgggtaacg  gttagcacag  acaggctgag  tggggaccct   36480
cagtatgact  ctgttttatg  acacctcttt  ggatgtgtgt  catctttgtg  acccttcagt   36540
ttgctttctt  cttcccttt   agcattcctt  gaagaaaaga  ggaacccggt  ctctggggaa   36600
gacagataag  aagcctactg  cacaggtagg  acctctgtac  ccatcacact  ccctgcagtt   36660
ggtagtttgg  atgcccatac  caacttcaag  tgtcctgagt  agtcccccag  aggtccctat   36720
cccttcccaa  tgtctctcct  gccctccttc  ccctatgcat  tttttttggct  tccccattta   36780 gttcctccaa  gcccactccg  accccatcct  tacacactcc  tggacccaca  agttgataac   36840
ccaacatagg  gacggataga  cccaagggga  gtcggtccct  ccgcagcttg  actgccaccc   36900
gactgagaca  aatcagcttt  ccagtctgtt  tcctcatgcc  ttcctgttct  gtgggtttgt   36960
tggaagaact  ggataaaaat  gtcatgtcgt  gcacaggcca  gaatcctgtt  agcagccaag   37020
gcaccttttg  aacggtttcc  catttagcag  tcatcatatg  acaacaatgt  ttctccccac   37080
tttttttttt  gtttgtttgt  ttgttttttt  cccgagacag  tgtttctctg  tatagctccg   37140
gctgtcctag  agctcacttt  gtagaccaag  ctggcctcga  actcagaaat  ccacctgcct   37200
ctgcctccca  agtgctggga  ttaaaggcat  gcgccaccac  gcccggctct  gcccactttt   37260
agagatgggg  caggaatggc  catagtcaca  tgtctgaagg  tcacctgctc  ccagacttcc   37320
agattgtagg  tagtgtgtct  tgggctctca  atattgatgt  ccctgctctc  tatcctgtgg   37380
cctccaggcc  ttgagagcca  agctgattca  cccctgtgtt  ctccgacagt  cagggcaccc   37440
cagaatcctg  tggctgggtc  caagctgaca  ctaaccttcc  ttgttgttgc  ctgtctccgt   37500
gtccattggg  ctgcaggagg  atagtgcaga  cctgaagtgc  cagctgcatt  ttgcaaagga   37560
ggagtcggcc  ctcatgtgca  agaagctcac  caagttggct  aaggagaacg  acagcatgaa   37620
ggaggagctg  ctcaagtaca  gatcgctcta  tggggacctg  gatgcagccc  tgtcggcaga   37680
ggagctggcg  gatgctccgc  actcccgtga  gactgagctg  aaggtgcacc  tgaagctggt   37740
ggaggaggag  gccaacctgc  tgagccggcg  catagtggag  ctggaggtgg  agaaccgtgg   37800
cctgcgagcc  gagatggacg  acatgaagga  ccacgggggt  ggcgggggtc  ccgaggccag   37860
gctggccttc  tcttctctgg  gtggtgagtg  cggggagagc  ctagccgagt  tgcggcgcca   37920
cctgcagttc  gtggaagagg  aggctgagct  gctgaggcgc  tcctcagctg  agctggagga   37980
ccagaacaag  ttgctgctga  acgagctggc  caaataccgc  tcggagcacg  agctggacgt   38040
gacgctgtcg  gaggacagct  gctccgtgct  cagcgagccc  tcgcaggagg  agctggcagc   38100
```

```
cgccaagctg cagatcggcg agctcagcgg caaggtcaag aagctgcagt atgagaaccg    38160
cgtgctcctc tccaatctgc agcgctgtga cctggcctcc tgccagagca cacgcccat    38220 gctggagacg gacgctgagg ctggggactc tgcgcagtgc gtgcctgccc tctgggtga    38280 gacgctggag ccccacgccg cccggctgtg cagggcccgt gaagccgagg cgctgcccgg    38340
cctacgggag caggccgctt tggtcagcaa ggccatcgac gtcctggtgg ctgatgccaa    38400
tggcttctca gtcggcctcc gcctgtgcct ggacaatgag tgtgctgact tgcgactgca    38460
cgaggcgcct gacaacagcg agggccccag ggatgccaag ctcatccacg ccatcctggt    38520
gcggctgagt gtgttgcaac aggagctgaa cgccttcacc cgcaaggcag atgtggcctt    38580
ggggagctct ggcaaggagc agcctgagcc cttccctgct ctgcctgcct gggctccca    38640 gggccctgct aaggagatca tgctgtccaa agaccttggc tctgacttcc aggtaagatg    38700
ctacatgttc tgaaccaggc acatgacaga aggacacaaa gccccaggta cacaacttca    38760
caactgccct gcagggagca gtcctggtca tcacctagaa cataaccagc cctaaggcag    38820
ccatggttca tctccctgtt ctctggtttt attcgtcttt gagctttata taaattctat    38880
agactaaaca cagcagtgcc tggctgtgtt ctctcagcca actatttgct gttacaggta    38940
ggaaaaacaa ttatttattc tcacctaact aggaataagc ctgccgactc agcaaactgc    39000
ctggtatgcg tttactatgg atagggatta attctgaggt cccatctttt tgctagactt    39060 cccgttttc tccctttccc tctcctcttc cagtgctggg gacacaacgc aggacctcat    39120
acatgtaagg caagaacccct accattgagc cacatccctg gccccttctt tttaaaaaca    39180
tttttgagcc aggcgtggtg gcacacgcct ttaatcccag tacttgggag gcagaaccag    39240
gcagatttct gagttcgagg ccagcctggt ctacagagtg agttccagga cagccagggc    39300
tatacagaga aaccctgtct taaaaacgg gaaaaaaag aaaagaaaa aaaaaaaaa    39360 aaagaaagtt tgcatatgtg tgtgcaggtg tgtgtgtgtg tgtgtgtgtg tgtgtgtgtg    39420
tgtgtaccca cagaaggcag agcaaagtgc tggagccccc agagctagag ttgaaggtgg    39480
ttgtgagctc cttgattagg gtgctagaag ctgaactcgg gtccttttaa agagcattaa    39540
tgtatcttaa ctgttgagcc atttctctag ggtagccccc tccttttcc atctcttttg    39600 taactaaaat tattacacgt atttggtggg gttcagggg agccgttgtg cacatgtggt    39660
ggtcacagga gtcagtctca gatggtcctg gggatcagct caggcttggt agcaagtacc    39720
tttacctggt cagctcgctt gccagatccc cacatcccac ttcttttgg ttttttcgag    39780 gcagggtttc actgtgtagt cctgctgtcc tggaactcac tctgtaggcc aagctaaccc    39840
tgaactcata tagagatctg cctgcctctg ccccccccac cccccacaaa tgctgggatt    39900
aaaggtgtgt gtcatcaccg cccaccacca gtccataata ttaaatttaa aaaatatatt    39960 taaactttt gatcaacttt tgagaagctt agccttgata cccatgacag gctacccaga    40020
aaaactaaaa cggaaaagac acttgttgaa aaatttaaaa tgcattagtg caaaagcaaa    40080
acgtaaacat ttgacgcaaa tataaaaata aacgaacacc tcgtgtgcct acctaccact    40140
tcctgccgat gtctctgtac accgtcttga ctggtgacgt tcagtgcagc agccatgtgg    40200
ggatgtgccg cgatggtaaa ggatcagcct tagttggcgg cacaggttct atccccagta    40260
cagaacagaa acaacccaaa actcccaaga caaattttaa aaattaaatt aacgaagcat    40320
aggattgagc tgcagttcct tcgttgtagt tacacatcgc agatgcttga ggctggctgc    40380 gtgctggag cgcccctct gatccttccc acacagcctt tcctgggcct gggcttcatg    40440
ttatggctac tgtcgctggg cagtgtgctt cctcacaccc tgcattccct gtccgcaggc    40500
```

```
tgggatacct tgtggatggt ccccacccctt cgtgcttaac acgggatggg tggtgatctg    40560
cagaaccagg gagggatagg agccccactc gaaaggtccc accgcctagc gaggggaat     40620 taattagtca atctgtcaag cctgtgaatg tgacatgaga aatggttttt atcaaccagg    40680
aacttgtcct agatcttgaa ggggctcaga tcattgagag aaggaacacg gtaggtcgaa    40740
ggaacaggac agagttgtga ggctgggctg cagagagcgt ggagtggtgt ggttttcatc    40800
ctgagagaat ggcgggagat tgctgtgtgt ggccctgcac tgcatgggac cgggcgggta    40860
gtggcttcag ctgtgctgct gtggcttcag atcgcttctt gaaaggggag gcccgtgttg    40920
agtctccctc ttcctgaagt aagagtgagc agggaccaca cgggtcaccg acagggtgat    40980
agaattgttt cagagggctt tgcgtaagag ccattcacaa aattaatgtt tccacttgcc    41040
ccactgctcg ttatgcaata agcaaatgag ttgtggcctc gcaccctggg aaggccaatt    41100
cacccaggct ccctctcatg tggacaaagc ccattatatg gcagaggcct ggtggggacc    41160
tttgttgcac tccttgggcc tctccctatg gatctcttct gcttttagcc acctgacttc    41220
agagacctgc ttgagtggga gcccaggatc cgagaggcct tccgtaccgg ggacttggag    41280
tccaagcctg accctagtcg gaacttcagg ccctaccgag ctgaagataa cgattcttat    41340
gcctctgagg tgggtctagg cctaagcagg ctgttgggtg gaagccgatt gcctcctgaa    41400
agcaggcagg gtgcccttg gaggaggatg gtataggttt taagcattta aacttctgac    41460
agccaaggca aaaaagaaa gaaagaaaga aagagagaga gagagagaga gagagagaga    41520
gagagagaga gagagagaga gaaagagaaa agggaatttg aatcaatccc gtggtttagt    41580
tagaggaagc ttagctggat atgggacatg atatcaaact gtaatcccag tgtcaggacg    41640
ctgaggcagc ctgaatgctg agctggaggc catcttgaaa tgactaactt atgtagcaga    41700
gaagcaatgg cctctccatt taggctgttt gagttcatgc tgtgactttc tgggtgctgg    41760
ctgtgagatc tcgggtacgt catttcactc tcgaaaattg tcaggtttgc cacagacaag    41820
tacagagcct cataggattg ttggcctggc ctccacgggt tgaggatgag gtcggtgtcc    41880
gtgacaagtc acatggactc agggatcctg agtgctgagt cactctgctg gtctggtggt    41940
gtgaccttcg acatgtccac tcccatgggc ccggcttcc caccacaaca gttataatcc    42000
ctagagttgc taagattctc tgatctttga gaagttccct gtcctcctga gcctgggaaa    42060
ctccctggaa ctgaagggtc caactgccta gtgaggtggt ctggatgtcc tcataaccat    42120
ggcgaaggag gaagaggaag agcgttgtct ggggctggag agatggctca gtggttaaga    42180
gcaccgactg ctcttccaaa ggtcgtgagt tcaaatccca gcaaccacat ggtggctcac    42240
aaccatctgt aatgggatct gatgccctct tctggggtgt ctgaagacag ctacagcgta    42300
cttacatata ataaataaat cttaaaaag aaaaaagaaa agaaaagcac tgtctggaca    42360
aggagctaag ctgtagtgct gtgtagcctt agctttgatc cccagtcagg agatggatag    42420
acagagagaa gggagggag agaggaagaa gaggaggagg aggaagaaga ggaagaagag    42480
gaggacgatg actacgttga agcaacctga gatgcttaga tctcgttttc tgagaagaaa    42540
ataggcttgt ttgtttgtgt tggctcattt acaccttgac tccgtttcct tcattcttac    42600
cgattagcta tgactaagca cagcgccaac ccccagttca agagcgatgt gcaggggcag    42660
gcgcctgact tctatttaag aggttttttt ttttgtttc tttgttgagc cagggtctca    42720
gtaattatat tatgcttact tcaaacttac catcctcctg cctacaactt ccaagtgctg    42780
ggattacagg cacatgacag tttgcccaga tctgcagaga ttttttaatac agaacaggta    42840 tacaagacac gcctcgtatc actgcagaga cggccaaatt atattattgg ccacattttt    42900
```

```
tttcacagca ggaacctgct atgcctggga ccatgtccac tcttctgttc ctgtgcagcg   42960
tgttagagtc aacattcctg ttaccagaaa tacttaacac ttgtcttttg cgatggagtc   43020
ttactgtgtt gctcaggctg gcctcagact cacaggttcc ggtgatccgc ctgcttcatg   43080
cccacttcat ctcatctaaa aaatgttgtt actggggaat aacagcaaag tagtgatgga   43140
tggggctgca gctcagtgat gaggcacttg ctcagcacgt gtgaggcctt gtgcccacac   43200
aaggcagggt cttgctatgt aacccagcac cagtgcacac acatggactc acatgcacac   43260
acaagcagac acgtgtgtac acacacatgc actgcacatg dacacaccca tgtaccacac   43320
atgcatacac attcatacat gcctgcacac atatgcacac atacatgcat gtattagtca   43380
gggttctcta gagtcacaga acttatggat agtctctaga tagtaaagga atttattgat   43440
gacttacagt cggcagccca attcccaaca atggttcagt cgcagctgtg aatggaagtc   43500
caaggatcta gcagttactc agtctcacgc agcaagcagg cgaaggagca agagcaagag   43560
ctagactccc ttcttccaat gtccctatat tgtctccagc agaaggtgta gcccagatta   43620
aaggtgtgtc ccaccacacc tttaatccca gatgaaaggc gtagcccaga ttaaaggtgt   43680
gttccttaaa ctccgagatt caatcttctg gaatccatag ccactatggc tcaagatctt   43740
caaaccaaga tctagataag gatctccaag cctccagata agggtcactg gtgagccttc   43800
caattctgga ttgtagttca ttccaaatat agtcaagttg acaaccagga atagccacta   43860
caatgcatta cacatggata cacacatgca ccacacatgc atgcacatac atgcacatac   43920
acacacacgg ggaagggcag agatggagaa aggaaggaga atgggtgcct atggcttttg   43980
acaaactgaa cacttctctc cccttttggtg cttttgggcag ggtcttgcta tgtaacccac   44040
gctggcctca agctcatgac ttcctgtttt gtaagtaaca tctagaatca taagaagact   44100
ctagacatct gtgttcccta ctagtctgct gtctgtctgt ctgtctatct atctatctat   44160
ctatctatct atctatctat ctatctatct tgtgtgtggg tatgtgcaca tggtatataa   44220
gtcagcggac agtttatagg agttggttct ctcctcccac catgtgggtc ccagggatca   44280
aacccaggtc ctgacgcttg gctgcaagca cctttatctg ctgagccatc ttgacagccc   44340
aagaacaaat taacttcatt tagctctaaa tgcttttaaa acacaatttc ccccagaaaa   44400
tggagaattt ggttagcttt tttaaaatga tcttactcca tagttactga aatccacaaa   44460
taatcacaat taaacttctg ggcagcatta ttacatgaag aaacaaagaa aagcaagatc   44520
attctgtagt taaccacacc gacgttcacc gtagttctgt tacgtaacaa cgctcaaaga   44580
cagcatctgt gacggaacat ctggatggaa cttaacacat acagatccac taaacacatc   44640
tgaaacctca tttatctttt aaactgcgtc taaatttgta attatagaca gtgccctagc   44700
ttgggagtgg caagcaccta tagccccagc tacctggggg agctgaagta gggggatacc   44760
ttgagctcag gagtttgcca ccagcctgtg agactctaca tcagaaataa gtaatcaatt   44820
acatttaatc agttaatttg atcaattaaa gagactatga caacgttgt gacttacatt   44880 gagtttgcac aggattttc ttttctgcag ctacgtttgc aagagagaaa tgttaaaatt   44940
atattgggaa gatttgacac gtactgtttt gtgtaattgt cctgatgacc cgctaggcaa   45000
ggacagtgct gtgcctcgta gaggtgactc ccatccagtt ttctgttgac tccttactgc   45060
ttctgttctt tgaccacagc ctgtgtcttc tccttcctcc ttgtctgtcc cctccaccct   45120
acctccctcc tgcagatcaa ggatcttcag ctggtcctgg ccgaggccca cgacagcctc   45180
cggggcttgc aagagcagct gtcccaggag cggcagctcc ggaaggagga ggctgacagc   45240
ttcaaccaga aaatggtcca ggtgggtttg taccacaggt ttgtgttttt tgtttttttta   45300
```

```
ctgactatag cttgtctcag aagggaaggt aaaggggcca tgggatagct ctttggtaga   45360
acacttgacc agcgcgtgag aagctctggg ttctgttccc agcataggaa gaaatcaaac   45420
actactaaaa agaaggggac aacactgggg aaacccaagc ttccccaccc ctgcgctctg   45480
ccagtttgtg gttgtcagca gctacactga gctggagcca atcacatggt aatagttttc   45540
tgggtgacgg tgagcctgct taatatttct gggtcttgct tggttgtgtt tgtttgagaa   45600
agggtttctc cgtgtagccc tggttatcca cttgatatgt tgactgggtt gattttaact   45660
cacagaaatc ctcctgcttc tgtctcccgg gtgctgggat taaagacata cagcaccacg   45720
cctgtctctg tttcatgtct ttttttaaaa aaatttttt taaagaattt ttacttttaa   45780
ttacatgtag atgtgtatgt aaatgtgcat gcctgtgtag gtatgtgtgt atgtatgtgt   45840
atatatatat atatatgcat gtttgtgtaa gtgtatgtgc atagatgcat gtctgtgtag   45900
gtgtctgcag aaaccagaag tgtcaggttt cctttgatct gcctaatgtg ggtgctagga   45960
attgaatccg ggtcctagta ctcttaacca ctgagccatt tctccagctc ttgtttcatc   46020
tcttggcctc agtttcctgt ctgtgaaatg gtgcccgtat caaacctggc tgtggatcag   46080
atctataata gcatttcttt cttaaaaaaa aaaagattca ttttatttta tatatatgag   46140
tacactgtag cggtcttcag acacaccaga agagggcatc agatctcatt acagatggtg   46200
gtgagccacc gtgtgggtgc tgggaattga acacaggacc tctggaagag cagtcagtgc   46260
ttttaaccgc tgagccatct ctccagcccc tgtaataaca tttcttttct tttcttttct   46320
tttcttttct tttcttttct tttcttttct tttcttttct tttcttttct tttcttttct   46380
tttcctttct ttctttcttt cttttctttct ttctttcttt ctttctttct ttctttcttt   46440
ctcttctttc gagacagggt ttctctgtgt agccctggct gtcctggaac tcactttgta   46500
gaccaggctg gcctcgaact cagaagtccc cctgcctctg cctcctgagt gctgggatta   46560
aaggtgtatg ccaccatacc cggctataac atttcttaaa ccttaatgtt gaggctggtg   46620
agatgggtaa agacacttgc caccaagcct cacaacttgg gtttgatccc caggaccac   46680 acagggagag agagctaacc tgcctgagtc ttctgaccag cacacacatg ccacggcagc   46740
catgcccacc catacacata caaaacagta agagagtgta aaaattaaaa agcacctcat   46800
tggacggccc gtggaaccca ccgtgaacac atgatagcct gcaggcctca tactcctccc   46860
ttataagata ccctcacttt accgattggt ggtgcgtggt aggatgaact gaagaggcag   46920
gcagactgca gacaggagca cagagcagtc cagtcgtgct ttgctcagag ctgtacatcc   46980
caggctccct tagctgtgaa ccagtgttac ttactccctg gggtgcttct tgtttctcag   47040
ccttctttaa cccagcatgc cttgctctgc acccaccctc tctctgccgt ccccactcac   47100
cagtgtgagc acgtgggaaa cacctgctgc tctgtgggtg ctcagagtat ggtgtccaga   47160
gatcgttcct caggctgttt gctcagggtt ttgagatggg atccctccct ggcacctggg   47220
ctcacctatg agactacgct gggcggctga gctttcatag gtgggttctg gagagtgaac   47280
tctggtcttt gtgcttgtct agagggcact ttagtgactg ctctctccag cccactgctg   47340
ctgcttgtga gagttcttct tcccaggata caatgggctg ctggtagtag aagccctggc   47400
ggggggtccc cagtaggcac ttgccatcag tgttcccctc tacccttgtc tggttctgca   47460
atcaactggg gcctcccttg ctcacccctg tcaatgacag ctgaaggaag accagcgagg   47520
ggcgctgctg agacgggagt ttgagctgca gagtctgagc ctccagcggc gactggagca   47580
gaagttctgg agccaagaga agaacatcct ggtgcaggag tccagcagt tcaagcacaa   47640 ctttctgctg ctcttcatga agctccggtg gttcctgaag cgctggcggc agggcaaggt   47700
```

```
tctgcccagc gaagaggatg acttcctgga ggtatggctg agcatagcct tagcgcgggg   47760
ctggaagaat gggagcgtgg cacctgagtt ctgcctcttg tccctaacag tacctggttg   47820
ggagtaggtc acatgctatc tggactgctt gccgccgggg tctcccggtt tgttgaatgt   47880
ggtttctcaa accaggtgaa cagcatgaag gaactgtacc tgctgatgga ggaagaggag   47940
atgaacgccc agcactcgga taacaaggcc tgcacagggg agagctggac ccagaacacg   48000
gtgtgtttaa ccccttcggg tcctacctta actgtgtgta actcgttcat taatgagcgc   48060
ttcctgctat cttctcagcc ctgacaggac acagggtctg tggatgctta ttgcttggat   48120 tctgcccac cagtttctca gtgctagggg gacatgccag ggtagtgaca gaaggccaat   48180
gtcacaagta agggaagcag ttcgcccgtt tgttttatag gaaacagtgt tagagaatgg   48240
gggtcccgtg tccgtgcgtt tccatggatg aatagggget tgtccaattc agaatageca   48300 aaaaaggcca tattgaaccc agaggacagc atgtgctgag gtgtggcaag atgtgctgga   48360
gtgctgctgg ccagtgggac attgtgggag ggtgaggata taccaggcca gggacatacg   48420
aagagagacc ttaagtaaga actgtcaaat caagccacag gttggagagg gcggtggagt   48480 cacccccctag ggttctatag tgagctagag tgagggcgag cagtgtgaaa ggcaccagga   48540
aagaggtttg ggatccagtc tggcgccatt tgagggacat cagtcagaga ggagagacct   48600
gcagcctgga gcccgctaag cctaggtgag gttgtttctc tgcgtttggg cagagtagct   48660
gctcctggaa tagacttcat tgtgtatgag acttgctgct cagctgagct atttaggaca   48720
ggccttcagc cccattttac tggtgagagg acctgaggag agctctctgg agctggtagg   48780
gccccagctg gactcctggg tgagtctgct atgccagggc tgccctttct gccttcataa   48840
agttcctgac caggccttac tctgccggca gcctaatgag tgcatcaaga ccctggccga   48900
catgaaggtc accctgaagg agctgtgctg gctgctccag gacgagcgtc ggggtctgac   48960
tgaacttcag cagcagttcg caaaggccaa ggccacctgg gagacagagc gtgcagagct   49020
caagggccac gcctcgcagg taagcctccc tgcttgttag ggacggtccc ttcctttttc   49080
ccggcccagc tctagacagg caggtctcgg aggaggatgc taaggatgca cagggtcccc   49140
tgcacctcac cgtgtgcccc agagagattg acaggaatgt aggctgcact gtggactcac   49200
agaacgcttc cacgccagcc tgcgcgtcat atcctgcatg gctcctaata daccggacta   49260
gggtgttgag agggtgaaga aaagacagac agacacaagg atacacagat agctgggatc   49320
aggcgatctg gactctctat ggagctctgg aaactcagcc tatttaccat gaagttggtg   49380
gtcattaatg cagataaccc gggtggtggg gattatggtg taccacagta tcagggggaca   49440 agctcagcaa atctgagcag gagcgctctg taggggagct gtctccaggc tgcgaatgtt   49500 ggaggggget gctgtggcgg acatcttcat acactaataa catcgcccac acacagagga   49560
aggctttgcc gtttccctct gagtctcacc ctggtgggac aaatggcttt gccatgtctc   49620
cctgggtccc acggtcgcca ggtatctgtg acgtgactgt acccatttca agagtacaca   49680
taagctcagg acctgactca cgagggcgtc ctctgccctc acacctgtac ttggtaacag   49740
gctgcacact cctgtctggg ctctgctggc tgccacccte atttgttttc ttctttcttc   49800
ctaaggactc ccagcccctg ctacctggct ctaatgtgtt cctcatactc aaattgggtc   49860
tcccctcaca gccacccagc ctgactaaca gcgctctcac cagcatcccc aggggctgga   49920
catctgctgt gtgcctgggg gcaagttgtt tccccactct gatctgacaa ataggaaggt   49980
agaaatgctg tctctgcttc tctggactgg gcccctggcc gcctccagca catcttggct   50040
tccgggtgcc ttccttgcca tctgtggcca tgggagacag gcatgctgaa ggtctctgct   50100
```

```
ggccagatgg ccaagcaggc ccagaggagt taggtttctc tcctaggtat taagtagcag   50160
gcttgctctt gccccccagg cttctgacct tcttgttccc atgggtgcat ttccacccte   50220 gcctggtgtg tggagactcc ttgagtttcc ctgagccctg cgctcttcct caccctgtgg   50280
gtatccatct tcttccagcg ttccccgctg cccctcactg ctccccaggc ccagccgtcc   50340
caggagctct ggctctcgga ccagcctcat aaggatcagc gttctagatc catgggcagt   50400
gagtcttgag gctgtatgtt tctttcctgc ctccccatga tgaggtcgag gctgagaaaa   50460
atatgctgga ccattcctgc gccagcgtat tatgtgactg tgtgtacatc tccctgtgca   50520
gggcctctgg gacaaggtga ggcccagctt tcaaggggta gcagtgggga ataaagaatg   50580
tcttccaccc gtggaagctg gtgctcctgg taagaactga taaatgtttg gttatcagta   50640 gccgggctc tccttttgt agcaggatgt ggaatgctta tctagcccct tggagccacg   50700
gtgagggaca ggaagtggtg ctttgcttac agaggcttag gaagagaaca ttgggttcgg   50760
ggtcagtctt gtatgtagaa agggggtccat agcacagaga gtccctgaag acctccccag   50820
tatgggtttg gagccagtgt cccctgccac tatccagcta gctggtgctt cttcctgcag   50880
atggagctga aggctgggaa gggtgccagt gagaggcccg ggcctgactg gaaggctgca   50940
ctgcagagag agcgggagga gcagcaacac ctcctggcag agtcctacag cgccgtcatg   51000
gagctgacga ggcagctgca gctgagcgag cgccactgga gccaggagaa gctgcagctg   51060
gtggagcggc tgcagggaga aaagcagcag gtggagcagc aggtgaagga gctgcagaac   51120
cgcctcagtc aggtgaggag gctctggtgc agtgatagct ggagcccagg gcacagggga   51180
agccgccaga gtcgggccct tcccttccca gcacaccaca tggcagcctc ggtgatcgca   51240
tcttacatct tagcagttgc aataaggaag tgatcttgtc tcacgagttc tcactgagca   51300
ggtgtcgatc ttgtgcccat tggtggggcc tgtcgagacc caggacccaa aagggaagag   51360
ccaagagtgg tttccatagg aaagcgagag tcctcagacc agaatgggaa accaagacct   51420
aagtattaca aaatccttat tccgtccggc tccctccctt tgctctgcag gtatacatct   51480
gtggagagat ctctgtctgg tttggttttc actaattgag tcattgtctt ccgaggagag   51540
ccttgctcgg tttaactgct gtttgactcc cactcattcc gcgtggacag agtccaggct   51600
ccatgtttga tttggagcag gtgacgtcac tcagttggta cagcactgcc ctagcacgca   51660
tgaagccctg ggctggattc ccagcaccac aggaacaatg tgtggcagct catggctgtc   51720 agttttggt aggtaaaggc agaaaggtta gaggttcaag gtcatcaccc tcagctactt   51780
agtgagtttg aagccagcct ggtttacatg aaaccttgtc tcaaaaaacc aaaccaaaca   51840
aacacaccag cagaaagcag ccctctactg tcctgtgcac aggtgtatat gtgaacagta   51900
tttacaatgc tgtagtcaca ggctctcaca tggatagaga gtgagagaaa gagaacttca   51960
gggggctttc cccactgttc tcgtgtctgt ctgtctgtct gtgtgcagtg cgcagactcg   52020 cttgcttct ttcttgccag ttcttatgac tctccagtct ttggactcac ctaatccccc   52080
tgagagccac catctttgtc ttgtcagccc gccattttaa accctctcag tcctgtaagg   52140
ccacttccca gaagagaaga acgagccaaa atgtcctgtt aatgacagga cagaaacatg   52200
ccagctcctc acatctgttg gatttttttt ttttaaagat ttacttgttt ttatgtagat   52260
gcgtgttttg cttgcttact tacatgtaca cacaccatat tcctgttcat attctctggc   52320
tagtgtcaga tttctcagtt atagatggtt gtgagctgcc gtgtgggtcc tgggaactga   52380
gcctgagtcc tctggaaaca agtgctttta actgctgagc catctctgta gccctaacat   52440
ctgatagatt cttttttttt tttttttggt ttttttttt ttgagacaag gtttctctgt   52500
```

```
gtagctctaa gtgtcctgga atttgctgtg tgtagaccgg gctgacttca aactcacaga   52560
gatcctcctg cctctgcctc ccaaatgctg ggattgtagg catgcaccac cactgcccaa   52620
cttttaatat catttttta  tgatttggaa atcattaacc aaatcaatgc cctgctgaat   52680
gaggtgtgag cacaccgctg ggacctgcca gctcgtgggt gctcgctctt gtgcttaatt   52740
tcccagcagc gcccacctat ggaatttgct gacttcctag ctcggctcct gcaaccttt    52800 gatgctgatt tgtttccctg cattcaagcc caagctgcat cctgtatttc ttattttctt   52860
cctccttttt cccttcccc  tgtcctttct ttctttgttt gtttgttttg agactacata   52920
tctcaatatt tggcccagac tagcctggca tgctcagttc tcctgagcta ggatgacaga   52980
ggtcagcccc aacatctgta taagctgtgc tctagatgaa accagcttgg tcaagcaacc   53040
agcagagcaa cagataggaa gagtatcttt agtcagtgtt cttccccacg aagagtcacc   53100
ttgaccatcg cagctcttaa aaggaaacat ttaatcgggg ctggttggct gttccagagg   53160
tttcctccct tttcgtcatg ttgagcagct tggtggcctg caggcagact tggtgctggt   53220
gaggtggctg agagttctac atccagatcc aaaggcagca cgaagagaga gtgacaatgg   53280
gcctggcttg agcatttgaa agttcaaatg ccccgccccc cagtgacaca cttcctccaa   53340
tgaggccacg cctcctaata gtgccactcc ctataagcct atgggtctca ttttttttt    53400 tttaaatatt tgtctttctt ttttttttt  taatttatta tatgtaagta taagtacact   53460
gtagctgtct tcagacactc cagaagaggg catcagattt cattatggat ggttgtgagc   53520
taccatgtgg ttgctgggat ttgaactcgg acttttgga  agagcagtcc gtgctcttaa   53580
ccactgagcc atctcgccag cccctatggg tctcattttt attcaaacta ccacaaaggg   53640
gctcctagcg ctaatcaaat cccctctgat ctctgggctt cctctacaca aggaggatgg   53700
ctgttcaatc ttcttatctc tcaggacagc caagggaata aagagctag  ccacaagaat   53760 ggtgcgttgc tcctaggtcc ccccctccc  ccactgggc  cttggcttac atcttcatct   53820
gtgattgctg ttcattcatg ctgagatgac ttttgttgct gccctcccac ccccattctg   53880
tttgtcttac attgggttcc aagtaagcag agcttgagat gggggttcag gtgcaaacag   53940
gtagccagcc tgtcctggtg ttgcttagga cttcattgca cctctgggaa atggaaggca   54000
aagcctactt gcttttcag  aactgaaagg gtttggggtg gggggagcct tactaacact   54060
ggggaagctg gggggcggg  gggtggggaa ctagggcgag tcgtcccctg tgggagcgaa   54120
gtggtgatgc ggcgcccgtc atctcagctg ctgtctgaac tgctccacat ctgggccctc   54180
cttctgttga ctttatcctc tcacctgcta cttggaaata atctcagttg tactggctcc   54240
tatgtctgct atgaggacta attgagctga tgagcacatg caaatgggcc ccctggaatt   54300
gtggtactcc agggaacacc tcaggactca gcaggttcgc agcatggtcc ccgagtgaaa   54360
tagctactgc ttgtctgccg ccctagctgt tctgtgaact gccgtgcaga gtaatgtagc   54420
aacagctcct gttaactcta tcagccaggt cagcaagatg cctgccagta gctgtttgta   54480
ttactggttt ccaaatccac cttgtgcggg gctcagaggt actatctatt gagaagccaa   54540
tgccggacat atgttgtggg tgggtcatgt ggcttataga attgagactg gggagtggcc   54600
ctgctcagag taaccctgcc cgccagcata cacacttttc tctttctcag ttgcagaagg   54660
ctgccgagcc ctgggtcctg aagcactcag acatggagaa gcaagacaac agctggaaag   54720
aggtgagagc atccctgcta cccacatcct attggcccgg actgtaccag aaaattcctt   54780
gcttgtgaga aatgtaacag agggatgcta actctgtccc agaagccaca ccctcactac   54840
accctgggct cccgagcccc agagtcacta ccccatgact gctgtccatg aatgtggact   54900
```

```
tgggaagggt tctctgctgt ggaagaaacc ccaggccagt tcagtcatac ctcaacagaa    54960
agcaggcctt ctaagtagct gtgtggtctt gggtgagtca ctctccatct ccgggcccca    55020
tttcctcatt gccctggcct catcctgagt gggtcggtgg ggtgacactg gaggaattca    55080
cacataaggt caggggggact gttaatagaa cacagagctg aggaacaaag ggtacataca    55140
ggtccctcat gtcgtccctc ctcatgatgg cgtgaagaaa tggcacccca ctcaggatat    55200
ggggctacaa aagcctattc tggagaactg aagcagagag gattttgagg ggctcacagg    55260
gctagtgatg cgcttctggt tactcatggg ccccgagggc tgcgtctcta gacccagagt    55320
gggaaaatct cacaatcact gtcatggcca tcaactgtac agtggctgtc atggaaaaag    55380
ttctgtctca agtggtccct ctttctctgg tccctctttg cactgcagat atctgagcct    55440
ggctcccatt gccattgtaa gggggtgaga ggtaacggtc cagacagtta gattgctact    55500
gacggcgtct taccctccag aggagacaac tcacgtgtgg agtcttgggc tcagttccca    55560
cgtgggtctg atgtcatcac ccatcacaca ctggtcacca gaactgatct tcttgtctct    55620
tcctttgaca ggcacgaagt gagaagaccc atgacaagga gggtgtctct gaagctgagc    55680
tcgggggaac tggcttaaag aggtgctggc cactcatccc ccaattctgt cctctacccc    55740
acagctctgg cccatgccct atagactttt ggctttgact ctctctactc ccctgctccg    55800
tgtgtccact cccaccccca tgagagttgg gagaaccacc agatgttccc ccctcccttg    55860
ggaccccagg cactcgggaa ctggagagcc tggggtcaca aggattgcag gctgcagttt    55920
aatgttgatt ctgggtatgg aaaactggag cctcagctgc acttgctgac aaagaagcca    55980
tttggctcct ttgagggttc tcttttctc cctggaattt gaatcatggt agatatccat    56040
ttgggggatt attaggcagt gtctattagg cctactacta tgctatggcc aagaggatat    56100
gcaagaatag cattctcatc attaagaccc tccatgacct gggcagtggc agtgcacacc    56160
tttaatcgca gcactcagga ggcagaggca ggcggatttc tgagttcgag gccagcctgg    56220
tctacagagt gagttccagg acagccaggg ctacacagag aaaccctgtc ttgaaaaaaa    56280
accaaaaaat aaaaaaattt taaaaagacc cttcatgaaa aagagagga atagtacaga    56340 acagaacatt ctagagtgag gggctcactg gagtcagaag gccaggtgta gatctaactc    56400
tgccattcct agcacagggg ccttgggtgc ctccctctct ctagtgggtg aattggagat    56460
gcccacagag ccgtgcagtg accagtcatg tgtggtagag gattccagta gcaaaccaaa    56520
cctggatgtg aaatagggaa tgaaggcagc cagcggatca aaggaatttc aaatgatcca    56580 tggggggtggg aagagggggg tggggggggag aggcagctgg gatcctatca agatgtcatg    56640
gggtagctgg aactcaggat tgctgaggaa cctggaagcc agcagaggcc gaacccctca    56700
gagatccccc agcacaggtg tgaggaagcc aggtacttaa ctccagattc caccattgtg    56760
tgctaagggc tgtgttctgg ggattgaaag agctgtttct gccttcctct gcccagaggc    56820
caaccatgat cctagcattt gtgctactta agcgtgtaaa gagggtttga ggaggcagca    56880
gccagatgtc tacaagagat aggcaagaca ggcttggtcc ccacggcatg tccactttgt    56940
tatttcccac taacccccatt ttcttccttt acttttccca ggaccaaatc agtctcctcc    57000
atgtctgagt ttgaaagttt gctcgactgc tccccgtacc ttgctggcgg ggatgcccgg    57060
aacaagaagc tgcccaacgg ccctgctttt gcctttgtga gtactgagcc agtggagcct    57120
gagaaagacg ccaaggagaa ggcggggctt tccacccggg actgtagcca cattggtagc    57180
ttggcctgtc aggaacctgc agggagacag atgcagcgca gctacacggc tccagacaag    57240
acgggaatcc gagtctacta tagtccgcca gtggcccggc gcctgggtgt ccctgtggtc    57300
```

```
catgacaagg agggcaagat cctcattgag ccaggcttcc tcttcactac cgccaagccc    57360
aaggagtcag ccgaggctga cgggctggcc gagagctcct acagccggtg gctttgcaat    57420
ttctcccggc agcggctgga tggaggatcc ggggccagca cctcgggttc cggacctgct    57480
ttccccgcct tgcatgactt tgagatgtcg ggcaacatga gtgacgacat gaaggagatc    57540
accaactgcg tgcggcaggc catgcgctcc ggctctctgg agaggaaggt aaagaacaca    57600
tccagccaga cggtaggcgt ggccaccgtg ggcacccaga ccattcggac ggtcagtgta    57660
ggtcttcaga ccgacccacc ccgcagcagc ctccacagca agagctggtc accccgcagc    57720
tcctcgcttg tgtctgtgcg cagcaagcag atctcttcct ccctggacaa ggtccattct    57780
cgcattgagc ggccatgttg ctcgcccaag tacggctcac ccaagctcca gagacgatcg    57840
gtgtccaagc tggatagcac caaggaccgc agcctgtgga acctgcacca gggcaagcaa    57900
aatggctccg cctgggctcg ctccaccacc acacgggata gccctgtact gaggaacatc    57960
aatgatgggc tttctagcct ctttagtgtg gtggagcact ctgggagcac cgagtctgtg    58020
tggaaactgg gcatgtctga ggcccgaacc aaacctgagc ctcccaagta tggcattgtt    58080
caggagttct tccggaacgt gtgtggccgg gcaccgagcc ccactactgc agcaggcgag    58140
gaaagctgca agaaaccaga gcccctttcg ccagccagct accatcaacc cgagggtgta    58200
tccaggatcc tgaacaagaa ggcggccaag gcaggtggta gcgaagaggt cagacccacc    58260
atgctgtccc aggtggggaa ggatggcatc cttcgggatg gagatggatc cttgatcctt    58320
cccagtgagg tatgggtgga ctttacccct cattcagaat ggggattag cctagaaagt    58380 tcaaattctt ctgttttgtg ctgttctgtg ttttgcttct cttctgtaaa gtttcatgta    58440
gcccaggcta gccttgaact ttctgtgtgt gtgtgtgtgt gtgtgtgtgt gtgtgtgtgt    58500
gtgtgtgtgt gtgtgtattt aaatatgtcc ttttttgtttg gtttggcttt tgttttttgtt   58560 tttttttcaag acagagtttc tctgtggagc cctggctgtc ctagaactca ctctgttgac    58620
caggctggcc ttgaactcag aaatcctcct gcctctgcct cccaagtgcc caagtgctgg    58680
gattaaaggc atgcaccaaa aatatgtcct ttttatttt ttagaaggaa agcaacagca    58740
gttcagggct agagtgtggt ttgatggtaa aaacacatgc gtagcacagg gaagccctga    58800
attcaatccc aacacttcaa aagagataga aggagaaag gagtgtgtta ctgagacatg    58860
ttaggtgctt agtgggcacc atgtcacatc ctttacatgc cctgtttgat cggatcctca    58920
cgacactgag aaacacaata cattttttcat tgttgagaag aggagagaaa gattcttcgt    58980
agagtgtcac ttgcctagca agtggcagag ctgagagagt gtttgggttc tacagcaagg    59040
cttttcacca tctctttgtt cttatgataa ttaaaaaatg aataatccca gcaggtggga    59100
ggcaaaggca ggtggatctt tgaggcaagt ctggtctaca gccagggtta cacagagaaa    59160
ccttgtttca agaacaaaca aacaccaacc cccccaccca cccactcaca aataataaag    59220 aaaagaatg aatgtaccta aatacacatc aaaagtgtat ctggaatcct cagtactccg    59280
gatatgatag cacatgccct tagtcccagc acttgaatag ctgagactga agcaccacgg    59340
gttgaggcca gcctggacta catcgtgaat tcaaaggcca gctggagcta cacagtgtga    59400
ccctgacaca aagaagcaaa cagagagtaa attggaacta aggatgtagc tcagtggtag    59460
agcacctgcc tggcttgctc aagcccctaa attccatcac tatggggtgg gggtgggggt    59520
gttggaaaat acgtatttcc attcagtaga acaccataga gccttaagga ctaagaccca    59580
ggagctgggg agatggctca gccgttaaga gcactggctg cttttccaga ggacctgggt    59640
tcaattctca gcacccacat gatggctcac aactgtctat agctctactt ccagggcatc    59700
```

-continued

| | |
|---|---|
| tgacaccttc ttccaaactc tacgggcact ccatacttgc ggtgcacaaa cacgcgtgca | 59760 |
| ggcaaacttc ccaaacacaa gccaagctgg tcgtgtctgc gtagagtgtt gagaatctca | 59820 |
| acctcggaca gcgtctgcct tctctgtgcc ttgcagactt tattagaatg tggatccatt | 59880 |
| gttgccctaa taggagtaat atggtctaga gcagagttgc agctcctgcc tcagcatgag | 59940 |
| acatggctga attctggtgc ctgggtggct gtagcccagg cttcaggctg ctgctgatct | 60000 |
| cttctctgtc tctcccagg atgccgtatg tgactgtagc gcccagtcac ttgcctcctg | 60060 |
| cttcatccgg ccatcccgca acaccatccg gcactctcct tccaagtgca ggctgcaccc | 60120 |
| ttcagagtca ggctggggcg gggaggagag ggcagctccc cagtgagtcc ctgagcaacc | 60180 |
| aagcacccac ctcaagcagc ccagaccctg gagatgaggc aagggctcgt gtcctcagcc | 60240 |
| tcagtccatc caggaggaat ggcagctgtg ccactgccac agaagagctt tcacattaag | 60300 |
| gtaaagcaag gtgtcttgct gactgctggg cagtgacctc tgatttccag gggaagaca | 60359 |

<210> SEQ ID NO 11
<211> LENGTH: 76771
<212> TYPE: DNA
<213> ORGANISM: Homo sapiens

<400> SEQUENCE: 11

| | |
|---|---|
| cgctgagcag cgacgccgag tccgcggccg ggggcccggc gggggtccgt acggggcagc | 60 |
| cggcccagcc cgcgccctcc gcgcagcagc cccgcggcc gcccgcctcc ccggacgagc | 120 |
| cgtcggtggc cgcgtcgtcg gtgggcagca gccgcttgcc gctcagcgcc tcgcttgcct | 180 |
| tctccgacct caccgaggag atgctggact gcgggcccag cggcttggtg cgggagctgg | 240 |
| aggagctgcg ctcggagaac gactatctca aggtgggggc gccggggtag aaagggaggt | 300 |
| cgcaggggtc gccggctgtc acagtcccgc gggcctgagg caccagccgg ccctccttcc | 360 |
| cactgaacaa tccggagaaa ggggcccaag ccctctgggg accactctga ggtggatctg | 420 |
| ggctcccctc atcccccccg cccctctca actttatttg ggaagcgcgc tcctgaaaaa | 480 |
| gaccttggaa ctggctacag ggccctaacc tgggagcggg gacttgagaa gctttggag | 540 |
| cgttctggga ggcgttgctg aggtgggggt gggtagccag ggaagggatg gatctctgcc | 600 |
| ttcagctgcc cagaacctcc acgcccagc tctccttctt gggacgggat tgatagacac | 660 |
| cgccgccagg gaaacctgtg gccatcccct gcccaggaaa ggcctgaatg ccatcctgag | 720 |
| tcgttaccca gggcttttcc gggcgcaggc ctgtctctgc ctgcctttct gggcgggtcc | 780 |
| agtttgaaag catgacatct gggaacatcc ccttggctgg agtccacttc cgcccagcct | 840 |
| aacggtccca cagcctggag gatgatgtcg tgggagaacc ggttcagagg cagcttccta | 900 |
| aatcccagga cagtgtcttt tgccctccct ggggcagacc ttgtgcacac aacagcccca | 960 |
| ttggcccctc gtggccagtg cctttccatg ttcgcagtga gaggagggca actgcccacc | 1020 |
| tggaacagga cttccctgtg gccatgtggg gaccctaggg cttcccccgg acagcaggct | 1080 |
| ttgcctttgc tttttcagtg gacatgagca cctactgggt gccagccggg ctccatctgc | 1140 |
| acgcttccag gtgccatggc agctttaggg acagcccagc ttgcacgtgt tgacctctcc | 1200 |
| ctggaggct ggaagcttcc tgagctctcc tgccgctggc tgggcacggt tttggaggag | 1260 |
| gctgaaatgt tgccgactct tgtcagtgga tgatggcctg gcacaacacc cagagtgccc | 1320 |
| ctggctgtgg agctcacagc atgctgctgg tttatgtctg ccctcagcac ttaggtttta | 1380 |
| acttttcctt gtggctcttc tgaccaaatg ggcttctccc tcattagagt gttggtgtct | 1440 |
| tgctcaacta tgtctctgtc tccccatttt ccccgggatc tgctctccag cctgagttct | 1500 |

```
gtaaatgctt gtagtatgga aggacaaggt ctgtctgaat caagagacac ctttccccaa    1560
gccaggcctc agtctcctca tccgttaaat gggaggatgt cttcccaagg gccgggttcg    1620
gtgttggcaa ctgggagttc agtcggctct ttgagtcttc agaagccggt ggtaaggaga    1680
gggcaagtgg aaggtgagga ggaggaggga ggtgacgagc caggacaagg gtcttttgct    1740
cctgccctct tggtgctctg agctgcttcc agtgagtgct gcctgaattg gccttaaccg    1800
aaactctgag ttcctcaccc ctgcctcccg gttcctgcta ctcactctgg tgaaggggga    1860
tgggttgcag agctttgctt cagggctcct aggcacccat ctccatgggc ccctgtccat    1920
cccaggaagt catcaggctc tgacccaaag tctgtttgag gcacccatga ctgtttaaag    1980 ggaaaacag tcccaggagg ctggggttg agcccgggat ctcacagggg ccggggtcca     2040
gctggggaca tcccacgttt gggccaagat ggaaccgtaa tttccaccat tcattcagtg    2100
gctcaggctt cgtgctgcta ttggatctgg ggtctgtcgc ttcctgacgg cgtgatcttt    2160
ggcaagttac ttaaaggccc tggacctttg ctttctcatt tgtaaaaatg ggacagtaac    2220 acgcttttcca acctcaacgg ttaaatgagc tgattcctgc aaacaccatt agagcacctg    2280
gtatgtagta aacctctgat cactgctctt gtcagaggca cggacatgt ttccatgtgc     2340 acccagcctg ttctcttgtg gattctgtga gggcagaata gatcctcttc atcacccaag    2400
gcaggctggg ctctttctcc tggcccctca ttggttcatt cggcagctgt ttatttagaa    2460
cctgccgtgt gctagggcag atctgggata cagctgtgga caagggagga tgaggtgtct    2520
gttttcatag gcttttggg gagaccgaaa ttaaacaata gtcatacaag aaatcacaac     2580
acagatcata atgagggtaa aggggacagt ttgccaggag cacacgaagg tggggctgg     2640 ggtgcacagg gaggctgagg gctgcaggat gccgtggagc caactgagtg agggtctgga    2700
gtaagaagat ttcaggctaa gggaaattgg aatgctcgtt gagttcaaga acagcgctaa    2760
ggccagagag gggaaggagt gtgggtaaga gaggagagca aggccagccc atgccacttc    2820
tcactgtgta catttgggtt agtcccttaa cttctctgta tatctgttta tcccagccgc    2880
cagcctcaca gaggcagggt caaaatccag agactaaatg tggaccataa atagagggt    2940 tattactgga ggtgttgtgt tgtttattcc acagatggga aaactgtggc cagagtgggt    3000
cccagagcag ggtcgctagg ctgccagggc ttggagtaag catgtgttag actcttgatg    3060
tgttttctgc ctttctggac tactttgcct ctaagatgca gaaactgagt acaagggaaa    3120
ggactccaaa tccccagtat gtcccctgca ggagcagagt tgaaggaggt cccaccaggt    3180
ctggtgggtg gccctgctca ggcttacctc cccccttgtag gggtcactgg gaactgtcaa    3240
ctgcgaagga ctgtgatctc cagtctggta tggtctgctc tggggtccaa gtgaggaaag    3300
cataaatcgg gcaactctct cccagtgaga agatagaagg agcttctaca gagaaggtag    3360
tgagctcact gtcactttaa ttattcagag agaggcggga tgaccttgca tgcttggata    3420
aagatagagg gtttgtggaa tgattgcttg agaagggttc agagggagat tgatgtggtg    3480
gctgcagttg agctgcctga ccttgggtcc cttctagcca aggaagtctg aaggttatta    3540
actactgagg tgccaggatt ctaagatgca gctttagctg ccgagcagac acgtcacctg    3600
agaccttcaa agacccggtg atctgaggtc ttccagcctt tcatcaccac taaccattaa    3660
gcacgtacca tgtggccaga acatgtagga acccactggg tgtggatgga ggaatctgag    3720
agttggagtc tgaagacctg actttgaaac ctgactctcc cgtttactgt gtggccatgg    3780
gcaagttacc tggcttctct gagctgcttt ttttctcatc tgtataataa aggtgatggg    3840
gcctggcgca gtgactcacg cctgtaatcc cagcactttg ggaggccaag gcgggcggat    3900
```

```
cacctaaggt caggagttcg aaaccagtct ggccaacgtg gcgaaacccc atctctacta   3960
aaaatacaaa aattacccag gcgtggtcgt gggcgcctgt aatcccagct actcaggagg   4020
ctgaggcagg agaatcactt gacccctggga ggcagaagtt gcagtgatcc agatggcgc   4080 cactgcactc tagcctgggc aacagagtga aactcttgtc tcaaaaaaaa ataagtaaag   4140
gtgatggaac ctgcctggac aacctcatac gatggtcatc aggaatcagg gaagtgtgaa   4200
tagacaagaa aacattttgc aagcagtgaa cccaagtcgc ctgaggaatt gttattattc   4260
atagccaata ggcagacagg atgtctgtgt cttcattctt ggaggaactg ggagaatgca   4320
ggagggtgga tttccttagt tttagaatgt taatacatca gtagctgccc cagggagaac   4380
ggaaaggtgt gatcaccttc cctgccgtgt gtgtgtgtgt gtgtgtgtgt gtgtgtgtgt   4440
gtgtgtgtgt gtgtgtgtgt gtgtgttttc cctccttggt gattctagat gtgagtgaag   4500
tgcagccagt gtgtgtgtgt gtgtgtgtgt gtgtgttttc cctccttggt gattctagat   4560
gtgagtgaag tgcagccagt gtgtgtgtgt gtgtgtgtgt gtgtgtgtgt gtgtgtgttt   4620
tccctccttg gtgattctag atgtgagtga agtgcagcca gtctagatgt cagctcagaa   4680
gggcctggag gaagcaccta atccatcccc acttgccatt ttacagatca gtaaatggag   4740
gctctaaatt acatagccag gattccaacc caggtttgtc taactctggg cctgttcttt   4800
ctgcagtgtg accagagcag tgagcttttg gttgttaact agcgtgtcta ggctgagaca   4860
catttggtga gaggaatcct gtcatgggcc aggctctagg ctaaggcatg ctgggggccc   4920
ggagcctggg ggaggtgggg gttagtggag gatgtttgtg tgtgcatgtg tgtgagattg   4980
ttccttctgt aacatggggg acaagcacgc ccgcccaggg ccgtgaggac ccttttcaat   5040
gtgaggacgc agatggagtg cacagtgagt gttagtgtgt cccagtcatt gccgatccct   5100
tatccgttcc tccaggcatt cattcattca ttcaacacat atttccccag tggctcctgg   5160
gtaccaggcc ctgtgctggg tgtctggacc cagtggccac gtagtaggct tctgcatgta   5220
gctcttctct tcttggctcc caggagctac agggggagga ctctagtctg tcactgggtg   5280
gaggagagga ggtcaccaca gtcagcaaag ctcttggctg ctccttaccc tgagtcccag   5340
ccgcagcctc cttggggctg agcctgtgtc cctgggcata ctctgtcttg cacatacaaa   5400
tgcacatata ctgttcacag ctcaagctca gagacacaca gccacttgca cacatctcac   5460
agacccatcc agtgactcgc tggtgttgga tgctttcaga agcacgcctc cagacagatt   5520
agagaggata ctcactcaga gaagtgcaca aacccatgca gccacacaac tcccattcta   5580
tcacacgcac acatcaccaa acagacacaa cggaggctca gaccctgctg caaccccac    5640 gtcagaaaca cattctcata tacacatctt acacccctag acacacccgg atatgtccca   5700
gagacagact gacatcctgc agacacactc agacttatca gaagtacaca tgtaggcgga   5760
gacacaaacc cacacagacg ttatacacac acactagcat ccacagaagt ctgcacatct   5820
acccttgcca ggctggccca ggcacaagct caccacccgg gtacctcccc tgcctcttct   5880
acaaagagag cagcagagac ttgcacacct acccgaggct tacagacacc caccaagggg   5940
actcccacat gcacatcagc agggacacag cacagtctgg catgcaaaca ttaggcatgt   6000
agcatttgcc cacaggagcc agaggctctc aaaccaggga acctagacac acgcacacac   6060
gtgcgcgcac gcacacacac acacacacac gctgtgacat ttcatccaca cacagaaaca   6120
ggaaatcctg gtctgtgtct ccctggagct aatgtgtaca aactactact gttttcagtg   6180
gctcactaga cttacttcta caaggctgct gggaacacta aggagtgtgg ccagggcctt   6240
gactttgtaa ccttctggag ctgggggtct tggggtcctg ggtggtgggt ggatggggt    6300
```

-continued

```
ggtaggtctt gaagtcagaa gaagctacac cgaagtcccc caggtccctg atgcccagct    6360
cctgggccca gggccagtgg ggctgagtga agtggaccga ttgtcgagct gcccacagaa    6420
gaaacactgc ccgggggcaa ctcccttcta atctccttgg aatttcctgc tggccctatc    6480 tccccttct  cccctgttc  ccttgctggg ggctgcagag ggccatgcca ctcccatcta    6540
taaagggtgc cccattctgg ctggggaatg atggaggcaa gggtagaggt ggctagagga    6600
gctatgggag ctcagaggag ggacttggca gacttcctgg aggaggaggt gtccttggag    6660
ctggggagtt agcctcaagt ggctgtctct gtgcccagct cttagaacag tgcctgccat    6720
gttgtagggg ctcaataaat atgtgtacaa ttaagtgaaa ggcagtaggc agggcctgga    6780
ggtggaccac aggcttgaaa cggaaaagct ggagggagtg gtgggagctg gcagggatgg    6840
ggagagtctg ggaaggggcg ttgggctggc ttggaaggg  cattgaatgc caagccaagg    6900
gagcaccttg ctgggagtgg tcttgttgca gcaaagctgc agccacctcc ttttatgtgt    6960
ctgcagccct gggcctgagg cctgccctgc cggagaggcc tggggaggga ggagagccag    7020
gctgtgtggt ctaggggcca actccacctc tggagtcaag tctggagcca aacctcactg    7080
tgtcacctcc tccgtgtgca tgctgtccct gtgcaaaccc ctcaccaaga ctccgtcttc    7140
ctcctgtaaa atggggatgt gatcctttct agtgggcac  ttgggaggct gacagctcag    7200
atgttctgtg cacctagcac catcctggca cagaggaggg gaggaggccc cgtgtcttgc    7260
atagcctccg gggcagagag agtcccctag gaaaggggcg cagctaagtt caagcaaggg    7320
cctgcccagc agccaaggtt ttcactgagg tcattcccct agtccccaca tgcatgacct    7380
catccatggt cacgttcact ccccttggtg ccggaaggaa cttggagctg gggtgctcca    7440
tgccaggctg accctggcat cactggaggc ctcagtcagc actgcatcta cctgctttgc    7500
ggtagtgagg cacagcaggg gtcagagcag gtggaagcag caggccagcc ctttgttctc    7560
cgaggtccag ggtggttggg agagagcact gtgatctgga gccaagctga ctgggctgga    7620
atcccagctc tgccttttcc tttctgagct ttcccttct  gagcctcggt ctcgtcatct    7680
gtagaatggg gatgtggatg tccttgcccc gcacgttgcc gtgagggttc cgtaagagaa    7740
agtgtgcagg tgtgggtccc attagccagg tctggctcct gggaaggacc cgacagcact    7800
tggcgcttgc ctgttatatc tggctctggt gtgaccccg  tgaccccagg ttaagctggg    7860
tgcttgatga caggggctgt gcttggctct gggtgtccct ctgtgggtgt tggcttgggg    7920
catcagtctg agtgttatgc acagagctgc actgcatttt gggcaccccc aaacgtatat    7980
ccctgtctgt gtccccccctt ccctccccca cggcgtcgtg tcactcttcc ctgaatggcc    8040
caggctagtg cctccagctt agtaactggt gatacacatt tgctaatgga aggacacctt    8100
tggcggcccc tcattctcaa atggaggtga atcatctctc actgcctgag ccacaaggaa    8160
aagctcagcc tctatgaaaa aaattctggg gttccctagc taggctggat cagctgaaca    8220
tctttactct ggttggggcc caggcctgct ttgggtcttc tgggctcgag tcagttgcac    8280
cagcctctcc cctccccgcc tctccttgac cctaccccat ggtggagcag cctgtgtggt    8340
cctgcctccc acagcctcac ccaccctgc  ccgcccaag  ctctgcgggt gctggacaca    8400
ccccggcctc tgtcccgtgc tcttgctctt cccatccggc ctttgtgctt gcagttcccg    8460
gctccttccc ttggtttctt cctccacctt tgagcgctca gccccagcag cagctccca    8520 ggtcaggctc ctgtgtcaga caccttggag ctccctggag cttcctttgg ggcatttacc    8580
acgatgttga ttagattatt aatggggtaa tgataggttt catgccatca ctgccccacc    8640
tttccctgca tgagggcagg gaccttccag ggtaattagc tccttccttt tacaaaggga    8700
```

```
gaaactaagg cccagagagg ttaaggggct tgttagaggt catgcagcct gtaagtggca    8760
agaggcaaga ctggggtctt gtgcttctct ccaggatgcc aggcaggggg aatggcaggg    8820
gtgtgaagtg ctggggtgtc ctggagcttc aggctttgtg ccttgggcc actctctttg     8880
gagctttgcc ttctatccct aaagacctca gacccctgct ctgagttttt gagatttcgc    8940
tgcaacccag agggtgtttg ggggatgttt taaacacatc caggtccaga tgctgccttc    9000
cttcctgttc acatggaaag gatgggagga aactgtcagg cgcttcctga cacgaatgcc    9060
ccagaggccg tagggcctgt ggatatctcc ctgctctgcc aggtaaggcc ttgaatggga    9120
gagtgacaac agtgacaagc cagatgtggc cttggtgggc agtggtctct taccaacaac    9180
aaccaccaca cacacacaca cacacacaca cacacacccc tccctgatag               9240
agcatctgta gtgtctcttg tgcagaactg taccagacgg atctgggagg ctcactcctg    9300
actggctgcg tagaccttat cttcctgggc ctccgtttgc ttgtctgtga aatggggata    9360
aaataataat agtgcctgcc tctaaggatc atcactgagc aagagataat ggcttttctg    9420
tctcagtccg gtgtctggaa cgcattaaac gcttgtcaat gttagctatt gttatcgtca    9480
ccattgttca ttataagact gtctagtcca gcttatagga gctccaactg gacctgaatc    9540
ctggctgtgc cacttagtgt gtgaccctgg gcaacatact tgacctctgt gaggttcctc    9600
tcccatcggg gattgctcgg gctgcagtga gagaatgtgc actccctggc ggggatcagg    9660
ggtgcacagg gagcatctca tttcttggca ttggagaggc gggtccaggc cccagtcttc    9720
cctcattatt cccaaccaga ggagcaggac gtggtgagtc tccagggcca ggcagcctct    9780
gtgttgtctg gagtggggac atcatgtggc acggtgatgc caggctgcgt gtcctggcct    9840
tctttccccg ggacctttt tttttttttt tggagacga agtctcactc tgtcgcccaa     9900
gctggagtgc agtggcgtga tcttggctca ctgcaacctc cgtctcctgg gttcaagtga    9960
ttctcctgcc tcagcctccc gagtagctgg gactacaggc atgtgccatc atgcctggct   10020
aattttttgta ttttttagtag agacgggggtt tcatcatgtt ggccaggctg gtctcgaact  10080
cctgacctca ggtgatccac ccgcctcagc ctcccaaagt gctgggatta caggtgtgag   10140
ccaccatgcc cggcctcatc aggacctttg atgcaacttc ctgaaaactg gaccctagct   10200
tcttcgcaag gatgctaagc tagattgagc tctggggtgg gagacaggtg cccagagtcc   10260
cccctcccac tcagtgctat cccctccagg gactgtggga ttgtccctg tccttctcaa    10320
ggccttctg tccctgggta tgaagggatt gagtctttgg tttccctccc ctgctgctgt    10380
gcccagagtg tttgcatttg ggctgagaag tggagctctg cggagttttt tgcatatcct   10440
tttttggggt ccaagtgtga tgatctcatc tggagccttg acagactcct ggggaccgg     10500
cagaagggac ggcagatggc tgccctggcc tcttgggtgg ggctggcatg ccgcccctgt   10560
ggccactgcc ggcccactcc acagagcagc ccttccgggg ctggggtgag tggcccgggc   10620
ccgggcagga gacgagtggc ccagagccag ggtggcagat gggaggcagc ccaggcctcg   10680
gcctgaggga gggaccatgg tggccagggc agtatgggag caggcgggcc aggcggaggc   10740
tcccgttcct ctgtagtgtg gttgctgcct cgcagagtga aggttctggg cctctcagct   10800
cagctctgtc attcttctgg gttggtctgc ccgtcggagg gcttgttggg ccctgaac     10860
ctggggagga ggtggtacat ttgggtaagg tttgaatct ggcagggctg tggcctggt     10920
gttgctgggc tgggacttga gccccaccac tggggtctga agcacccatg ggcattagct   10980
tcacagaatc aaggaattag attcaaacac aggagcgctg actagaagta gttttctgta   11040
ggggagtaga acaggggggat tctcctcccc tctgagggcc tgtgtattca ttcagcacct   11100
```

```
ctttattgag ctgttctgtg tgtcccaggc actgtgctgg gctctgtcct cctgacatca   11160
catcctggtg gtagagactg acattctgca ggcaaacaga caaataaaac gctgagtatc   11220
acaaataagc ctatgatata tgccaagaaa gaaacaaggg attaagatgg acgtaatggg   11280
cctggaggag catggaaggc ttctcagagg aggtggcatt tcagtggaga cttgaggcag   11340
aaggcaagcc agcagggcag agatggggga cagggaaatc caggcagagg aaactgcaag   11400
gccaaaggct ttgaggtggg acaggtgagg tggctgctgg ttgcctacga cccaagtggc   11460
tgctgtgttg ccagtgagag gaggcgtcga gggagatgaa gatggagaag tggacggggc   11520
ttaggccagg cagggcctgt atgctgtacg atgggatttg ggttttcttt tgtatgtgat   11580
gaaaagtcac tggaggtttt gttttgcttt gcttttttgct ttttgggtt ttaggtcagg   11640 tgtactgggt atatatatac aatatactgt acaatatact gtacaactat atacaatata   11700
ctgtataata tattgtacaa atatatacaa tatactgtac aatatattat acaaatacat   11760
acaataaaat gaattttggc aaatgcatcc agttctgtag ccaccaccac aaccaagata   11820
tagaacagtt ccttcacacc ccaaatttca ccctgtgagg tcagttcctc tctcgatttc   11880
agaccctgac aaccaccggg actgttttct gtccctagag ccttgccgtt tccagagtgt   11940
caaaaacaga ctcatacagt gtgtagccta ctcagtctgg cttccttccc taagcttcct   12000
gcatgtgagc ttcctccatg ttgcaggtgt cagcagttct ttccttttca tcgctgagta   12060
gtattctatt gcgtggacgt accacagttt atcattcacc agctgaggga catttgggtg   12120
attcccaggt tttggtgatc attggagaat tttaaacagg agaaatttt aaacagtttt    12180 aaccacattt taaacatggt tttagaaaaa atcactcact gtactgaatg gagaacaaat   12240
tagttgggag cagagtgacc atcataagga ttaaatccaa taatttggtg atggatctgg   12300
cccaccatag gcactcacta attgttcaaa caaaagggct gtgccctggg acagtcaggg   12360
aggcttttgg tggaggtggc tttttttttt cttttttttt tggtcaaaca cagtctcatt   12420
ctgtcatccc ggctggagta tagtggtgcc atcttggctc actgcaacct ccacctcctg   12480
ggttcaagca attctccgcc ttagcctcct gagcagctgg gattacaggc gtgcaccacc   12540
acgcccggct aattttttgt atttttatag agacggtttc gccatgttga ccaggctggt   12600
cttgaagtcc tgacctcaag taatccgtcc gtctcggcct cccaaagtgc tgggattaca   12660
ggtgtgagcc actgcgctct gctggaggtg gcttttgagg tgggaaacag gtgtggagta   12720
ggagtcccag gcagtacaga gtcccatggg agtgggtggg ctcagattcc agctccccgc   12780
ccctgagcca gccttggcat atgtagagtt gctagaatat ggtctgtagg ggtcatatca   12840
gagttcccca gggacactag gggctgactc ttgggtggga ggtagctgag ggacttccgc   12900
tctggaagtc tcttccttgg tggctggcaa gaggcaacct gctcctgcct ttgggagcct   12960
catgtcccct tggttctctc cgtgtcctcc cagctgggag ctgttgctgg gttcagacca   13020
catgctgcca cttgtgtttc tgcagagggt cctggtgttt ggtcactttc atctccagcc   13080
ccacagctca ccagctgctg caggccaatt ccgtcatagc catgcatctg gagccacgtg   13140
caaaggttcc agtgggcccc aaatctaaac ttcccccgc tgtcctcagt gtacaaacgt    13200
aaatcatttt atatctgcgt gggtttctga tagaaagtaa tctttcttag aacacttaaa   13260
gtgtgattta ccagcccagg ctggtaaatc actaaagcaa gacccctct ctacaaaaaa    13320 tacaacattc agccaggcat ggtggtgtgt gccagtagtc ccagctactc aggaggctga   13380
agtgggagga tgactttagt ccaagaggtc aaggctacag tgagctgtga tcaagccact   13440
gtgctccagc ctgggtgaca cagagggacc ctgtcttaaa gaataaaata agtaaaaagt   13500
```

```
gtgatttgaa agtggagctc tgcttctccc gcctgtattt catttcaaca tttaaagtta   13560
tatcttattt tggctgggtg cggtggctca cacctgtaat cccagcactt tgggaggccg   13620
aggcgggtgg attacctgtc aggagttcaa gaccagactg tctaacgagg cgaaaccccg   13680
tctctactaa aaatacaaaa attagccaag cgtggtgctg catgcctgta atcccagcta   13740
ctcgggaggc tgaggtggga gaatcgtttg aaccccagag gcagaggttg cagtgagctg   13800
agattgcacc attgcactcc agcctgggta acaagagtga aactccgtca aaaaaaaaa   13860 aaaaaaaaag gaaaccaact atattgaaac acagttatta aagtatttt aaattacaac   13920 atagtaatat gtgtgcttat taactcataa attctggtga cagatctaac tagcataatt   13980
tcaaactact gatgagtgta aataatattt tgacatttt gcagcaactg ttatatgata   14040
tgaaaatacc tgtgattttt ttttggtggc aaagtcacag atattactca tataatgatg   14100
atttgttcat aggcccagaa tagaaggaaa tgctacattt tacttagagg tcagtgaaaa   14160
ggaagatgtg atttccaag ttcatggact ccctgagttc tggttccaag gaaagatctt   14220
gaagttggtg gttggacttt gagtcctgct tggaggtctc accccctccc cctgcctgtt   14280
tgcgtgtgct tgggcaccac ccaccttccc tgtgcttctc tgaagttctt catctgtaga   14340
acatggatga tggttcctgt cttccttac tgggagtggg gggttcagtg aggatctgtg   14400
agatgattca gatggaatgt cttgtaaac tgtgaagccc tctgctgctg tgcaagatct   14460
tgctattatt agcagtagtg tgagctcatg tttggctgtc cggcccagcc gggaccaaga   14520
ggctcttcct ggacaattct cccaggattc ttgggaatca gtccatcgag gggagcaggt   14580
ttgcctttga gaggctgctt cctgcaggct gagctcatgg tttggcaggg ggtggacaga   14640
gatgcacctt gtgggcaggg agtgggtggg tgagcaggag gttccctacg tagacagacc   14700
ctgcctaccc tccttgggtg gcataggga ctgcgaccag ttctgatctg cccaggctct   14760
ccctctctca tttttattta gagacagggg tctcactctg tcacctagcc tggagtgcag   14820
tggtgcactc atggctcaca gcagcctgga actcctgggc tcaagtgaac ctcctgcctc   14880
agcctcctga gtagctgggg actacaggca catgcccagc taagttttta aattttta   14940 tttttttgta gagacggaga ctcactgtgt tgccaaggct ggtcttgaac tcctgtcttc   15000
ctaactcttt gcagctggct gggagttgtg gactgggcag gacagaagct atactctttt   15060
tttttttttt tttttgagt cagactgtct ctgtgtcact caggctggag tgtagtggtg   15120
caatccttgc ttattgcagc ctcaacctcc caagctcaag tgatcctcct gttgcagcct   15180
cctgagtatc tgaggctaca ggtgtacagc accatgcctg gctaatttt aatttttg   15240 tagagatggg gtctcgctat gttgtccagg ctggtctcaa actcctgagc tcaagggatc   15300
ttccctcttt ggcctctgca aagtgttgcg attacaggcg tgagccaccg cgcctggccc   15360
catactcatt ctttaattcc tacatctacc catagacagt gacaggtacc tgctctgtgc   15420
cacggtctgc cctgggtgat gctgaggact agacacaaac cagcccctgc ccttctccct   15480
agctcttggg gaagattgac atgaaaacag acaaatacaa cctaaaatta ccagcacaac   15540
ggaccataga tttcagagtg tggggtttga atcagagtct gggaaggaaa tgttctggaa   15600
ggatgagata gtcaggagtc agcctggcaa aggccgttct agcagaggga atagctgaac   15660
aaattggaag agcacagtta tgacgcactg acccagggcc acgtggcttg tttggaatcc   15720
agccccgcag gtcccttgct caagcagctc tgcgaagctt ctgagcctcg tctcctcatc   15780
tgcaaaacag gaacgttttc agcacctacc tcacagggtc ggtaagagga ttaaactgtc   15840
aactgataat gcacgtactg cctgtgcggg ggcctggtaa ttagtgagcc tcctaatagg   15900
```

```
tggtagccgt gttttgtttg ttgaaacagt ctgtctctgt cgcccaggct ggagtgcatt   15960
gttgcaatct cagctcactg caacctctgc ctctgggttt caagcgattc tcctgcctca   16020
gcctcccgag tagctgggat tacaggcaca cgccaccaag cctggctaat tttttttgtat  16080 tttttttgtag agatggggtt tcaccatgtt ggtcaggcaa gtctcaaact cctgacctca  16140
ggtaatccat ccgcctcggc ctcccaaagt gctgggatta caggcgtgag ccgccgtgcc   16200
tggccaatgg tagccatttc taaagtcaca gcctatttgg acgctggagg gctggggtaa   16260
ggcgggagta gggaggagac caggggctgg ctcaggaccc ggtaagggga cttggaccta   16320
ctgcagaagc tggtgagaac cggtggaaga gatagaaagc cgtctacctt cttcagattt   16380
tctccaaaaa cagctattaa ctgtaatcag agcaaaaaag cattctctag aaagggaagc   16440
actgcctatc ctggcagcag tgtgggtgcc ctggtccccc atcctccccc atgctcctat   16500
tccccgtttc tagtccagct aaaaaatctg ggttagcttc aagagtagcc tttaaggtga   16560
agaggtcaac ttgaaggagg tggccaggcc gtggtggggc tgagggtcag gggccccaag   16620
gctctgaggt gggcactacc aggcactgtg ccctttgttt gtctggcaga ggatgaggct   16680 tggggttttcc ccagtggtgt tgaggggatt tttttttttt ttttgagaca cagtctcgct   16740
ctgttgccca ggccggagtg cagtggtgcg atcttggctc actacaacct ctgcctccca   16800
aattcaagca attctcttgc ctcagcctcc caaacagctg ggattacagt cgtgagccac   16860
cacagctggc taattttat atttttagta gagacaaggt ttcaccatgt ctacaacttt    16920
gttccatagc cacgaggcct actgagtcca gtggagctgg gcctctccct ccccacttcc   16980
acacagttag ggggtctggg agctgggaga ggctcttcag aaccactgag ctgtctgtga   17040
aggagctggg aagcctgtgc tcctcacccc cacctcccag ggcccccac ccccagctcc    17100 ttcagttgga tctgtcactg gagagctctc ctgggatgga ggcccagact gcatgaccac   17160
agagccccag aacattctta ggctccctga ggactgtgaa cctctggaac agaacaaagg   17220
cctgccctct gggtcccctc cccaagcccc agcagcacct ctcctagccc cacctcgggc   17280
ccggaaagcc cagcgcccct gcctaagtcc tgcattcgcc agcctctccc gcccacgtcc   17340
ctgcagaccc agcctggggc cacaagcctg cctttgtcag ctcaccctct cacgtggggc   17400
cgtgccagca ggggctaacg ggcattctgc ctgcagctgg gactagcccc ctgagaggcc   17460
taggcccccc tggagagatg gaactggcgt gaatgcaaca tcttgggctg tcacaaattg   17520
actgtggtga agggcaggcc ttggggagac agctgctcat gtgagaacta tcattcattc   17580
attcacttat tcaaaggatg cttgctgaga tcctgctctg tgtcaggccc tggcatgggg   17640
acttgtgctc agagacctga ctcttgccct tttaggggg gaaataacta gaaggaaacg    17700
cccttcatca gaatcccttg gggggctcac cctaggagtt tctgattcag caagtctggg   17760
ttgggacatg agaatttctc acaaattcac cagtgatgct gatgttactg gtccaggaac   17820
tgcactttga gagccactgt aattcaggta ttgtaattat gcatggatta tgttttcttt   17880
ttcttttctt cttcttcttc ttctttttttt ttttttttg agacagaatc ttgctctgtc   17940
acccagggtg gagtgcagtg gtgtgatctc agctcactgc aatgtccatc tcctgggttc   18000
aagcaattct cctgccttag tagctggtat tacaggcacc tgccaccatg cctggctaat   18060
tttatatttt tagtaaagac aggggtttcac caagttgccc aggctggtct cgaactcctg   18120
acctcaaatg gtccgcccgc ctcggtctcc ccatagtgct gggattacag gcgtgagcca   18180
ctgcacctgg cctgttttct ctattttcaa aactgtctct atgatcatgt tttactttta   18240
gagacaggtt cttgctctgt tacccaggct ggagtgcagt ggtgcaatca tagttcaaca   18300
```

```
gaaccccaac ctcctgggct caaacaatcc tcccacccca gcctcccaag tagctggggc    18360
cacaggtgca ctaccagacc aggtaatcca tccacctcag cctcccaaag tgctgggatt    18420
acaggcatga gccaccgcac ctggccaatg atagccattt ttaaagtcac ggcctatttg    18480
gatgtaatac attattatta ttgttgttat tattattatt attattattt ttttttttgta   18540 gagatgaggt cttactgtgt tgcccaggct ggtcttcaac tcctgggctc aagtgatcct    18600
cctgcctcag cctctcagag tgctgggggtt acaggggtga gccactgtgc cctgccagtg   18660 ctttattttta ttttatttta ttttattttt ttctgagaca gagtctcgct ctgttaccca   18720
ggctggagtg cagtggcatg atctcagctc actgcaacct ccgcctcctg ggttcaagca    18780
attctcctgc ctcagcctcc tgaatagctg ggattacagg cgtgcaccac cacgcccggc    18840
taattcttat atttttagta gagatggggt ttcaccatgt tggccaggct ggtctcaaac    18900
tcctgacatc gtgatctgcc ggccttggcc tcccaaagtg ctgggattac aggcgtgagc    18960
catcgtgccc gacctggcct gttttataaa taagaaaatc agtcatttaa aagttaaaaa    19020
aaatgatttc caaaaatgac tctagtgctc tgggtgtgat cttgtgtaag agatgttacc    19080
tcccatgatc taaatgtcat gcatttgtta atgtagccca gcatcatagg gttgtgtgca    19140
tttccccttg gttcaacctg agcttggggt ccacttagac cctcctattc tttccatcac    19200
catatcctgt cattttaact ttctagagat aataagtgag gtgctggtaa ccggcatggc    19260
taggatttga acacagatcc atctggaggc tggcctagcc taccggcttg cacttcctga    19320
gtgatctttc cttcatgctt ccttcaccgg ctgcctgaaa cagcgcgtgg atccttcact    19380
tcctcatttt tttaactggt gtgatcattt actgttccac ttcctcctct ccactctggt    19440
tctgtccacg tggtatgctg gtggggtggt gagtctatga gggtggaggt gggggtgggg    19500
ggctggcaaa gtgactgttc tctgcagccc caggagtcaa accgatgggc aggaaaacct    19560
ctcgagcttg tgagaactgg cctggagggc agggctccct aaccctgact ctgagttaaa    19620
tccatccagc ctcaggggggc gctggcaacc ccagtcgtac cccttcctc acagggagcc    19680 atcctaccag gctgaccatt ggaagagcag agcagtcctc cccatctggg caggcaggag    19740
tgaagagaga gaaccccatg tttgttcctt tcacaggcac aaaatcagat cccccttcct    19800
cccagcccca gcgagggtgt ggtgaggggt gctcggacag aagccagagg tgtccctctg    19860
acgggagcag agtggacact ccctcctccc agtggcagca tgaggaggga ggaatacgag    19920
accccacttc ccagtccctt cctttccgtt ttctttgggg aaagacgggt agggagagct    19980
gaggaatccg gctctccaga tctgccctct ccagggccca cagaggcctt cttgcccctt    20040 ggaccccccca cccctgcttc catcactgcc atcctcggtg cttcccctgg ctcctcaggg   20100
atgcctttag caggtcattc atccctggtg actctgtttc tctttttttt tattttgtga    20160
gacagaggct cgctctgctg cccaggctgg agtgcagtgg tatgatcttg ggtcactgca    20220
acctctgcct cccaggttca aatgattctc ctgcttcagc ctcccgagta gctgggatta    20280
caggtgccca ccaccatgcc tggctaattt ttgtattttt agtagagacg ggatttcacc    20340
atgttggcca ggctggtctt gaactcctgg cctcaggcga tctgaccgcc ttggcctccc    20400
aaagcgctgg gattacaggc gtgagccacc gcacctggcc agtttcccctt cttagtatac    20460 aatcttattt aaatcattcg gtcacattaa gagtaggtat tatcattccc atttgtgact    20520
aggttttcac atttgtatga gacataataa ttatgcattt cttctgcgta attctacttc    20580
cctccccctt acacttagta tctaatgatt gttgcacatt cgtatgtctt ttttgttgtt    20640
tttgacctga ctaaacatgc atgcatccat tcagttaata tttgttggga ggctaccacc    20700
```

```
tgctaggcca aatggggttg cctccaggca ctcatggttt ggctgggaga caaactatta  20760
aacatagaat tgcaaatttg ctaataatga ttacaaagga gaagtgagga acagctggaa  20820
gctgatgaca gcggtagcag aagctgcctt caggaagtga ggtcatactc ttaccctctc  20880
tgcttaaaac ccaaacccag gccaggcatg gtggcttatg cctgtaatcc cagcactttg  20940
ggatgctgag ctaggcagat tgcttgagct cagttcatga gcaacctggg caacatggca  21000
aaaccctgta tacacacaca cacacacaca cacacacaca cacacacaca cacacccac   21060 cccccacccc cgatgtgggg ttgtgtgtct ttggtcccaa ctacttggga ggctaaggtg  21120
ggagggtggc ttgagcctgg gaggcagagg ttgcagcgag ctgagatttt gccaccgcac  21180
tccagcctgg gtgacagagt gagacccat  ctcaaaacaa aagcaagcaa acaaatccca  21240
aacccaaatt ctatttggcc cttcacagta ccatgtggtt gactcctgtc agtttcctca  21300
gcctcaaatt aacccagtag ctgccctggc ctccttgctg taccttgaca cactgagctc  21360
tttcctgcct ctgagccttg gcacacactg ttccctctgc ctggaataac ctctcccct   21420 agctttctcg gctgttcctt cttgtctcag ctcaaatgtc tcttttgtag agatggcctc  21480
cctgatcatg tcccctaaca tagcaccccc cctcaccccta tcatataact catgttgttt  21540
ggtttcattt tggctttgtc tttatagcac ttaacagtat ctgaggtttg ttttgtttt   21600 tttttcttgg agatagggtc tcactctgtc acccaatggt gcaatctcgg ctcactgcat  21660
cctctgcctc ctaggttcaa gtgattctca tgcctcggcc tcccgagtag ctgggattac  21720
aggcgtgaac caccacgctg ggctcatttt tttttttttt tttttttttt ttttgtattt  21780
ttagtagaga cagggtttca ccatgttggc caggctggtc tcaaactcct gacctcaaat  21840
gatccaccca cctcggcctc ccaaagtgcc gggattagag gtgcgagcca ctgcgcccag  21900
ccaggtgtct tttgttatta ttattttctg gtttactgtg tatcttcctg gtgaagcttg  21960
gggctccata cagagtatat agaagggggct ggacccaccc cattgtccct ccctgccct   22020 gcgcttagca cagggcctac ctaggacgta catagttgat gctcatccat gtttcttttt  22080
ttttgagacg gagtctcgct ctgtcgccca ggctggggtg cagtggtgcg atctcggctc  22140
actgcaagct ccgcctcctg ggttcacgcc attctcctgc ctcagcctcc cgagtagctg  22200
ggactacagg caccgccac  catgcccagc taattttttg tattttaat  agagacggat   22260 tttcaccatg ttagccagga tggtcttgat ccaacctcgt gatccgccca tctcagcctc  22320
ccaaagttct gggattacag gcatgagcca ccgtgcccaa cctcatccat gtttcttaaa  22380
tggcctctcc tgcttcccca gtgtgttcct gttgcttctg taacaaatca ctacaaattt  22440
agtggcttaa aagaacacca ggccaagggc acggtggctc atgcctgtaa tcccagcaat  22500
ttgggaggcc gaggcaggct gattacgagg tcaggagatg gagaccatcc tggctaacac  22560
ggtgaaaccc cgtctctact aaaaataaaa aaaaaaaatt agccaggcgt ggtggcgggt  22620
gcctgtagtc ccagctactc aggaggctga ggcgggagaa tggcgtgaac ccaggagggg  22680
gagtttgcag tgagccgaga tagcgccact gcactccagc ctgggcgaca gagcgagact  22740
ccgtctcaaa aaaaaaaaaa aaacaccagg ctgggcaggg tggctcatac ctgttcccag  22800
cactttggga ggccaaggcg ggcagatcgc ttgaggtcag gagttcaaga ccaacctggc  22860
caacatggtg aaaccccgtc tccactaaaa atataaaaaa tcagctgggt gtggtggtgg  22920
gcacctgtaa tcccaactac ttgggaggct aaggcaggga gaatcgcttg aagtagggag  22980
gaggaggttg cagtgagctg agattgtgcc actacactcc agcctgggca acagagtgag  23040
actccgtctc aaaaacaaca aaaaaatgaa caccagatta ttatcttctg atcctggagg  23100
```

```
tcaaaggtct agaaatcaag gtttgggcag ggctgcattc ctcgggaagg ctccagggga   23160 gaaaccttt  ccttgccttg agaggcaccc ccttcctccg tcatcacagc cccttcctcc   23220
aacatcaaag catctcactc cagcctctgc ttctgtttcc ctgtcttggg atccttaatt   23280
tactcatatt tgcaaagtct cttttgccat gtaaggcaac attcacagat cctgggaatg   23340
tgaacatgga cgtcttggta ggtctgtcat tcagcctgcc acatccaggt cccccacggt   23400
gcttcattca gtcctaggtg tggccagtac tccggcctcc tagctgctac tgtgggccca   23460
gtgacctgac tcttccttcc ctccgcagga cgagattgag gagctgcggg ccgagatgct   23520
ggagatgcgg gacgtctata tggaggagga cgtgtatcag ctgcaggagc tgcgacagca   23580
gctggaccag gccagcaaga cctgccgcat cctgcagtac cggctgcgca agccgagcg    23640 ccgcagtctc cgtgccgccc agaccggcca ggtggacggc gagcttatcc gtggtctgga   23700
gcaggatgtc aaggtcagcc tgggctcggg tgcccttgtt gctgggatgg gaccacaagt   23760
ctaagtgggg cccaggttgg ccttgcatct catttccgtg tgtccatggc caagttctac   23820
cacctctctg ggcctcagtt tcctcatcta agtaggaatt cctggtgaac ccacagggct   23880
tctatcaagg gtatcccaaa atgatatcat aaatatgaatc cttcctacta gcagcagcta   23940 ctgtttttt  ttttccttt  gagacagagt ttctctcttg ttgcccaggc tggaatgcaa   24000
tggcgcgatc tcagctcact gcaacttctg cctcccggga tcaagcgatt tctcttgcct   24060
cagcctccca agtagctggg attacaggca cctgccacca cacccggcta atttttgtat   24120
ttttagtaga gacagggttt caccatgttg gccagcctgg tttcgaactc ctgacctcag   24180
gtgatctgcc caccttggcc tcccaaagtg ctggggttac aggcatgagc cactgcgcct   24240
ggctgagaag ctactgttta ttgagtatca accaccacct ggtgctagcc tctaattgtc   24300
cccgcacagt tccatggggg tttcttttc  ttcttgtttt tttagagaca aggtcttgct   24360
ctgttgccta ggtatcaggc agtgatgtga tcatagctca ctgtagcctc cacctcctgg   24420 gctacccca  cctcagcttc ctgagtagct gggactacag gcacacacca ccacacctgg   24480 ctaattttc  tatatgttgt agagatgggg tctcattatg ttgcccaggc tggtctcaaa   24540
cttctgggct caagtgatcc tcctgccttg gcctcccaaa gtgctgggat tacaaggatg   24600
agccacggtg tcaggcagag gttccttaat tatgctaatg aaaagtagtg aaggcctcga   24660
gaccatcctg gctaatacag tgaaaccctg tctctactga aaacacaaaa aattagccag   24720
gtgtggtggc aggcatgtgt agtcccagct actcgggagg ctgaggcagg agaatggcgt   24780
gaacccacga ggcggagctt gcagtgagcc aagatcgtgt caccactgca ctccagcctg   24840
ggcgacagag cgagactccg tctcaaaaaa aaaaaaacaa agagaagtag tgaaggccta   24900
gagttggtca aggctggttt aaatcttggc tccaatatac ctgaactta  ttattttgag   24960 caaagtcatc aatttcagtg tcctcatctg taaaatgggt ttgcagcaat ctctatctca   25020
cagggttata tgaggattaa atgaaataat gcgggctggg cacagtggct catgcctgta   25080
atcccagcac tttgggaggc cgaggcgggc agatcacctg aggtcaggag ttcgagacca   25140
gcctggccaa catggtgaaa ccccatctct actaaaaata cacaaattag ccgagtgtgg   25200
tggttcccgc ctgtaatccc agctactcag gggctgagac aggagaatcg cttgaacccg   25260
ggaggcggag gttgcagtga gctgagatcg cgccactgca ctccagccag ggtgacagag   25320
tgagactccg tctcaaaaat aataataata ataataataa taataataat aataataata   25380
atgtgggtaa aatgccagca taaggactca aaaatgttag ctatcattat ttccattttc   25440
ttgatgaaga atctgaggtt cagagaaaag caatacctgc cgaaggtcaa ggggcgctca   25500
```

```
gtgtgttggt ggcagagccc aggctcatga gcctcccaag cctccagctt ggcctcactg    25560
ctctctgctt caggaagcag gggaagggtg ggtgggaggt tggcaggtgg gatgtccccc    25620
tgcctgtctt cggaagctct ggtctggtgg tgagaactcc agggccccca ggcccggccc    25680
tctgccctca gaactcagcc cagtgtgatc tggtgacacg aggagctggg atggggccct    25740
agggaggctt cctgcagggg tgacttctga gtgaaggccc aagggagaag tgggcctgag    25800
ccaggaaggg ggaaagagga aggtggcaga agatggctcc tgtgaggacc caggggagcg    25860
gcaggatgcg agtcagccac acacttacct ggggagaagt cccttctgtt ggaagacact    25920
ggcaaactca agccctatag cctttccagt ggaatataaa agaaaaacct ttgttaaggg    25980
accagggaga gccatggttt caaaggccag cagaaccagg ggaggtaaac aggagtgcct    26040
gttccaggaa gctgctggcg cccctgtgg tcttgttggt gcacaatggg attgtagtgc     26100
tgtcctacac atgaggcaac caatggttgt gtctccgcca gaggtggagg ctcatgcctg    26160
taatcccaga atcccagcgc tttgggaggc tgaagtggga ggatcgctag aggccaatag    26220
ttggaaatca ggctgggcaa catagcaaga ccctatctct acaaaaaaat aaaaaaaatt    26280
agcagaggct gggggtggtg gctcacacct gtaatcctag cactttggca ggccgaggcg    26340
gatggatcac ctgaggtcag gagttcgaga ccagcctggc caacatggtg aaaccccggc    26400
tctactaaaa atacaaaatg agccgggtgt ggtggtacac gcctgtactc ccagctactc    26460
aggaggctga ggcagatgaa tcgcttgaac ctgggaggcc gaggttgcag tgagctcaca    26520
ccattgcagt ccagcctggg tgacagagtg aaactctgtc tcaaaaaaaa aaaaaaaaa     26580 aaaaaaatt agctgggcgt ggtggcaagt gcctatagtc ccagctatat gggaggccaa     26640
ggccagagga ttgcttgagt ccaggagtta aaggtttcag tgagctatga ttgcagcact    26700
gcactccagc ctgggcgaca gagcgacaag gtctctctct aaaagaaaaa aaagaatgag    26760
ttagtttcca agttcaaagc gtacctctac ttgacagggc agctcccggg catattcaga    26820
ttccaatcac tgggttggga ggggtggggg gtggtggggg aaggcagtag ggaggagatg    26880
gggaggggga gggaatagct ggagaagctc agaggaatct gcgtttgggc atatagtgga    26940
ggatttctgg gagggacaca aaaaaatgtc agacttcaga aagatgagga agaggcggag    27000
gagaggctgg gacctggagc tagctgccgg ctgcggcgcc tccgtgggtg gagctagagc    27060
agcggcggcg gcggcgggga ggcgggtgtg gggagcgggt gtgtggctct ccggagtctg    27120
ggcggagagg aggggccgtt tctgttgggg tttgaattag ccaatcagca tccctcttgc    27180
ccttccctcc ctcctctccc cacgctgcag ctggagcgct gagctcatct gcgggcctgg    27240
ggcctgagct ggatggacac ctctggccac cacctgagc cccatgtgct ggggtcgttc     27300
tgggggtttt tgggaagtta tcagaatgct gctttccctg gcatcgtctt ggagggcttg    27360
atggacccga gtggggaggg ggcggcgct gcctaggagg gtacctctgg gacttccca     27420 acttgctctg ccagctccgt ggtccatgcc ctgacttgcc cctaccgctt ggtgcctcat    27480
tttccccttc tgttaaatgt ggcttttgac cagctgaatc ctcagggctt ttgagctcct    27540
gtggttttat ggagcagagg ggtattggtg gggtggggtg gggggtcatg aataaaacca    27600
caggcctcag tgcccccccc caaccccag ctctccctct ctgctggtcc tcaccgttga     27660
caggacctac agaacctcgg tggggccttt gcccagcatg aggagggcaa ggtcacgggg    27720
cggagagctg ctgtgccacg tttgctgtgt ggccttgggt aagttccttc acatctctga    27780
gcttgttttc tcatggaaaa tggagataaa atgagtccct ccctctagag gtttttgtga    27840
ggataaaatg aaataattca agtgaagaga gtattaaata ctaggtctgg aaataaacat    27900
```

```
gtattggttg tggttttctt tttctttttt tttttaaggc agggtctcac tctgtcaccc    27960
aggctggagt gcagtggtgt gatctcagca acctctgcct cctgggttcc agcaattctc    28020
ctacctcagc ctcccaagta gctgggatta caggcatgcg ccaccatgtc cagctaattt    28080
tcgtattttt agtagagatg gggtttctct gtgttggcca ggctggtctc taactcctga    28140
cctcaggtga tctacccacg tcggcctccc aaagtgctgg gattacaggt gtgagccacc    28200
atgcctggtc tggttgtggt tttcttattg ctgagaagaa ctcacacagc aagtataagt    28260
tcttctgagc aatacatcag taggactact agtagtagta ggctagtagg actggttggt    28320
agtagtagta gactagtagt ctgggggcga gggtaggcca ggatctcagc ctcccagggt    28380
ggataaaaat caccaggagg gcttgttcac aacatacatt cccaggaccc gtgaggagct    28440
gagaccggat acaaggaggt caggtccagg gaatctggga tctaaactct ggtctaaagt    28500
gactcctgtg ggaagccaag gacacaccag gagcacgccc ccttcctcag atacagatgt    28560
tgctggagaa aatgttctgg ctttgggttt cattcctagg tgacctgtgc aggttacctc    28620
ccttctttga gcctcacttt cctcatctgt agagtggggg tgacattcct accctcctgg    28680
ggtttgtagg aggattcagc cacacggagt ccagaatgct gcctggccag gggatgctct    28740
tccttttttc ttttttttt ttttttgag atgaagtctt gctctgtcac ccaggctgga    28800
gtacagtagc gtgatcgctg ctcactgcaa cttccacctc ccgggttcaa gcaattctcc    28860
tgcctcagcc ttccgagtag ctgggattac aggcatgcca ccatacccag ctaattttg    28920 tatttttta gtagagacgg ggtttcaccg tgttgaccgg tctggtctcg aactcctgac    28980
ctcaagtgat ctgccggcct cggcctccca aagggccaga attacaggca tgagccacca    29040
tgcccggcct tgttttcttg tttctttctt tctttcttga acatagtct ctctttgtca    29100 cccaggctgc agtacggtgg ctgatcacag ctcactgcag ccttgacctc ctgggctctc    29160
aagggatcct cctgtctcag cttcctgagt agctgatact gcaggcacac accatcatgc    29220
cctgctaatt ttaaaaagtt tttatagaga tgggggtctc cctattttgc tcaggctggt    29280
cttgaactcc tggcctcaag cagtcttcct acctcgacct cccaaagtat tggaattaca    29340
ggcgtcagcc accatgcccg gccaggagct gctcttcgt gagagctccc atccctctcc    29400
ctgaggatca ggatgacaga ggcccaggag ccgaggggcc tgatgcctgg ggagcagggg    29460
ctggaggctg ctagttgcac ttggcaggag ccaggcccta gcgctgtaaa cagtgacctc    29520
atggctgagt gcatttgttt atggtttagg gatttgccct ggttttcgga agccgcagct    29580
gccgcgcctc ccttagtatc tcagccccc taccttgagg gtagctggga ggatcaaatg    29640
ggatagacac gtgggccct tcaaatgcct gacacagtaa gcccactgtt ggggtttatt    29700
attaatactt gtattgttga tgttaatgta atgtgttttc acgcattggg cctatacggc    29760
aaaatcagcc tgagagtgag actttagagt tgacccactc gatttcaaac cttagttcta    29820
tagccttcct agctgtgtga ccttgggaag tgacctttcc tttctgagcc tcagaatggg    29880
gataataatc aaagtgcttc ccaacgggat gaaaagcacg tggtgagcac ccggggatg    29940 ttccagctga ttctgtaaat cacttgtgag ggccgagggg gccaggacc actgaggctc    30000 actgaggagc agggacaagc ccaggccaca gggctcctgc ctcccagtct ggctgcctgg    30060
agttgtgatt ttttttttc ttttttctgag acaaagtatt gctctgtcac ccaggctgga    30120
gtgcagtggt gcaatctcag ctcactgcaa cctccgtctc ctgggttcaa gcaattctcc    30180
tgcctcagct tctcaagaag ctgggattat aggcatgtgc caccacgcct ggctaatttt    30240
tgtattttta gtagagacag caaagacggg gttttaccat gttggccagg ctggtcctga    30300
```

```
actcctgacc tcaagtgatc tgcccgtctc agcctcccaa agtgttggga ttataggcgt    30360
gagtcatcgt gcctggcctg tgctttcttt tgatacagca gccatcaggg aaagggagta    30420
aataggaaag ggattccatg gagaatgggg cagaagggaa ctggggaatc atggagagga    30480
tgggagggga tgaaatccat agagttgttc atgaacccca gaggatccag aaatccacat    30540
ggattgtgac ttcttgatgg ggactggtag cctccccagg tggaggacat ggtggagatg    30600
gggcatcccc gcaggtggag aggagctggc ccagatggga gctcatttga gagaggagcc    30660
ctcaccccag ccaggggtgc agcccttcct ggatagtggg tggggttggc atttgagggc    30720
agcctcttca gccctgcgag ggcaggtacc actccccatg tatattcagt cattcactca    30780
ttcatctccc tccctttcca cttgttggac ccttggattt atttgttcat ccaacaagca    30840
tttattaggc acttagtgtg tgcctgacgc tgcgctgctg ctgggacaca tagatatgaa    30900
tgaggccaag tatgtctgcg gccttgatct ctgtaccccca ccactcctgc ctccagtgcc    30960
taagcaggat gagtgagtga gtgagttagt gagtgagtat gagtgagtta atgaatggaa    31020
tgttgatcag gacaggggct tactgggtga cctaacagcc ccaaactggg gaccatgttt    31080
aaataactta acctgggtca catagccagt aaatgctgga actgggcttg aatctagttt    31140
tcctatctgc aaagcccttg ttctgatact gaggggttgt tctccccact tcgtggatga    31200
ggaaggtctg gtaccagag aggctgtggg aggagcctca tgggcccgct cctggctgtc    31260
ctacgagatc ctcgggcaga acaggcagt ggcagtgcag ggagggagag gccatgcctg    31320
gtttcctttc tggtcgttgt ttttcctggc ctgcctcata cattgccaag gggtccgtgc    31380
cgagctgggc ttcggcccag gcagaggtca gagccaggga gggccctctt cccttctggc    31440
aaggaggagg cacaacagtc atttccgaga ccagcaggca tgggttgctg ggctctctgc    31500
cccacatgga gttcctgctg gcgaaacctg ggcacccctg ggaaaccctg ggctatactg    31560 gccccctcagc caaaccccctg gggctcccag cccagctcaa cccacactgg cttttgcgtga    31620 ccctgagtga gtcacttctg ctctgagctc cagtttcctt gtaaaatggg gacaggattg    31680
gggtgaagat gggtgagttt ggcatgcagt aggtattcac caaacagtag ttcccaatgt    31740
acatagagat ggagtctggt tgcaatttcc cagcccagaa gggccttcct tcctcatccc    31800
tgcaggcctc ctttcctggc ttccctcaac cagccagcag gggacagaac agagggtgtc    31860
taccaggaat ggggtgctgt tgctacagag tcctggacca ggatcagaga ttgcagctcc    31920
tctagcttct ttctgtaggg atgacttgga catctgccca ccctttgtca ttttgggcct    31980
gttctacatc ccagacaact agatataggt ctcagggtca cactgtgacc tccagcgatc    32040 atgccccttct ctgggcttca gttccttgga gcagcagcta ccagtcaccc agaactcact    32100
gtgtgcaggc cccaggccaa ggcttttgtg taatagctgg ttcagttatc ctgtcgggcc    32160
tgtaaggttg accctgttat cactgcgttc attttatagt tgaggagact gaggtacaga    32220
gaggaaaatt gccttgccca ggactacatg ctggtcactg gcagagatgg gattcagtgg    32280
tctagggccc atcttctctg ggtttccact gcagctcaat cccctctctg ttttgttttg    32340 cttttgctttg ttttgttttt aggagacagg gtctcgctct gttgcctagg ctggagtgca    32400
gtggcacaat catagctcac tgcaacctcg aactccaggg cccaggtgat tcttccatgt    32460
tggcctcctg agtagttggg cctgtaggtg tgtgccacca tgccaagcta acttttttgg    32520 gtttttttgta gaggtggggt cttgctatgt tccccaggca catctcgaat tcctgggctc    32580
aagcgatccc cctgcctcgg cctctcaaag tgtgggattc caggtgtgag ctaccgtgtc    32640
cagcccctca aagtgttggg attacaggtg tgagctactg tacccagttc ctcagtctcc    32700
```

```
tccctttaag atgagcttct ggccctccca caggcttttg tgaggactgg gcaagtggtg   32760
gctgggagag gctttggaag tgtgaagagc ccaggtaggc aggcacagtg gctcatgcct   32820
gtaatctcag ctactcggga agctgaggca ggaggatccc ttgaggccac aagttcaaga   32880
ctctcctgga ccacatagtg agacccgtt tcttttt att tatttattta tagacaaagt   32940
tttgctctta ttgcccaggc tggagtgcag tggcatgatt ttggctcacc gcagcctctg   33000
cctccctggt tcaagcaatt ctcctgcttc agcctcccaa agtgctggga ttacaggcac   33060
ctgccaccac gcctggctaa ttttttgtat tttagtaga gatggggttt caccatgttg   33120
gccagtctgg tctcgaactc ttgacctgag gtgatccacc tgtctcgacc tcccaaagtg   33180
ctgggattac aggtgtgagc cactgcgccc ggctgagacc ccgtgtctac ataaaaatgc   33240
aaaaattagc cagttgtggt tatgcatacc tgtagtccca gctactcagg aggctgaggt   33300
gagaggattg cttgagccct ggagttcaag cctgcagtga gacatgattg caccactgca   33360
ctccagcctg ggagacatag tgagaccctg tctcaaaaaa aaaaaaaaa aaaaaagcct   33420 caggtaaatg aaaaggcatt cctgagaaca gggtcttccc agctttctgg ggctgtgctg   33480
tgatacagat gctgagagct tgcggtacct aggtttgggt tttggttcta ctgcttcctt   33540
catgagtttc ttggtctctt tgtgcctcag tttgctcatc tgcagcgtgg cagtgatgcg   33600
ataggaacct gcctgtctct agggttgccc tgctgtgaaa gtcgggtggt cagtgggact   33660
tgcagtgggg gctctcctca gcctgctcac atccttctct ctcccacccc tgcacaggtc   33720
tctaaggaca tctccatgcg gctgcataag gagctcgagg tggtggagaa gaaacgggcg   33780
cggctggagg aggagaacga agagcttcgt cagcggctca tcgagactga gctggctaag   33840
caggtgctgc agacggagct ggagcgaccg agagaggtga ggacctcatg catccagcag   33900
ggccagccta gggcaggtgg gcacatgcaa gcccccccaa gccagtgtct ctgtgagccc   33960
ccgcttgtgg gaaatgggca gcttatgcct ccctggcaag gttgtttatt cattcattcc   34020
tccaacatgc atttcctgag cacctactgt gtaaattgtg tgctggacac taaggttaca   34080
atggtgaaca aaacacaccc agttcctgtc ctcaggagc tcacgggta atgagagaga   34140 gagtcattca tcaaagaacc acagccgctg tgggaggatt aactgagaaa acatgcaaca   34200
atgtcaggca tggggctcag ccctctgtgc ctcagtttcc ttacctatac aatggggcag   34260
tggtgccctg agtcattgtg aggaccaaca ggaataacgc atgtggagtg gctgcaagag   34320
actgcgagat cctgccattt ggtgtgaagt cagtgcaggg gctgggtctc aggccagtgt   34380
ctctggggta ctggtgcttc ccgaatgtga ccctgagaca cattcctgtc tgtgtttgtt   34440
catgccagtt cctcccctgg cagaccttct cctcctgttg tgtgttgggt atacagtgtg   34500
ttatgcgccc tgcttgacag tttatctcaa acatttcat gctaacaagg ttgcgatcat   34560
gcccattttg tggatgagca aacagcccct gagagagagg gagggacaac ctcaaggcca   34620
tgcagggctc agggggttct gcagaatgcc ggctagaaac catcagccta ggtgtccctt   34680
aaaggctgga atccccccat tccagggttc tgtgttccaa atggcctggg gtggcttctg   34740
gccctagagg cagagccagg ccttagctct ctgcctgctg atgagatatg aggatcgtgc   34800
attcttctag ggcacactcc tcgctgcagg cgctgcctgc cttcctcccc cgagggcgag   34860
cctgccagtg tccttggact gagacaccac agcccaaggc cagaacattc ctccagccat   34920
ccttcccact gggtgtgttg gtgtgatgtg ccaatgccct ctcagtgtgc agggagagga   34980
ggcgtttgct gctaagggtg gctagccccc tcccttcatt cagctgccca cccccatggc   35040
ctggcccata acacggagca ccatcttcac accgtcttgc tgctgcaacc cttgatagtg   35100
```

```
aaaaggggag acaatttctg aaagcatctt aaggtcacgg tacaagtaat gaaactgagg    35160
ctcaggagga acagcttgcc tgagttcacc cagcctctcc ttagcagaga tgtggctgga    35220
accctgaagc cacttcccct ctctaagtct cagtttcttt atctgtgaca tcaggataag    35280
caagcaaaca aacaagcaaa gcctgcacgg tggctcacac ctataatccc agcactttgg    35340
gaggccaagg tgggcagatc tcttgagcct aggagttcga ccagcctg gcaacatag     35400 tgaaactctg tctctataaa gaatgcaaaa attatccagg tgtggtggtg cctgcctgta    35460
gtcccagcta cttaggaagt ggaggctgca gtgaggtgag atcgcaccac tgcactccag    35520
cctgggagac agagtgagac cctatctcca aaaaaaaaa aaaaaaaaa aaggggggtc    35580 caggcacagt ggctcacgcc tgtaatccca gcactttggg aggctgaggt gggtggatca    35640
cctgaggtta ggagttcaag accagcctgg ccaacatggc gaaaccccat gtctactaaa    35700
aatacaaaaa aaaattagct gggtgtggtg gcgggcacct gtaatcccag gtacttggga    35760
ggctgaggca ggagcatctc ttgaacctgg gaggtggagg ttgcagtgag ccagattgc     35820 gccactgcat tcattccagc ctgggcgaca aaagtgaaac tccatctcaa ataaataaat    35880
aaataaataa ataaataaat aaataaagca ggatgataac tgtacgcagc ctatgaggtt    35940
gtttaggatc attaataaga ttatgtagcc atagaatact atgaagaaat taaaaagaat    36000
aagatagtat ggcagttcct caaaattaa acatagaaca atcatatgat ccagcaatct    36060
cacttctagg tatatcccaa agaattgaa agcagagact caaagagata tttacacacc    36120
cgtgttcata gcagcataac tcacaatagc cagagggtag aagcaaccca aatgttcatc    36180
aacagaggaa tggataaaca aagtgtagta cacatgtata atggaaaact attcaacctt    36240
aagaaggaat gaggctgggt gtggtggctc atgcttgtaa ccccagcatt ctgggaggca    36300
gaggtgggca gattggttgg ggctaggagt tcaagaccag cctgagcaac atggcaaaac    36360
cccgtctcta caaaaatac gaaatttagc caggcatctt tgtgcatgcc tgtagtccca    36420
gctactaggg aggttgaggt gggaggatca cttgagccca agaggttgag gctgcagtga    36480
gctatgatgg tgccactgga ctctagcctg gctatagag tgagaccctg catcgagagg    36540
gagagggaga aggagaggga gggggagggg ggaggggga ggggagggga gaggggagg    36600 gggagggaga gggggaggg gaggggagg gggaaacag aaaagaaaag accagcactt    36660
tgggaagcca aggcaggcgg atcatgaggt caggagatca agaccatcct ggctaacacg    36720
gtgaaacccc gtctctacta aaaatacaaa aaaaattag ccaggagtga tggcgggcac    36780
ctgtagtccc agctactcag gaggctgagg caggagaatg gcatgaaccc cggaggtgaa    36840
gcttgcagtg agctgagatt gtgccactgc actccagcct gggcgacaga acgggactcc    36900
gtctcaaaga aaaaaaaaa agaaaagaaa gtatttggaa tttatttgtg aaattttaa    36960 aagaggtaaa gcttgtaaag agcccttgt ggtgcctggt acagagtagg tgctcaagaa    37020
acactggttc acatcctttt gcagctggtg tcagtgaggc tggtctagct ctcctcgcgt    37080
gccctgtggt gtctcaggct tgtgcacagg aggcggagc ctgtgtttat tatttgctgt    37140
ttatcctctc cctcctccgt ctctttcctg acatggtttc tatggagacg agggtccctg    37200
agcaattctt ctgccagagc ctcagtccca tcatcaagat ctgccgttgc atcctgaca     37260 ggctgccgag gtggtgctgt cacccggctg ggaacaggag ccctggcct gagctgatgt     37320 ggttgccatg gagacagctc tccgctagag agaagggagg tggcagaccc tggccgaggg    37380
ctgcggtggc actgttgccc agctaccctc tcttccagtg tcacacccct ccttgtgttt    37440
taggcagaaa gccaatacga gtgttgacgt gatttattat ggtatagctg ctgtgtttga    37500
```

```
gccctcactc tgtgccaggc accacagaag ccttgaccac accagcacat tgtttaaccc   37560
tccaacagcc ttcccacgga catggtgtgg ttgtcttatt ttataggtgc cactgtttgt   37620
tggcaatttt aaaatcatga tttaattccc atatcataca actcaccatt taaaagtgta   37680
cagtttgggc tgggcacagt ggctcacacc tgtaatccca gcactttggg aggccaaggc   37740
gggtggatca cctgaggtca ggagttcgag accagcctga ccaacatggt gaaaccccac   37800
ttctactaca aatacaaaaa ttagccaagt gtggtggtgg gcgcctgtaa tcccagctac   37860
ctgggaggtt gaaataggag gagaattgct tgaacccggg agctggaggt tgcagtgagc   37920
cgacatccca tcattgcact ccagcctagg caacaaagcg agactctgtc tcaaaaaaaa   37980 aaaaagtgt acaattcaga ccagacacag cactttggga ggccgaggca gcaggattgc    38040
ttgagcccag gagtttgaga ccagcctggg caatatattg agacccttgt ctctacaaaa   38100
atttaaaaaa ttagctggac ctgatgacac aagcctgtgg ttccagctac caagaggtt    38160 gaggtgggag aattgcttga gcctgggaaa cggaggttgc agtgagccaa gatcacgcca   38220
gtgtactcca gcctgggtga cagagcgaga ccctgtctga aaaaaaaat taaaataaaa    38280 acaacaaaaa ataaaagtgt ataatttagt gattttagt tatattcatga tgttttgtag    38340 cgtcaccatt atctaattcc agaacatttc catggcccca aaaagtaacc tcatgcctat   38400
gaacagtcac tccccactcc ccctttccct cttgccccca gcaaccactc atccgctttc   38460
tgtctctgga tttgcctgtt ctggatgctt catccaaatg gagtctttgg tgactggcct   38520
cttttactta gcatcaggtt ttcaaggttt atccatccat gttgaagaat gtagcaggac   38580
ctcattcctc tttatggctg agtaatcatc cattgtgtgg gtatatgacc acattagatt   38640
tgtccattta tctgggttgt tttggctact atgaataatg ctgctgggaa cattcatgtg   38700
cacgtttctg agattctgtg ttagttctct tgtgtagatc ccagggagta gaactgcagg   38760
atgtagacgt gactggggaa agacaaagat gggattcaaa cccaggactc cacatctctc   38820
aaacccgcac tgactcttct ggtgttgccc ctatgctcct tgccccaccc ttgctctcct   38880
aggaccctgt tgtgtcttca gaaacctgga agaggctgcc cactcctgtg actgcttcct   38940
tccctggcac agccttctca tccggaattc ctacctggtg ggctaggaag gggctgatag   39000
ttcaaagccc ggttctgcct tttttccaga cttggcactt acttgcaagt gactgtaacc   39060
ttgcggaaat gatataactg ctctagcgct tagtttattt attttattat tatttttggg   39120
ggagacaaga gtcttgctgt gtcactcagg ctagagtgta gtggcacgat catggttcat   39180
tgcagcctca aacttccggg ctcaagagat cctcctgcct cagcatccca agttgttggg   39240
actataggcg cacgccacca cacctggcta atttcgtatt tttgaaagag atggggtctc   39300
tcactatgtt gcccaggctg gtctcaaact cctgggctca agctatctgc ccttctcagc   39360
ttcccaaagt gctgggatta caggcatgag ccatcgtacc cagcctagtt tgtttataaa   39420
attggaatat tatccctact tctcagaggt gtttgtgaaa attaaacaag acaagcaagt   39480
aaagtgctta acacagacta aggacttatt attttcatta gtgtcacaac caccgtgagg   39540
gctgcgggtc tggagaagca tttgtcttag ttaaataaat acatttctgc ttcctctggc   39600
aaggagctct gtgtctagag ctgccagttg cccgggaaag gagcagctac gttgccaatc   39660
ttcacgtgca gttggctcca tctgtccttg tgacatttga tttggggcca atgtttaaaa   39720 cactcttttgt tttctccccc aagtgatctc tccctaatca agagccacat ggcctctctc   39780
tgtggccatt tcagccactc aggaggaaga atgaatgcct aaatctttga ggtacacccc   39840
caaccccaag ttccttctag aatctacagt aggccgggca cagtggctca cgcctgtaat   39900
```

```
cccaacactt tgggaggtca aggcgggtgg atcacttggg ttcaggagtt cgagaccagc   39960
ctgggcaaca tggcgaaatc ccatttctac aaaaaataca aaaaattagc cagatatggt   40020
ggtgcacacc tgtagtctcg gctactcagg aggctgaggc atgagaattg cttgaacctg   40080
ggaggcggag gttgcagtga gccgagatca tgccactgca ctccagcctg ggcgacagag   40140
tgagaccctg tctcaaaaaa aaaaaaaaaa gaatctagag taaattttgt acctgaagca   40200
cagtctgtgc tttcagtgag accttttcaa acatctcctc cagatttggt gaaaatctgc   40260
cctgctgttt tggcagaaga ttcattttgt tccttggaag gttggccttt gtttcttggc   40320
caaagtgggg caggaaggtg tttgagtgca gaggcccctc cagagctgtg ctcaggcagc   40380
tctctcctgg gctgaaggaa agacaaggga ggacatagct caggcttctc ctagaagcct   40440
gtagacaggg agatgcttag aggtaccaca ctggctgctc aaagatggcc ttgtgagttg   40500
ctggcgagtg gggaagcccc tgttgcatgc caggccacag agtttgtcct cagggctggg   40560
catgtcccca ggccttgcgg ctgcattcct gctgggcct aggcaccgcc ctgccttgtc   40620
ctgccctccc aaggcccaga gccagaacat ctgcctcttg ggcagagact ggcttcatcc   40680
ctgggggctc cacaaagggg ctctgacagg ccctggcttt cttgcggggt gcagccccc   40740 agccacctgg ccagctgctg ccgtgcagag gggaggaagg tctttgtgca ctctgagccc   40800
gccttgtttt ccctccagaa tggcagggct gtgtgggagc ccacatggct tagataaggt   40860
gggggaagtg tcaggtccta ccagaaaagg gtggaactcg tctcctctgc ccccaaccct   40920
gctttctggt gagattcaag ccactcagct cattcacacc ttttctctgc ctgctggaaa   40980
ggtgtttggt gacttcttgg ggaaagtata ttttaaaaac cttttataat gacttttccc   41040
ttccccccag caggtagtag tatgtgctta gcagaaaaag attagaagat tcgaataagc   41100
catagggaat ttctgtgtgg atggggaggt gcatatactt ccaataagtt tttctatgta   41160
tacatatatg tgtatttaaa tgtaaacgtg aatatgcttt ttttcttttt tggagacaag   41220
gtctggctct gttgcccagg ctggagtgca gggacgtgat cttggctcaa tgtaacctcc   41280
accttgcggg ctcaagcaat tctcccacct cagcctccca agtagctagg actacagaca   41340
catgccacaa cacccggcta agaatatgca ttttgtctgt tttgtttttg ttcttgtttt   41400
tgagacagag tttctctctt gttgcccagg ctacagtgca gtggtgtgat ctcggctcac   41460
tgcaacctct gcctcctggg ttcaagtgat cctcctgcct cagcctcccg agtagctggg   41520
attacaggca tgcaccacca tgcccggcta attttttttt ttgtattttt agtagagacg   41580
gggtttctcc atgttggtta ggctggtctt gaactcccga cctcaggtga tccacccacc   41640
tcggcctccc aaagtgctgg gattataggc gtgagccact gcatccagcc agaatatgta   41700 tttttttaatc taaaaagta atataaactc agtgaagcaa aaatatcatt agaaaagcac   41760
acagatgcat gcctagcata cctccaagga caagctgcag tgctctggtt acgttggttg   41820
ccttggggcg ggataactgg gtgactgggt tcactgtatt cttctatgtc cttttgaat   41880 gttgaaccat gcaactttgt tatctattca aaaataatag aaataataaa acccataaat   41940
taaagaagaa agccttccct aactgcctcc ttcaattcta ctcctcagcc tgacccagca   42000
tcagcagttt gctttgtatc tttccaggtc tttctctagt ctcatacaat gcaggtttct   42060
atatattttt aaactctttt ttttttttga cacagagtct tactctttg cccaggctgg   42120 agtgcagtgg tgtgatctcg gctcactgca accactgcct catgggttca accgattctc   42180
ctgccccagt ctcctagta gctgggatta caggtgcctg ccaccacacc tggctaattt   42240
ttgtattttt agtagagaca gggtttcact atgttggcca ggctggtctc aaactcctgg   42300
```

```
cctcaggtga tccaactgcc tcagcctccc caaaagctgg aattacaggc atgagccacc   42360
acacccagcc atttctttct tctttctgtg gctgagtaaa tattctgttg tgtggataga   42420
ccacattttt ttaatccatt ctaaagttgg tggacatatt tgggttatag gctttgtttt   42480
gctggtcact tctttcccca aacagagtgt ctgagagact ttaccatgtc agtgaatctc   42540
atgatccctt agtactttga atggctttag gtgatctcat tcattcacat gtgatgcctg   42600
accccttggt acctatgcag acccctggct ctcctctctg tcacttcact tccttcctcc   42660
agggagtctg cagtcattgg tgggctctg  gtcacctaat ccatggccca gtgttataaa   42720
tgagaaaatg gaatttcagg gagaggaaag ggttcaccca gggatcataa actcagcgtt   42780
gcaagggccc cagagttcaa ctcccagctg aggccacagc ccttcccact cagcttgtaa   42840
taggtgggcc tagatccttc catagcctga tggtctgagc ccacagcacc cccttgcatg   42900
ctatacgggg gtctgcttct gtgtgcgccg tccagggccc cactggctgc ccttgtctgc   42960
tgcctcctgg ctcttgtgga aggactcgtt ttctgaccca tagccctgtt tcctcctctt   43020
cccttccagc ttttgaaagc tcccaggtca gcacttctca aatactggct cctggctctt   43080
ggcacccagc gtctgaaata tcagcctctg cctccctgcc tcatttgcat ttcaaaaggt   43140
ctctttagga tttgattgag ctctaagata ttctgtactt aggagtccat ctggagctct   43200
ccttgcctgg cacagaggat ccgacctgca cttcagaatc acctgaaagc atttgaaaaa   43260
tactgatgtc tcagacctac ctcagaccac cagtattttt tctttttttt ttttttttg   43320 agtaattctg atgtgtacca ggttgagaac cactgtgctg gctacactct ggccctcatc   43380
agagaagaca cattttctcc taccaactct ttggaatttg gtcaagagct atgtcaagaa   43440
ctggtcccag gtcagctgtg ggtgtactgt gagaccttgg acaagtccct gcccctctgt   43500
cttggtttca gaaaaatggg actcagatta gatcagtggc tgtcactttc agggatgggg   43560
tgtgagaggt ggggggatgga gcaagcatgt atccaaatca cctggggcca ttttcaaaaa   43620
tataccagcc caccttgaaa agtcaaaaca acctaagcaa ggttttatac atacaccacc   43680
accaggaatc cccctcctc  tcttgggagg aagcgctcaa aagaatcgtg catctaattg   43740
aatgacttct ttaaacattg agaaatttca gtaattgtta ttgtaacatt tcctccaatt   43800
ccctctgtag ggcttgtgcc atttggcatt cttgccagca atttatgaac cttttgtttt   43860
ctctatagct tcaccaatag aatatgtcgt cagatatttg gattttgcc  aatctgatag   43920 gtgagaaacg gtatctcagt gtaattttaa tttgcattta tctaacagga gtggggttga   43980
atatcatcat gtgccttgat gtcttcatgt gccatgatcc atttgccttt cttttcctgt   44040
gaactgtttt tcatatctct agcctatttt cctacaggtc tgctggcctt ttaatgctct   44100
gtttgtgaaa ctctttccat atttaggata tcaaccctttg ttggtgttg  tacattgcag   44160 atatttttc  agagtttgtc atttatgttt ttacttttct taaggtgttt ttatttccat   44220
gcagaatttg cttgtataat caaatgtatc tatttttcc  cctattgctt ctggattta   44280 aacatcttat ttttttgagg tggagtcttg ctatgttgcc taggctagtc tcaaactcct   44340
caatgcaagc aatcctctca cctcagcctc ccaaagtact gggattacag gcatgagcca   44400
ctatgccaga ccagcttctg gattttgaa  tcactgtttg ccatcagtct cttatgacca   44460
tttctaagcc tcatgtgtaa ttacgatttg ttatattcat tttattgttg ttgtttgttc   44520
tttgagacag ggtcttgcta tgttggccag gctggtctca aactcttggc ctcaggcaat   44580
cctcctgtct tggcctccca aagtgttggg attacaggca tgaactacca catccagcct   44640
ccatattcat tttatccatt agtattcatt ctgaattaca gttcccacta gatgtcagtt   44700
```

```
tcatgaagac aggattttct ctgagatgga gatttgcatg cagaggttta tggaagagtc   44760
tccttgggaa caacaccaca gggagtgagg cagagctgga agctgaatta caccagtgat   44820
ctcaggcgat cccatgggga gctctggagc taggatggcc ctccctgtag agctgaggca   44880
aggggtcatg gacccatccc tggatgtggg ctccatccac ggatagcacc tgcccttgga   44940
caaggtggtt ctcctcaacc aatggctgtc gctgggagag gtactcagct ttgaggtctc   45000
agctctggga atgagtgtct cagttccgaa ggggaatctg gcaaagcac cacaacatcc   45060 tccctggttc actgctgtgt tctctacacc tacctacctg gcgcttgata ggtgctcagg   45120
aaatcctttg atgaaagaca aatgagaaca gaaacacagc tttccaagtc ttcgccgagg   45180
ccaactgggt cacacatggg agcaggctgg aggggaggag ccctgagcag gtgtttttag   45240
aatcatcttc tccaatgctt ctggcctatc tcccattgct gctcactggg tgatctggag   45300
ggctcctctt actcaacagt cagtgccatc agggtggggt ggcctgggga ctggggccct   45360
ccctggaccc tgggcactgt gacagctctc tgcatgtgca tcattctgtg agctttcagt   45420
cctgactttt ttttttttt ttaattaaat ctcacttcag cattccttga agaaaagagg   45480
aacccgctcc ctggggaagg ccgataagaa gactttggtg caggtaattc ccagcagccc   45540
ccgtaggaag gttttattct gaagacctga gcctgactct aagtggcctg gggatcccag   45600
attctgccct gtcctcccct tgctcatttt ccttttttc ttttcttttt ttttttttt   45660 tttgagacgg agtcacactc tcttgcccag gctgcagtgc agtggcacaa tctcagctca   45720
ctgcaacctc tacctcccag gttcaagcaa ttttcatgcc tcagcctccc gagtagctgg   45780
gactacaggc gtgcaccacc acacctggct aatttttgta tttttagtag agacagggtt   45840
tcaccgtgtt gaccaggctg gtcttgaact cctggcctca gcaatccac ctgcctcggc   45900 ctcccaaagt tctgggatta caggtgtgag ccactgcgcc cggccccctt gctcattttc   45960
ttagtttcac tgcccacttt atttcccaaa accacatcct gagcccatgg ttcttagatg   46020
cttagatgct cgctccccac cccagccagg aacttagcaa gcagcactac agtcaaatcc   46080
aaaggtctag agttggagac ccaggcttga atcttggctc tgccacttga ctgccatgtg   46140
attggagcga gtcattttga gtttctgggc tccatttcct atctatccct gtcttggggg   46200
ttcattggaa gaattggatg aagtactata tgcagcaaag gccacatacc gttagctcct   46260
agtggtatgg gattgtcaga gtgccaggcc ctttcatcc ttagctcatt taatcccgtc   46320
tgtggctctg ggagggaggt aatgttaccg ccccatttta ctgatgaaac tgtagtggca   46380
gcagttgctc atcagtatgt cacctgttcc tgtactccca ggctatgtgt ggcgcccat   46440 ccttgctgtc atttcaacat ctaccctct gcgtctcccc cggaccctta gctccttgag   46500
ggtctggctg tgtctgattc atccctgtgt tcccagcaca tagtgctccc caaaatgcca   46560
tggctggtac tgagactccc agcactaacc ttcctgggtt gtgtctgtct ctgtggtccc   46620
aggaggacag tgcagacctg aagtgccagt tgcactttgc aaaggaggag tcagccctca   46680
tgtgcaagaa gctcactaag cttgccaagg agaatgacag catgaaggag gagctgctga   46740
agtaccgctc gctctatggg gacctggaca gcgcgctgtc agccgaggag ctggcgatg   46800 ccccccactc gcgggagacc gagctgaagg tgcacctgaa gctggtggag gaggaagcca   46860
acctgctgag ccgccgcatc gtggagctgg aggtggagaa ccgaggcctg cgggctgaga   46920
tggacgacat gaaggatcat ggaggtggct gtgggggtcc tgaggcacgc ctggccttct   46980
ccgcgctggg tggcggagag tgcggggaga gcttggcaga gctgcggcga cacctgcagt   47040
ttgtcgaaga ggaggccgag ctgctgcggc gctcctctgc cgagctcgag gaccagaaca   47100
```

```
agctgctgct gaacgagctg gccaagttcc gctcggagca cgagctggac gtggcgctgt  47160
cggaggacag ttgttctgtg ctcagcgaac cttcacagga ggagctggcg ccgccaagc   47220 tgcagatcgg cgagctcagc ggcaaggtca agaagctgca gtacgagaac cgcgtgctcc  47280
tctccaacct ccagcgctgt gacctcgcct cctgccagag tacgcggccc atgctggaga  47340
cggacgccga ggccggggac tctgcccagt gtgtgcctgc tcccctgggc gagacacacg  47400
agtcccatgc ggtccgactc tgcagagcca gggaggccga ggtgctgcct gggctgagag  47460
agcaggccgc cctggtcagt aaggccatcg atgtcctggt ggctgatgcc aatggcttca  47520
cggctggcct ccggctgtgt ctggacaacg agtgtgctga cttccggctg catgaggccc  47580
ccgacaacag cgagggcccc agggacacca agctcatcca tgccatcctg gtgcgcctga  47640
gcgtgctgca gcaggagctg aatgccttca cgcggaaggc agatgcagtc ctcgggtgct  47700
ctgtcaagga acagcaggag tccttctcat cactgccccc cttgggctcc caggggctct  47760
ctaaggagat tcttctggca aaagaccttg gctcagactt tcaggtaagg tgcctcatgc  47820
acagatccta ttatttattt ttttcctttg ttttgttttg tttttcttga datagggtct  47880
ctccccgctg gccaggctga agtgcagtgg tgcaatctca gttcactgca gcctcgatat  47940
cctgggctct agccattctc cccccctcac tctcctgagt acctgggact acaagtgagc  48000
accaccacac ccagctaatt tttatttatt ttttatttt tttgagacgg agtctcgctc    48060
tgtcacccag gctggaatgc agtggcgcaa tctcggctca ctgtaacctc caactcccag  48120
gttcaagcga ttctcctctc ttagcctccc aagtagccag gattacaggc gcctccatc   48180 atgcctggct aattttttgta tttttagtag agatggggtt tcaccatgtt ggccaggctg  48240
gtctcgaact cctgacttca agtgatccga ccgcctttgt ctcccaaagt ctgggatta   48300 caggtgtgag ccactgtgcc tggccataat ttttaaattt ttttgtagag atggaatctt  48360
gccatattgc ccaggctggt cttgaactcc tgagcttaag tgatccacca gcctcagcct  48420
cccaaagtgc taggactata ggtgtgagcc actgtgtgtg gcctaatagt cacattttaa  48480
atgttcagta tttgtgtgtg tctagtagag tggatctaga atatttcatc cttgcagctt  48540
gtccttctaa atccttctct acacatctat catatatttg ttttccacc cagattgctt    48600 tatatctatt gttactacac aacttatatt tttaacgcaa tgtatcagtt tgttaattta  48660
tgatgccttg tctgttgttc acacagttttt tgtgctcact gctgaagatg tcatgattag  48720
caaaaacaga tatgattccc cctctcatgg tccttatcat ctagtggggc agagtcaccc   48780
aaaatatcat gtcagtgaat gtgcaattag acactgagag aggaatctga aggaagcgta  48840
catggtttta tgaacaagga acttgaccta gaccctatgc tgagggaagg cctctgatct  48900
gaccagaggt cagagggatg gatggctggg ggaacacagt gttttcagca gagcaaatag  48960
cctgtgcaaa gacacagctc agatcagagg cggaaggagc gtggtgtgtc caggacactg  49020
agtgaagaga caatgtgaag ctggactgca ctgagcatgc gggaggtttg atcttcatcc  49080
tcagagcaat ggcagggaat ttttcatttc cagggaaaga gagcgattta gcactttctt  49140
tttttctttt atctttttt ttttttttt ttttttgag acagagtctt actctgtcgc     49200
ccaggctgga gtgcgtggc acgatctcag ctcactgcaa cctccgcctc ctgtctccgc   49260
cttccgggta gctgaaatta caattctcct gtctccgtct cctgggtagc tggaattaga  49320
ggcatgcccc accacacctg gctaattttt gtatttttaa tagagatggg gtttcacgat  49380
gttggccagg ctggtcttga actcctgacc tcaggtgatc cacctgcctc ggcctcccaa  49440
agtgttggga ttgcaggtgt gagccatcgt gcccttctga gatttagcac tttctttta   49500
```

```
acaactatac agtggatatg tgccataatt tctttaactc aagacctgtt gatccggttt   49560
catcttgctt ttttaagcaa gcacattgcc tttttttttt tttttttttt ttttttaaag   49620
aaacagtctt gctctgttgc ccacgctgga gggcaatggt atgatcacag ctcgctgtag   49680
cctcaaattg tagatggaat tacaggcaca tgccactgtg cccatagact gctctatgtt   49740
atctcccttt tggttcttct tgaaagaggg atgaacagag gtcacacatg tgataggaca   49800
gtttgggctg actcaaaagg tttgtgcaca aggcacacat tcagaaaatc acttcgcact   49860
tacctactca ttcatccttt cagcaaacat tcattaaacg gcagcagtgc ccccagctgg   49920
ggctgggtct ggggttgcaga ggtgaatcta ccagggtccc agccctcagg tgggtggttc   49980
aagcctctta gggagcgcag aggcctgggg tgggtgtttc tggcacccct cgggcccctc   50040
cccatggtga tctttggttt gttctgcctg tgcctctggg tgcagccacc tgacttcagg   50100
gacctgccgg aatgggagcc caggatccga gaggctttcc gcactggtga cttggactct   50160
aagcccgacc ccagccggag cttcaggcct taccgagctg aagacaatga ttcctatgcc   50220
tctgaggtgg gtctaggcct gagcaagcat gggattgggt aggaggagag tgactgagcc   50280
ctgtcaaaag cagagtggtc catatatcac ttagctggtg aggatatggg tttggggcat   50340
tccatttggt tccaggcttc ttggcagcca aggccagaag ggaaataagg aagtttggga   50400
cattctcatg gcctgatcca aggaaactta taaactcatc tgcataaatt attttttctt   50460
ctgtactaaa ttccactggg aatttaacaa tttatgtaat ttaatggaac tactcatgta   50520
tgtagcagga aggcagcagt ctctatagcc aggcagtttg ggtttcaatt gtggatccac   50580
tctattctgg ctgtgagatc ttggataagt cattttacct ctctgattct cagttttctc   50640
acatgtaaaa tgaaggtgcc tcacagggtt gttgaaagga ttaaatacat gaaaagccat   50700
agcttaaggc atggtccaca ttgggtgagg atgaggagga ggaggaggat gattatgatg   50760
ataatgacac atctctggga ctcaggggac ctgagttcaa gtctcagttc taccagtgtt   50820
cctgtgtgac cttggacaga tttctacctt ctggccacag cttccccatc tgtaacggga   50880
gggttagagt gaatggtagt tattgaattg ctaggattct ttgatcctca gggaattctg   50940
ggtagttctg agccccttct aagcctgctg agcttctcct tgctcttcat aatgagcctg   51000
aagcaggaaa aggctcctac ggactgggtg gagtatccct gaaaccctga accttgcaga   51060
gtcctatgta ttttccagcc tgagcaccttt tctgagcatc tcttggaaga caactctgta   51120
gtcccaggaa ggtcagccca tgactatgtg ggaaggagaa gctcacttga agctgatgga   51180
tcagactctc taagtgagct tcctggaagc catggcaaaa agagaaaaaa ctgagataac   51240
ttagttgtca ttttctaaga aaaggaaata ggcctattct ttttttttgtt tttttttttt   51300 tagactgagt ctcgctctgt tgcccagtct ggagtgcagt agtgcgatct tggctcactg   51360
taacctccat ttcctgagtt caagcgaatc tcgagcctca gcctcccag ttaggtggga   51420 ctataggcgt gcgccaccat gcccagctaa ttttcgtatt tttagtagag acagggtttt   51480
gtcatgtcac ctaggctggc ctcaaactct ggggctcaag tgatcttccc gtctcagcct   51540
tccaaagtgc tggtattaca ggcgtgagcc actgtgccct gccaggaaat aggcctattc   51600
tataggctta cctgtagaaa aaatgatttc ctgcacacat tcaattattt gtttcattca   51660
gccactcttt attgagtagt gacaattgcc cagtgctgtt gaccactgag ttcagggagg   51720
aaaccaggga cagcagacag tatgtagccc tgcaaaaatt tttaatgcaa aacagatata   51780
gaagatatac ctcaagtcac tgtgccttcc actgccaaat catcatatta ttgaccatat   51840
aatgaatgtt tactttctca cagagggaca tttgccatgc ctaggaaggt tttatgtagg   51900
```

```
agttctgggg ccaggcacgg tgactcacac ctgtaatttc agcactttgg gaggcccagg   51960
tgggcagatt gcttaagcct aggagttcga gatgagcctg ggcaacatgg caaaatcctg   52020
tctctatcaa aaatatacaa aaattagcca ggcgtggtgg cgggtgcctg taatcccagt   52080
taattgagag gctgaggcag gataatcgct tgaacctggg aggcagaggt tgcagtgagc   52140
caagatcacg ctcaaagctg gcgaaactcc gttgaaagag agagagagag agagagagag   52200
agagagagag agggagagag agaaggaggg gagggtgggt gaaggttgga ggtcagaagg   52260
tcttcacata gttcccactg gttacattta ttgtgtgtgt ccatgtcctt tgtatgtttt   52320
tttatggagg cctatagcgt ttttggtttt gtttttctac tttctgttgt agtataacat   52380
aataacatac atacaataaa ggacactgtc cttaagggta ccactgaatg gattgttaca   52440
tatgtataga tccattaagc atcttttaag tcccatcatt tagtatctaa gttgtttcta   52500
aaatattgca attataaaca atgaaacaat gaacatcttt gtgaatcaaa cttagttttc   52560
ccagtacctt attaagataa atttcagaga gaaagaaca agttccaatg gtaacaaaag   52620
ccagatttga tatgtactgt ttcatttaat catcatgacg accctcagag gtggggacag   52680
tcattctgcc tgatttgtat ttggacagct tgggtccaac atcccatcgt tcccctacca   52740
ctgtcatcct tagatcacaa tttctatcca cttcttcctc tctctccctc ctcattatct   52800
gtgtcccctg tctgtaccac agatcaagga gctgcagctg gtgctggctg aggcccacga   52860
cagcctccgg ggcttgcaag agcagctctc ccaggagcgg cagctacgaa aggaggaggc   52920
cgacaatttc aaccagaaaa tggtccaggt gcgtggtgcc cagcgctttc caggcagcta   52980
ttcctacagc ctctctgagc tggaagcaga ggccttgagg atctatgggc cctctgaagt   53040
caagaaagtc aggggaggct gggtgtggtg gctcacgcct gtaatcccag cactttggga   53100
ggccaaggca ggcagatcac ttgaggccag gagtttgaga ccagcctggc caacatggaa   53160
accccgcctc tactaaaaat acaaaaatta gccaggcgtg cactagcacg cctgtaatcc   53220
cagctactca ggaggctgag gcaagagaac cgcttgaacc caggaggcgg aggttacagt   53280
gagccgagat catcccactg tattctagcc tgggtgacag agtgatatct aaaaaaaaaa   53340 aaaaaaaaa agaatgaaag aatgtcaagg gaaacctgag tcttcagccc ctgtgccctg   53400
ctgggatgtt attgtccttg ccattgtgca ttagttgtgt aacagggctg tcattggcgg   53460
cctgtgggac ctggggccag tcctgttttc tctcaggacc tcagtttccc atttatgaaa   53520
tggtgccctc atcaggcctg gcttctaatc aagataatag ttctggaata acatttgtta   53580
agcccttact gtatggtggg cctgtccaat gcactttcta cccattatgt cttttaatcc   53640
ttgtgccctc ccttatcacc attttgcaga tggggaaact gatgcccaga gagctggagt   53700
gctctgccca gggttgcaca tccagagtgt ggcagggctg ggcctctaat ccaggtccct   53760
ctgttaggca tgacactgca ttgcttccta gggtgttgcc tagtcatcag ctgtcctcaa   53820
ccctggcacg ccctttgctc tccatgcgtc accoctccct gctatcatcg ctcaccctcg   53880
caggttcctc attgaacatg agcattcgtg tgagacattt ggtgcccagg aggtgctcag   53940
tatatgatgt catggttttt tagagccagg gtcaaatccc agctccttca atgatgtgtc   54000 actgttttg caggagcaga gggcagtgct catctgaata gattgcgcca cgtgtggtgg   54060
gatccccggc agggatcact cacaggcacc acccagactt tcctccctgc ccctgtccag   54120
gggcccagaa aggggtgggg gagaggacag ggccctgggg ttgctcaagc tcttgtcccc   54180
cggcagctga aggaggacca gcagggcg ctcctgaggc gggagtttga gctgcagagt   54240
ctgagcctcc agcggaggct ggagcagaaa ttctggagcc aggagaagaa catgctggtg   54300
```

```
caggagtccc agcaattcaa gcacaacttc ctgctgctct tcatgaagct caggtggttc   54360
ctcaagcgct ggcggcaggg caaggttttg cccagcgaag gggatgactt cctcgaggta   54420
agattgggcc agggactggg actgggagtg tgggctgggg agagagggac agggaaggga   54480
cgcccagctg gtattgacac aactcctagg ctcacatacc tgccatcagc atgcaggctt   54540
ccttcctgca ttcgttgctt tttttttttt ttttccgaga tggagtctca ctccagccca   54600
ggctagagtg cagtggtgca atctcagcct gctgcaatct ccatctcccg ggttcaagca   54660
attctcctgc ctcagcctcc cgagtagctg ggattacagg cacatgccac catgcccagc   54720 taattttttgt attttaagta aagacagggt ttcttggccg ggtgcggtgg ctcacacctg   54780
taatcccagc actttgggag gccgaggcgg gtggatcacg aggtcaggag atcgagacca   54840
tcctggctaa catggtgaaa ccccgtctct actaaaaata caaaaaatta gccaggtgtg   54900
gtggcgggtg cctgtagtcc cagctactcg ggaggctgag gcgggagaat ggcgtgaacc   54960
caggaggcgg agcttgcagt gagcctagat tgtgccactg cactccagag tgggagagag   55020
agcaagactc cttctcaaaa aaaaaaaaaa aaaaaaaaaa aaaagacagg gtttctccat   55080
gttggccagg ctgatctctc aaactcctga cctcaagtaa tccacctgcc ttggcctccc   55140
aaagtgctgg gattacaggc atgagccacc atgcctggcc aaaagatatg tttacttaac   55200
aagagggagt aggctggctt aaaaacattg gtgatagtac aggtggtatt aggatgtggc   55260
aggaaacgtg ggggcggagc tctgggaatg taagaagctt agaaaggacc cacctgaccc   55320
attcatgccc cagtctatgc aggacccttt gctgctcaaa gcccttgcgt cctgtcatca   55380
gcacagcagc acacatcaac acatcaggga agagaagggg acttacaagg atgtcagacc   55440
ttggtcacac tcatcttagt tgacattgtt cactttggcc gtgtccttt gggttcaggt   55500 acctcgagtc tagcccaggc ttggccctcc tctagtccag gctgctctct gtagtcccct   55560
gtccagatcc agtagggagc attggcatgc ctcaagttgc cacttacgcc atcagggta   55620 ctccagagga gcccagatgc cccaggagcc aggcaagaca gttagacctg agtgtgtagc   55680
aagaccctgc atcacccctat ctcagtgggg ctcatcattc tcgcaggcca ccagctcctc   55740
cccagggcct catgggagag tcactaccgc cattccatag gcccacaccc tgctgccctg   55800
gccctgcagt gcctgacaca gggccgcccc tgggagcatt cgcctcggtc ctcctgtccg   55860
aagctgtctc ttctgtgacg tttggaaaca taggagccct ctcacctgtt tggaagtctc   55920
acaggcctct ggatgaagcc cagtttaagg gaatgacctg caggccacac agtctatatt   55980
ttaagtcagt ttgtctcaga cgaaccctcc acatttggtg aaaacctttc tagccatttc   56040
catatcctag agtaaaagag agagaaactt actttaggga aaaaaaatta gggcataaac   56100
atagaaaatt ggctaggtgc agtggctcac acctgtaatc tcagcacttt gggaggttaa   56160
ggtgggcaga tcacttgaga tcaggagttc gagaccagtc tggtcaacgt gatgaaaccc   56220
tgtctctact aaaaatacaa aaattagctg gaacggtgg tgcacactgg tagtcccagc   56280
tactcaggag cctgaagcaa gagaatctct tgaacctgca aggcagaggt tgcagtgagc   56340
taagagcatg ccattgcact ctagcctgga tgacacagtg agactccatc tcaaaaaaaa   56400
aataaagaga cacagaaaat tacataacat atataattaa gaaatatata catttaccaa   56460
aataagcata attaataaga tataaacata atcatgctgg gcatggtggc tcgcgcctgt   56520
aatcccagca ttttgggagg ctgaggcagg aggattgctt gagcacagaa ggtgactcgc   56580 tccctttttgt cttatttcca tcctgaacta ggtccctgat ctccttggct ggccctggac   56640
tcttgcccag aatctatcag caagcagtcc aaccccccag caaggtccct tctgtccacc   56700
```

```
caaacctttg gtcaccctta tgtagcattg tgggagtgcg tgtggccttt tcatttcaac    56760
cacagtgcct gccttgaccc agcctgtcaa catggttatt tcagagtgac tctcagggat    56820
gcttcctggt ctttggggca aatagatgt  cgtgggaggc taggagggcc tgactatcca    56880
gccgtgctcc tcgacctaca tggtgcccaa ggttggaatt aaaatttggg aaaacttccc    56940
acctgctgtt aagcatggtt tttaaaaaac aggtgaacag catgaaggag ctgtacttgc    57000
tgatggagga agaggagata aacgctcagc attctgataa caaggcctgc acggggaca    57060 gctggaccca gaacacggtg tgtttccagc cccttcccgg tcctgttgtg tccattcatt    57120
cctttgtctg ctcagtaatc aattcctact gctttctctg accccattcc tggacattga    57180
agttgcaagt tattgcctgg tcatcccagg gcagtaacag agtccagatg atggactgtg    57240
gggtcatagg caagacagca agtaattctc tttgcagtat aggggacaat atcacggtga    57300
aggggtcatg gatgatgggt tttgaaggat gtataggagt ttacctaata gagaataggg    57360
gaaagactat tctggaccaa gagaactctg tgtgccaagg tgtggcaagg tgttctggta    57420
ttgagtatgg cttgggaggt acatggtaag ggtaaggata tcaggctaga gtcatctgaa    57480
gaggggcctt gtggtctagg gtcaggaacc ttcaaatcaa gccataagtc agagagaaca    57540
gtggggtcag gatcccaggg tcacacacgg tgagctgggg tagggatggg aaatgagggc    57600
atgggcccag gagagaagat ttgggacaga atcaggcaaa ctgagggagt ctccatgaat    57660
tagaccccac atctggcctg cagcgggtca gagaggcaga tcctgagtga ggagaaggac    57720
ccacggcaca gacgctgcag agccttgaag aagccagatg attcagctca gagttaggct    57780
gaataattat tactgtaact gcagggtttt ttcttggtgt cagatttggg cctcatgtca    57840
gcctaggagg tagccagggc tgggcctgtc attcccattt tatgggtgag atgacctagg    57900
gaggttgtgg gacttgcctg aggcctcgtg aagtcccaag ctggactcct aggtgagttc    57960
tctgaaccca ggttcccctc cctacccac  agaggctctt gactcaggtt ttgcctcctg    58020
tctgcagccc aatgagtaca tcaagacact ggccgacatg aaggtgacgc tgaaggagct    58080
gtgctggctg ctccgggatg aacgccgtgg tctgacggag cttcagcaac agtttgccaa    58140
ggccaaggct acctgggaga cagagcgggc agagctcaag ggccatacct cccaggtgag    58200
ccccccacct gtcagacgcc tctcccctta ctctcagcca agcctttagc tgtcagatct    58260
gggagtagaa taccaaggcc atgctcctag aggaataaga atgccgttgc ttcacctgtg    58320
gcccagagag ggcaagagac ttgcctaaag tcacacagca agggtatcag aaacggtggg    58380
gaatgggagt cacagaggaa gggaaggaag gtggggatt  gcgccctggg ctcacaggtg    58440
aggctggtgc acatcccac  tgcctgctgt cctcatttgc tccttcattt cctcataagc    58500
actccctcag ccccaactgc ctggctctat tttgctccct ccacgcaaaa tggggggcctc    58560 ccctcccaac tccccagcgt gccccccaaag gagccttaac caggagccct ggggggtttgg    58620 tgtctgctgt gtgcctgagg gtgacttgct gcctcctttg gcctgaaaag tgagagggtg    58680
ggcttcttcc cactcagaga gaatgctctg accctgcagc ttgggctcca gcttcttcca    58740
tccagcctgc cctgctgca  agctgccttc ccaggcgtca gcagcctctg ggaggcaggc    58800
actccgatgg tctctgctgg acagatgaca aaactggcac agaggagtta aatttatctc    58860
ccaaggtcac ccggctaata agtgtcagac tggcccttgc tcccccaaac ctctaacccc    58920
tggctccctg tgaccccaat tccacctcct tttttttttt tttttttttt tttgagacgg    58980
catctcactg tgtcactcag gctggagtgc agtggtgcaa tcttggatca ctgcaacctc    59040
cgcctcccgg gttcaagaga ttctcctgcc tcagcctgca aagcaactgg aattatagat    59100
```

```
ggcacaccac catgcccagc taattttttgt attttttagta gagatggggc tgcaccatgt   59160
tggccaggct agtcttgaac ttctgatctc aagtgatctg ccggcctcag cctcccaaag   59220
cgctgggagt actggcgtga ccaccactc ccggccccaa ttccaccttc ttcccactgc    59280
tcacagtctc ctggctactt cctggggcca ctactctccc ctcctaaccc tcttccagat   59340
ctcacagctc cctccatctg catattccac ggtgtccct gcacctgctg ccccaaaga    59400 cctgggcatt tcaggtgctc ctcccaccaa gaacctgacc agctcatggg ggttaatggg   59460
gggcattgag tctaaaggtt gcacattccc tttcctgcca ctctgaggtt tgaggccaag   59520
aaaaccatct tgctggaatg accactagta atctttctga gtttttatga ggatactgac   59580
atcatgcctg aaaagcccac agaagagcat ggcttataga aagagctctt caaaccctta   59640
ttgtgtggag gggttagggg ttagttctga gtggggagga ctaagctggg ttagtcccta   59700
gtgaggggtc ttctgagggg acctctcccc ttttccccgc tggcacccag gagggaagga   59760
gagagaaggg ccaagaggag tggcctcctg ctgccagctg cttagtctgc ttcttttccgc  59820 agatggagct gaagacaggg aagggggccg gggagcgggc agggcccgac tggaaggcag   59880
ccctacagcg ggagcgtgag gagcagcagc acctcctagc tgagtcctac agcgctgtca   59940
tggagctgac tcggcagctg cagatcagtg agcgcaactg gagccaggaa aagctgcagc   60000
tggtggagcg gctgcaggt gagaagcagc aggtggagca gcaggtgaag gagctgcaga   60060
accgcctaag ccaggtgagg cccacccctg ccaagccgct tccacccgca agggagagtt   60120
gctacagaaa tgattcagaa gcaggaactc cttcaggtat agctggatct aggtgctcat   60180
ccagtgaggt ctggcacacc atctccttca ggtatagctg gatccaggca cttagagaat   60240
gcagtgggaa ctagattttt ctttctgctt cagcctgtca ggcctgcttt cctctgtgtt   60300
agctttactc ttaaacaagc tattcccaaa tatggccact gttagtttca tgctcatatc   60360
ttacagctta gcaagtacag tggattggcc agatatgagt catgtgccca ccctggagc    60420 ctacccaaac ccaggaacca agagggagga actaagagtg gttcccatgg gaaaattggg   60480
aggcctccaa tcaaaagaag gaggaaagga aaagcaatca ttgaccctca ctccccatta   60540
tagttcactt catgcagcca ggcaccacct accataggct gctctgctcc actcttgatt   60600
ttgacttttc cctttctttc acttttattt ttatttactt atctatttat ttgagacaga   60660
gtctcactct gtcacccagg ctagagagca ctctcggctc actgcagcct ccgcctccca   60720
ggttcaagtg attcatgtgc ttcagcctcc tcagtagctg ggattacagg cgtgtgctac   60780
cacagccggc taattttttat atttttagta gagatagggt ttcaccatgt tggccaggct   60840
ggtctcaaac tcctggcctc aagtgatcct cccgcctcag cctcccaaag tgctgggatt   60900
acaggagtga gccaccatgc ccggccttac ttttatttta tttatttta tttatttatt    60960 ttttctttga dacagtctta ctctgtcgcc caggctggag tacagtggtg tgatctcagc   61020
tcactgcaac ctccacctcc cgggttcaag tgattctcct gcctcagcct cccgagtagc   61080
tgggattaca ggcacgtgcc accacacccg gctaatttt tatttttagt agagatgggg    61140
ttcaccatgt tggccaggct ggtctcgaac tcctgacctc aggtgatccg cccgcctcgg   61200
tcttccaaag tgctgggatt acaggcatga accaccgcgc ctggccttac ttttaatttt   61260
aattacgtaa atcaggactt catctttata taatgttcac atattacaaa ggtacatttc   61320
agcctactcc ctcccttct tgtcatttt ttttaatgaa aaaagttgt ttttttttt       61380 tatgagagat gaggtcttac tgtatggccc aggctggact tgagctcctg gtctcaagcc   61440
atcctcctac ctcagcctcc cgagtcgctg ggcctttctt tctatttaaa tttatattta   61500
```

```
cagggttttg ttttgtttgt tttttaatca tcaatcaaat tttaatgtcc atttatttat   61560
actttgtgtc tttcctggag agctgttcac aagagtatgg aggccttcct tattcagtgt   61620
gactggtgcc tggtgttcct agtgtggaga tactatgatt tgttatctac agtgattaaa   61680
tctagattgt ttccagtttt tcactattga aagttgtgac ctgaagctgg ttgtggcaat   61740
gtgtgcctgt agtcccagct acatgagagg ctaaggtggg aggattgctt gagctcagga   61800
aatcaaggct gcagtgagcc atgatcatgc cactgcactc cagcctgggc aacagagtga   61860
gacttcgtat ctaaaaaaag aaaaaaaaag ttcaagttgt gcctcagtga acatctccac   61920
acatatattt ctgcacacgc atgaatattt cagtaggata gattcctaga ggtgaaattg   61980
ctaaatccaa gggcatatgc atttatagtt gatggtaact gccaggccgc cttctagaaa   62040
ggctttgccc atgtaccctc ctgccagctg cacagtgaga aggacaagaa ggccctttt    62100 gctttatctt tgccagttcc tgtgattacc aatctttgaa atgtctgccc aagttagggt   62160
gtgaaatgct atctcattgc tttactttgc atttctctga cttctactga aggtgagcat   62220
ttttcatgag tttatggatc ttaggtattt cctcttccta atgttctctt cagtacttca   62280
acagccttgc aaggtcacgt tcatgaaacc ccttttcag atgaggagac tgaggcaaag    62340
tgatttgccc aaggtcataa agtgagtaag ggagaggacc agaatctggc agaactccca   62400
gatctggaaa gttcctggtc ctgggccatg cccactttcc tgcaggtaaa gagctccttt   62460
gaggttcaca cttgctagga ggctgtgctt ggggagtgca ggatggcagg ctgactaaca   62520
aatcccagaa ccatccaggt accatgtgga aagcaggtca gatgcatgca tctgtttgca   62580
ccatcaaacc aaattcctgt ctataaaaga ataattcctt cttattatat taacaacaaa   62640
atgtttctaa aatgattctg aaattatgaa acaagcttca tgtcatccct ggggaacatg   62700
tcagcccaca ggcgtgtctt gtcagctcat cagggcacgg gttccatgtt ctgctgttgt   62760
tctcacatca gagacttgcc ggccctctag ctccagcctc ttgtgtctct gacattcttc   62820
tgcctcctgc acttttaaacc aaatccccca aagcagcatt cttcttaca ctggactgac    62880 gattaagcca gactggtgaa agcaacagag tggctggtgg aaagagcttt ctgaccagga   62940
gtccccagtc cttacctggc tccaccaggt acaaccccag tcaagtcacc tctgatctct   63000
gggcctcatc tgtaaaataa ggatgaccat tcttgacctt ctcatcttgc aaggcagcta   63060
tggaaataaa gtgagatagc cagaagattc aaagtgcttc ttaagcccac ccctgtctgg   63120
ggcttggttt gattctatgg tctttcatctc tcattgctgt ttgctgatgt tagtgttatt   63180
tccctccttc ccttccctcc cttcctccct cccttcttct ttcttcgttt cttttcttttc  63240 ttattttgag acaaggtctt gctctgtcac ctaggctgga gtgcagtggc accatctcag   63300
ctcactgcaa cctccgcctc ccaggctcaa gtgatcctcc cacctcaacc tctcgtgcag   63360
ctgggagcac actctaccat gcctggctaa ctttttattta tttatttatt tatttattta   63420
tttatttatt tattttgag atggagtttc actcttgttg cccagactag agtgcaatgg   63480
cgcgatcttg gctcaccgca acctctgcct cccgcgttca aacgattctc ctgcctcagc   63540
ctcctgagca gctgggatta caggcttata ccaccacgcc tgtctaattt tttgtatttt   63600
tagtagagac agggtttctc catgttggtc aggctggtct cgaactccca acctcaggtg   63660
atccacctgc cttggcctcc caaagtgctg ggattacagg tgtgagccac cgtgcccggc   63720
aacttttgta tttttttgta gagatggggt ttcgccgtgt tgcccaggct gatcttaaac   63780
tgctaggctc aagtgatcct cccacctcag cctcccaaag tgctgggatt atagttgtga   63840
gctgccacac ctggcctagt gttattttca ttgttgccct tattactgtt tgtctcatgt   63900
```

```
tgagtttctt agaagcaaag ccctagacat gaattcaagt acaagtaagg tgaccaaccc   63960
atgctggctt gcctgggact gagcgcgttc ctgggacttt gacttttaaa actagaatag   64020
tcctagccgt agcctactag ttttttttag aactgagggt tctggacat gggactttca    64080 atgcaaacac tgagaaagtc ctgggcaaac caagatgagt tggttaccct gtgtgcaagt   64140
gatttgttaa cggatggagt caggatgggg aaggggaaga aaccacgtaa gatatgcttt   64200
cagatgaagt ctgccctcgg cctgacccca tgacatgccc aggagtgtaa acagtaaatc   64260
accccacagt ttggtccacc ttaaggcaag gggtctgcct tttgggccgg tcttttggac   64320
ccctgtcttt gtctgtcatt ggcagtgatt cggttctaat tgcccaaggc aatcctccag   64380
agaaggctgt agtgtcagat ggtacagatg gagccaccaa caatgggaag tgctacacga   64440
tcattcactc agtcagctgc ccaacctctt ctctcagtct tgatcctctc atctgccaaa   64500
tggaaataac cacaagaaca cctatcatac actgtttctg tgaggattaa atcaactaat   64560
gcggccagac gcggtgcctc acacctgtaa tcccagcatt ttaggaagtc gaggcaggcg   64620
gatcacctga gtcaggagtt caagaccagg ctggccaaca tgtgaaaccc gtctctacta   64680
aaaacacaaa aattagccag gcgaggtggc tcatccctgt aaatgccagc cactcgggag   64740
gctgaggcag gagaattgct tgaacctggg aggcagagtt tgcagtgagc tgcgatcgta   64800
ccacagcact ccagtctgga caacagagta agaccctgtc tcaaaaaaaa aaaaaatta    64860 actaatgtgt gcataggaga taggttccat cacaagccac ctggaagtga tggagctcca   64920
aagaggggag agaagcagag gcccctcaag gcccagcagg aaaaagtgcc gagatccata   64980
aatgacggcc actgtggatg gagcagtggg ggtgcctgga tcttacattt gccactctga   65040
tgggatgtag ctgctgctta gctagtctag ctgttctgtg aattgtaaca tgaattcaca   65100
tagtcatggc tgttactata ttaggtataa tgacatctag aaggatgcct gcaagtagtt   65160
cctttattta tcattttcca aatccaccag gcagagtggg gcgctctgag ctgctaccca   65220
ctgagaaggt ggcccttgt ccatgatgta ggttctgtgg gctgcagagt ggagtctggg    65280
gaatggcctt gcttagagca gggtcctgca taccagcttt gcccattacc gacccaccct   65340
ctctgccctt gcccagctgc agaaggctgc cgaccctgg gtcctgaagc actcggagct    65400
ggagaagcag gacaacagct ggaaggaggt gagtggggcg gctgctgcca tgctatcttg   65460
gctcctggct gcaccataaa ggtccctgct tgtgggggac atgagaggaa gttgctaacc   65520
ctgtctcata ggtcacaccc ttgcaccttg ggctcctcag ccctggagtc tgtatctcat   65580
ggttcctgcc tcaaaaaaat aaaaaaaaaa cccaaccacc cagggactgg gctaagtgag   65640
ggggtagggt tgaggaggaa gaagacaagc ccaccaccag ctgagcagtg gaccactgga   65700
tgctttgttg cagtcaccac atttggatta aattttaagt ggtccctttc cttgggtggg   65760
tcactcttgg agctctgatt ggcccagcct ggatcacata tggtggggga gttggatgca   65820
gggcagccag aaactgacca tgctagatca ttgatgacat cattcctgct ctccggatga   65880
ggagattcaa gcactgaggt cggggctggt ctcttgttcc atgcccttag tgctctggtg   65940
gccagaactg accccttcctg tctctcttcc ttgacagaca cgcagtgaga agatccacga   66000
caaggaggct gttccgaag ttgagcttgg aggaaatggt ttaaagaggt gcttgcatgc    66060
tggtcccctc tctgcctct ctgaccggcc ccacagcctc gccctctcc acctcctgct     66120 gcgccctgca cccactctac ctgctttcac cgcagccctg ccccgcccct ttgccctctt   66180
cctgccgcca ccccaccgca tccaagttgg gagagcatcg ggatatggtt tctctggaac   66240
ccgagccact caggagctgg aaggcttggg gcagtgggaa ttccaggctg ctgcatgttg   66300
```

```
tttgagtccg ggaatggaac acaggtggaa acaaaacatt ttgctcctct tgggattctt   66360
ttctcctgcc tctggagtta ggagagtcaa gattgacctc tattcctggg attattgagc   66420
agcatccttt gggcccagcc ctgtgctatg gccaaggaga ccccacccc aagaccataa    66480 ggaccacgtc tccactgtta ggaaacccat gaaaggagtc agggaaacag aacccccagc   66540
cgctatcaga ccagcccaga agcaaggcag gcgggacagg ctgtggagcc agagggccag   66600
gtttgaatgc cagccctgcc agttctagct ctatgacctt gaccttgagc agtactttcc   66660
atctctgtct agtggggatg ataggagctg cctcttgaag ttaatcagag tggtctgaca   66720
cgtgcatttc catatgcctg gtgtgttcag tgattcaggc aataggtgtg ccaggagctt   66780
catggcgtct tagtttgggt tcccccataa gcaaaccctg agacaaagat ttaagtgcaa   66840
atggtttatt tgggacagaa tttcaggaaa cacttggaag tgagacaggg aagggaaagc   66900
agccgataaa aggagcttca accaggttat tccacgggca actggagttc aggctgtcgg   66960
aggaactcag ggagccagag gagaacatgc agcttagagt catcccacca caaggaggct   67020
ggggcacttg ttcaccatat cccacctatt gtttgttgag ggctgtgttt aggggtgtga   67080
actcattaac tctgtgctat ctctagcttc ggtttgggcg tgtgttttgt ttttttttgtt   67140 tttgtttttt ttttgaggca gagttttgct ctgtctccca gggtggagtg caatggcaca   67200
atcttagttt actgcaacct ccacctccca ggttcaagca attctcctgc ctcagcctcc   67260
tgagtagctg gggttacagg ctaacgccac cacgcttggc taattttgt attttacta    67320 agagataggg ttttaccatc ttggtcaggc tagtctcaaa ctcctgacct caggtgatct   67380
gcctgcctca gcatcccaaa gtgctgggtc tagcttcttc tatgtgtagg acagccaagt   67440
atgatcccac aggcagaaaa aaaaaccatc agatagagaa tggtggagta tgcagttcag   67500
agtatgcagt tttaggtgta taggtgaaag tgcaaagaga ggccaggtgc agtggctcat   67560
gcctctaatc ccagcatttt gagaggcaga ggcaggaaga tctcttgagg ccagaagttt   67620
gagaccagcc tgggcaacat agggagatcc ccatctctac aaaaaatttt taaaaatta    67680 gccaggtgtt aggctgggca cagtggctca catctgtaat cccagcactt tgggaggctg   67740
aggcgggtgg atcacctgag gtcaggagtt ccagaccagc ctggccaaca tggtgaaacc   67800
ccgtctctac taaaaataca aaaattagct gggcgtggtg gcgcacgcct gtaatttcat   67860
ctgctccgga tgctgagaca ggagaatctc ttgaacctgg agggtggaag ttgtagtgag   67920 ccagatcat gccactgcac tccagcctgg gtgacagaac aagactctgt ctcaagaaaa    67980 aaaaagaaa aaaaaagcc aggtttggtg gtgcacacct gtagtcccag ctactctgga     68040
ggctgaaatg ggaggatcac ttgagcccag gagtttgagg ctgcagtgag ctattattgc   68100
actactgcat tccagcctgg gtgacatatc aagacctgtt tgggagaaaa aaaaaaaaaa   68160
gaaaatgcag acagaatgtg ggactgggca ccaacaacat ctctacaaga ggtgaacaag   68220
acggtcctgg tctttgccct cacgcagcac acggaccagg tggtagacc agagtgtgcc    68280 ctcagtgtta tttccactaa taacgacgtt tcctcctctg tccttcgcag aaccaaatct   68340
gtttcttcca tgtctgagtt tgaaagtttg ctcgactgtt ccccttacct tgctggcgga   68400
gatgcccggg gcaagaagct gcctaacaac cctgcctttg gctttgtgag ctccgagcca   68460
ggggatccga agaaagacac caaggagaag cctgggctct cgtcgaggga ctgcaaccac   68520
ctgggtgccc tggcctgcca ggaccccca gggaggcaga tgcagcgcag ctacacggct    68580
cctgacaaga cgggcatccg agtctactat agtcccccgg tggcccggcg cctcggagtc   68640
cctgtggttc atgacaaaga gggcaagatc attatcgagc ccggcttcct cttcaccaca   68700
```

```
gccaagccca aagagtcggc cgaggctgat gggctggctg agagctccta tggtcggtgg   68760
ctctgcaact tctcacggca gcgcctggac ggaggctcag cgggcagccc ctcggcggcc   68820
gggcctggct tcccagcggc cctgcatgac tttgagatgt caggcaacat gagtgatgac   68880
atgaaggaga tcaccaactg tgtgcgccag gccatgcgct ccggctcact ggagaggaaa   68940
gtgaagagca catccagcca gacggtgggc ctggccagtg tgggcacaca gaccatccgc   69000
acggtcagcg tgggcctgca gaccgaccca ccccgcagca gcctccatgg caaggcctgg   69060 tcacccccgca gctcttcgct cgtgtctgtg cgcagcaagc agatctcctc ctccctggac   69120
aaggtccatt cgcgcatcga gcggccctgc tgctccccca gtatggctc accaaagctc   69180 cagaggcggt ctgtgtccaa gctggacagc agcaaggacc gcagcctgtg gaacctgcac   69240
cagggcaagc agaacggctc ggcctgggcc cgctccacca ccacgcggga cagccctgta   69300
ttgagaaaca tcaacgatgg actctccagc ctcttcagtg tggtggagca ctcagggagc   69360
acggagtctg tctggaaact aggcatgtct gagacgcggg ccaagcccga gcctcccaag   69420
tacggcattg tgcaggaatt cttccgtaat gtgtgtggcc gggcaccgag ccccacctca   69480
tcagcaggag aggagggcac caagaagcca gagcccctct ccccagccag ctaccatcag   69540
ccagagggtg tggccaggat cctgaacaag aaggcagcca agttgggcag cagtgaggag   69600
gtcagactca ccatgctccc caggtgggg aaggatggtg tcctccggga cggagatgga   69660
gccgtggtcc ttcccaatga ggtaggtggg tgggatctgt cctttctctt agtaggtgga   69720
gttagtatat aagtccaag ctcttttggt ttttaagttc agagatatgg gccgaggtgg   69780
gtggatcgcc tgagatcagg agttcaagac cagtctggcc aacatggtga accccatct   69840 ctactaaaaa tacaaaaatt ggccaggcgt ggtggcatgc acctgttgtc ccagctgctc   69900
tggaggctga ggtaggagaa tcacttgaac ccagtaggcg gaagttgcag tgagctgaaa   69960
ttgtgctatt gcactccagc ctgggtgaca gactaagact ccgtctcacc aaaaaaaaaa   70020
aattatctat ctgtctgtct gtctgtctgt ctgtctgtct gtctgtctgt ctatctatct   70080
atctatctat ctatatatct atatatataa aataaaaatt cagggatatg gccatgtgtt   70140
ccaggaagtt cttatgctgg tctaggatag agttggaagg tcccagacct ggaacaacac   70200
agacctgatg gtcacatggt ctgaattcca agagactagt gagcatggct taactagcag   70260
cttttgctcc acccaccaga gactgccagc atcccctcca gggaaggggc cttactgctc   70320
tcctgccacc cagtggtgtg ctagagccag cttgtttggc ttgcaggagc caattgtcag   70380
catctctgtg ggttttttt ttttattgt ttttgttttt gttttgagag aagtctcgtt   70440
cttgtccccc aggcttgagt gcaatgactc aatctcggct cactgtaacc tccgcctcct   70500
gggttcaaac aattctgtct ctgcctccca gtagctggg attaaggcac ctgccaccat   70560
gcccggctaa ttttttgtatt ttttagtaga cggggttt caccatgttg gccaggctgg   70620
tctcgaactc ccgacctcaa gtgatccgcc caccttggcc tcccaaagtg ttaggattac   70680
aggcgtgagc caccgcgcct ggccacatct ctgtgtttaa catcaccttg gtaccttgag   70740
attggccaca gtgggaggat ttacagcata aaaattggta aacactacaa atcgggctc   70800 ctcctatcac tcctggaaaa ctaattgtta aacattagcg ggcataccac ttctccaccc   70860
catcaagact tcacacctaa gtgctcacat ttcctctgag aatctttcac accccactcc   70920
tgctatcagt ttcttataag ttaattagta aaccttattt gaatgttagt gagcattatt   70980
tgaatgtgtt agaatgtgca taagttaact ttgcagaaag ggaaggaaat gtatttgaag   71040
gatggcatgt tttataaaac ccaagagtag gaacctgaca acctcagcag cttctccctg   71100
```

```
tcttcctctc ctctctttaa gcttcaccct ctctgatatc atattcctcc ttttctctg   71160 tttctctctc tgttgcattt gcacaaggac tgggtgggct gtcccagctc tgactttaca   71220
acatcttcca gttcaagccc ctaggagaga ctgacacaaa tccctgtctc ccaattccac   71280
atttctgaaa gaaggaaact ctgattggtg cagctagagg cgagtgtacc ccttggtcca   71340
gtctatggct gggagtggta ccatgtggtc tgctgtgggg cacagagaca tgagaagggc   71400
tgtgtgtgga atgggctgtg atagactcaa acattctact tttctattat tgtacgttta   71460
ggtggtttct agtttgtccc tactgcaaat aatgctgtgg tgaacatctt ggtgcaaaat   71520
cattttttta catttcagac tatttcctta ggtataagtt gcagaaatga gattaaagga   71580
taatagaata taaatgtggc cgggcgcggt ggctcatgcc tgtaatccca gcactttggg   71640
aggccgaggc gggtggatca caaggtcagg agtttgagat cagcctggcc aatatggtga   71700
aaccctgtct gtactaaaaa tacaaaaatt agccgggcat agtggtggtc acctgtagtc   71760
ctagctactc aggaggctga ggcaggagaa tcgcgtgaac ccaggaggcg gaggctgcag   71820
tgagctgaga tggtaccact gcactccagc ctgggtgaca gagtgagact ccatctccac   71880
acaaaaaaaa aaatataaat gttttaaagt tatttgataa atactgccaa attgttttc   71940 aaaagtgtgc catatctaca gcttccagca gtgtgtggcg agtgcgttac ttttctatac   72000
tctcactcag ctggctgaca tttaaaaaca tcttttaaat atttattcct tttttggcca   72060
ggtgcaatgg ctcatgtctc taatcccagc actttgggag actgaggtgg gcagatcact   72120
tgagctagga gttcaagacc agtctgagca acatggtgag agctcatctc tacattaaaa   72180
aaaaaaaaaa agaggccagg catggtggct tacgcctgta atcctagcac tttgggaggc   72240
cgaggcaggt ggattgcctg agctcaggaa tttaagacca gcctgggcaa cacagtgaaa   72300
ccccatctct actaaaaaat acaaaaaatt agccaggcgt ggcagcatgc gcctatagtc   72360
ccagctactc gggaggctga ggcaggagaa ttgcttgaag ccgggaggtg gaggttgcaa   72420
caagctgaga ccacgccact gcactctagc ctgggcaaca gagcaagact ccatctttta   72480 aaaaaaaaa aaaaaaaaa agggccaggc gtggtggctc acacctgtaa tcccagcact   72540
ttgggaggcc gagagaggtg gattgcttga agccaggagt ttgagaccag cctggccaac   72600
gtagcaaaac cctgtctcta cttaaaaaat acaaaaattg gccgggcgca gtggctcacg   72660
cctgtaatcc cagcactttg ggaggctgag gtgggtggat catgaggtca ggagatcgag   72720
accatcctgg ctaacacagt gaaaccccgt ctctactaaa aatacaaaaa gttagccagg   72780
cgtggtggca ggcgcctgta gtcccagcta ctcgggaagc tgaggcagga gaatggcatg   72840
aacccgggag gcggagcttg cagtgagccg agatcgcgcc actgcactcc agcctgggtg   72900
acagagcgag actccatctc aaaaaaaaaa aaaaaaaaa atacaaaaat tagctgggca   72960
tggtggcaca tgcttacagt tccagccact tgggtgattg aggcatgaga attgctggaa   73020
cccaggaggc agtgagccaa tatcgcacca ctgcactcca gcctgagcaa cagagtgaga   73080
ctctgtctca aaataaata aataataaag tctcaaggca ggaaaaaagc aagtgtctca   73140
gtctgaaggc tgtcaggcag gaagaattct cttacttgag ggagagtaag ccctcttgtt   73200
ctgttcaagc ctttaactga ctggatgggg tccatgttag ggagaattcg cttttttttt   73260 ttttgagac ggagcctcac tctgtcaccc aggttggaat gcagtggtgt gatctcggct   73320
cactgcaacc tctgcctccc aggttcaagc gattcttgta cctcagcttc ccaaccaagt   73380
agctgggatt acaggcacat gccaccacgc ccggctactt ttttattttt agtagaaata   73440
gggtttcacc atgttggcca ggctggtctc gaactgctaa tctcaagtga tccgcctgcc   73500
```

```
tcagtctccc aaagtggtgg gataacagac gtgagccact gcgcctggct gagaatttac   73560
atgttaatct catctcaaag cactctgaca gaaacaccca gaacaatgtt ttacgtaata   73620
tctcggcacc tgtggcccag tcatattgaa tataaaatta accatcactt ccatataacc   73680
agcaccacat caagaaacaa cagcacaaag ctggctggat tttgaatgtt gattttaaag   73740
ttgatccaaa tattgttcag tatgtaaaat gtgcgtgcta cccattgacc cagtagttct   73800
tcttttacga aggtagccta tggaaatatt cacagagatg gataaagaaa aataaaaaga   73860
ggctgggcgc agtggctcac ccaatcacct gaggtcggga gtttgagacc agcctgacca   73920
atgccgagaa accccatctc tactaaaaat acacaattag ccgggcgtgg tggcacatgc   73980
ctgtaatccc agctactcgg gaggctgagg caggagaatc gctcgaaccc gggaggcaga   74040
ggttgctgtg agctgagatc gcatcattgc actccagcct gggcaacaag agctaaactc   74100
tgtctcaaaa aaaaaaaaaa aagaaaaga aagaaaaag aaaaaagag agaggggagg   74160 aaatcaaagc tcaagagagg ttaagtaaat ctcccaaggt cacacagcta gtaattggca   74220
aagctgggat ttaaccaagc agtttggctc tatcacagca cttttatttt atttatttat   74280
ttatttattt ttgagacgga gtctcgctct gttgcctagg ctggagtgca gtggcacgat   74340
cttggctcac tgcaagctcc gcctcccagg ttcacgccat tctcctgcct cagcctccta   74400
agtagctggg actacaggca cctgccaccg cgcccggcta attttttgta tttttagtag   74460
agacggggtt tcagatggtc tcgatctcct gacctcgtga tccacccgcc ttggcctccc   74520
aaagtgctgg gattacaggc atgagccacc gcgcccgggc cattttatt atttttttaaa   74580 gagatggggt cttgctctat tgctcaagcc agagcccagt gacacaatca tagctcactg   74640
ctgccttgac ctcctgggct caaaggatcc tcctgtctca gcctcccaca tggcccagcc   74700
cagcagcact ttttttttt tttttttttg agatggagtc tcactctgtc ccccaggctg   74760
gagtgcagtg atgtgatctc ggctcactgc aacctccgcc tcctgagttc aagccgttct   74820
gctgcttcgg tctcccaagt agctgggact gcaggaatgt gccaccatgc ccgggtaatt   74880
tttgtatttt gagtagagat ggggtttcac catgttggcc agcctggtct tgaactcctg   74940
acctcaggtg atccacctgc catagcctcc caaagtgctg gcattacagg tgtgagccac   75000
catggccagc tgtccagcag cactttttt ttttttttt ttttcagatg gagtcttgct   75060 ctttcacccca ggctggagtg cagtggcaca atctcagctc actgcaacct ccgcaccctg   75120
ggtttaagcg attctcctgc cctagcctcc cgagtagctg gactacagg cgcatgccac   75180 catgcccagc taattttgt attttagta gagatggggt ttcaccatgt tggccaggat   75240
ggtctcgatc tcctgacctc gtgatccacc tgcctcagcc tcccaaagtg ctaggattac   75300
aggcatgagc caccgtgcct ggcagcagca cttttgatca ttatttctgt ttattggtaa   75360
tagtaaaaaa ttagaaacta cccagatgta cataaaaagt gaattgggc caggcacagt   75420 ggctcacacc tgcaatccca cactttgga aggccgaggc gggcagatca ctagaggtca   75480
ggagtttgag cctgaccaac atgctaaaat ccctctcta ctaaaatac aaaaattagc   75540 taggcatggt ggcacacgct tgtaatctta gctactggg aggctgaggc acaagaatca   75600
cttgaatccg tgaggtggag gttgtagtga tcaagatcg taccactgca ctccagcctg   75660
gggaacagag caagattctg tctaaaaaat aaaaaataa aaaagcgaa ttgggtatat   75720 aaatcagtta tttctatcta gtgaaatggt acagagacac taaaaagaa ggcgatcagc   75780 caggcatggt ggctcatgcc tttgggaggc atgagcaccc aaaggtgcta attccagcag   75840
tttgggaggc tgaggcagga ggatcgcttg agcccaggag ttcaagacca gcctgagcaa   75900
```

-continued

```
catagtgaga ccctgtctca aacgaaaaaa aaggataaaa aggaaggaga tctagacata  75960
cctagtgaca gaaaagtgtt cgtgttttac agttgcaaaa taagctgtca ttttggtaaa  76020
tgtatgttaa gaatctcttt ggcgtgcagg accatggaca gtgtccactg tcctctctgt  76080
atagcctaga atatattaca atgaacttcc attaccgctc taatgggaga agaacaacag  76140
aaagaaaaaa ttggtccagt gaggagcttc agcccctggg aactggttta tggccgagtc  76200
tcagttcctt gcctggcata ccacacagct catggtggtc catgtctcct ggctcctctt  76260
gacttcctgc ctccctgcct ccctcttcct aggacgctgt ttgtgactgt agtacccagt  76320
ctctcacctc ctgcttcgcc cgatcgtccc gctctgccat ccgccactct ccttccaagt  76380
gcaggctgca cccttcagag tccagctggg gtggggagga gagggcactc cccccagcg  76440 agtgacagag cagccaagct ccccgcctca accagcccag ccctggata gcagaaggga  76500 accagcagag acgagacgag gtgaggcgag gggctgtgtc ctcagcattg cctggccctg  76560
gagggacagc agtgatgcca ctgccagaat gcagctttca catcaaggta aagccgggtc  76620
tcctgctggc ccctgggtgg tgagcttcga cttcccaggg gaaggcagtg agtgggagag  76680
agaccaaacc tgggcttccc aagcatccac tgagagatct gtcaagagcc gatccctggg  76740
tcctaagaga gagccttgcc tggttctgcc c                               76771
```

US 8,530,174 B2

SOGA POLYNUCLEOTIDES AND POLYPEPTIDES AND USES THEREOF

RELATED APPLICATIONS

This application is a 35 U.S.C. §371 national phase application of PCT Application PCT/US2010/037,472, filed Jun. 4, 2010, which claims the benefit under 35 U.S.C. §119(e) of U.S. Provisional Patent Application Ser. No. 61/184,392, filed Jun. 5, 2009. The entire contents of each of these applications is incorporated herein by reference.

STATEMENT OF FEDERAL SUPPORT

This invention was made, in part, with government support under grant numbers DK075573, DK056350, and ES010126 from the National Institutes of Health. The United States government has certain rights to this invention.

FIELD OF THE INVENTION

The present invention relates to the identification of polynucleotides and polypeptides involved in insulin and adiponectin signaling and regulation of glucose production. The invention further relates to the use of the identified polynucleotides and polypeptides, and inhibitors of the polynucleotides and polypeptides, in the regulation of glucose production and the monitoring and treatment of metabolic disorders such as diabetes.

BACKGROUND OF THE INVENTION

Adipose tissue exerts a powerful effect on glucose metabolism by regulating the concentration of circulating adiponectin (Goldline et al., *Lancet* 362:1431 (2003)). High adiponectin in the lean state is linked to elevated insulin sensitivity whereas low adiponectin in the obese state is linked to insulin resistance and diabetes (Arita et al., *Biochem. Biophys. Res. Commun.* 257:79 (1999); Hotta et al., *Artererioscler. Thromb. Vasc. Biol.* 20:1595 (2000); Maeda et al., *Diabetes* 50:2094 (2001); Weyer et al., *J. Clin. Endocrinol. Metab.* 2001, 86:1930 (2001)). Endogenous glucose production is elevated in diabetes (Wahren et al., *Annu. Rev. Nutr.* 27:329 (2007)). Studies in mice and liver cells show that adiponectin lowers glucose production by increasing the insulin sensitivity of the liver (Berg et al., *Nat. Med.* 7:947 (2001); Combs et al., *J. Clin. Invest.* 108:1875 (2001); Combs et al., *Endocrinology* 145:367 (2004)).

The signal transduction pathway of adiponectin is currently linked to (a) adiponectin receptors that bind to the full-length or the carboxy-terminal 'globular' fragment of adiponectin, (b) binding of the intracellular domains of adiponectin receptors 1 and 2 to the adaptor APPL1 and (c) the activation of AMPK, a signaling intermediate that reduces the gene expression of rate limiting enzymes for glucose production (Combs et al., *J. Clin. Invest.* 108:1875-(2001); Combs et al., *Endocrinology* 145:367 (2004); Tomas et al., *Proc. Natl. Acad. Sci. USA* 99:16309 (2002); Yamauchi et al., *Nat. Med.* 8:1288 (2002); Shklyaev et al., *Proc. Natl. Acad. Sci. USA* 100:14217 (2003); Nawrocki et al., *J. Biol. Chem.* 281:2654 (2006); Andreelli et al., *Endocrinology* 147:2432 (2006); Mao et al., *Nat. Cell Biol.* 8:516 (2006); Brooks et al., *J. Biol. Chem.* 282:35069 (2007); Yoon et al., *Exp. Mol. Med.* 41:577 (2009); Wang et al., *J. Biol. Chem.* 282:7991 (2007)). However, the inhibition of glucose production by this pathway is not completely clear.

Glucose production depends on autophagy, a regulated mechanism of intracellular degradation that is inhibited by insulin (Amherdt et al., *J. Clin. Invest.* 54:188 (1974)). Autophagy provides the biochemical intermediates for glucose production through the hydrolysis of proteins, glycogen and triglycerides (Mortimore et al., *Annu. Rev. Nutr.* 7:539 (1987); Kotoulas et al., *Pathol. Res. Pract.* 202:631 (2006); Singh et al., *Nature* 458:1131 (2009)). Insulin inhibition of autophagy in isolated hepatocytes is linked to the activation of mTOR (Blommaart et al., *J. Biol. Chem.* 270:2320 (1995); Kanazawa et al., *J. Biol. Chem.* 279:8452 (2004)). Hence, reports that AMPK, an essential mediator of adiponectin action, inhibits mTOR and stimulates autophagy are perplexing (Shaw et al., *Cancer Cell* 6:91 (2004); Meley et al., *J. Biol. Chem.* 281:34870 (2006); Xu et al., *Cell Death Differ.* 14:1948 (2007); Liang et al., *Nat. Cell Biol.* 9:218-(2007); Meijer et al., *Autophagy* 3:238 (2007); Cheng et al., *J. Biol. Chem.* 279:15719 (2004); Hoyer-Hansen et al., *Mol. Cell.* 25:193 (2007)).

The present invention addresses previous shortcomings in the art by providing a novel polynucleotide and polypeptide that connects insulin, adiponectin, and glucose production and that can be used for diagnostic and therapeutic methods.

SUMMARY OF THE INVENTION

The present invention is based, in part, on the identification of a novel polypeptide named Suppressor of Glucose by Autophagy (SOGA), also known as Target of Adiponectin (TOA), and the role it plays in insulin and adiponectin signaling and glucose production. The invention is based further on the use of this polypeptide, polynucleotides encoding the polypeptide, and inhibitors thereof, in the regulation of glucose production and the monitoring and treatment of metabolic disorders related to glucose levels, such as diabetes.

Accordingly, as one aspect, the invention provides an isolated polynucleotide selected from the group consisting of:

(a) a polynucleotide comprising a nucleotide sequence at least 70% (e.g., 75%, 80%, 85%, 90%, 95%, 97%, 98%, 99%, 100%) identical to a nucleotide sequence selected from the group consisting of SEQ ID NOS:1 and 3 and encoding a functional SOGA polypeptide;

(b) a polynucleotide that hybridizes to a nucleotide sequence selected from the group consisting of SEQ ID NOS:1 and 3 under stringent hybridization conditions and encodes a functional SOGA polypeptide;

(c) a polynucleotide encoding a functional SOGA polypeptide comprising an amino acid sequence at least 70% (e.g., 75%, 80%, 85%, 90%, 95%, 97%, 98%, 99%, 100%) identical to an amino acid sequence selected from the group consisting of SEQ ID NOS:2 and 4; and (d) a functional fragment of any of (a) to (c).

The invention further relates to vectors and cells comprising the polynucleotides of the invention, and methods of recombinantly expressing the polypeptides of the invention.

Another aspect of the invention relates to isolated SOGA polypeptides or functional fragments thereof encoded by the isolated polynucleotides of the invention. Functional fragments include, without limitation, C-terminal fragments of about 80 kDa and about 25 kDa. In some embodiments, the polypeptide is part of a fusion protein.

A further aspect of the invention relates to agents that inhibit the expression and/or activity of SOGA polypeptides or polynucleotides, including antibodies, antisense oligonucleotides, ribozymes, siRNAs, and small molecules.

An additional aspect of the invention relates to pharmaceutical compositions comprising the polypeptides, polynucleotides, or inhibitory agents of the invention.

A further aspect of the invention relates to non-human animals genetically modified to express the polypeptide of the invention or to inhibit expression of the polypeptide of the invention.

Another aspect of the invention relates to methods of decreasing glucose production in a cell or decreasing autophagy in a cell, comprising contacting the cell with the polypeptides or polynucleotides of the invention.

A further aspect of the invention relates to methods of decreasing blood glucose levels in a subject or of increasing insulin sensitivity in a subject, comprising delivering to the subject the polypeptides or polynucleotides of the invention.

Another aspect of the invention relates to methods of increasing glucose production in a cell or increasing autophagy in a cell, comprising contacting the cell with an agent that decreases the expression and/or activity of the polypeptides or polynucleotides of the invention.

Another aspect of the invention relates to methods of increasing blood glucose levels in a subject or of decreasing insulin sensitivity in a subject, comprising delivering to the subject an agent that decreases the activity of the polypeptides or polynucleotides of the invention.

An additional aspect of the invention relates to a method of measuring the response of a subject to a treatment for diabetes, comprising determining the circulating level of the polypeptides of the invention in the subject after administration of the treatment and comparing it to the circulating level of the polypeptide in the subject before administration of the treatment.

Another aspect of the invention relates to a method of predicting the clinical outcome of a diabetes treatment in a subject, comprising determining the circulating level of the polypeptide of the invention in the subject after administration of the treatment and comparing it to the circulating level of the polypeptide in the subject before administration of the treatment.

Another aspect of the invention relates to a method of identifying an agent that binds to the polypeptides of the invention, comprising contacting the polypeptide or a functional fragment thereof with a test agent under conditions whereby binding between the polypeptide or a functional fragment thereof and the test agent can occur; and detecting binding between the polypeptide or a functional fragment thereof and the test agent.

An additional aspect of the invention relates to a method of identifying an agent that modulates the activity of polypeptides of the invention, comprising contacting the polypeptide or a functional fragment thereof with a test agent under conditions whereby modulation of the activity of the polypeptide or a functional fragment thereof can occur; and detecting modulation of the activity of the polypeptide or a functional fragment thereof upon contact with the test agent as compared to activity of the polypeptide or a functional fragment thereof in the absence of contact with the test agent.

A further aspect of the invention relates to a kit comprising a reagent for determining the expression and/or activity of the polypeptides and/or polynucleotide of the invention.

BRIEF DESCRIPTION OF THE DRAWINGS

FIG. 5 shows that the concentration of SOGA in plasma corresponded with circulating levels of adiponectin.

FIG. 10 show the sequence (SEQ ID NO:2) and predicted functional domains of SOGA.

FIGS. 13A-13B show detection of recombinant SOGA.

FIGS. 14A-14D show the circulating levels of adiponectin and SOGA in humans and mice.

DETAILED DESCRIPTION OF THE INVENTION

Figure 1:
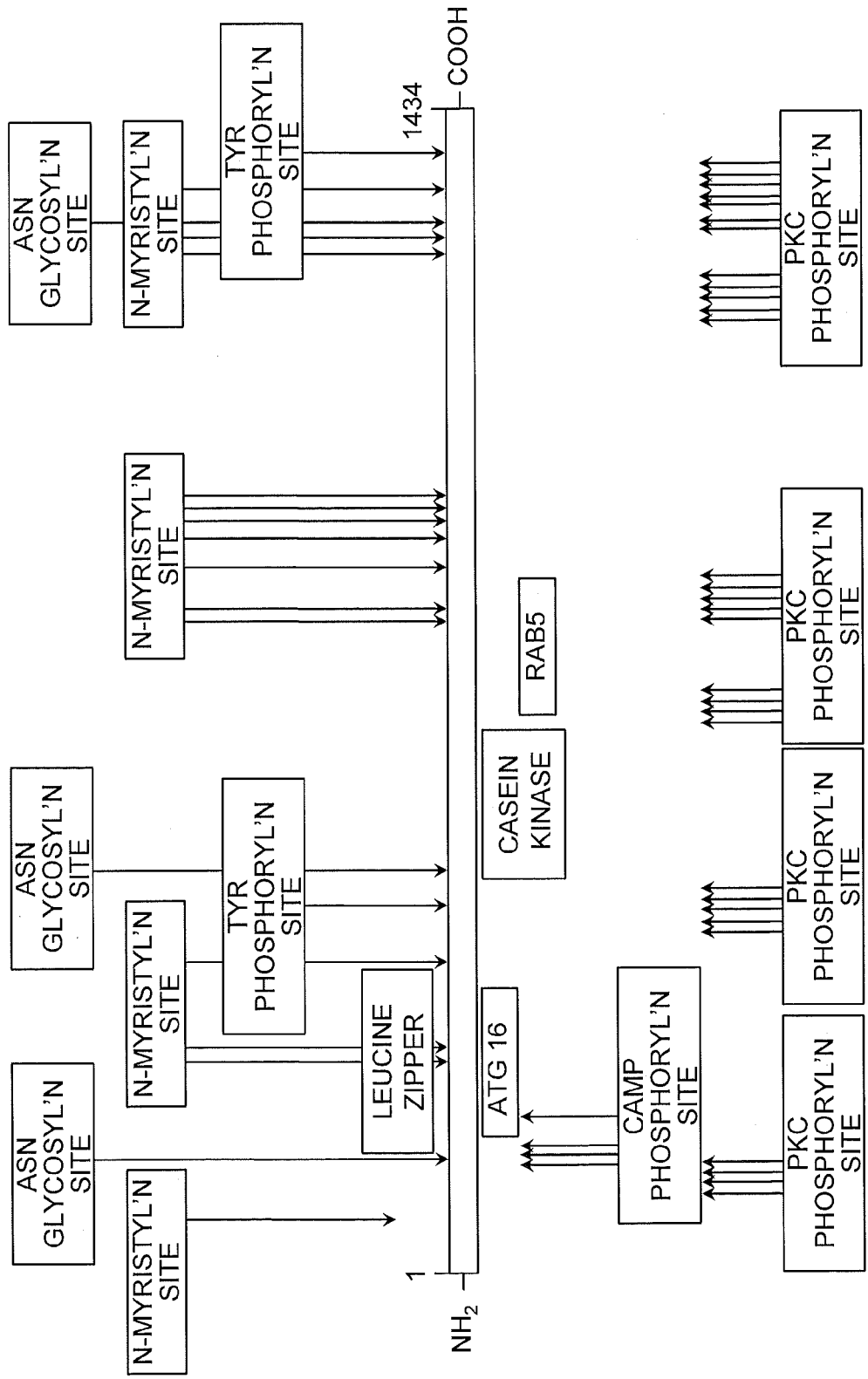
FIG. 1 shows an amino acid sequence analysis of SOGA for conserved functional domains.

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

I. Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in the ability to inhibit glucose production of at least about 50% or more as compared to the activity of a polypeptide consisting of the recited sequence.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject (e.g., in the case of diabetes, reduction in glucose levels or increase in insulin sensitivity). Those skilled in the art will appreciate that the therapeutic effects need not be complete or curative, as long as some benefit is provided to the subject.

By the terms "treat," "treating," or "treatment of," it is intended that the severity of the subject's condition is reduced or at least partially improved or modified and that some alleviation, mitigation or decrease in at least one clinical symptom is achieved.

The term "control sample," as used herein, refers to a tissue or cell sample that is used to compare the level of expression and/or activity of a SOGA polypeptide to the level of expression and/or activity in a sample of interest. The control sample may be, for example, from a normal (i.e., non-diseased) portion of the same tissue or cell type in the subject, from a different tissue or cell type in the subject, from a matched individual, or may be a standard derived from the average of measurements taken from a population of subjects. In another embodiment, the control sample may be from the disease tissue of the subject, e.g., at the time of diagnosis, prior to treatment, or after a stage of treatment.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" can refer to a nucleic acid or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose. In certain embodiments, the polypeptide is at least about 50% pure, e.g., at least about 60%, 70%, 80%, 90%, 95%, 96%, 97%, 98%, or 99% or more pure.

An isolated cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, 250, 300, 400, 500, or more consecutive nucleotides of a nucleic acid according to the invention. In some embodiments, such fragments can comprise, consist essentially of, and/or consist of oligonucleotides having a length of less than about 8, 10, 12, 15, 20, 25, 30, 35, 40, 45, 50, 75, 100, 150, 200, 250, 300, 400, or 500 consecutive nucleotides of a nucleic acid according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, 300, 400, 500, or more consecutive amino acids of a polypeptide or amino acid sequence according to the invention. In some embodiments, such fragments can comprise, consist essentially of, and/or consist of peptides having a length of less than about 8, 10, 12, 15, 20, 25, 30, 35, 40, 45, 50, 75, 100, 150, 200, 250, 300, 400, or 500 consecutive nucleotides of a nucleic acid according to the invention.

The term "functional SOGA polypeptide," as applied herein, refers to a polypeptide that substantially retains at least one biological activity normally associated with the naturally occurring SOGA polypeptide (e.g., the ability to inhibit glucose production, protein binding, ligand or receptor binding). In particular embodiments, the "functional" polypeptide substantially retains all of the activities possessed by the naturally occurring polypeptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and suppression of glucose production can be measured using assays that are well known in the art and as described herein. In certain embodiments, the "activity" of a SOGA polypeptide is defined as the ability to inhibit glucose production in a population of isolated hepatocytes (either primary hepatocytes or a hepatocyte cell line).

The term "functional fragment," as applied to a polypeptide, refers to a fragment that substantially retains at least one biological activity of the full length polypeptide, e.g., the ability to inhibit glucose production. By "substantially retains" biological activity, it is meant that the fragment retains at least about 20%, 30%, 40%, 50%, 60%, 75%, 85%, 90%, 95%, 97%, 98%, 99%, or more, of the biological activity of the full length polypeptide (and can even have a higher level of activity than the full length polypeptide). A "non-functional" fragment is one that exhibits little or essentially no detectable biological activity normally associated with the polypeptide (e.g., at most, only an insignificant amount, e.g., less than about 10% or even 5%).

The term "functional fragment," as applied to a polynucleotide, refers to a polynucleotide that encodes a functional fragment of a polypeptide.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, and adenovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., *Canadian Patent Application No.* 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. USA* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. It is clear that directing transfection to particular cell types would be particularly preferred in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in viva as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass both peptides and proteins, unless indicated otherwise.

A "fusion protein" is a polypeptide produced when two heterologous nucleotide sequences or fragments thereof coding for two (or more) different polypeptides not found fused together in nature are fused together in the correct translational reading frame. Illustrative fusion polypeptides include fusions of a polypeptide of the invention (or a fragment thereof) to all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

II. SOGA Polynucleotides and Polypeptides

In one aspect, the invention relates to an isolated polynucleotide encoding a SOGA polypeptide or a functional fragment thereof. In one embodiment, the SOGA polypeptide is a mammalian SOGA polypeptide, e.g., human or mouse. The cDNA, polypeptide, and genomic sequences of mouse SOGA have been deposited in GenBank under Accession No. H977045 and are disclosed herein as SEQ ID NOS:1, 2, and 10, respectively. The cDNA, polypeptide, and genomic sequences of human SOGA are disclosed herein as SEQ ID NOS:3, 4, and 11, respectively. The polynucleotide can comprise cDNA sequences, genomic sequences, synthetic sequences, or combinations thereof.

```
Mouse SOGA cDNA Sequence
                                                             (SEQ ID NO: 1)
agttgggcctggagctggcgctgagcagcgacgccgagtctgcggcgggcggccggcgg    60 ggacccgcaccgggcagccgccccagccagcgcagtcggggcagcagcctccgcggcccc  120 ccgcctccccggatgagccgtcggtggccgcatcgtcggtgggcagcagccgcttgccat  180 tcagcgcctcgctagccttctccgacctcaccgaggagatgctggactgtgggcccggag  240 gcttggtgcgggagctggaagagctgcgttccgagaacgactatctcaaggatgagattg  300 aggagctacgggctgagatgctggagatgcgggatgtctacatggaggaagacgtgtatc  360 agctgcagtaccgactgcgtaaggctgagcgccgcagcctccgcgctgcccagacaggcc  420 aggttgatggggaactcatccgaggtctggaacaggacgtcaaggtctctaaggacatct  480 ccatgcggcttcacaaggagctggaggtggtggagaagaagcggatgaggctggaggagg  540 agaacgaggggcttcgacagaggctcattgagacagagctggccaagcaggtgctacaga  600 cggagctggatcgtcccagagagcattccttgaagaaaagaggaacccggtctctgggga  660 agacagataagaagcctactgcacaggaggatagtgcagacctgaagtgccagctgcatt  720 ttgcaaaggaggagtcggccctcatgtgcaagaagctcaccaagttggctaaggagaacg  780
```

-continued

```
acagcatgaaggaggagctgctcaagtacagatcgctctatggggacctggatgcagccc   840
tgtcggcagaggagctggcggatgctccgcactcccgtgagactgagctgaaggtgcacc   900
tgaagctggtggaggaggaggccaacctgctgagccggcgcatagtggagctggaggtgg   960
agaaccgtggcctgcgagccgagatggacgacatgaaggaccacgggggtggcgggggtc  1020
ccgaggccaggctggccttctcttctctgggtggtgagtgcggggagagcctagccgagt  1080
tgcggcgccacctgcagttcgtggaagaggaggctgagctgctgaggcgctcctcagctg  1140
agctggaggaccagaacaagttgctgctgaacgagctggccaaataccgctcggagcacg  1200
agctggacgtgacgctgtcggaggacagctgctccgtgctcagcgagccctcgcaggagg  1260
agctggcagccgccaagctgcagatcggcgagctcagcggcaaggtcaagaagctgcagt  1320
atgagaaccgcgtgctcctctccaatctgcagcgctgtgacctggcctcctgccagagca  1380
cacgccccatgctggagacggacgctgaggctggggactctgcgcagtgcgtgcctgccc  1440
ctctgggtgagacgctggagcccacgccgcccggctgtgcagggcccgtgaagccgagg   1500
cgctgcccggcctacgggagcaggccgctttggtcagcaaggccatcgacgtcctggtgg  1560
ctgatgccaatggcttctcagtcggcctccgcctgtgcctggacaatgagtgtgctgact  T620
tgcgactgcacgaggcgcctgacaacagcgagggccccagggatgccaagctcatccacg  1680
ccatcctggtgcggctgagtgtgttgcaacaggagctgaacgccttcacccgcaaggcag  1740
atgtggccttggggagctctgcaaggagcagcctgagcccttccctgctctgcctgcct   1800
tgggctcccagggccctgctaaggagatcacgctgtccaaagaccttggctctgacttcc  1860
agccacctgacttcagagacctgcttgagtgggagcccaggatccgagaggccttccgta  1920
ccggggacttggagtccaagcctgaccctagtcggaacttcaggccctaccgagctgaag  1980
ataacgattcttatgcctctgagatcaaggatcttcagctggtcctggccgaggccacg   2040
acagcctccggggcttgcaagagcagctgtcccaggagcggcagctccggaaggaggagg  2100
ctgacagcttcaaccagaaaatyguccagctgaaggaagaccagcagagggcgctgctga  2160
gacgggagtttgagctgcagagtctgagcctccagcggcgactggagcagaagttctgga  2220
gccaagagaagaacatcctggtgcaggagtcccagcagttcaagcacaactttctgctgc  2280
tcttcatgaagctccggtggttcctgaagcgctggcggcagggcaaggttctgcccagcg  2340
aagaggatgacttcctggaggtgaacagcatgaaggaactgtacctgctgatggaggaag  2400
aggagatgaacgcccagcactcggataacaaggcctgcacaggggagagctggacccaga  2460
cacgcctaatgagtgcatcaagaccctggccgacatgaaggtcaccctgaaggagctgt   2520
gctggctgctccaggacgagcgtcggggtctgactgaacttcagcagcagatcgcaaagg  2580
ccaaggccacctgggagacagagcgtgcagagctcaagggccacgcctcgcagatgggagc  2640
tgaaggctgggaagggtgccagtgagaggcccgggcctgactggaaggctgcactgcaga  2700
gagagcgggaggagcagcaacacctcctggcagagtcctacagcgccgtcatggagctga  2760
cgaggcagctgcagctgagcgagcgccactggagacaggagaagctgcagctggtggagc  2820
ggctgcaggagaaaagcagcaggtggagcagcaggtgaaggagctgcagaaccgcctca   2880
gtcagttgcagaaggctgccgagccctgggtcctgaagcactcagacatggagaagcaag  2940
acaacagctggaaagaggcacgaagtgagaagacccatgacaaggagggtgtctctgaag  3000
ctgagctcggggggaactggctuaaagaggaccaaatcagtctcctccatgtctgagtttg  3060
aaagtttgctcgactgctccccgtaccttgctggcggggatgcccggaacaagaagctgc  3120
ccaacggccctgcttttgcctttgtgagtactgagccagtggagcctgagaaagacgcca  3180
aggagaaggcggggctttccacccgggactgtagccacattggtagcttggcctgtcagg  3240
```

-continued

```
aacctgcagggagacagatgcagcgcagctacacggctccagacaagacgggaatccgag    3300
tctactatagtccgccagtggctcggcgcctgggtgtccctgtggtccatgacaaggagg    3360
gcaagatcctcattgagccaggcttcctcttcactaccgccaagcccaaggagccagccg    3420
aggctgacgggctggccgagagctcctacagccggtggctttgcaatttctcccggcagc    3480
ggctggatggaggatccggggccagcacctcgggttccggacctgctttccccgccttgc    3540
atgactttgagatgtcgggcaacatgagtgacgacatgaaggagatcaccaactgcgtgc    3600
ggcaggccatgcgctccggctctctggagaggaaggtaaagaacacatccagccagacgg    3660
taggcgtggccaccgtgggcacccagaccattcggacggtcagtgtaggtcttcagaccg    3720
acccaccccgcagcagcctccacagcaagagctggtcaccccgcagctcctcgcttgtgc    3780
ctgtgcgcagcaagcagatctcttcctccctggacaaggtccattctcgcattgagcggc    3840
catgttgctcgcccaagtacggctcacccaagctccagagacgatcggtgtccaagctgg    3900
atagcaccaaggaccgcagcctgtggaacctgcaccagggcaagcaaaatggctccgcct    3960
gggctcgctccaccaccacacgggatagccctgtactgaggaacatcaatgatgggcttt    4020
ctagcctctctagtgtggtggagcactctgggagcaccgagtctgtgtggaaactgggca    4080
tgtctgaggcccgaaccaaacctgagcctcccaagtatggcattgttcaggagttcttcc    4140
ggaacgtgtgtggccgggcaccgagccccactactgcagcaggcgaggaaagctgcaaga    4200
aaccagagccccttcgccagccagctaccatcaacccgagggtgtatccaggatcctga    4260
acaagaaggcggccaaggcaggtggtagcgaagaggtcagacccaccatgctgtcccagg    4320
tggggaaggatggcatccttcgggatggagatggatccttgatccttcccagtgaggatg    4380
ccgtatgtgactgtagcgcccagtcacttgcctcctgcttcatccggccatcccgcaaca    4440
ccatccggcactctccttccaagtgcaggctgcacccttcagagtcaggctggggcgggg    4500
aggagagggcagctcccagtgagtccctgagcaaccaagcacccacctcaagcagccca    4560
gaccccCggagatgaggcaagggctcgtgtcctcagcctcaghccatccaggaggaatggc    4620
agctgtgccactgccacagaagagctttcacattaaggtaaagcaaggtgtcttgctgac    4680
tgctgggcagtgacctctgatttccaggggaagaca                           4716
```

Mouse SOGA Polypeptide Sequence
(SEQ ID NO: 2)

```
MLDCGPGGLVHKLEELRSENDYLKDEIEELRAEMLEHKDVYMEBDVYQLQYRLRKAERRS    60
LRAAQTGQVDGELIRGLEQDVKVSKDISMRLKKELEVVEKKRMRLEEENKGLRQRLIETE    120
LAKQVLQTELDRPREHSLKKRGTRSLGKTDKKPTAQEDSADLKCQLHKAKEESALMCKKL    180
TKLAKENDSHKEELLKYRSLYGDLDAALSAEELADAPHSRETEIKVHLKLVEEEANLLSR    240
RIVELEVKNRGLRAEMDDMKDHGGGGGPEARLAFSSLGGECGESLAELRRHLQFVEREAE    300
LLRRSSAELEDQNKLLLNELAKYRSEHELDVTLSEDSCSVLSEPSQEELAAAKLQIGELS    360
GKVKKLQYENRVLLSNLQRCDLASCQSTRPMLETDAEAGDSAQCVPAPLGETLEPHAARL    420
CRAREAEALPGLHKQAALVSKAIDVLVADANGFSVGLRLCLDNKCADLRLHEAPDNSEGP    480
RDAKLIHAILVRLSVLQQELNAFTRKADVALGSSGKEQPEPKPALPALGSQGPAKEIMLS    540
KDLGSDFQPPDFRDLLEWEPRIREAFRTGDLESKPDPSRNFRPYRAEDNDSYASEIKDLQ    600
LVLAEAHDSLRGLQEQLSQERQLRKKEADSPNQKMVQLKEDQQRALLRREFELQSLSLQR    660
RLEQKTOSOEKNILVQKSQQPKHNFLLLFMKLRWFLKRWRQGKVTPSKKDDFLEVNSMKE    720
LYLLMEEEEMNAQHSDNXACTGESWTQNTPNECIKTLADMKVTLKSLCWLLQDERRGLTE    780
LQQQFAKAKATWETERAELKGHASQMELKAGKGASERPGPDWKAALQREREEQQHLLAES    840
```

-continued

```
YSAVMELTRQLQLSERHWSQEKLQLVERLQGEKQQVEQQVKELQNRLSQLQKAAEPWVLK   900
HSDMEKQDNSWKEAHSEKTHDKEGVSEAELGGTGLKRTKSVSSMSEFESLLDCSPYLAGG   960
DARNKKLPNGPAFAFVSTEPVEPEKDAKEKAGLSTRDCSHIGSLACQBPAGRQMQRSYTA  1020
PDKTGIRVYYSPPVARRLGVPVVHDKEGKILIEPGFLFTTAKPKKSAEADGLAESSYSRW  1080
LCNFSRQRLDGGSGASTSGSGPAFPALHDFEMSGNMSDDMKEITNCVRQAMRSGSLERKV  1140
KNTSSQTVGVATVGTQTIRTVSVGLQTDPPRSSLHSKSWSPRSSSLVSVRSKQISSSLDK  1200
VHSRIERPCCSPKYGSPKLQRRSVSKLDSTKDRSLWNLHQGKQNGSAWARSTTTRDSPVL  1260
RNINDGLSSLFSVVEHSGSTKSVWKLGHSEARTKPEPPKYGIVQKKFRNVCGRAPSPTTA  1320
AGEESCKKPEPLSPASYHOPEGVGRILNKKAAKAGGSEEVRPTMLSQVGKDGILRDGDGS  1380
LILPSEDAVCDCSAQSLASCFIRPSRKTIRHSPSKCRLHPSESGWGGEERAAPQ        1434
```

Human SOGA cDNA Sequence (SEQ ID NO: 3)

```
cgctgagcagcgacgccgagtccgcggccgggggcccggcggggtccgtacggggcagc    60
cggcccagcccgcgccctccgcgcagcagccccgcggccgcccgcctccccggacgagc   120
cgtcggtggccgcgtcgtcggtgggcagcagccgcttgccgctcagcgcctcgcttgcct  180
tctccgacctcaccgaggagatgctggactgcggggccagcggcttggtgcgggagctgg  240
aggagctgcgctcggagaacgactatctcaaggacgagattgaggagctgcgggccgaga  300
tgccggagatgcgggacgtctatatggaggaggacgtgtatcagctgcagtaccggctgc  360
gcaaagccgagcgccgcagtctccgtgccgcccagaccggccaggtggacggcgagctta  420
tccgtggtctggagcaggatgtcaaggtctctaaggacatctccatgcggctgcataagg  480
agctcgaggtggtggagaagaaacgggcgcggccggaggaggagaacgaagagcttcgtc  540
agcggctcatcgagactgagctggctaagcaggtgctgcagacggagctggagcgaccga  600
gagagcattccttgaagaaaagaggaacccgctccctggggaaggccgataagaagactt  660
tggtgcaggaggacagtgcagacctgaagtgccagttgcactttgcaaaggaggagtcag  720
ccctcatgtgcaagaagctcactaagcttgccaaggagaatgacagcatgaaggaggagc  780
tgcCgaagtaccgctcgctctatggggacctggacagcgcgctgtcagccgaggagctgg  840
ccgatgcccccactcgcgggagaccgagctgaaggtgcacctgaagctggtggaggagg   900
aagccaacctgccgagccgccgcatcgtggagctggaggtggagaaccgaggcctgcggg  960
ctgagatggacgacatgaaggatcatggaggtggctgtgggggtcctgaggcacgcctgg 1020
ccCtctccgcgctgggtggcggagagtgcggggagagcttggcagagctgcggcgacacc 1080
tgcagtttgtcgaagaggaggccgagctgcCgcggcgctcctctgccgagctcgaggacc 1140
agaacaagctgctgctgaacgagctggccaagttccgctcggagcacgagctggacgtgg 1200
cgctgtcggaggacagctgttctgtgctcagcgaaccttcacaggaggagctggcggccg 1260
ccaagctgcagatcggcgagctcagcggcaaggtcaagaagcLgcagtacgagaaccgcg 1320
tgctcctctccaacctccagcgctgtgacctcgcctcctgccagagtacgcggcccatgc 1380
tggagacggacgccgaggccgggactctgcccagtgtgtgcctgctcccctgggcgaga  1440
cacacgagCcccacgcggtccgactctgcagagccagggaggccgaggtgctgcctgggc 1500
tgagagagcaggccgcccctggtcagtaaggccatcgatgtcctggtggctgatgccaatg 1560
gctccacggctggcctccggctgtgtctggacaacgagtgtgctgacttccggctgcatg 1620
aggccccgacaacagcgagggccccagggacaccaagctcatccatgccatcctggtgc  1680
gcctgagcgtgctgcagcaggagctgaatgccttcacgcggaaggcagatgcagtcctcg 1740
ggtgctctgtcaaggaacagcaggagtccttctcatcactgccccccttgggctcccagg 1800
```

```
ggctctctaaggagattcttctggcaaaagaccttggctcagactttcagccacctgact  1860
tcagggacctgccggaatgggagcccaggatccgagaggcttccgcactggtgacttgg   1920
actctaagcccgaccccagccggagcttcaggccttaccgagctgaagacaatgattcct  1980
atgcctctgagatcaaggagctgcagctggtgctggctgaggcccacgacagcctccggg  2040
gcttgcaagagcagctctcccaggagcggcagctacgaaaggaggaggccgacaatttca  2100
accagaaaatggtccsgotgaaggaggaccagcagagggcgctcctgaggcgggagtttg  2160
agctgcagagtctgagcctccagcggaggctggagcagaaattctggagccaggagaaga  2220
acatgccggtgcaggagtcccagcaattcaagcacaacttcctgctgctcttcatgaagc  2280
tcaggtggttcctcaagcgctggcggcagggcaaggttttgcccagcgaaggggatgact  2340
tcctcgaggtgaacagcatgaaggagctgtacttgctgatggaggaagaggagataaacg  2400
ctcagcattctgataacaaggcctgcacggggacagctggacccagaacacgcccaatg   2460
agtacatcaagacactggccgacatgaaggtgacgctgaaggagctgtgctggctgctcc  2520
gggatgaacgccgtggtctgacggagcttcagcaacagttttgccaaggccaaggctacct 2580
gggagacagagcgggcagagctcaagggccatacctcccagatggagctgaagacaggga  2640
agggggccggggagcgggcagggcccgactggaaggcagccctacagcgggagcgtgagg  2700
agcagcagcacctcctagctgagtcctacagcgctgtcatggagctgactcggcagctgc  2760
agaccagtgagcgcaactggagccaggaaaagctgcagctggtggagcggctgcagggtg  2820
agaageagcaggtggagcagcaggtgaaggagctgcagaaccgcctaagccagctgcaga  2880
aggctgccgacccctgggtcctgaagcactcggagctggagaagcaggacaacagctgga  2940
aggagacacgcagtgagaagatccacgacaaggaggctgtttccgaagttgagcttggag  3000
gaaatggtttaaagagaaccaaatctgtttcttccatgtctgagtttgaaagtttgctcg  3060
actgttcccettacctcgctggcggagatgcccggggcaagaagctgcctaacaaccctg  3120
cctttggctttgtgagctccgagccaggggatccagagaaagacaccaaggagaagcctg  3180
ggctctcgtcgagggactgcaaccacctgggtgccctggcctgccaggaccccccaggga  3240
ggcagatgcagcgcagctacacggctcctgacaagaegggcatccgagtctactatagtc  3300
ccccggtggcccggcgcctcggagtccctgtggttcatgacaaagagggcaagatcatta  3360
tcgagcccggcttcctcttcaccacagccaagcccaaagagtcggccgaggctgatgggc  3420
tggctgagagctcctatggtcggtggctctgcaacttctcacggcagcgcctggacggag  3480
gctcagcgggcagccctcggcggccgggcctggcttcccagcggccctgcatgactttg   3540
agatgtcaggcaacatgagtgatgacatgaaggagatcaccaactgtgtgcgccaggca   3600
tgcgctccggctcactggagaggaaagtgaagagcacatccagccagacggtgggcctgg  3660
ccagtgtgggcacacagaccatccgcacggtcagcgtgggcctgcagaccgacccaccc   3720
gcagcagcctccatggcaaggcctggtcaccccgcagctcttcgctcgtgtctgtgcgca  3780
gcaagcagatctcctcctccctggacaaggtccattcgcgcatcgagcggccctgctgct  3840
cccccaagtatggctcaccaaagctccagaggcggtctgtgtccaagctggacagcagca  3900
aggaccgcagcctgtggaacctgcaccagggcaagcagaacggctcggcctgggcccgct  3960
ccaccaccacgcgggacagccctgtattgagaaacatcaacgatggactctccagcctct  4020
tcagtgtggtggagcactcagggagcacggagtctgtctggaaactaggcatgtctgaga  4080
cgcgggccaagcccgagcctcccaagtacggcattgtgcaggaattcttccgtaatgtgt  4140
gtggccgggcaccgagccccacctcatcagcaggagaggagggcaccaagaagccagagc  4200
```

-continued
```
ccctctccccagccagctaccatcagccagagggtgtggccaggatcctgaacaagaagg 4260 cagccaagtttgggcagcagtgaggaggtcagactcaccatgctcccccaggtggggaagg 4320 atggtgCcctccgggacggagatggagccgtggtccttcccaatgaggacgctgtttgtg 4380 actgtagtacccagtctctcacctcctgcttcgcccgatcgCcccgctctgccatccgcc 4440 artctccttccaagtgcaggctgcacccttcagagtccagctggggtggggaggagaggg 4500 cactcccccccagcgagtgacagagcagccaagctccccgcctcaaccagcccagcccct 4560 ggatagcagaagggaaccagcagagacgagacgaggtgaggcgaggggctgtgtcctcag 4620 cattgcctggccctggagggacagcagtgatgccactgccagaatgcagctttcacatca 4680 aggtaaagccgggtctcctgctggcccctgggtggtgagcttcgacttcccaggggaagg 4740 cagtgagtgggagagagaccaaacctgggcttcccaagcatccactgagagatctgtcaa 4800 gagccgatccctgggtcctaagagagagccttgcctggttctgcccatgccaccctcttg 4860 ga                                                         4862
```

Human SOGA Polypeptide Sequence
(SEQ ID NO: 4)
```
MLDCGPSGLVRELEELRSENDYLKDEIEBLRAEMLEMRDVYMKEDVYQLQYRLHKAERRS    60
LRAAQTGQVDGELIRGLEQDVKVSKDISMRLHKELEVVEKKRARLEEENEELRQRLIETE   120
IAKQVLOTELERPRKHSLKKRGTRSLGKADKKTLVQEDSADLKCQLHKAKEESALMCKKL   180
TKLAKENDSMKEELLKYRSLYGDLDSALSAEELADAPHSRETELKVHLKLVEEEANLLSR   240
RIVELEVENRGLRAEMDDMKDHGGGCGGPEARLAFSALGGGECGESLAELRRHLQFVEEE   300
AELLRRSSAKLEDQNKLLLNELAKPRSKHRLDVALSEDSCSVLSEPSQKKIAAAKLQIGE   360
LSGKVKKLQYENRVLLSNLQRCDIASCQSTRPMLETDAEAGDSAQCVPAPLGETHESHAV   420
RLCRAREAEVLPGLREQAALVSKAIDVLVADANGFTAGLRLCLDNECADFRLHEAPDNSE   480
GPRDTKLIHArLVRLSVLQQELNAFTRKADAVLGCSVKEQOESFSSLPPLGSQGLSKEIL   540
LAKDLGSDFQPPDFRDLPEWEPRIREAFRTGDLDSKPDPSRSPRPYRAEDNOSYASEIKE   600
LQLVLAKAHDSLRGLQEQLSQERQLRKKEADNFNQKHVQLKEDQQRALLRREFELQSLGL   660
QRRLEQKFWSQEKNMLVQESQQFKHNFLLLFMKLRWFLKRWRQGKVLPSEGDDFLEVNSM   720
KELYLLMEEEEINAQHSDNKACTGDSWTQNTPNEYIKTLADMKVTLKELCWLLRDERRGL   780
TELQQQFAKAKATWETERAELKGHTSQMELKTGKGAGERAGPDWKAALQREREEQQHLLA   840
KSYSAVMELTROLQISERNWSQKKLQLVERLQGEKQQVEQQVKELQNRLSQLQKAADPWV   900
LKHSELEKQDNSWKETRSEKIHDKEAVSEVELGGNGLKRTKSVSSMSEFESLLDCSPYIA   960
GGDARGKKLPNNPAFGFVSSEPGDPEKDTKEKPGLSSHUCNHLGALACODPPGRQMQRSY  1020
TAPDKTGIRVYYSPPVARRLGVPVVHDKEGKIIIEPGFLFTTAKPKESAKADGLAESSYG  1080
RWLCNFSRQRLDGGSAGSPSAAGPGFPAALHDFEMSGNMSDDMKEITNCVRQAMRSGSLE  1140
RKVKSTSSQTVGLASVGTQTIRTVSVGLQTDPPRSSLHGKAWSPRSSSLVSVRSKQTSSS  1200
LDKVHSRIERPCCSPKyGSPKLQRRSVSKLDSSKDRSLWNLHQGKQNGSAWARSTTTRDS  1250
PVLRNINDGLSSLFSVVEHSGSTESVWKLGMSKTRAKPEPPKYGIVQEFFRNVCGRAPSP  1320
TSSAGEEGTKKPEPLSPASYHQPEGVARILNKKAAKLGSSEKVRLTMLPQVGKDGVIRDG  1380
DGAVVLPNEDAVCDCSTQSLTSCFARSSRSAIRHSPSKCRLHPSESSWGGEERALPPSE   1439
```

One embodiment of the invention is an isolated polynucleotide selected from the group consisting of:

(a) a polynucleotide comprising a nucleotide sequence at least 70% (e.g., 75%, 80%, 85%, 90%, 95%, 97%, 98%, 99%, 100%) identical to a nucleotide sequence selected from the group consisting of SEQ ID NOS:1 and 3 and encoding a functional SOGA polypeptide;

(b) a polynucleotide that hybridizes to a nucleotide sequence selected from the group consisting of SEQ ID NOS:1 and 3 under stringent hybridization conditions and encodes a functional SOGA polypeptide;

(c) a polynucleotide encoding a functional SOGA polypeptide comprising an amino acid sequence at least 70% (e.g., 75%, 80%, 85%, 90%, 95%, 97%, 98%, 99%, 100%) identical to an amino acid sequence selected from the group consisting of SEQ ID NOS:2 and 4; and (d) a functional fragment of any of (a) to (c).

In another embodiment, the isolated polynucleotide is selected from the group consisting of:

(a) a polynucleotide comprising a nucleotide sequence selected from the group consisting of SEQ ID NOS:1 and 3 or a fragment thereof that encodes a functional SOGA polypeptide;

(b) a polynucleotide encoding a functional SOGA polypeptide comprising an amino acid sequence selected from the group consisting of SEQ ID NOS:2 and 4 or a functional fragment thereof; and (c) a polynucleotide comprising a nucleotide sequence that differs from the nucleotide sequences of (a) or (b) above due to the degeneracy of the genetic code.

In one aspect, the invention relates to SOGA polypeptides and functional fragments or homologs thereof. The SOGA polypeptide can be from any species expressing SOGA, such as mammalian SOGA, e.g., human or mouse SOGA. As used herein, the term "homolog" is used to refer to a polypeptide which differs from a naturally occurring polypeptide by minor modifications to the naturally occurring polypeptide, but which significantly retains a biological activity of the naturally occurring polypeptide. Minor modifications include, without limitation, changes in one or a few amino acid side chains, changes to one or a few amino acids (including deletions, insertions, and substitutions), changes in stereochemistry of one or a few atoms, and minor derivatizations, including, without limitation, methylation, glycosylation, phosphorylation, acetylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., inhibition of glucose production), e.g., about 30%, 40%, 50% or more. SOGA activity can be measured as disclosed herein. Other biological activities may include enzyme activity, receptor binding, ligand binding, a cell signal transduction event, etc.

Functional fragments of SOGA polypeptide include any fragment that substantially retains at least one biological activity of full length SOGA polypeptide. In one embodiment, the functional fragment is a C-terminal fragment of SOGA. In certain embodiments, the C-terminal fragment begins immediately after the internal signal sequence of SOGA. In other embodiments, the functional fragment is a C-terminal fragment of about 80 kDa or 25 kDa.

In exemplary embodiments, the polypeptide comprises, consists essentially of, or consists of the amino acid sequence of the polypeptide disclosed herein and in the GenBank accession numbers listed above or a functional fragment thereof. In another embodiment, the isolated polypeptide comprises, consists essentially of, or consists of an amino acid sequence that is at least 70% identical, e.g., at least 75%, 80%, 85%, 90%, 95%, 96%, 97%, 98%, or 99% identical to the disclosed amino acid sequence or a functional fragment thereof (and polynucleotide sequences encoding the same).

The polypeptide of the invention also include functional portions or fragments (and polynucleotide sequences encoding the same). The length of the fragment is not critical as long as it substantially retains at least one biological activity of the polypeptide. Illustrative fragments comprise at least about 4, 6, 8, 10, 12, 15, 20, 25, 30, 35, 40, 45, 50, 75, 100, 150, 200, 250, 300, 400, 500, or more contiguous amino acids of a SOGA polypeptide.

Likewise, those skilled in the art will appreciate that the present invention also encompasses fusion polypeptides (and polynucleotide sequences encoding the same) comprising a SOGA polypeptide or a functional fragment thereof. For example, it may be useful to express the polypeptide (or functional fragment) as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the polypeptide may be produced, e.g., fusion proteins comprising maltose binding protein or glutathione-S-transferase. As another alternative, the fusion protein can comprise a reporter molecule. In other embodiments, the fusion protein can comprise a polypeptide that provides a function or activity that is the same as or different from the activity of the polypeptide, e.g., a targeting, binding, or enzymatic activity or function.

Likewise, it will be understood that the SOGA polypeptides specifically disclosed herein will typically tolerate substitutions in the amino acid sequence and substantially retain biological activity. To identify polypeptides of the invention other than those specifically disclosed herein, amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table.

TABLE 1

| Amino Acid | | | Codons |
|---|---|---|---|
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |
| Valine | Val | V | GTA GTC GTG GTT |

TABLE 1-continued

| Amino Acid | | | Codons |
|---|---|---|---|
| Tryptophan | Trp | W | TGG |
| Tyrosine | Tyr | Y | TAC TAT |

In identifying amino acid sequences encoding polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); praline (−1.6); histidine (−3.2); glutamate (−3.5); glutamine (−3.5); aspartate (−3.5); asparagine (−3.5); lysine (−3.9); and arginine (−4.5). Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Thus, the hydrophilicity of the amino acid (or amino acid sequence) may be considered when identifying additional polypeptides beyond those specifically disclosed herein.

In embodiments of the invention, the polynucleotide encoding the SOGA polypeptide (or functional fragment) will hybridize to the nucleic acid sequences specifically disclosed herein or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and conditions represented by a wash stringency of 50% formamide with 5×Denhardt's solution, 0.5% SDS and 1×SSPE at 42° C., respectively) to the polynucleotide sequences encoding the SOGA polypeptides or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the SOGA polypeptides have at least about 70%, 80%, 85%, 90%, 95%, 96%, 97%, 98%, 99% or higher sequence identity with the nucleic acid sequences disclosed herein and in the GenBank accession numbers listed above or functional fragments thereof and encode a functional polypeptide or functional fragment thereof.

Further, it will be appreciated by those skilled in the art that there can be variability in the polynucleotides that encode the polypeptides (and fragments thereof) of the present invention due to the degeneracy of the genetic code. The degeneracy of the genetic code, which allows different nucleic acid sequences to code for the same polypeptide, is well known in the literature (See, e.g., Table 1).

Likewise, the polypeptides (and fragments thereof) of the invention include polypeptides that have at least about 70%, 80%, 85%, 90%, 95%, 96%, 97%, 98%, 99% or higher amino acid sequence identity with the disclosed polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blastmustl/edu/blast/READMME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Those skilled in the art will appreciate that the isolated polynucleotides encoding the polypeptides of the invention will typically be associated with appropriate expression control sequences, e.g., transcription/translation control signals and polyadenylation signals.

It will further be appreciated that a variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polypeptide coding sequence can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.,* 4:432 (1997)); and the rapamycin-inducible system (Magari et al., *J. Clin. Invest.* 100: 2865 (1997)).

Other tissue-specific promoters or regulatory promoters include, but are not limited to, promoters that typically confer tissue-specificity in hepatocytes. These include, but are not limited to, promoters for albumin, hepatocyte nuclear factors, transthyretin, $\alpha_1$-antitrypsin, and the hepatitis B virus core promoter. In other embodiments, the promoters typically confer tissue specific in renal cells. These include, but are not limited to, promoters for ksp-cadherin, erythropoietin, γ-glutamyl transpeptidase, kidney androgen-regulated protein, vacuolar $H^+$-ATPase B1 subunit, and AQP2. In other embodiments, the promoters typically confer tissue specific in muscle cells, e.g., skeletal muscle and/or cardiac muscle. Skeletal muscle cell promoters include, but are not limited to, promoters for β-actin, Pitx3, creatine kinase, and myosin light chain. Cardiac muscle cell promoters include, but are not limited to, promoters for cardiac actin, cardiac troponin T, troponin C, myosin light chain-2, and α-myosin heavy chain.

Moreover, specific initiation signals are generally required for efficient translation of inserted polypeptide coding sequences. These translational control sequences, which can include the ATG initiation codon and adjacent sequences, can be of a variety of origins, both natural and synthetic.

The present invention further provides cells comprising the isolated polynucleotides and polypeptides of the invention. The cell may be a cultured cell or a cell in vivo, e.g., for use in therapeutic methods, diagnostic methods, screening methods, methods for studying the biological action of SOGA polypeptides, in methods of producing the polypeptides, or in methods of maintaining or amplifying the polynucleotides of the invention, etc. In another embodiment, the cell is an ex vivo cell that has been isolated from a subject. The ex vivo cell may be modified and then reintroduced into the subject for diagnostic or therapeutic purposes.

In particular embodiments, the cell is an untransformed cell or a cell from a cell line of a gluconeogenic tissue, such as liver, kidney, skeletal muscle, or cardiac muscle.

The isolated polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a SOGA polypeptide or functional fragment thereof operatively associated with the promoter, and, optionally, a termination sequence including a stop signal for RNA polymerase and a polyadenylation signal for polyadenylase.

Non-limiting examples of promoters of this invention include CYC1, E1TS3, GAL1, GAL4, GAL10, ADH1, PGK, P1105, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus $^{35}S$, CMV $^{35}S$ minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro baciliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, $\alpha$-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell $\alpha$-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

It will be apparent to those skilled in the art that any suitable vector can be used to deliver the polynucleotide to a cell or subject. The vector can be delivered to cells in vivo. In other embodiments, the vector can be delivered to cells ex vivo, and then cells containing the vector are delivered to the subject. The choice of delivery vector can be made based on a number of factors known in the art, including age and species of the target host, in vitro versus in vivo delivery, level and persistence of expression desired, intended purpose (e.g., for therapy or screening), the target cell or organ, route of delivery, size of the isolated polynucleotide, safety concerns, and the like.

Suitable vectors include plasmid vectors, viral vectors (e.g., retrovirus, alphavirus; vaccinia virus; adenovirus, adeno-associated virus and other parvoviruses, lentivirus, poxvirus, or herpes simplex virus), lipid vectors, poly-lysine vectors, synthetic polyamino polymer vectors, and the like.

Any viral vector that is known in the art can be used in the present invention. Protocols for producing recombinant viral vectors and for using viral vectors for nucleic acid delivery can be found in Ausubel et al., Current Protocols in Molecular Biology (Green Publishing Associates, Inc. and John Wiley & Sons, Inc., New York) and other standard laboratory manuals (e.g., Vectors for Gene Therapy. In: *Current Protocols in Human Genetics*. John Wiley and Sons, Inc.: 1997).

Non-viral transfer methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal derived systems, polylysine conjugates, and artificial viral envelopes.

In particular embodiments, plasmid vectors are used in the practice of the present invention. For example, naked plasmids can be introduced into muscle cells by injection into the tissue. Expression can extend over many months, although the number of positive cells is typically low (Wolff et al., *Science* 247:247 (1989)). Cationic lipids have been demonstrated to aid in introduction of nucleic acids into some cells in culture (Feigner and Ringold, *Nature* 337:387 (1989)). Injection of cationic lipid plasmid DNA complexes into the circulation of mice has been shown to result in expression of the DNA in lung (Brigham et al., *Am. J. Med. Sci.* 298:278 (1989)). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell surface antigens of the target tissue (Mizuno et al., *No Shinkei Geka* 20:547 (1992); PCT publication WO 91/06309; Japanese patent application 1047381; and European patent publication EP-A-43075).

Liposomes that consist of amphiphilic cationic molecules are useful as non-viral vectors for nucleic acid delivery in vitro and in vivo (reviewed in Crystal, Science 270:404 (1995); Blaese et al., *Cancer Gene Ther.* 2:291 (1995); Behr et al., *Bioconjugate Chem.* 5:382 (1994); Remy et al., *Bioconjugate Chem.* 5:647 (1994); and Gao et al., *Gene Therapy* 2:710 (1995)). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Feigner et al., *Proc. Natl. Acad. Sci. USA* 84:7413 (1987); Loeffler et al., *Meth. Enzymol.* 217:599 (1993); Feigner et al., *J. Biol. Chem.* 269:2550 (1.994)).

Several groups have reported the use of amphiphilic cationic lipid:nucleic acid complexes for in vivo transfection both in animals and in humans (reviewed in Gao et al., *Gene Therapy* 2:710 (1995); Zhu et al., *Science* 261:209 (1993); and Thierry et al., *Proc. Natl. Acad. Sci. USA* 92:9742 (1995)). U.S. Pat. No. 6,410,049 describes a method of preparing cationic lipid:nucleic acid complexes that have a prolonged shelf life.

Expression vectors can be designed for expression of polypeptides in prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSecl (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers Virology 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA and RNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

Polypeptides and fragments of the invention can be modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Another embodiment of the invention relates to homologs of the polypeptides of the invention that are peptidomimetic compounds that are designed based upon the amino acid sequences of the functional polypeptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with biological activities qualitatively identical to that of the functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbon A, dimethylene and ketomethylene bonds, are known in the art to be generally useful substitutes for peptide bonds in the construction of protease-resistant peptidomimetics.

III. Inhibitors of SOGA Polypeptides and Polynucleotides

As one aspect, the invention provides agents that inhibit the expression and/or activity of SOGA polypeptides or polynucleotides. These agents can be used to inhibit or downregulate the SOGA signaling pathway, e.g., in a cell or a subject.

In one embodiment of the invention, decreasing the expression and/or activity of a SOGA polypeptide comprises decreasing the level of a nucleic acid (DNA or RNA) encoding the polypeptide or the level of expression of the polypeptide from the nucleic acid. Numerous methods for reducing the level and/or expression of polynucleotides in vitro or in vivo are known. For example, the nucleotide sequences for the human and mouse SOGA polypeptides are disclosed herein. An antisense nucleotide sequence or nucleic acid encoding an antisense nucleotide sequence can be generated to any portion thereof in accordance with known techniques.

The term "antisense nucleotide sequence" or "antisense oligonucleotide" as used herein, refers to a nucleotide sequence that is complementary to a specified DNA or RNA sequence. Antisense oligonucleotides and nucleic acids that express the same can be made in accordance with conventional techniques. See, e.g., U.S. Pat. No. 5,023,243 to Tullis; U.S. Pat. No. 5,149,797 to Pederson et al. The antisense nucleotide sequence can be complementary to the entire nucleotide sequence encoding the polypeptide or a portion thereof of at least 10, 20, 40, 50, 75, 100, 150, 200, 300, or 500 contiguous bases or more and will reduce the level of polypeptide production.

Those skilled in the art will appreciate that it is not necessary that the antisense nucleotide sequence be fully complementary to the target sequence as long as the degree of sequence similarity is sufficient for the antisense nucleotide sequence to hybridize to its target and reduce production of the polypeptide. As is known in the art, a higher degree of sequence similarity is generally required for short antisense nucleotide sequences, whereas a greater degree of mismatched bases will be tolerated by longer antisense nucleotide sequences.

For example, hybridization of such nucleotide sequences can be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS, and 1×SSPE at 42° C.; and/or conditions represented by a wash stringency of 50% formamide with 5×Denhardt's solution, 0.5% SDS and 1×SSPE at 42° C., respectively) to the nucleotide sequences specifically disclosed herein. See, e.g., Sambrook et al., Molecular Cloning: A Laboratory Manual 2nd Ed. (Cold Spring Harbor, N.Y., 1989).

In other embodiments, antisense nucleotide sequences of the invention have at least about 70%, 80%, 90%, 95%, 97%, 98% or higher sequence similarity with the complement of the coding sequences specifically disclosed herein and will reduce the level of polypeptide production.

In other embodiments, the antisense nucleotide sequence can be directed against any coding sequence, the silencing of which results in a modulation of a SOGA polypeptide.

The length of the antisense nucleotide sequence (i.e., the number of nucleotides therein) is not critical as long as it binds selectively to the intended location and reduces transcription and/or translation of the target sequence, and can be determined in accordance with routine procedures. In general, the antisense nucleotide sequence will be from about eight, ten or twelve nucleotides in length up to about 20, 30, 50, 75 or 100 nucleotides, or longer, in length.

An antisense nucleotide sequence can be constructed using chemical synthesis and enzymatic ligation reactions by procedures known in the art. For example, an antisense nucleotide sequence can be chemically synthesized using naturally occurring nucleotides or various modified nucleotides designed to increase the biological stability of the molecules or to increase the physical stability of the duplex formed between the antisense and sense nucleotide sequences, e.g., phosphorothioate derivatives and acridine substituted nucleotides can be used. Examples of modified nucleotides which can be used to generate the antisense nucleotide sequence include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomet-hyluracil, dihydrouracil, beta-D-galactosylqueosine, inosine, N6-isopentenyladenine, 1-methylguanine, 1-methylinosine, 2,2-dimethyl guanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopenten-yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleotide sequence can be produced using an expression vector into which a nucleic acid has been cloned in an antisense orientation (i.e., RNA transcribed from the inserted nucleic acid will be of an antisense orientation to a target nucleic acid of interest).

The antisense nucleotide sequences of the invention further include nucleotide sequences wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues can be modified as described. In another non-limiting example, the antisense nucleotide sequence is a nucleotide sequence in which one, or all, of the nucleotides contain a 2' lower alkyl moiety (e.g., $C_1$-$C_4$, linear or branched, saturated or unsaturated alkyl, such as methyl, ethyl, ethenyl, propyl, 1-propenyl, 2-propenyl, and isopropyl). For example, every other one of the nucleotides can be modified as described. See also, Furdon et al., *Nucleic Acids Res.* 17:9193 (1989); Agrawal et al., *Proc. Natl. Acad. Sci. USA* 87:1401 (1990); Baker et al., *Nucleic Acids Res.* 18:3537 (1990); Sproat et al., *Nucleic Acids Res.* 17:3373 (1989); Walder and Walder, *Proc. Natl. Acad. Sci. USA* 85:5011 (1988); incorporated by reference herein in their entireties for their teaching of methods of making antisense molecules, including those containing modified nucleotide bases).

Triple helix base-pairing methods can also be employed to inhibit production of SOGA polypeptides. Triple helix pairing is believed to work by inhibiting the ability of the double helix to open sufficiently for the binding of polymerases, transcription factors, or regulatory molecules. Recent therapeutic advances using triplex DNA have been described in the literature (e.g., Gee et al., (1994) In: Huber et al., Molecular and Immunologic Approaches, Futura Publishing Co., Mt. Kisco, N.Y.).

Small Interference (si) RNA, also known as RNA interference (RNAi) molecules, provides another approach for modulating the expression of SOGA polypeptides. The siRNA can be directed against polynucleotide sequences encoding the SOGA polypeptides or any other sequence that results in modulation of the expression of SOGA polypeptides.

siRNA is a mechanism of post-transcriptional gene silencing in which double-stranded RNA (dsRNA) corresponding to a coding sequence of interest is introduced into a cell or an organism, resulting in degradation of the corresponding mRNA. The mechanism by which siRNA achieves gene silencing has been reviewed in Sharp et al., *Genes Dev.* 15:485 (2001); and Hammond et al., *Nature Rev. Gen.* 2:110 (2001)). The siRNA effect persists for multiple cell divisions before gene expression is regained. siRNA is therefore a powerful method for making targeted knockouts or "knockdowns" at the RNA level. siRNA has proven successful in human cells, including human embryonic kidney and HeLa cells (see, e.g., Elbashir et al., *Nature* 411:494 (2001)). In one embodiment, silencing can be induced in mammalian cells by enforcing endogenous expression of RNA hairpins (see Paddison et al., *Proc. Natl. Acad. Sci. USA* 99:1443 (2002)). In another embodiment, transfection of small (21-23 nt) dsRNA specifically inhibits nucleic acid expression (reviewed in Caplen, *Trends Biotechnol.* 20:49 (2002)).

siRNA technology utilizes standard molecular biology methods. dsRNA corresponding to all or a part of a target coding sequence to be inactivated can be produced by standard methods, e.g., by simultaneous transcription of both strands of a template DNA (corresponding to the target sequence) with T7 RNA polymerase. Kits for production of dsRNA for use in siRNA are available commercially, e.g., from New England Biolabs, Inc. Methods of transfection of dsRNA or plasmids engineered to make dsRNA are routine in the art.

MicroRNA (miRNA), single stranded RNA molecules of about 21-23 nucleotides in length, can be used in a similar fashion to siRNA to modulate gene expression (see U.S. Pat. No. 7,217,807).

Silencing effects similar to those produced by siRNA have been reported in mammalian cells with transfection of a mRNA-cDNA hybrid construct (Lin et al., *Biochem. Biophys. Res. Commun.* 281:639 (2001)), providing yet another strategy for silencing a coding sequence of interest.

The expression of SOGA polypeptides can also be inhibited using ribozymes. Ribozymes are RNA-protein complexes that cleave nucleic acids in a site-specific fashion. Ribozymes have specific catalytic domains that possess endonuclease activity (Kim et al., *Proc. Natl. Acad. Sci. USA* 84:8788 (1987); Gerlach et al., *Nature* 328:802 (1987); Forster and Symons, *Cell* 49:211 (1987)). For example, a large number of ribozymes accelerate phosphoester transfer reactions with a high degree of specificity, often cleaving only one of several phosphoesters in an oligonucleotide substrate (Michel and Westhof, *J. Mol. Biol.* 216:585 (1990); Reinhold-Ilurek and Shub, *Nature* 357:173 (1992)). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, Nature 338:217 (1989)). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., *Proc. Natl. Acad. Sci. USA* 88:10591 (1991); Sarver et al., *Science* 247:1222 (1990); Sioud et al., *J. Mol. Biol.* 223:831 (1992)).

In another embodiment of the invention, decreasing the expression and/or activity of SOGA polypeptides comprises decreasing the activity of the polypeptide. Polypeptide activity can be modulated by interaction with an antibody or antibody fragment. The antibody or antibody fragment can bind to the polypeptide or to any other polypeptide of interest, as long as the binding between the antibody or the antibody fragment and the target polypeptide results in modulation of the activity of the SOGA polypeptide.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric antibody. See, e.g., Walker et al., *Molec. Immunol.* 26:403 (1989). The antibodies can be recombinant monoclonal antibodies produced according to the methods disclosed in U.S. Pat. No. 4,474,893 or U.S. Pat. No. 4,816,567. The antibodies can also be chemically constructed according to the method disclosed in U.S. Pat. No. 4,676,980.

Antibody fragments included within the scope of the present invention include, for example, Fab, Fab', F(ab')$_2$, and Fv fragments; domain antibodies, diabodies; vaccibodies, linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)).

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fe), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al, and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Polyclonal antibodies used to carry out the present invention can be produced by immunizing a suitable animal (e.g., rabbit, goat, etc.) with an antigen to which a monoclonal antibody to the target binds, collecting immune serum from the animal, and separating the polyclonal antibodies from the immune serum, in accordance with known procedures.

Monoclonal antibodies used to carry out the present invention can be produced in a hybridoma cell line according to the technique of Kohler and Milstein, *Nature* 265:495 (1975). For example, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in *E. coli* by recombinant techniques known to those skilled in the art. See, e.g., Huse, *Science* 246:1275 (1989).

Antibodies specific to the target polypeptide can also be obtained by phage display techniques known in the art.

Various immunoassays can be used for screening to identify antibodies having the desired specificity for the polypeptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). A two-site, monoclonal-based immunoassay utilizing monoclonal antibodies reactive to two non-interfering epitopes on the polypeptides or peptides of this invention can be used as well as a competitive binding assay.

Antibodies can be conjugated to a solid support (e.g., beads, plates, slides or wells formed from materials such as latex or polystyrene) in accordance with known techniques. Antibodies can likewise be conjugated to detectable groups such as radiolabels (e.g., $^{35}S$, $^{125}I$, $^{131}I$), enzyme labels (e.g., horseradish peroxidase, alkaline phosphatase), and fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In one embodiment, the activity of SAGA polypeptides is inhibited using aptamers. Recently, small structured single-stranded RNAs, also known as RNA aptamers, have emerged as viable alternatives to small-molecule and antibody-based therapy (Que-Gewirth et al., *Gene Ther.* 14:283 (2007); Ireson et al., *Mol. Cancer. Ther.* 5:2957 (2006)). RNA aptamers specifically bind target proteins with high affinity, are quite stable, lack immunogenicity, and elicit biological responses. Aptamers are evolved by means of an iterative selection method called SELEX (systematic evolution of ligands by exponential enrichment) to specifically recognize and tightly bind their targets by means of well-defined complementary three-dimensional structures.

RNA aptamers represent a unique emerging class of therapeutic agents (Que-Gewirth et al., *Gene Ther.* 14:283 (2007); Ireson et al., *Mol. Cancer. Ther.* 5:2957 (2006)). They are relatively short (12-30 nucleotide) single-stranded RNA oligonucleotides that assume a stable three-dimensional shape to tightly and specifically bind selected protein targets to elicit a biological response. In contrast to antisense oligonucleotides, RNA aptamers can effectively target extracellular targets. Like antibodies, aptamers possess binding affinities in the low nanomolar to picomolar range. In addition, aptamers are heat stable, lack immunogenicity, and possess minimal interbatch variability. Chemical modifications, such as amino or fluoro substitutions at the 2' position of pyrimidines, may reduce degradation by nucleases. The biodistribution and clearance of aptamers can also be altered by chemical addition of moieties such as polyethylene glycol and cholesterol. Further, SELEX allows selection from libraries consisting of up to $10^{15}$ ligands to generate high-affinity oligonucleotide ligands to purified biochemical targets.

In another embodiment, the method of decreasing the activity of a SOGA polypeptide comprises delivering to a cell or to a subject an agent that decreases the activity of a SOGA polypeptide, the agent administered in an amount effective to modulate the activity of the polypeptide. The agent can interact directly with the SOGA polypeptide to decrease the activity of the polypeptide. Alternatively, the agent can interact with any other polypeptide, nucleic acid or other molecule if such interaction results in a decrease of the activity of the SOGA.

The term "agent" as used herein is intended to be interpreted broadly and encompasses organic and inorganic molecules. Organic compounds include, but are not limited to, small molecules, polypeptides, lipids, carbohydrates, coenzymes, aptamers, and nucleic acid molecules (e.g., gene delivery vectors, antisense oligonucleotides, siRNA, all as described above).

Polypeptides include, but are not limited to, antibodies (described in more detail above) and enzymes. Nucleic acids include, but are not limited to, DNA, RNA and DNA-RNA chimeric molecules. Suitable RNA molecules include siRNA, antisense RNA molecules and ribozymes (all of which are described in more detail above). The nucleic acid can further encode any polypeptide such that administration of the nucleic acid and production of the polypeptide results in a decrease of the activity of a SOGA polypeptide.

The agent can further be an agent that is identified by any of the screening methods described below.

In one embodiment of the invention, the agent is a modulator of the insulin and/or adiponectin signaling pathways that directly or indirectly inhibits SOGA expression and/or activity. For example, the agent can be an activator of AMPK such as AICAR (N1-(β-D-ribofuranosyl)-5-aminoimidazole-4-carboxamide). In another embodiment, the agent can be a PI3 kinase inhibitor such as LY294002. In a further embodiment, the agent can be an inhibitor of adiponectin such as rapamycin.

IV. Inhibition of Glucose Production

Increases in SOGA polypeptide levels and/or activity result in the inhibition of glucose production in cells. Thus, the SOGA polypeptides and polynucleotides of the invention can be used in methods in which a decrease in glucose production is desired for research, diagnostic, and/or therapeutic proposes. These methods can be carried using techniques to increase the expression and/or activity of SOGA polypeptides in a cell, in a tissue, and/or in a subject.

One aspect of the invention relates to a method of decreasing glucose production in a cell, comprising contacting said cell with a polynucleotide, polypeptide, or fusion protein of the invention in an amount effective to decrease glucose production in the cell.

Another aspect of the invention relates to a method of decreasing autophagy in a cell, comprising contacting said cell with a polynucleotide, polypeptide, or fusion protein of the invention in an amount effective to decrease autophagy in said cell.

The cells to be contacted can be in vitro, ex vivo, or in vivo (e.g., in an animal model of disease or a patient). Cells can be contacted with a polynucleotide or polypeptide of the invention by any means known in the art and as described herein.

A further aspect of the invention relates to a method of decreasing blood glucose levels in a subject, comprising delivering to said subject a polynucleotide, polypeptide, or fusion protein of the invention in an amount effective to decrease the blood glucose levels in said subject.

Another aspect of the invention relates to a method of increasing insulin sensitivity in a subject, comprising delivering to said subject a polynucleotide, polypeptide, or fusion protein of the invention in an amount effective to increase insulin sensitivity in said subject.

In one embodiment, the subject is one that is in need of decreased glucose levels and/or increased insulin sensitivity. The subject can currently have or be at risk for a carbohydrate-related metabolic disorder such as diabetes mellitus (Type I or Type II), alcoholic ketoacidosis, diabetic ketoacidosis, nonketotic hyperosmolar syndrome, and new onset diabetes (NOD), such as in cancer patients undergoing chemotherapy, immunosuppressed patients, post-operative patients, and trauma patients. In certain embodiments, the methods of the invention encompass methods of treating a subject having a carbohydrate-related metabolic disorder such as diabetes, comprising delivering to said subject a polynucleotide, polypeptide, or fusion protein of the invention in an amount effective to treat the disorder.

In one embodiment, increasing the expression and/or activity of a SOGA polypeptide comprises delivering a nucleic acid encoding the polypeptide or a fragment or homolog thereof to the cell or tissue or subject. In another embodiment, increasing the expression and/or activity of a SOGA polypeptide comprises delivering the polypeptide itself or a fragment or homolog thereof to the cell or tissue or subject.

In one embodiment, the methods comprise delivering to the subject an isolated SOGA polypeptide. In exemplary embodiments, the polypeptide comprises, consists essentially of or consists of the amino acid sequence of the polypeptide disclosed herein or a functional fragment thereof. In another embodiment, the isolated polypeptide comprises, consists essentially of, or consists of an amino acid sequence that is at least 70% identical, e.g., at least 75%, 80%, 85%, 90%, 95%, 96%, 97%, 98%, or 99% identical to the disclosed amino acid sequence or a functional fragment thereof (and polynucleotide sequences encoding the same).

In one embodiment, the polynucleotides, polypeptides, or homologs thereof of the invention are administered directly to the subject. Generally, the compounds of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. They can be delivered directly to a site involved in gluconeogenesis, such as the liver, kidney, and/or muscle. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 μg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Administrations can be single or multiple (e.g., 2-, 3-, 4-, 6-, 8-, 10-; 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

According to certain embodiments, the polynucleotides or vectors can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., Biochemistry 25:5500 (1986); Ho et al., J. Biol. Chem. 262: 13979 (1987); Ho et al., J. Biol. Chem. 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain, that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., J. Clin. Invest. 104:21 (1999)). Intravenous delivery of cholesterol-containing cationic liposomes has been shown to preferentially target pulmonary tissues (Liu et al., Nature Biotechnol. 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

The polypeptides and polynucleotides of the present invention can optionally be delivered in conjunction with other therapeutic agents. The additional therapeutic agents can be delivered concurrently with the polypeptides and polynucleotides of the invention. As used herein, the word "concurrently" means sufficiently close in time to produce a combined effect (that is, concurrently can be simultaneously, or it can be two or more events occurring within a short time period before or after each other). In one embodiment, the polypeptides and polynucleotides of the invention are administered in conjunction with anti-diabetic agents, including without limitation, (1) PPARγ agonists such as glitazones (e.g., ciglitazone, darglitazone, englitazone, isaglitazone (MCC-555), pioglitazone, rosiglitazone, troglitazone, BRL49653, CLX-0921, 5-BTZD, GW-0207, LG-100641, and LY-300512; (2) biguanides such as buformin, metformin, and phenformin; (3) protein tyrosine phosphatase-1B (PTP-1B) inhibitors such as ISIS 113715; (4) sulfonylureas such as acetohexamide, chlorpropamide, diabinese, glibenclamide, glypizide, glyburide, glimepiride, gliclazide, glipentide, gliquidone, glisolamide, tolazamide, and tolbutamide; (5) meglitinides such as repaglinide and nateglinide; (6) alpha glucoside hydrolase inhibitors such as acarbose, adiposine, camiglibose, emiglitate, miglitol, voglibose, pradimicin-Q, salbostatin, CKD-711, MDL-25,637, MDL-73,945, and MOR 14; (7) alpha-amylase inhibitors such as tendamistat, trestatin, and Al-3688; (8) insulin secretagogues such as linogliride and A4166; (9) fatty acid oxidation inhibitors such as clomoxir and etomoxir; (10) adenosine A2 antagonists such as midaglizole, isaglidole, deriglidole, idazoxan, earoxan, and fluparoxan; (11) insulin or insulin mimetics such as biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-NH$_2$); (12) non-thiazolidinediones such as JT-501 and farglitazar (GW-2570/G1-262579); (13) PPARα/γ dual agonists such as BVT-142, CLX-0940, GW-1536, GW1929, GW-2433, KRP-297, L-796449, LR-90, MK-0767, SB 219994, muraglitazar and reglitazar (ITT-501); (14) other insulin sensitizing drugs; (15) VPAC2 receptor agonists; (16) GLK modulators such as those disclosed in WO 03/015774; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine; (19) glycogen phosphorylase (HGLPa) inhibitors such as those disclosed in WO 03/037864; (20) ATP consumption promoters such as those disclosed in WO 03/007990; (21) TRB3 inhibitors, (22) vanilloid receptor ligands such as those disclosed in WO 03/049702, (23) hypoglycemic agents such as those disclosed in WO 03/015781 and WO 03/040114; and (24) Insulin-responsive DNA binding protein-1 (IRDBP-1) as disclosed in WO 03/057827.

V. Stimulation of Glucose Production

Decreases in SOGA polypeptide levels and/or activity result in the stimulation of glucose production in cells. Thus, inhibitors of the SOGA polypeptides and polynucleotides of the invention can be used in methods in which an increase in glucose production is desired for research, diagnostic, and/or therapeutic proposes. These methods can be carried using techniques to decrease the expression and/or activity of SOGA polypeptides in a cell, in a tissue, and/or in a subject, One aspect of the invention relates to a method of increasing glucose production in a cell, comprising contacting said cell with an agent that decreases the activity of a polynucleotide or polypeptide of the invention in an amount effective to increase glucose production in the cell.

Another aspect of the invention relates to a method of increasing autophagy in a cell, comprising contacting said cell with an agent that decreases the activity of a polynucleotide or polypeptide of the invention in an amount effective to increase autophagy in said cell.

The cells to be contacted can be in vitro, ex vivo, or in vivo (e.g., in an animal model of disease or a patient). Cells can be contacted with an agent by any means known in the art and as described herein.

A further aspect of the invention relates to a method of increasing blood glucose levels in a subject, comprising delivering to said subject an agent that decreases the activity of a polynucleotide or polypeptide of the invention in an amount effective to increase the blood glucose levels in said subject.

Another aspect of the invention relates to a method of decreasing insulin sensitivity in a subject, comprising delivering to said subject an agent that decreases the activity of a polynucleotide or polypeptide of the invention in an amount effective to decrease insulin sensitivity in said subject.

In one embodiment, the subject is one that is in need of increased glucose levels and/or decreased insulin sensitivity. The subject can currently have or be at risk for a carbohydrate-related metabolic disorder such as hypoglycemia, e.g., as a result of sepsis, malaria, or injection of insulin.

Agents that can be used in the methods of the invention include, without limitation, an antisense oligonucleotide, ribozyme, or siRNA that targets a SOGA polynucleotide, an antibody or antibody fragment that binds to a SOGA polypeptide, agents that modulate the insulin and/or adiponectin signaling pathways, and agents identified by the screening methods described below.

The agents of the present invention can optionally be delivered in conjunction with other therapeutic agents. The additional therapeutic agents can be delivered concurrently with the agents of the invention.

VI. Monitoring of Responsiveness to Treatment

The increased levels of SOGA polypeptide in response to administration of insulin and adiponectin provides the basis for monitoring responsiveness of a subject to anti-diabetic treatments. It is known that insulin treatment of diabetics is not effective 100% of the time and that certain drugs may induce adiponectin but do not necessarily lower glucose. Measuring the induction of SOGA in response to an anti-diabetic treatment may provide insight into the ability of a subject to respond to the treatment and can help identify subjects that are likely to respond or not respond to a particular treatment.

One aspect of the invention relates to a method of measuring the response of a subject to a treatment for diabetes, comprising determining the circulating level of a SOGA polypeptide or a functional fragment thereof in said subject after administration of the treatment and comparing it to the circulating level of the polypeptide or a functional fragment thereof in said subject before administration of the treatment.

Another aspect of the invention relates to a method of predicting the clinical outcome of a diabetes treatment in a subject, comprising determining the circulating level of a SOGA polypeptide or a functional fragment thereof in said subject after administration of the treatment and comparing it to the circulating level of the polypeptide or a functional fragment thereof in said subject before administration of the treatment.

In these methods, an increase in circulating levels of SOGA polypeptide or a functional fragment thereof subsequent to administration of an anti-diabetic treatment is indicative that the subject will respond to the treatment (e.g., the treatment will lower glucose levels). Conversely, if the circulating level of SOGA does not increase or increases less than a "normal" amount, the subject may not respond favorably to the treatment. The magnitude of the increase in SOGA polypeptide (e.g., a "normal" increase as compared to a "less than normal" increase in SOGA) can be classified based on average numbers in a population of similar subjects.

In one embodiment, determining the level of a SOGA polypeptide comprises determining the level the polypeptide. Determining the level of a polypeptide can be carried out by any means known in the art and as described herein, such as Western blots, immunoblots, immunoprecipitation, immunohistochemistry, immunofluorescence, enzyme-linked immunosorbant assays, and radioimmunoassays. Assays for expression and/or activity can be carried out automatically or partially automatically in a machine or apparatus designed to perform such assays, e.g., using computer-assisted methods. The results of the assays can be stored in a computer database and analyzed to produce predictive results. In some embodiments, the data can be analyzed, e.g., by comparing intra-patient results over time or before and after treatment or comparing inter-patient results to determine baseline and/or abnormal values in a population.

In a further embodiment, determining the level of a SOGA polypeptide comprises determining the activity of the polypeptides. The activity may be any activity associated with the polypeptide, including, without limitation, inhibition of glucose production, enzyme activity, protein interaction, receptor binding, ligand binding, a cell signal transduction event, etc.

In one embodiment, determining the level of a SOGA polypeptide comprises determining the level of a nucleic acid encoding the polypeptide. Determining the level of a nucleic acid can be carried out by any means known in the art and as described herein, such as Northern blots, dot blots, PCR, RT-PCR, quantitative PCR, sequence analysis, gene microarray analysis, in situ hybridization, and detection of a reporter gene.

One aspect of the invention relates to kits useful for carrying out the methods of the invention. One embodiment relates to kits for determining the level of expression and/or activity of SOGA, e.g., to assess responsiveness to anti-diabetic treatment, comprising a reagent for determining the expression and/or activity of a SOGA polypeptide or a functional fragment thereof. The reagents may be nucleic acids (e.g., an oligonucleotide that specifically hybridizes to a nucleic acid encoding a SOGA polypeptide and can be used as a hybridization probe or an amplification primer), antibodies (e.g., one the specifically binds to a SOGA polypeptide), or other agents that specifically recognize the polynucleotides or polypeptides of the invention.

The reagents can be conjugated to a detectable tag or detectable label. Such a tag can be any suitable tag which allows for detection of the reagents and includes, but is not limited to, any composition or label detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

In addition, the reagents can be immobilized on a substrate. Such a substrate can include any suitable substrate for immobilization of a detection reagent such as would be used in any of the previously described methods of detection. Briefly, a substrate suitable for immobilization of a detection reagent includes any solid support, such as any solid organic, biopolymer or inorganic support that can form a bond with the detection reagent without significantly effecting the activity and/or ability of the detection reagent to detect the desired target molecule. Exemplary organic solid supports include polymers such as polystyrene, nylon, phenol-formaldehyde resins, acrylic copolymers (e.g., polyacrylamide), stabilized intact whole cells, and stabilized crude whole cell/membrane homogenates. Exemplary biopolymer supports include cellulose, polydextrans (e.g., Sephadex®), agarose, collagen and chitin. Exemplary inorganic supports include glass beads (porous and nonporous), stainless steel, metal oxides (e.g., porous ceramics such as $ZrO_2$, $TiO_2$, $Al_2O_3$, and NiO) and sand.

The kits may further comprise other components useful for detecting expression or activity, e.g., buffers, cells, culture medium, enzymes, labeling reagents, containers, etc.

In one embodiment, the kit comprises an array of reagents for determining expression and/or activity. The array can comprise a substrate having a plurality of addresses. At least one address of the plurality includes a capture probe that binds specifically to a polynucleotide or polypeptide of the invention. The array can have a density of at least, or less than, 10, 20 50, 100, 200, 500, 700, 1,000, 2,000, 5,000 or 10,000 or more addresses/$cm^2$, and ranges between. The substrate can be a two-dimensional substrate such as a glass slide, a wafer (e.g., silica or plastic), a mass spectroscopy plate, or a three-dimensional substrate such as a gel pad. Addresses in addition to addresses of the plurality can be disposed on the array.

In one embodiment, at least one address of the plurality includes a nucleic acid capture probe that hybridizes specifically to a polynucleotide of the invention, e.g., the sense or anti-sense strand. Each address of the subset can include a capture probe that hybridizes to a different region of a polynucleotide. An array can be generated by any of a variety of methods. Appropriate methods include, e.g., photolithographic methods (e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another embodiment, at least one address of the plurality includes a polypeptide capture probe that binds specifically to a polypeptide of the invention or fragment thereof. The polypeptide capture probe can be a naturally-occurring interaction partner of a SOGA polypeptide. In one embodiment, the polypeptide is an antibody, e.g., an antibody specific for a SOGA polypeptide, such as a polyclonal antibody, a monoclonal antibody, or a single-chain antibody.

VII. Screening Assays and Animal Models

The identification of polynucleotides and polypeptides that are involved in insulin and adiponectin signaling and glucose regulation provides targets that can be used to screen for agents that regulate glucose production as well as models for studying these pathways in vitro or in animals.

One aspect of the invention relates to a method of identifying an agent that binds to a SOGA polypeptide or a functional fragment thereof of the invention, comprising:

contacting the polypeptide or a functional fragment thereof with a test agent under conditions whereby binding between the polypeptide or a functional fragment thereof and the test agent can occur; and detecting binding between the polypeptide or a functional fragment thereof and the test agent.

Another aspect of the invention relates to a method of identifying an agent that modulates the activity of a SOGA polypeptide or a functional fragment thereof of the invention, comprising:

contacting the polypeptide or a functional fragment thereof with a test agent under conditions whereby modulation of the activity of the polypeptide or a functional fragment thereof can occur; and detecting modulation of the activity of the polypeptide or a functional fragment thereof upon contact with the test agent as compared to activity of the polypeptide or a functional fragment thereof in the absence of contact with the test agent.

In each aspect above, the assay may be a cell-based or cell-free assay. In one embodiment, the cell may be a primary cell, e.g., an endothelial cell or a tumor cell, such as a breast tumor cell. In another embodiment, the cell is from a cell line, e.g., a hepatocyte, kidney, or muscle cell line or a tumor cell line. The cell may be contacted with the agent in vitro (e.g., in a culture dish) or in an animal (e.g., a transgenic animal or an animal model). In one embodiment, the detected increase or decrease in expression and/or activity is statistically significant, e.g., at least $p<0.05$, e.g., $p<0.01$, 0.005, or 0.001. In another embodiment, the detected increase or decrease is at least about 10%, 20%, 30%, 40%, 50%, 60&, 70%, 80%, 90%, 100% or more.

Any desired end-point can be detected in a screening assay, e.g., binding to the polypeptide, gene or RNA, modulation of the activity of the polypeptide, modulation of glucose-related pathways, and/or interference with binding by a known regulator of a polynucleotide or polypeptide. Methods of detecting the foregoing activities are known in the art and include the methods disclosed herein.

Any agent of interest can be screened according to the present invention. Suitable test agents include organic and inorganic molecules. Suitable organic molecules can include but are not limited to small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof) and nucleotides and nucleotide analogs. In particular embodiments, the agent is an antisense nucleic acid, an siRNA, or a ribozyme that inhibits production of a SOGA polypeptide.

Further, the methods of the invention can be practiced to screen an agent library, e.g., a small molecule library, a combinatorial chemical compound library, a polypeptide library, a cDNA library, a library of antisense nucleic acids, and the like, or an arrayed collection of agents such as polypeptide and nucleic acid arrays.

In one representative embodiment, the invention provides methods of screening test agents to identify a test agent that binds to a SOGA polypeptide or functional fragment thereof. Agents that are identified as binding to the polypeptide or functional fragment can be subject to further screening (e.g., for modulation of glucose production) using the methods described herein or other suitable techniques.

Also provided are methods of screening agents to identify those that modulate the activity of a SOGA polypeptide or functional fragment thereof. The term "modulate" is intended to refer to agents that enhance (e.g., increase) or inhibit (e.g., reduce) the activity of the polypeptide (or functional fragment). For example, the interaction of the polypeptide or functional fragment with a binding partner can be evaluated. As another alternative, physical methods, such as NMR, can be used to assess biological function. Activity of the SOGA polypeptides or functional fragment can be evaluated by any method known in the art, including the methods disclosed herein.

Agents that are identified as modulators of activity can optionally be further screened using the methods described herein (e.g., for binding to the SOGA polypeptide or functional fragment thereof, polynucleotide or RNA, modulation of glucose, and the like). The agent can directly interact with the polypeptide or functional fragment, polynucleotide or mRNA and thereby modulate its activity. Alternatively, the agent can interact with any other polypeptide, nucleic acid or other molecule as long as the interaction results in a modulation of the activity of the SOGA polypeptide or functional fragment.

With respect to cell-free binding assays, test agents can be synthesized or otherwise affixed to a solid substrate, such as plastic pins, glass slides, plastic wells, and the like. For example, the test agents can be immobilized utilizing conjugation of biotin and streptavidin by techniques well known in the art. The test agents are contacted with the polypeptide or functional fragment thereof and washed. Bound polypeptide can be detected using standard techniques in the art (e.g., by radioactive or fluorescence labeling of the polypeptide or functional fragment, by ELISA methods, and the like).

Alternatively, the target can be immobilized to a solid substrate and the test agents contacted with the bound polypeptide or functional fragment thereof. Identifying those test agents that bind to and/or modulate the SOGA polypeptide or functional fragment can be carried out with routine techniques. For example, the test agents can be immobilized utilizing conjugation of biotin and streptavidin by techniques well known in the art. As another illustrative example, antibodies reactive with the polypeptide or functional fragment can be bound to the wells of the plate, and the polypeptide trapped in the wells by antibody conjugation. Preparations of test agents can be incubated in the polypeptide (or functional fragment)-presenting wells and the amount of complex trapped in the well can be quantitated.

In another representative embodiment, a fusion protein can be provided which comprises a domain that facilitates binding of the polypeptide to a matrix. For example, glutathione-S-transferase fusion proteins can be adsorbed onto glutathione sepharose beads (Sigma Chemical, St. Louis, Mo.) or glutathione derivatized microtiter plates, which are then combined with cell lysates (e.g., $^{35}$S-labeled) and the test agent, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of SOGA polypeptide or functional fragment thereof found in the bead fraction quantitated from the gel using standard electrophoretic techniques.

Another technique for agent screening provides for high throughput screening of agents having suitable binding affinity to the polypeptide of interest, as described in published PCT application WO84/03564. In this method, a large number of different small test agents are synthesized on a solid substrate, such as plastic pins or some other surface. The test agents are reacted with the SOGA polypeptide or functional fragment thereof and washed. Bound polypeptide is then detected by methods well known in the art. Purified polypeptide or a functional fragment can also be coated directly onto plates for use in the aforementioned drug screening techniques. Alternatively, non-neutralizing antibodies can be used to capture the peptide and immobilize it on a solid support.

With respect to cell-based assays, any suitable cell can be used, including bacteria, yeast, insect cells (e.g., with a baculovirus expression system), avian cells, mammalian cells, or plant cells. In exemplary embodiments, the assay is carried out in a cell line that naturally expresses the polynucleotide or produces the polypeptide, e.g., hepatocytes or renal cells. Further, in other embodiments, it is desirable to use nontransformed cells (e.g., primary cells) as transformation may alter the function of the polypeptide.

The screening assay can be used to detect agents that bind to or modulate the activity of the native SOGA polypeptide (e.g., polypeptide that is normally produced by the cell). Alternatively, the cell can be modified to express (e.g., overexpress) a recombinant SOGA polypeptide or functional fragment thereof. According to this embodiment, the cell can be transiently or stably transformed with a polynucleotide encoding the SOGA polypeptide or functional fragment, but is preferably stably transformed, for example, by stable integration into the genome of the organism or by expression from a stably maintained episome (e.g., Epstein Barr Virus derived episomes). In another embodiment, a polynucleotide encoding a reporter molecule can be linked to a regulatory element of the polynucleotide encoding a SOGA polypeptide and used to identify compounds that modulate expression of the polypeptide.

In a cell-based assay, the agent to be screened can interact directly with the SOGA polypeptide or functional fragment thereof (i.e., bind to it) and modulate the activity thereof. Alternatively, the agent can be one that modulates polypeptide activity (or the activity of a functional fragment) at the nucleic acid level. To illustrate, the agent can modulate transcription of the gene (or transgene), modulate the accumulation of mRNA (e.g., by affecting the rate of transcription and/or turnover of the mRNA), and/or modulate the rate and/or amount of translation of the mRNA transcript.

As a further type of cell-based binding assay, the SOGA polypeptide or functional fragment thereof can be used as a "bait protein" in a two-hybrid or three-hybrid assay (see, e.g., U.S. Pat. No. 5,283,317; Zervos et al., *Cell* 72:223 (1993); Madura et al., *J. Biol. Chem.* 268:12046 (1993); Bartel et al., *Biotechniques* 14:920 (1993); Iwabuchi et al., *Oncogene* 8:1693 (1993); and PCT publication WO94/10300), to identify other polypeptides that bind to or interact with the polypeptide of the invention or functional fragment thereof.

The two-hybrid system is based on the modular nature of most transcription factors, which consist of separable DNA-binding and activation domains. Briefly, the assay utilizes two different DNA constructs. In one construct, the polynucleotide that encodes the SOGA polypeptide or functional fragment thereof is fused to a nucleic acid encoding the DNA binding domain of a known transcription factor (e.g., GAL-4). In the other construct, a DNA sequence, optionally from a library of DNA sequences, that encodes an unidentified protein ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the polypeptide that exhibited binding to the SOGA polypeptide or functional fragment.

As another cell-based assay, the invention provides a method of screening an agent for modulation of glucose production. In particular embodiments, the cell comprises an isolated polynucleotide encoding the SOGA polypeptide or functional fragment thereof. According to this embodiment, it is preferred that the isolated polynucleotide encoding the polypeptide or functional fragment is stably incorporated into the cell (i.e., by stable integration into the genome of the organism or by expression from a stably maintained episome such as Epstein Barr Virus derived episomes).

Screening assays can also be carried out in vivo in animals. Thus, as still a further aspect, the invention provides a transgenic non-human animal comprising an isolated polynucleotide encoding a SOGA polypeptide or functional fragment thereof, which can be produced according to methods well-known in the art. The transgenic non-human animal can be from any species, including avians and non-human mammals. According to this aspect of the invention, suitable non-human mammals include mice, rats, rabbits, guinea pigs, goats, sheep, pigs, and cattle. Suitable avians include chickens, ducks, geese, quail, turkeys, and pheasants.

The polynucleotide encoding the polypeptide or functional fragment can be stably incorporated into cells within the transgenic animal (typically, by stable integration into the genome or by stably maintained episomal constructs). It is not necessary that every cell contain the transgene, and the animal can be a chimera of modified and unmodified cells, as long as a sufficient number of cells comprise and express the polynucleotide encoding the polypeptide or functional fragment so that the animal is a useful screening tool.

Exemplary methods of using the transgenic non-human animals of the invention for in vivo screening of agents that modulate glucose production and/or the activity of a SOGA polypeptide comprise administering a test agent to a transgenic non-human animal (e.g., a mammal such as a mouse) comprising an isolated polynucleotide encoding a SOGA polypeptide or functional fragment thereof stably incorporated into the genome and detecting whether the test agent modulates glucose levels and/or polypeptide activity (or the activity of a functional fragment). It is known in the art how to measure these responses in vivo.

Methods of making transgenic animals are known in the art. DNA or RNA constructs can be introduced into the germ line of an avian or mammal to make a transgenic animal. For example, one or several copies of the construct can be incorporated into the genome of an embryo by standard transgenic techniques.

In an exemplary embodiment, a transgenic non-human animal is produced by introducing a transgene into the germ line of the non-human animal, Transgenes can be introduced into embryonal target cells at various developmental stages. Different methods are used depending on the stage of development of the embryonal target cell. The specific line(s) of any animal used should, if possible, be selected for general good health, good embryo yields, good pronuclear visibility in the embryo, and good reproductive fitness.

Introduction of the transgene into the embryo can be accomplished by any of a variety of means known in the art such as microinjection, electroporation, lipofection, or a viral vector. For example, the transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg can be incubated in vitro for varying amounts of time, or reimplanted into the surrogate host, or both. One common method is to incubate the embryos in vitro for about 1-7 days, depending on the species, and then reimplant them into the surrogate host.

The progeny of the transgenically manipulated embryos can be tested for the presence of the construct by Southern blot analysis of a segment of tissue. An embryo having one or more copies of the exogenous cloned construct stably integrated into the genome can be used to establish a permanent transgenic animal line.

Transgenically altered animals can be assayed after birth for the incorporation of the construct into the genome of the offspring. This can be done by hybridizing a probe corresponding to the polynucleotide sequence coding for the polypeptide or a segment thereof onto chromosomal material from the progeny. Those progeny found to contain at least one copy of the construct in their genome are grown to maturity.

Methods of producing transgenic avians are also known in the art, see, e.g., U.S. Pat. No. 5,162,215.

In particular embodiments, to create an animal model in which the activity or expression of a SOGA polypeptide is decreased, it is desirable to inactivate, replace or knock-out the endogenous gene encoding the polypeptide by homologous recombination with a transgene using embryonic stem cells. In this context, a transgene is meant to refer to heterologous nucleic acid that upon insertion within or adjacent to the gene results in a decrease or inactivation of gene expression or polypeptide amount or activity.

A knock-out of a gene means an alteration in the sequence of a gene that results in a decrease of function of the gene, preferably such that the gene expression or polypeptide amount or activity is undetectable or insignificant. Knockouts as used herein also include conditional knock-outs, where alteration of the gene can occur upon, for example, exposure of the animal to a substance that promotes gene alteration (e.g., tetracycline or ecdysone), introduction of an enzyme that promotes recombination at a gene site (e.g., Cre in the Cre-lox system), or other method for directing the gene alteration postnatally. Knock-out animals may be prepared using methods known to those of skill in the art. See, for example, Hogan, et al. (1986) Manipulating the Mouse Embryo: A Laboratory Manual, Cold Spring Harbor Laboratory Press, Cold Spring Harbor, N.Y.

A knock-out construct is a nucleic acid sequence, such as a DNA or RNA construct, which, when introduced into a cell, results in suppression (partial or complete) of expression of a polypeptide encoded by endogenous DNA in the cell. A knock-out construct as used herein may include a construct containing a first fragment from the 5' end of the gene encoding a SOGA polypeptide, a second fragment from the 3' end of the gene and a DNA fragment encoding a selectable marker positioned between the first and second fragments. It should be understood by the skilled artisan that any suitable 5' and 3' fragments of a gene may be used as long as the expression of the corresponding gene is partially or completely suppressed by insertion of the transgene. Suitable selectable markers include, but are not limited to, neomycin, puromycin and hygromycin. In addition, the construct may contain a marker, such as diphtheria toxin A or thymidine kinase, for increasing the frequency of obtaining correctly targeted cells. Suitable vectors include, but are not limited to, pBLUESCRIPT, pBR322, and pGEM7.

Alternatively, a knock-out construct may contain RNA molecules such as antisense RNA, siRNA, and the like to decrease the expression of a gene encoding a SOGA polypeptide. Typically, for stable expression the RNA molecule is placed under the control of a promoter. The promoter may be regulated, if deficiencies in the protein of interest may lead to a lethal phenotype, or the promoter may drive constitutive expression of the RNA molecule such that the gene of interest is silenced under all conditions of growth. While homologous recombination between the knock-out construct and the gene of interest may not be necessary when using an RNA molecule to decrease gene expression, it may be advantageous to target the knock-out construct to a particular location in the genome of the host organism so that unintended phenotypes are not generated by random insertion of the knock-out construct.

The knock-out construct may subsequently be incorporated into a viral or nonviral vector for delivery to the host animal or may be introduced into embryonic stem (ES) cells. ES cells are typically selected for their ability to integrate into and become part of the germ line of a developing embryo so as to create germ line transmission of the knock-out construct. Thus, any ES cell line that can do so is suitable for use herein. Suitable cell lines which may be used include, but are not limited to, the 129J ES cell line or the J1 ES cell line. The cells are cultured and prepared for DNA insertion using methods well-known to the skilled artisan (e.g., see Robertson (1987) In: Teratocarcinomas and Embryonic Stem Cells: A Practical Approach, E. J. Robertson, ed. IRL Press, Washington, D.C.; Bradley et al., Curr. Topics Develop. Biol. 20:357 (1986); Hogan et al., (1986) Manipulating the Mouse Embryo: A Laboratory Manual, Cold Spring Harbor Laboratory Press, Cold Spring Harbor, N.Y.).

Insertion of the knock-out construct into the ES cells may be accomplished using a variety of methods well-known in the art, including, for example, electroporation, microinjection, and calcium phosphate treatment. For insertion of the DNA or RNA sequence, the knock-out construct nucleic acids are added to the ES cells under appropriate conditions for the insertion method chosen. If the cells are to be electroporated, the ES cells and construct nucleic acids are exposed to an electric pulse using an electroporation machine (electroporator) and following the manufacturer's guidelines for use. After electroporation, the cells are allowed to recover under suitable incubation conditions. The cells are then screened for the presence of the knockout construct.

Each knock-out construct to be introduced into the cell is first typically linearized if the knock-out construct has been inserted into a vector. Linearization is accomplished by digesting the knock-out construct with a suitable restriction endonuclease selected to cut only within the vector sequence and not within the knock-out construct sequence.

Screening for cells which contain the knock-out construct (homologous recombinants) may be done using a variety of methods. For example, as described herein, cells can be processed as needed to render DNA in them available for hybridization with a nucleic acid probe designed to hybridize only to cells containing the construct. For example, cellular DNA can be probed with $^{32}$P-labeled DNA which locates outside the targeting fragment. This technique can be used to identify those cells with proper integration of the knock-out construct. The DNA can be extracted from the cells using standard methods (e.g., see, Sambrook et al., *Molecular Cloning: A Laboratory Manual* 2nd Ed. (Cold Spring Harbor, N.Y., 1989)). The DNA may then be analyzed by Southern blot with a probe or probes designed to hybridize in a specific pattern to genomic DNA digested with one or more particular restriction enzymes.

Once appropriate ES cells are identified, they are introduced into an embryo using standard methods. They can be introduced using microinjection, for example. Embryos at the proper stage of development for integration of the ES cell to occur are obtained, such as by perfusion of the uterus of pregnant females. For example, mouse embryos at 3-4 days development can be obtained and injected with ES cells using a micropipet. After introduction of the ES cell into the embryo, the embryo is introduced into the uterus of a pseudopregnant female mouse. The stage of the pseudopregnancy is selected to enhance the chance of successful implantation. In mice, 2-3 days pseudopregnant females are appropriate.

Germline transmission of the knockout construct may be determined using standard methods. Offspring resulting from implantation of embryos containing the ES cells described above are screened for the presence of the desired alteration (e.g., knock-out of the SOGA polypeptide). This may be done, for example, by obtaining DNA from offspring (e.g., tail DNA) to assess for the knock-out construct, using known methods (e.g., Southern analysis, dot blot analysis, PCR analysis). See, for example, Sambrook et al., Molecular Cloning: A Laboratory Manual 2nd Ed. (Cold Spring Harbor, N.Y., 1989). Offspring identified as chimeras may be crossed with one another to produce homozygous knock-out animals.

Mice are often used as animal models because they are easy to house, relatively inexpensive, and easy to breed. However, other knock-out animals may also be made in accordance with the present invention such as, but not limited to, monkeys, cattle, sheep, pigs, goats, horses, dogs, cats, guinea pigs, rabbits and rats. Accordingly, appropriate vectors and promoters well-known in the art may be selected and used to generate a transgenic animal deficient in expression of a SOGA polypeptide.

In another embodiment, animal models may be created using animals that are not transgenic. For example, animal models of diabetes or obesity are well known in the art and can be used to study the effects of regulators of glucose production.

VIII. Pharmaceutical Compositions

As a further aspect, the invention provides pharmaceutical formulations and methods of administering the same to achieve any of the diagnostic or therapeutic effects (e.g., inhibition or stimulation of glucose production) discussed above. The pharmaceutical formulation may comprise any of the reagents discussed above in a pharmaceutically acceptable carrier, e.g., a polynucleotide encoding a SOGA polypeptide or a fragment thereof or a vector or cell comprising the polynucleotide, a SOGA polypeptide or fragment thereof, an antibody against a SOGA polypeptide, an antisense oligonucleotide, an siRNA molecule, a ribozyme, an aptamer, a peptidomimetic, a small molecule, or any other agent that modulates the activity of a SOGA polypeptide, including agents identified by the screening methods described herein.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The agents of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the agent (including the physiologically acceptable salts thereof) is typically admixed with, inter alia, an acceptable carrier. The carrier can be a solid or a liquid, or both, and is preferably formulated with the agent as a unit-dose formulation, for example, a tablet, which can contain from 0.01 or 0.5% to 95% or 99% by weight of the agent. One or more agents can be incorporated in the formulations of the invention, which can be prepared by any of the well-known techniques of pharmacy.

A further aspect of the invention is a method of treating subjects in vivo, comprising administering to a subject a pharmaceutical composition comprising an agent of the invention in a pharmaceutically acceptable carrier, wherein the pharmaceutical composition is administered in a therapeutically effective amount. Administration of the compounds of the present invention to a human subject or an animal in need thereof can be by any means known in the art for administering agents.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, kidney or muscle). The most suitable route in any given case will depend on the nature and severity of the condition being treated and on the nature of the particular agent which is being used.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the agent can be administered in solid dosage forms, such as capsules, tablets, and powders, or in liquid dosage forms, such as elixirs, syrups, and suspensions. Agents can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the agent in a flavored base, usually sucrose and acacia or tragacanth; and pastilles comprising the agent in an inert base such as gelatin and glycerin or sucrose and acacia.

Formulations of the present invention suitable for parenteral administration comprise sterile aqueous and non-aqueous injection solutions of the agent, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an agent of the invention, in a unit dosage form in a sealed container. The agent or salt is provided in the form of a lyophilizate which is capable of being reconstituted with a suitable pharmaceutically acceptable carrier to form a liquid composition suitable for injection thereof into a subject. The unit dosage form typically comprises from about 1 mg to about 10 grams of the agent or salt. When the agent or salt is substantially water-insoluble, a sufficient amount of emulsifying agent which is pharmaceutically acceptable can be employed in sufficient quantity to emulsify the agent or salt in an aqueous carrier. One such useful emulsifying agent is phosphatidyl choline.

Formulations suitable for rectal administration are preferably presented as unit dose suppositories. These can be prepared by admixing the agent with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the agent. Suitable formulations comprise citrate or bis/tris buffer (pH 6) or ethanol/water and contain from 0.1 to 0.2M of the agent.

The agent can alternatively be formulated for nasal administration or otherwise administered to the lungs of a subject by any suitable means, e.g., administered by an aerosol suspension of respirable particles comprising the agent, which the subject inhales. The respirable particles can be liquid or solid.

The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the agent can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the agent can likewise be produced with any solid particulate medicament aerosol generator, by techniques known in the pharmaceutical art.

Alternatively, one can administer the agent in a local rather than systemic manner, for example, in a depot or sustained-release formulation.

Further, the present invention provides liposomal formulations of the agents disclosed herein and salts thereof. The technology for forming liposomal suspensions is well known in the art. When the agent or salt thereof is an aqueous-soluble salt, using conventional liposome technology, the same can be incorporated into lipid vesicles. In such an instance, due to the water solubility of the agent or salt, the agent or salt will be substantially entrained within the hydrophilic center or core of the liposomes. The lipid layer employed can be of any conventional composition and can either contain cholesterol or can be cholesterol-free. When the agent or salt of interest is water-insoluble, again employing conventional liposome formation technology, the salt can be substantially entrained within the hydrophobic lipid bilayer which forms the structure of the liposome. In either instance, the liposomes which are produced can be reduced in size, as through the use of standard sonication and homogenization techniques.

The liposomal formulations containing the agents disclosed herein or salts thereof, can be lyophilized to produce a lyophilizate which can be reconstituted with a pharmaceutically acceptable carrier, such as water, to regenerate a liposomal suspension.

In the case of water-insoluble agent s, a pharmaceutical composition can be prepared containing the water-insoluble agent, such as for example, in an aqueous base emulsion. In such an instance, the composition will contain a sufficient amount of pharmaceutically acceptable emulsifying agent to emulsify the desired amount of the agent. Particularly useful emulsifying agents include phosphatidyl cholines and lecithin, In particular embodiments, the agent is administered to the subject in a therapeutically effective amount, as that term is defined above. Dosages of pharmaceutically active agents can be determined by methods known in the art, see, e.g., *Remington's Pharmaceutical Sciences* (Maack Publishing Co., Easton, Pa.). The therapeutically effective dosage of any specific agent will vary somewhat from agent to agent, and patient to patient, and will depend upon the condition of the patient and the route of delivery. As a general proposition, a dosage from about 0.1 to about 50 mg/kg will have therapeutic efficacy, with all weights being calculated based upon the weight of the agent, including the cases where a salt is employed. Toxicity concerns at the higher level can restrict intravenous dosages to a lower level such as up to about 10 mg/kg, with all weights being calculated based upon the weight of the agent, including the cases where a salt is employed. A dosage from about 10 mg/kg to about 50 mg/kg can be employed for oral administration. Typically, a dosage from about 0.5 mg/kg to 5 mg/kg can be employed for intramuscular injection. Particular dosages are about 1 mal/kg to 50 µmol/kg, and more particularly to about 22 µmol/kg and to 33 µmol/kg of the agent for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of diabetes or other metabolic disorder.

The present invention is more particularly described in the following examples that are intended as illustrative only since numerous modifications and variations therein will be apparent to those skilled in the art.

Example 1

Identification of SOGA

Type II diabetes is associated with high glucose production. Obesity increases glucose production by lowering circulating levels of the hormone adiponectin. Therefore, type II diabetes can be treated by stimulating the adiponectin signaling pathway. Adiponectin lowers circulating glucose by inhibiting glucose production from the liver. Adiponectin inhibits glucose production by activating AMP-activated kinase (AMPK). AMPK stimulates fatty acid (FA) oxidation. The inhibition of glucose production by a signaling intermediate that increases FA oxidation is counter-intuitive because ATP generated from FA oxidation fuels glucose production. Furthermore, AMPK stimulates autophagy, a regulated mechanism of intracellular degradation that provides the biochemical intermediates for glucose production through the hydrolysis of proteins, glycogen and triglycerides. This deadlock led to the hypothesis that adiponectin inhibits glucose production through a novel mediator. Insulin inhibition of glucose production in the liver is mediated by the suppression of lysosome activity. We treated rat hepatoma cells with full-length recombinant adiponectin and identified the proteins that were bound to APPL1 in a co-immunoprecipitation assay using proteomics analysis. APPL1 was previously identified in a yeast 2-hybrid screen using the intracellular region of the adiponectin receptor. Proteomics analysis revealed a gene we are calling SOGA (also called TOA (Target Of Adiponectin)) that encodes a 161 kDa protein containing (1) a leucine zipper motif that enables binding to the leucine zipper motif of APPL1 and (2) Atg16 and Rab5-binding motifs that enable participation in membrane assembly for autophagy. The hydrolysis of proteins and glycogen by autophagy increases glucose production by producing biochemical intermediates for gluconeogenesis and glycogenolysis. Northern blot analysis revealed that SOGA is ubiquitously expressed as a 3.0 and a 4.5 kb mRNA. Our current hypothesis is that adiponectin stimulation of SOGA (NCBI Accession: FJ977045) can suppress glucose production.

We verified the expression of SOGA in the liver and other tissues by RT-PCR and Northern blot analysis. There are no publications describing SOGA, its gene, mRNA or amino acid sequence. The open reading frame of murine SOGA is derived from 16 exons. SOGA cDNA encodes a 1434 amino acid protein that lacks transmembrane domains. SOGA contains a leucine zipper motif that we predict allows SOGA to bind to the leucine zipper motif of APPL1 in our co-immunoprecipitation experiment (FIG. 1). The predicted regions of interest in SOGA include (1) a leucine zipper motif, (2) ATG16 motifs, (3) a Rab5 motif, (4) a casein kinase domain, (5) multiple myristoylation and glycosylation sites and (6) multiple kinase specific phosphorylation sites (FIG. 1). Amino acid sequence alignment shows that murine SOGA is 91% identical to human SOGA. When substitutions for similar amino acids are taken into account, murine SOGA is 95% identical to human SOGA. SOGA is a highly conserved gene in mammals but absent in lower eukaryotes like yeast. Our current model is that adiponectin signaling triggers SOGA binding to APPL1, a proximal target of the adiponectin receptor. Based on conserved domain predictions, SOGA binding to APPL1 contributes to adiponectin inhibition of protein degradation and glucose production. This may be accomplished through the binding of SOGA to APPL1, the proteolytic cleavage of SOGA and the secretion of its 25 kDa fragment.

Figure 2:
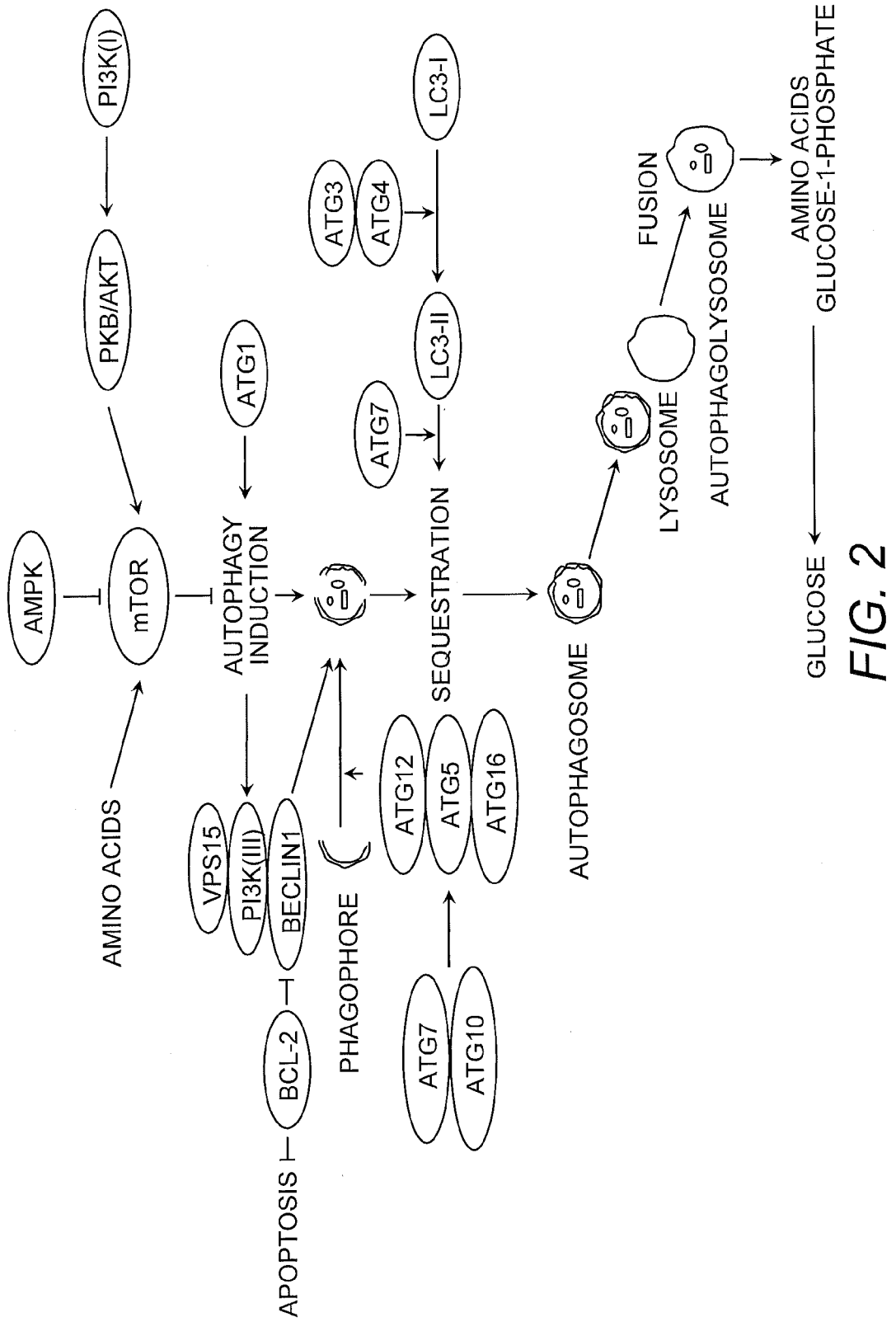
FIG. 2 shows the current model of autophagocytosis and the autophagy machinery showing mTOR and ATG 16 in black.

The formation of the phagophore, a primary step in autophagy, can lead to the digestion of proteins and glycogen providing the biochemical intermediates for glucose production (FIG. 2). Atg16-Atg5-Atg12 forms a protein complex that is essential for the formation of an autophagosome. Atg12 is covalently conjugated to Atg5 by ubiquitination-like reactions that involve Atg7 and Atg10. Overexpression of Atg5 and Atg12 in yeast causes an increase in autophagy that is absent in mammalian cells, suggesting the existence of a novel protein in higher eukaryotes. Although 31 autophagy-related (Atg) proteins have been identified in yeast, SOGA is highly conserved in mammals but bears little homology to any gene product in yeast. Thus, the study of SOGA can lead to the elucidation of the mechanisms governing autophagy in mammals.

We predicted that SOGA plays a role in adiponectin's inhibition of glucose production based on its binding to APPL1 under adiponectin exposure and the conserved functional domains of SOGA which include (1) a leucine zipper motif that enables SOGA to bind to APPL1, (2) an ATG16 (autophagy 16) motif that enables SOGA to initiate autophagy through the formation of the phagophore, (3) Rab5 motif (a small GTPase) that enables the fusion of the autophagosome and lysosome, (4) casein kinase domain that enables a downstream signaling cascade, (5) myristoylation and glycosylation sites that enable anchoring and (6) multiple kinase-specific phosphorylation sites that enable the modulation of SOGA by kinases and phosphatases (FIG. 1). Further insight into SOGA can increase our understanding of nutrient metabolism and lead to new ways of preventing and treating diabetes.

Figure 3:
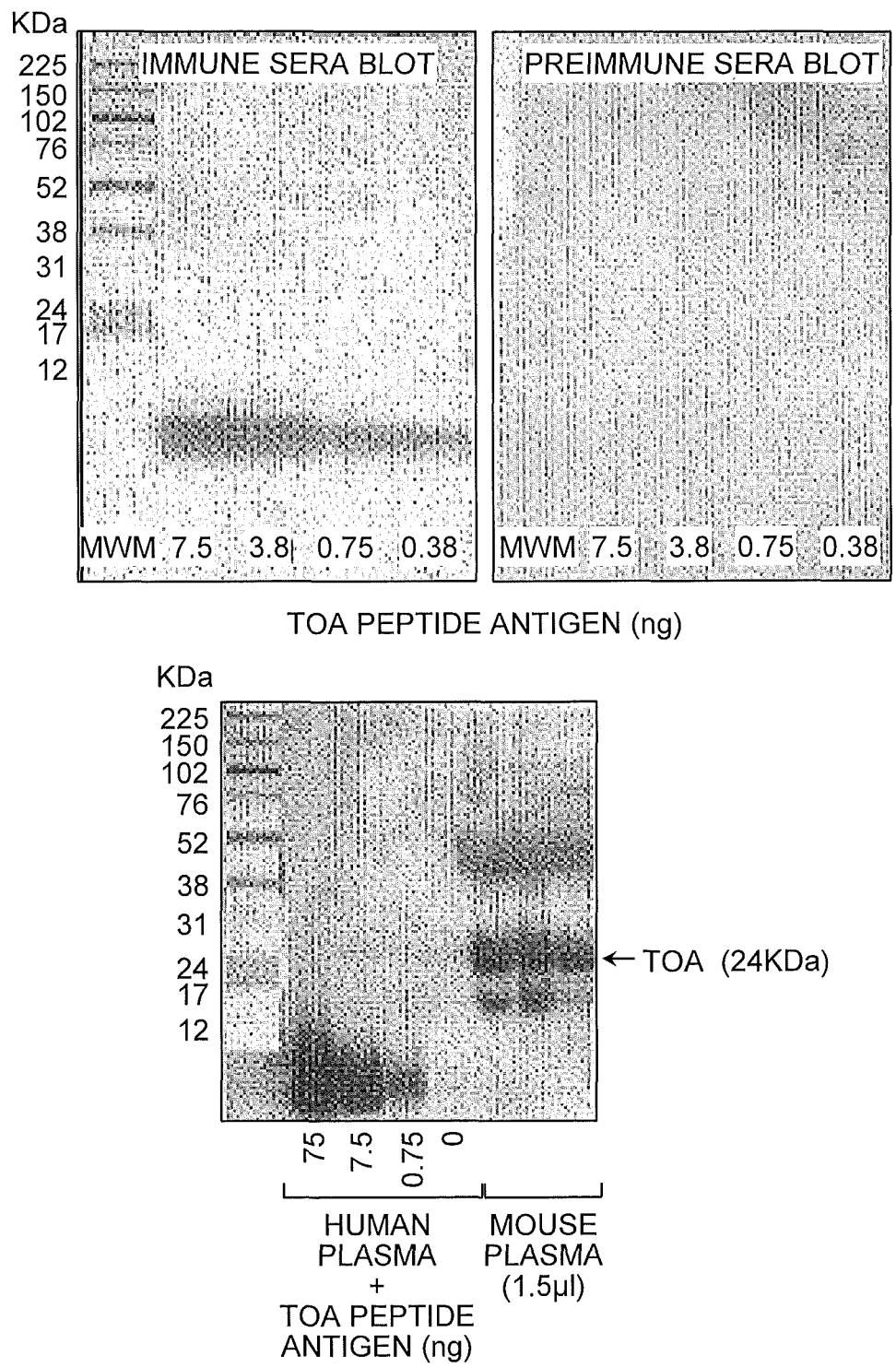
FIG. 3 shows proteolytic cleavage of SOGA yielding a circulating 25 kDa C-terminal fragment.
Figure 4:
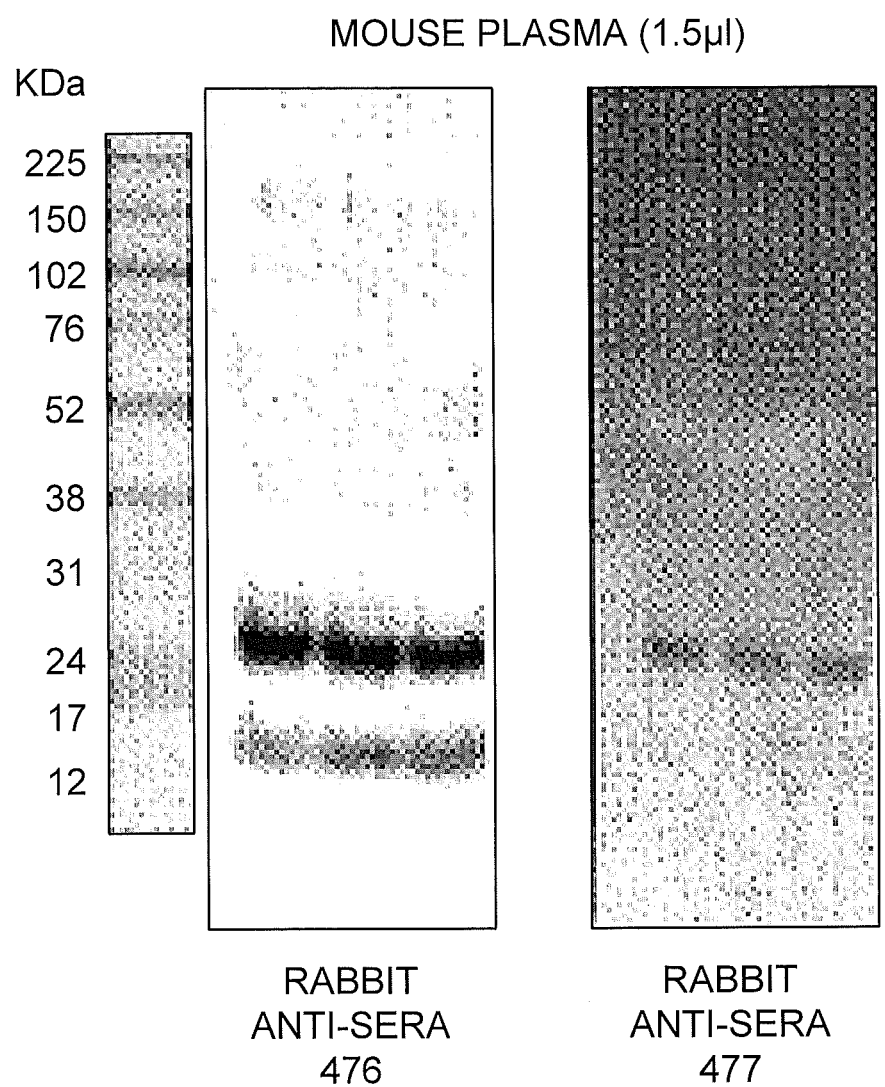
FIG. 4 shows that antisera from two different rabbits immunized with two different peptide antigens, 476 and 477, detected a 25 kDa band in mouse plasma.

Species specific (mouse) SOGA peptide antigen (476) was detected with immune but not pre-immune sera from New Zealand White rabbits (FIG. 3, left panel). The signal intensity is proportional to the peptide antigen concentration. Using our rabbit polyclonal antisera (476) that is specific for mouse SOGA, SOGA was detected in mouse plasma at 25 kDa but not in human plasma (FIG. 3, right panel). Antisera from two different rabbits immunized with two different peptide antigens, 476 and 477 specific for mouse SOGA, detected a 25 kDa band in mouse plasma (FIG. 4). Antigen peptides 476 and 477 correspond to overlapping amino acid sequences in mouse SOGA.

Figure 6:
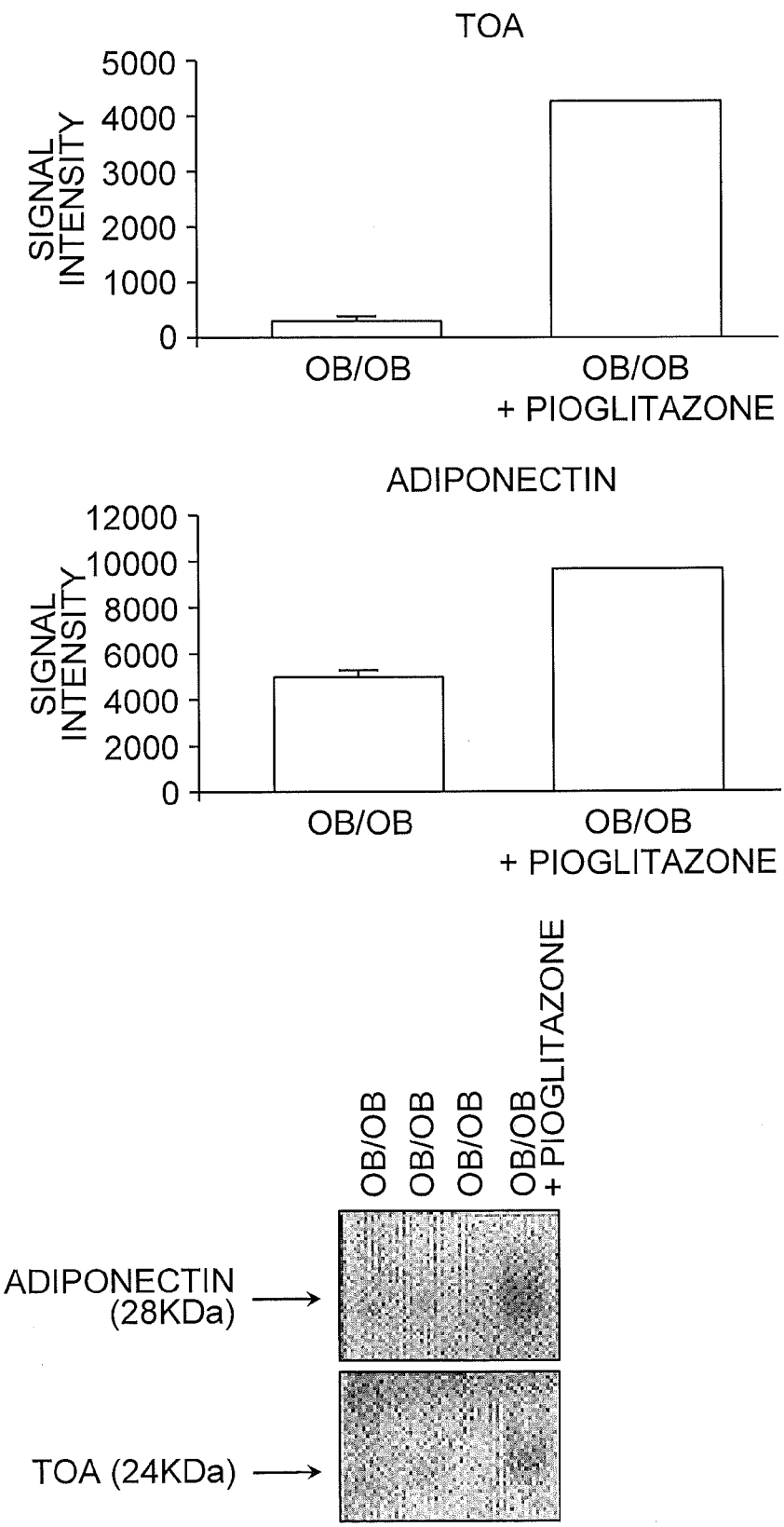
FIG. 6 shows western blot and densitometry of adiponectin and SOGA in ob/ob control mice and ob/ob mice treated with pioglitazone.
Figure 7:
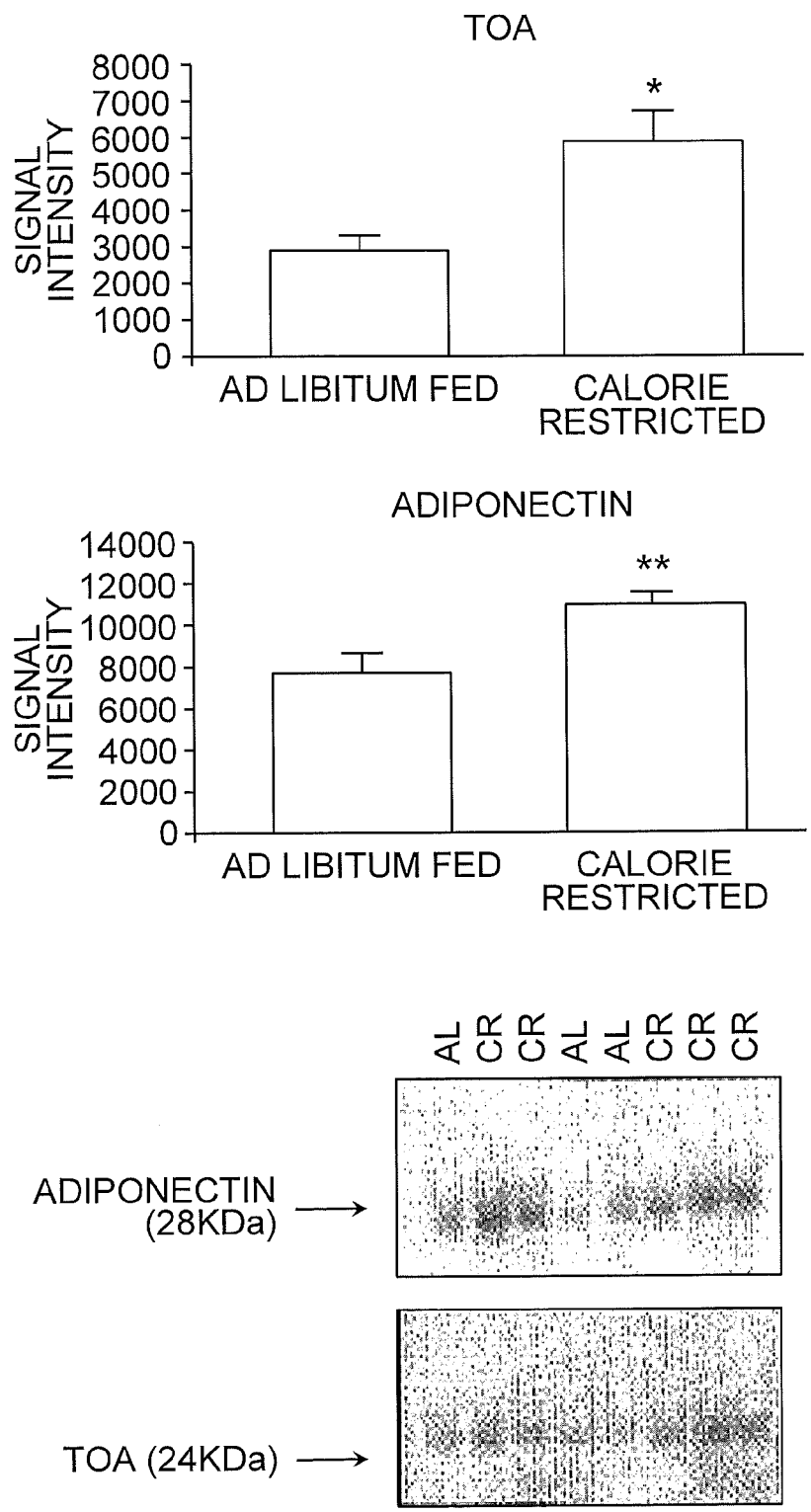
FIG. 7 shows western blot and densitometry of adiponectin and SOGA in ad libitum and calorie restricted fed C57B1 mice.
Figure 8:
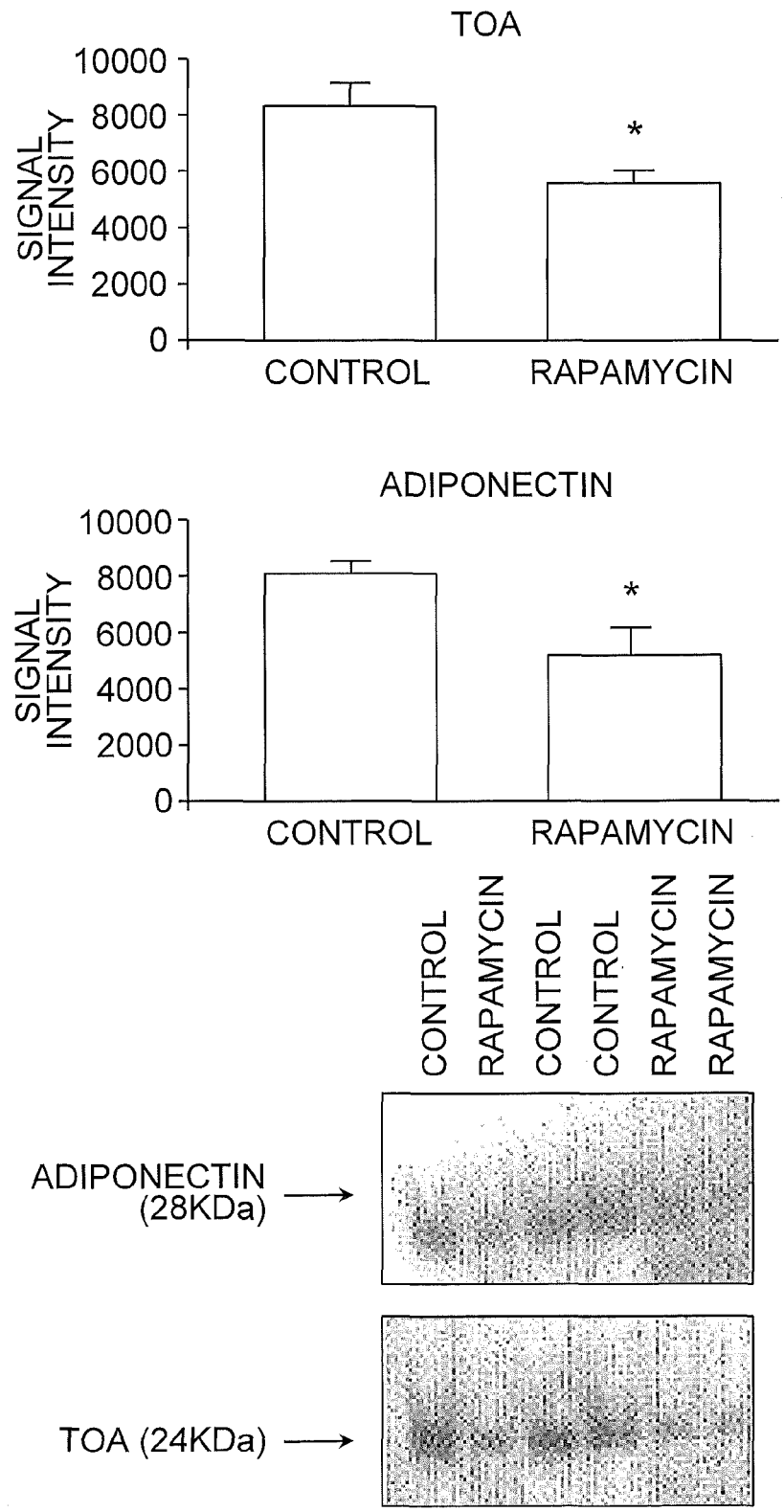
FIG. 8 shows western blot and densitometry of adiponectin and SOGA in rapamycin and control fed C57B1 mice.
Figure 9:
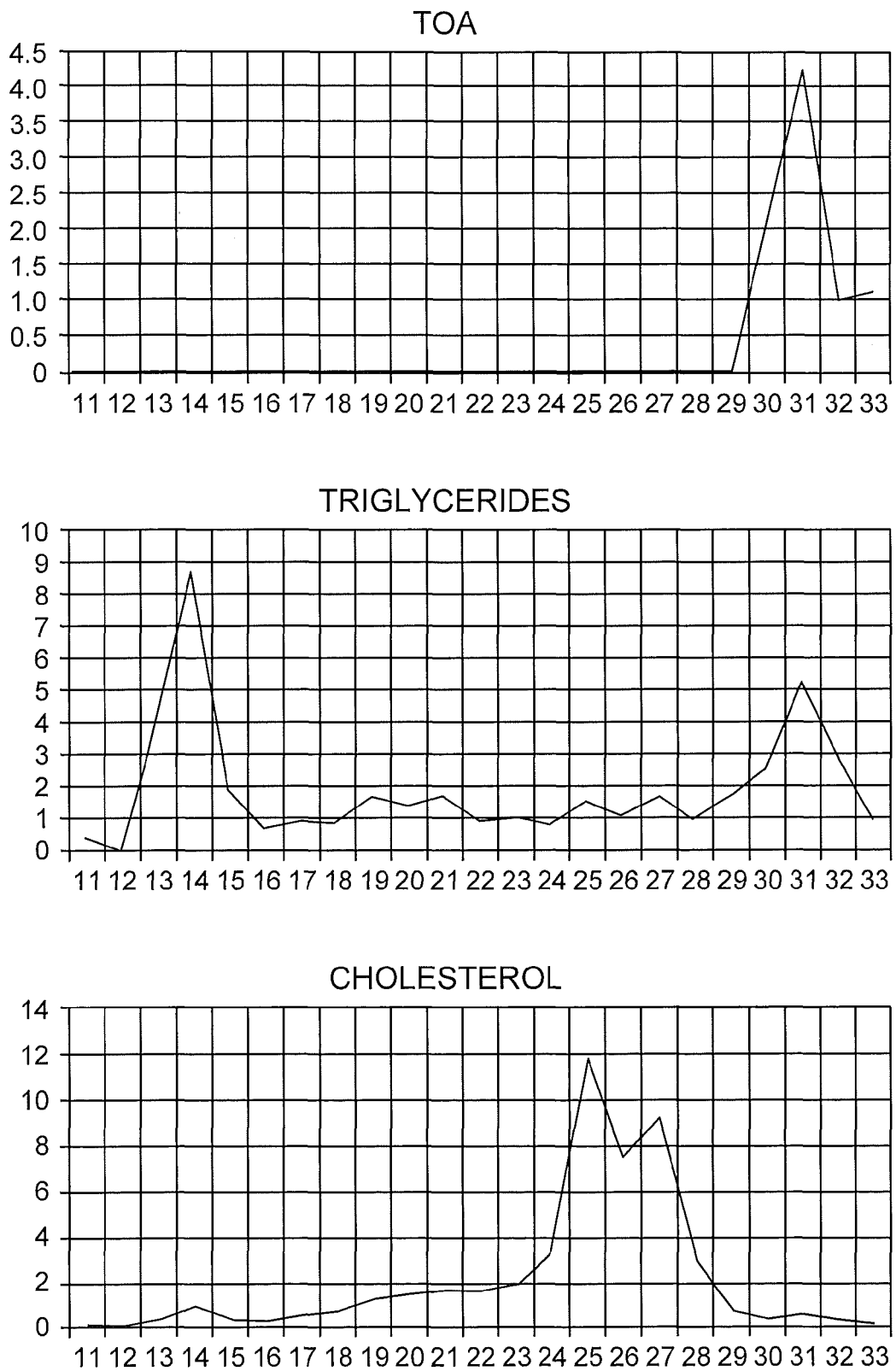
FIG. 9 shows FPLC fraction analysis of mouse plasma for SOGA.

The concentration of SOGA in plasma corresponded with circulating levels of adiponectin (FIG. 5). Plasma was sampled from young female C57B1 adiponectin null and wild-type mice. Western blot and densitometry of adiponectin and SOGA in ob/ob control mice and ob/ob mice treated with pioglitazone showed that adiponectin and SOGA were increased in ob/ob mice on pioglitazone compared to controls (FIG. 6). Western blot and densitometry of adiponectin and SOGA in ad libitum and calorie restricted fed C57 mice showed that adiponectin and SOGA were increased in calorie restricted mice compared to those fed ad libitum ($P<0.05$ for statistical significance) (FIG. 7). Western blot and densitometry of adiponectin and SOGA in rapamycin and control fed C57B1 mice revealed that SOGA was decreased in rapamycin fed mice compared to controls ($P<0.05$ for statistical significance) (FIG. 8). FPLC fraction analysis of mouse plasma for SOGA was performed (FIG. 9). Graphs show SOGA, triglyceride, and cholesterol levels in FPLC fractions 11-33.

In summary, SOGA (TOA) is a novel protein that we have identified through proteomics and a co-immunoprecipitation assay; it binds to APPL1 under adiponectin exposure. The SOGA gene contains Atg16 and Rab5-binding motifs that are indicative of autophagic activities; it is hypothesized that adiponectin stimulation of SOGA can suppress glucose production. SOGA peptide antigen was detected by immune sera from NZW rabbits; SOGA was detected at 25 kDa in mouse plasma but not human plasma. Two distinct antigens corresponding to overlapping segments of SOGA produced antisera that detected a 25 kDa SOGA. Circulating levels of SOGA were greatly suppressed in adiponectin null (−/−) mice. Adiponectin and SOGA were increased by pioglitazone, and calorie restriction, but were suppressed by rapamycin. FPLC analysis indicates that SOGA circulates below 100 kDa.

Example 2

Experimental Methods

Mass Spectrometry.

McArdle rat hepatoma cells were exposed to adipocyte conditioned media with or without adiponectin (Brooks et al., J. Biol. Chem. 282:35069 (2007)). Cell lysates were digested with proteomics grade trypsin (Sigma) and filtered through YM-10 molecular weight cutoff filters (Millipore, Bedford, Mass.). Tryptic digests were injected into an LCQ-Deca Ion Trap mass spectrometer coupled to a Surveyor HPLC system (Thermo Fisher Scientific, Waltham, Mass.). The solvent, 50% methanol and 0.1% formic acid, was delivered to the spectrometer at 200 μL/min. Peptide masses were acquired in positive mode using electrospray ionization under the following source conditions: spray voltage was 5 kV, sheath gas was 40 (arbitrary units), auxiliary gas was 20 (arbitrary units), and heated capillary temperature was 350° C.

Cloning of Murine SOGA.

Total RNA was obtained from primary mouse hepatocytes using Triazol reagent (Invitrogen). mRNA was isolated using Oligotex mRNA Kit (Qiagen). Primers used to clone SOGA were designed using publically available genomic and mRNA sequence data based on the open reading frame of SOGA peptides detected by mass spectrometry. The 4.7 kb SOGA cDNA was isolated by annealing two PCR products using overlap extension. RNA ligase mediated RACE (Ambion) was used to clone the sequence from the 5'-end of SOGA mRNA. The cDNA for human SOGA was cloned by a similar method.

Antibody Production.

Human- and murine-specific polyclonal antisera were produced in three New Zealand White rabbits (Franklin Rabbitry, N.C.) using a human-specific peptide antigen STQSLTSFARSSRSAIRHSPSKC (SEQ ID NO:5) and two partially overlapping murine-specific peptide antigens CSAQSLASC-FIRPSRN (SEQ ID NO:6) and SAQSLASC*FIRPSRNPIRHSPSKC (SEQ ID NO:7), where C* represents acemidomethyl cysteine. Synthetic peptides were purified by HPLC and analyzed on the LCQ-Deca Ion Trap mass spectrometer to confirm their molecular weight. Antigenic peptides (10 mg) were dissolved in 0.1 M $NaH_2PO_4$ (pH 7.2)/0.05 M NaCl and conjugated to keyhole limpet hemocyanin (KLH; 4 mg) before injection. KLH conjugated peptides were dissolved in 3 ml of 0.03% trifluoroacetic acid and added to 3 ml complete Freund's adjuvant (Sigma). New Zealand White rabbits (Franklin Rabbitry, Wake Forest, N.C.) were injected intradermally using multiple injection sites. After 5 weeks, each animal was reinjected subcutaneously with KLH conjugated antigen in 1 ml of 50% incomplete Freund's adjuvant (Sigma). Four weeks later, 20 ml of blood were collected and rabbits were reimmunized. Injections and bleedings were performed at monthly intervals thereafter. The antibody production protocol was approved by UNC's Institutional Animal Care and Use Committee (IACUC).

Hepatocyte Studies.

Mouse livers were perfused with a Krebs-Ringer-HEPES buffer containing collagenase (Sigma-Aldrich). Livers were isolated and cells were dispersed by gentle shaking and filtered through sterile nylon gauze. Cells were washed twice with sterile phosphate-buffered saline and purified by centrifugation in 50% isotonic Percoll (Sigma-Aldrich). Cells were resuspended with Krebs-Ringer-HEPES $Ca^{2+}$ buffer to a total volume of 10 ml. Viability was validated via trypan blue exclusion and routinely exceeded 90%. Freshly isolated mouse hepatocytes were plated at $10^5$ cells per well in 12-well culture plates coated with rat tail collagen I (BD Biosciences). Cells were maintained in Dulbecco's modified Eagle medium (DMEM; Caisson Laboratories), 25 mM glucose and 10% horse serum (HS). Adiponectin was provided from adipocyte conditioned media with or without adiponectin (Brooks et al., J. Biol. Chem. 282:35069 (2007)). SOGA siRNA, AICAR (500 μM) or LY293004 (10 nM) were introduced to the media 48 hours before the measurement of glucose production. siRNA sequences corresponding to base pairs 333-351 and 1988-2007 on the open reading frame of murine SOGA were selected using a rational design algorithm (Invitrogen). Transfection with a pool of 2 siRNAs targeting SOGA had a greater knockdown efficiency than transfecting with the individual siRNAs. Transfection was achieved by electroporation using the Mouse Hepatocyte Nucleofector Kit (LONZA) according to the manufacturer's protocol. In brief, freshly isolated mouse hepatocytes were diluted to $3\times10^6$ cells/tube in media without antibiotics and centrifuged at 2,000 rpm for 2 minutes. The supernatant was removed and the cells were resuspended in 100 μl of Nucleofector solution containing 100 nM of siRNA. The cell suspension was transferred to an electroporation cuvette which was placed in a Nucleofector I electroporation device and pulse charge was applied for 2 minutes using program T-28. Hepatocytes received 1.0 ml of media and were transferred to 12 well plates. SOGA expression, valine and glucose production were assayed 72 hours after siRNA transfection. Media was replaced with glucose-free DMEM containing MG-132 (10 µM), an inhibitor of the ubiquitin-proteasome pathway of protein degradation, for 6-8 hours to measure hepatocytes glucose production. Glucose was measured by colorimetric assay (Autokit Glucose CII) (Brooks et al., *J. Biol. Chem.* 282:35069 (2007)). Valine in the medium was measured by a HPLC (Waters) coupled TSQ-Quantum ultra triple quad mass analyzer (ThermoFinigan) in the Biomarkers Facility Core at UNC. Valine was measured in selected reaction monitoring mode (SRM) using the MS/MS transition of 118→72.

Lysosomal Activity.

Autophagic activity was estimated by lysosome and late autophagosome vacuole staining using LysoTracker Red DND 99 (Invitrogen), a membrane permeable fluorescent labeled basic amine with high affinity for the acidic interior of the lysosome and late autophagosome vacuole (Klionsky et al., *Autophagy* 4:151 (2008)). Cell medium was removed and replaced with GF/DMEM containing 50 nM LysoTracker Red. Cells were incubated for 30 min at 37° C. and the medium was replaced with GF/DMEM. Digital images were obtained at the Light Microscopy Facility at UNC with an Olympus 1×81 Motorized Inverted Microscope, a 40×11.30 Oil DIC lens, Camera pixel count: Hamamatsu C10600-1013 1344×$10^{24}$ using the acquisition software Velocity 5.3.2 (Perkin Elmer). Fluorescence Filter Cubes Specifications (Semrock, Inc.) were TXRED-4040B for rhodamine and Texas Red: Exciter 562 nm 20, Dichroic R 530-585/T 601-800, Emitter 642±20. Lysosome and late autophagosome vacuole number was determined from digital images as isolated punctuate staining, greater than background staining intensity threshold, distinct from lipid droplets in clearly demarcated cells containing two nuclei. Spot recognition and enumeration according to the foregoing definition was determined by two individuals.

Mouse Studies.

Mice were housed in ventilated isolator cage systems in a pathogen-free barrier facility maintained at 23° C., 55% humidity on a 12-h light/12-h dark cycle. Mice received a standard chow diet consisting of 73% carbohydrate, 18% protein, 4% fat and 5% ash (Purina). Young (3-6 month old) female C57B1/6J calorie restricted (CR) and ad libitum fed (AL) mice were maintained as previously described (Combs et al., *Diabetes* 52:268 (2003)). Adjustments were made to ensure that CR mice received 70% of the ad libitum food intake. Blood samples were collected at 1300 from the tail tip using heparinized capillary tubes (Fisher) and stored at −20° C. Male ob/ob mice (FVB background strain) received a daily dose of pioglitazone at 0.6 mg/kg BW in 0.025% (w/w) carboxymethylcellulose by oral gavage for 4 days. Control mice received carboxymethylcellulose by oral gavage for 4 days. Blood was collected from the tail tip on day 5 and analyzed for glucose, adiponectin and 25 kDa SOGA. Immediately after the collection of blood samples, ob/ob mice were sacrificed by cervical dislocation for tissue collection. Northern blot analysis for SOGA mRNA and 18S RNA was performed using 20 µg of liver RNA. NOD mice were bred and housed as previously described (Wong et al., *J. Immunol.* 176:1637 (2006)). Where indicated, diabetic NOD mice were injected with 5 units of insulin (NPH Human Insulin, Isophane Suspension; 100 U/ml Novolin; Novo Nordisk) 24 hours prior to blood collection. Adiponectin transgenic mice were produced as previously described (Combs et al., *Endocrinology* 145:367 (2004)). Glucose was measured by colorimetric assay. Adiponectin and SOGA were measured by SDS-PAGE analysis using 1 µl of plasma. The total concentration of protein in plasma, measured by BCA assay (Pierce), did not differ between groups. Experimental procedures were approved by IACUC.

Human Studies.

Thirteen healthy women between the ages of 20-63, body mass indexes (in kg/$m^2$) between 20.2 and 31.9, were included for this study. Inclusion was contingent on a good, age-typical health status, as ascertained by physical examination and standard clinical laboratory tests such as complete blood count, blood chemistries, fasting glucose, insulin, lipid and liver function tests, liver lipid content and the presence of no known chronic disease including diabetes. Subjects were admitted to the Clinical and Translational Research Center of UNC and placed on a balanced weight maintenance diet for 10 days (Fischer et al., *Am. J. Clin. Nutr.* 85:1275 (2007)). Circulating SOGA and adiponectin were measured from plasma samples collected from an intravenous catheter following an overnight fast. The race-ethnicity distribution of the participants was white (63%), African American (27%), Asian (6%), and Native American (4%), which reflected the local population characteristics of the Raleigh-Durham-Chapel Hill area. Plasma adiponectin and SOGA were determined by SDS-PAGE using polyclonal antisera against human adiponectin and human SOGA, horseradish peroxidase linked secondary anti-rabbit IgG. Circulating adiponectin and SOGA levels were measured by enhanced chemiluminescence (ECL) signal intensity. Human studies were performed under an IRB approved protocol (CTRC-2645; Study: 07-1158).

Statistical Analysis.

Student's t test was used to identify significant differences when data within groups showed a normal distribution and Wilcoxon-Rank Sum test was used when data did not show a normal distribution. P values less than 0.05 were considered significant.

Example 3

Identification of SOGA by Mass Spectrometry

Protein extracts from hepatoma cells exposed to adiponectin were digested with trypsin and analyzed by mass spectrometry. Mass spectrometry revealed a peptide, KVLP-SEEDDFLEVNSM (SEQ ID NO:8), encoded by a gene located on chromosome 2 in mice (2411) and chromosome 20 in humans (20q 11). Mouse liver RNA was used to clone the full length 4.7 kb SOGA cDNA (GENBANK ID: H977045). Northern blot analysis, using a probe recognizing the C-terminal end of SOGA, revealed a single dominant 4-5 kb band in the liver. The ORF of the cDNA clone predicts a 161 kDa protein that contains an internal secretory peptide sequence, FKHNFLLLFMKLRWFLKRWRQG (SEQ ID NO:9) (FIG. 10). On the basis of computational methods that incorporate signal peptide and cleavage site predictions, SOGA is cleaved between G at the end of the signal peptide and K at the beginning of at the peptide identified by mass spectrometry (Emanuelsson et al., *Nat. Protoc.* 2:953 (2007)).

FIG. 10 is a map showing the location of the conserved ATG16 and Rab5-binding motifs, the secretory signal peptide and the species-specific epitope in the predicted 161 kDa SOGA. The map also shows the predicted domains of the 80 kDa peptide detected in vitro and the 25 kDa peptide detected in plasma. FIG. 10 shows the amino acid sequence for murine SOGA (SEQ ID NO:2) showing the location of the Atg16 (232-375) and Rab5-binding (757-886) motifs underlined, the signal peptide (681-702) in bold, the tryptic peptide identified by mass spectrometry (703-718) shaded and the species specific domain (1392-1416) in a box. The position of the internal signal peptide explains why our antibodies, recognizing the species-specific epitope near the C-terminus of SOGA, detect an 80 kDa SOGA peptide rather than the 161 kDa SOGA protein.

Example 4

Function of SOGA in Primary Hepatocytes

Figure 11A:
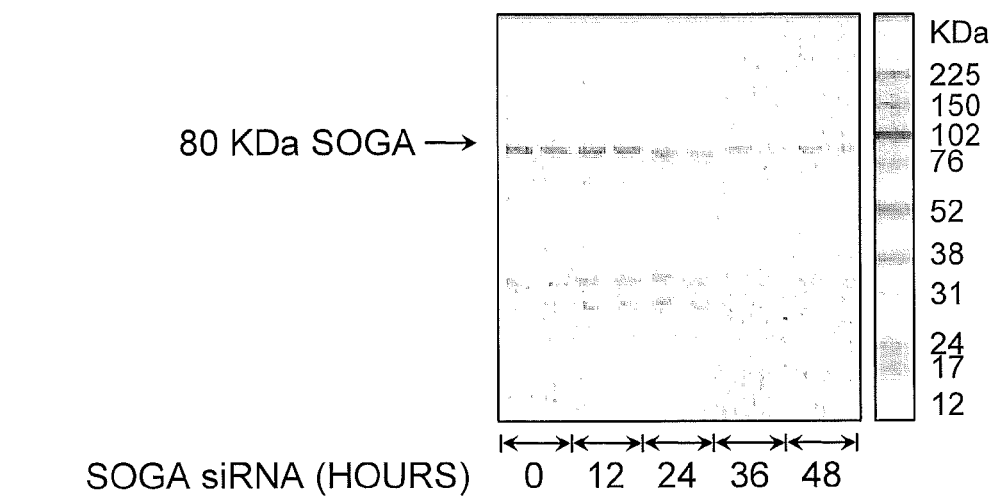
FIGS. 11A-11D show the function and regulation of SOGA in primary hepatocytes.
Figure 11B:
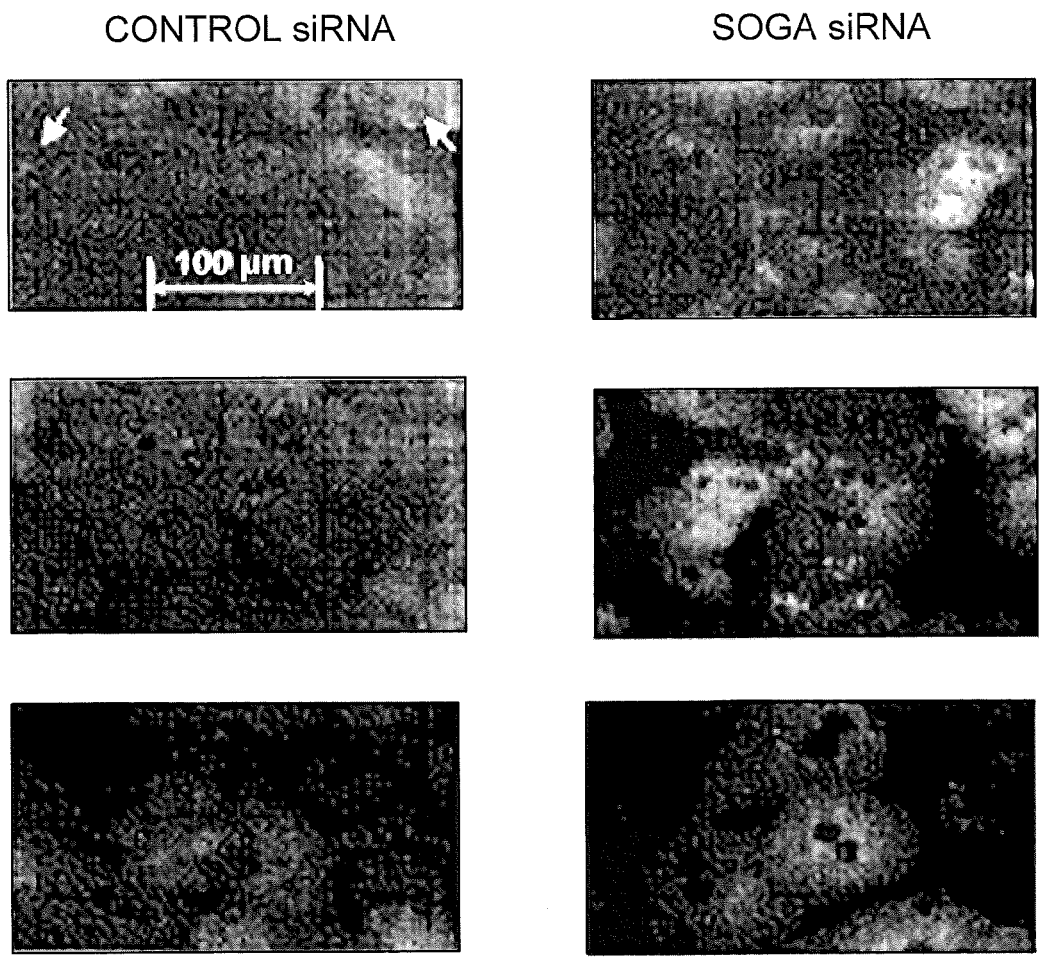
Figure 11C:
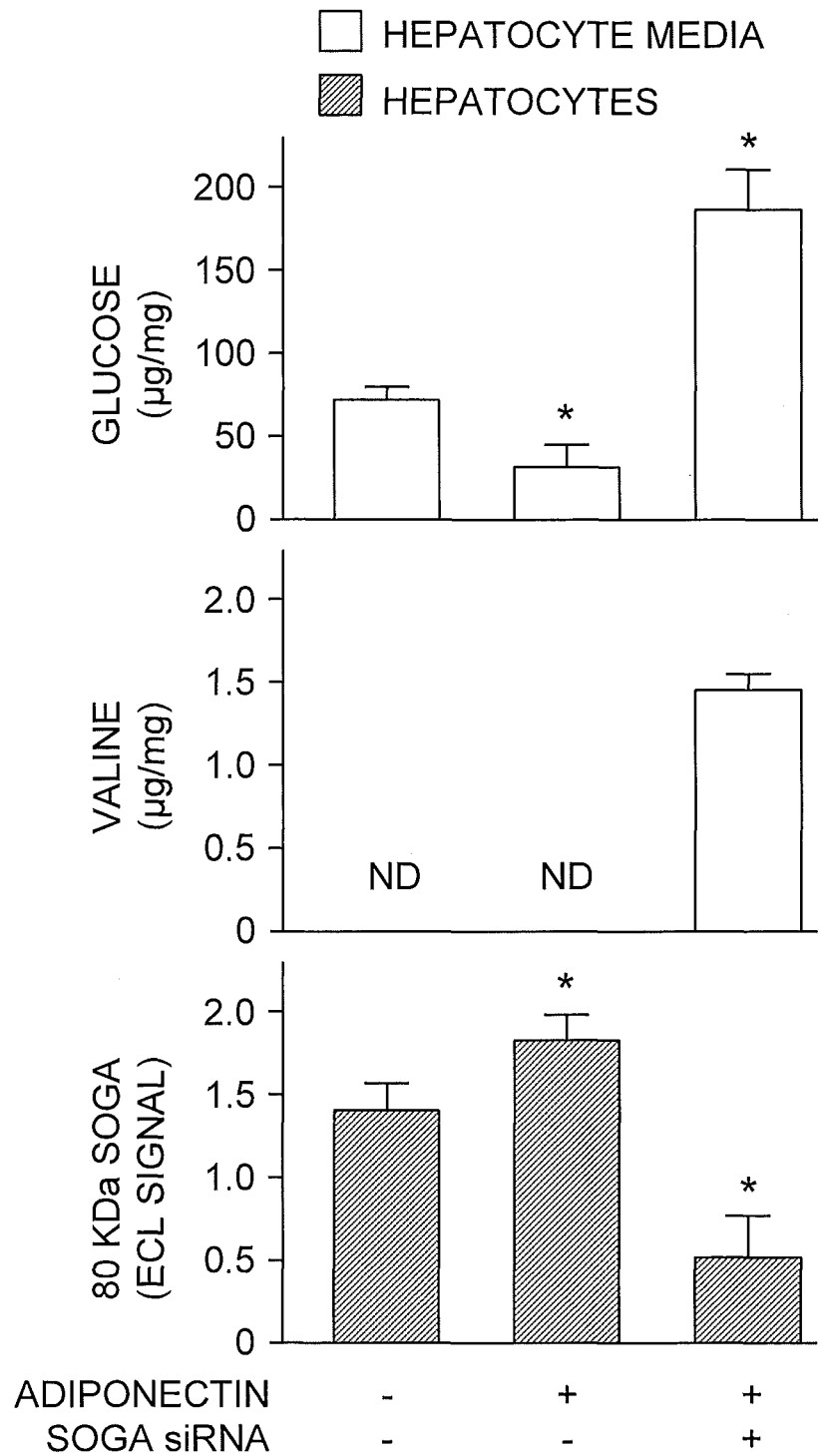

Consistent with the predicted position of the cleavage site, rabbit antisera recognizing the species-specific domain on the C-terminal region of murine SOGA recognized a single 80 kDa protein in isolated hepatocytes (FIG. 11A). FIG. 11A shows a representative SDS-PAGE of primary murine hepatocyte samples showing the knockdown of 80 kDa SOGA as a function of time after exposure to siRNA. siRNA suppression of SOGA caused a dramatic increase in lysosome and late autophagic vacuole number (2.0±0.2 per cell compared to 17.5±2.0 per cell where n=25-30 cells per group, $p<0.0001$) as indicated by isolated punctate acidotropic dye staining which provides correlative data on autophagy (FIG. 11B) (Klionsky et al., *Autophagy* 4:151 (2008)). FIG. 11B shows representative purified binucleate hepatocyte cultures transfected with control (left) or SOGA siRNA (right) stained with the lysosome-specific fluorescent dye LysoTracker Red. The hypothesis that SOGA inhibits autophagy is further supported by the reduction of total cell protein content 48 hours after siRNA suppression of SOGA (11.2 E 0.6 µg/well compared to 16.3±0.4 µg/well; n=4 per group; $p<0.05$). FIG. 2C depicts bar graphs showing the effects of adiponectin and SOGA siRNA on glucose and valine secretion in hepatocyte conditioned media (top and middle) and 80 kDa SOGA measured by densitometry of ECL (enhanced chemiluminescent signal) after SDS-PAGE (bottom). Adiponectin exposure caused a 40% increase of SOGA in primary hepatocytes and a 50% reduction in glucose production (FIG. 11C). siRNA suppression of SOGA blocked the inhibition of glucose production and stimulated valine secretion (FIG. 11C). The secretion of valine, an essential amino acid that cannot be metabolized, due to the absence of branched chain aminotransferase in hepatocytes, also suggests an increase in autophagy. These results support the hypothesis that the elevation of SOGA in response to adiponectin exposure is linked to the inhibition of autophagy.

Example 5

Figure 11D:
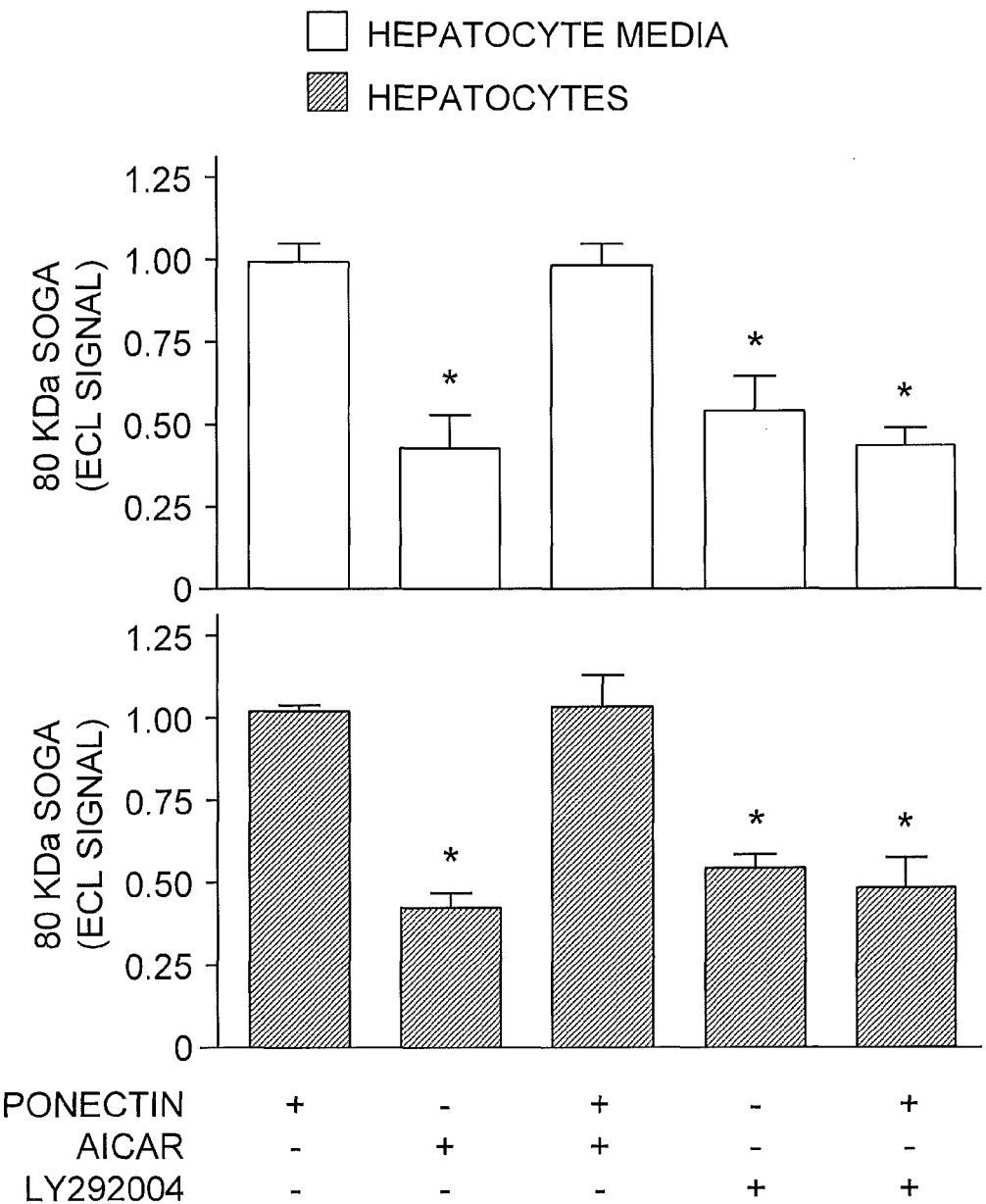

Regulation of SOGA in Primary Hepatocytes and the Correlation of Intracellular and Extracellular Levels of SOGA FIG. 11D depicts bar graphs showing the roles of AMPK and PI3K on adiponectin regulation of intracellular and extracellular SOGA levels. Primary hepatocytes were incubated in the presence or absence of 500 µM AICAR, a stimulator of AMPK, or 10 nM LY294002, a PI3K inhibitor. Bars represent mean values±SEM for n=4 per group where "*" indicates a significant difference compared to control (left bar) at $p<0.05$ by nonparametric Student's t-test. Grey and black bars indicate whether measurements were made in hepatocyte conditioned media or hepatocytes, respectively. The activation of AMPK by AICAR caused a decrease in SOGA that was blocked by adiponectin exposure (FIG. 11D). On the other hand, the inhibition of PI3K by LY294002 caused a decrease in SOGA that was not blocked by adiponectin (FIG. 11D). These observations suggest that adiponectin increases SOGA through the insulin signaling pathway through a mechanism that can be inhibited by AMPK. Consistent with the identification of an internal secretory signal peptide in SOGA, SDS-PAGE analysis revealed that the 80 kDa SOGA fragment is secreted in hepatocyte conditioned media. The reduction of intracellular SOGA by adiponectin and LY294002 was reflected in the levels of SOGA in hepatocyte conditioned media. These results suggested that extracellular levels of SOGA could be used as a biomarker of its intracellular activity.

Example 6

Circulating SOGA in Mice and Humans

Figure 12A:
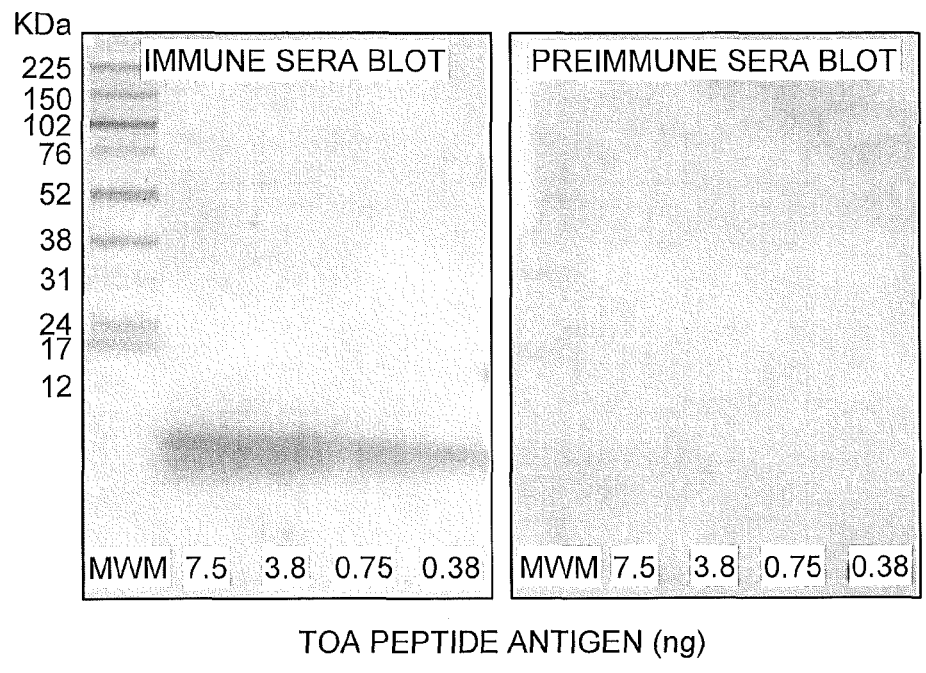
FIGS. 12A-12C show detection of circulating SOGA in mice.
Figure 12B:
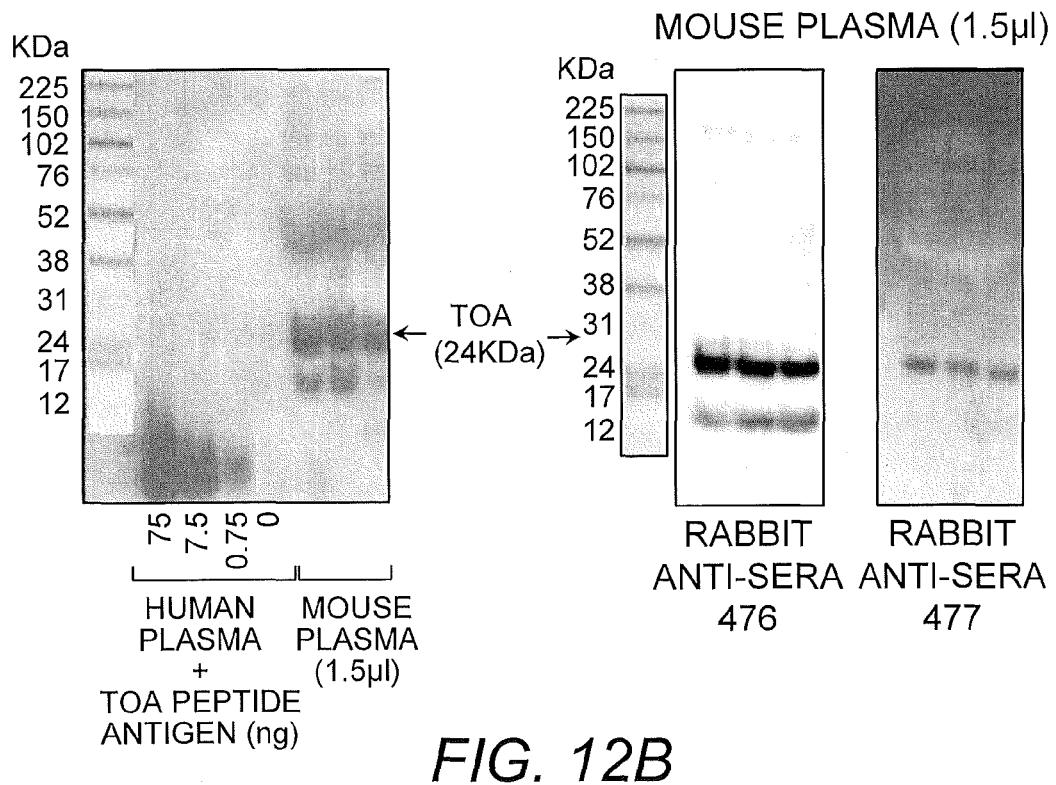
Figure 12C:
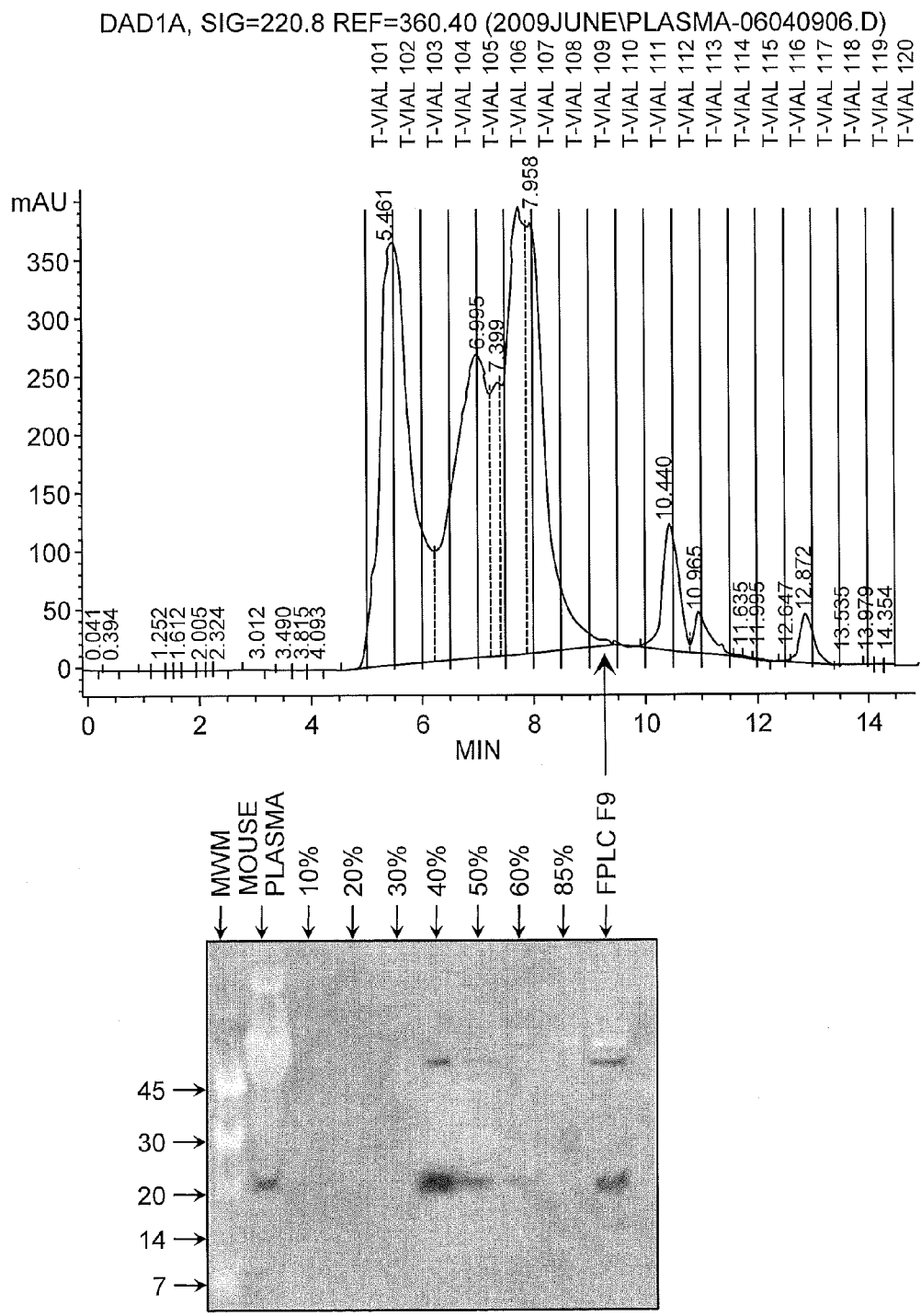

Antisera from 2 different rabbits immunized with two different peptide antigens, 476 and 477, detected a 25 kDa peptide in mouse plasma (FIG. 12A). SDS-PAGE shows the SOGA peptide antigen 476 was detected with immune but not pre-immune sera. The blot exposed to immune sera shows that the signal intensity is proportional to the peptide antigen concentration. FIG. 12B, left panel, shows that mouse-specific polyclonal antisera 476 detected a 25 kDa protein in mouse plasma but not human plasma. FIG. 12B, right panel, shows that antisera from two different rabbits immunized with two different peptide antigens, 476 and 477, detected a 25 kDa peptide in mouse plasma. Peptide antigens 476 and 477 correspond to overlapping amino acid sequences in the species specific epitope of SOGA. Peptide antigens used to produce rabbit antisera, SAQSLASCFIRPSRNPIRFISPSKC (SEQ ID NO:7) (antigen 476) and CSAQSLASCFIRPSRN (SEQ ID NO:6) (antigen 477), were analyzed by mass spectrometry to confirm their amino acid sequence. Rabbit antisera recognizing murine SOGA did not cross-react with any proteins in human plasma. FIG. 12C, top panel, shows a UV absorption plot for plasma proteins generated by HPLC. SDS-PAGE shows that 25 kDa SOGA eluted in fraction 9. For reference, the triglyceride peak (VLDL particle, ~400 kDa) and the cholesterol peak (HDL particle, ~200 kDa) were observed in fractions 1-2 and 5-6, respectively. HPLC analysis confirms that 25 kDa SOGA circulates as a monomer. FIG. 12C, bottom panel, presents SDS-PAGE showing SOGA precipitated out of HPLC fraction 9 in a 40% ammonium sulfate solution. Due to the presence of cysteine residues within the antigenic motif of SOGA, antibody detection of 25 kDa SOGA required the reduction of the sample with dithiothreitol. Based on the predicted sequence of 25 kDa fragment, the intramolecular disulfide bonds between cysteine residues on the carboxy-terminal end of SOGA should generate a fish hook conformation. Two observations indicate that 25 kDa SOGA circulates as a monomer. First, SOGA was detected at 25 kDa when plasma samples were reduced after SDS-PAGE. Second, by size exclusion chromatography of plasma proteins under native conditions, SOGA eluted at 25 kDa (FIG. 12C).

Recombinant 25 kDa SOGA was produced in *E. coli* and was detectable with the antibodies raised against full length SOGA. FIG. 13A shows a BsrG1 digest of murine 25 kDa SOGA clone in pET-DEST42 GATEWAY vector in 2% agarose. FIG. 13B shows a SDS-PAGE blot of recombinant 25 kDa murine SOGA, either without or with 6×His tag, produced in IPTG stimulated *E. coli* transformed with the pET-DEST42 GATEWAY vector. The left panel shows cross reactivity of our murine SOGA antisera with recombinant 25 kDa murine SOGA. The right panel shows a Ponceau red stained blot of total bacterial lysates after SDS-PAGE.

Example 7

Correlation between Circulating Adiponectin and SOGA

Figure 14B:
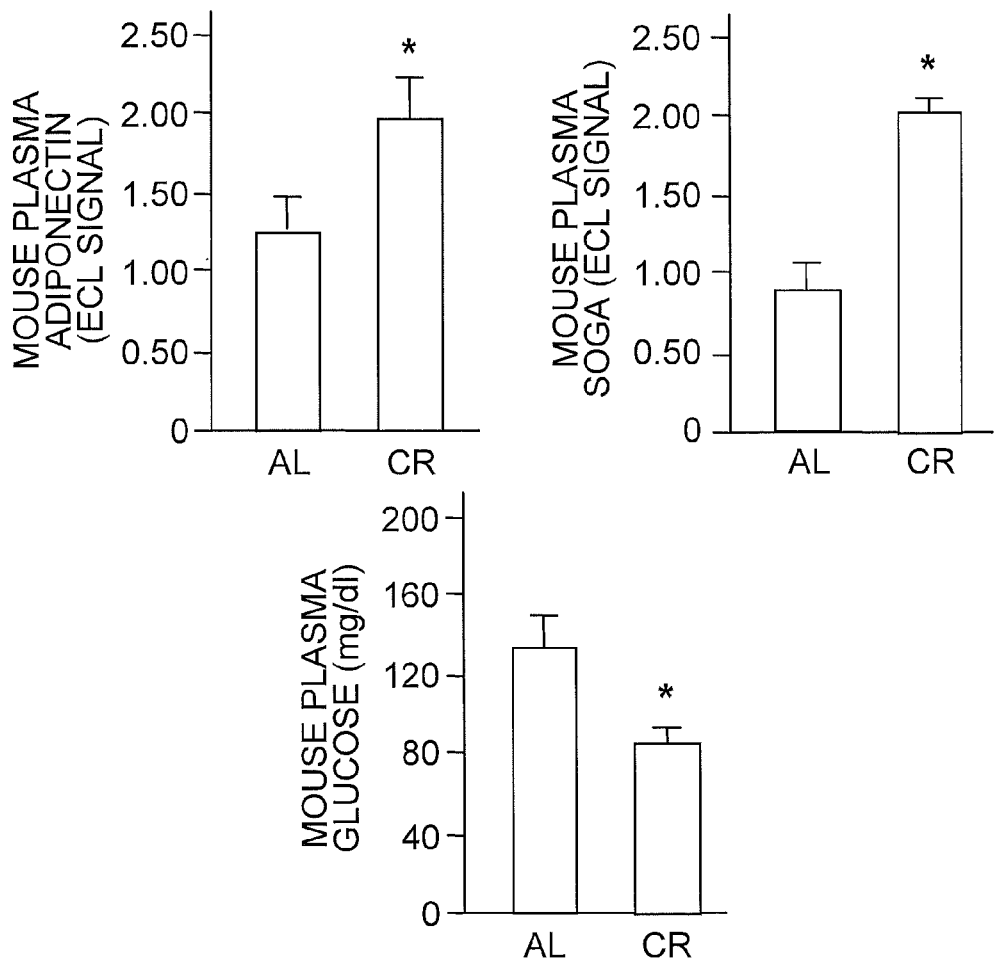
Figure 14D:
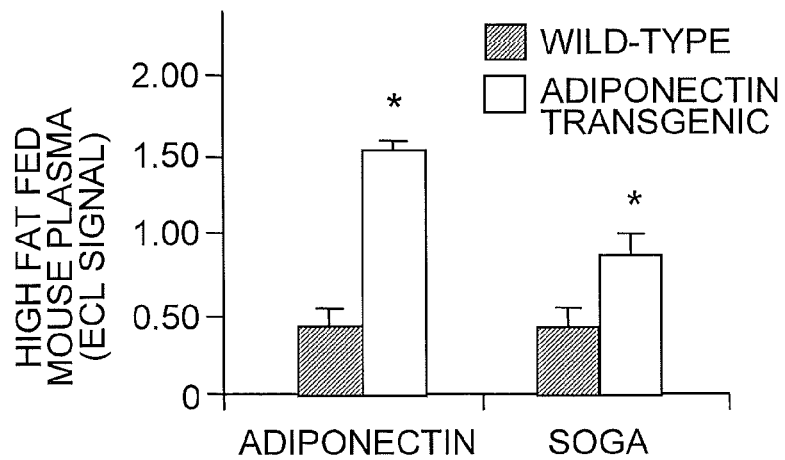
Figure 14C:
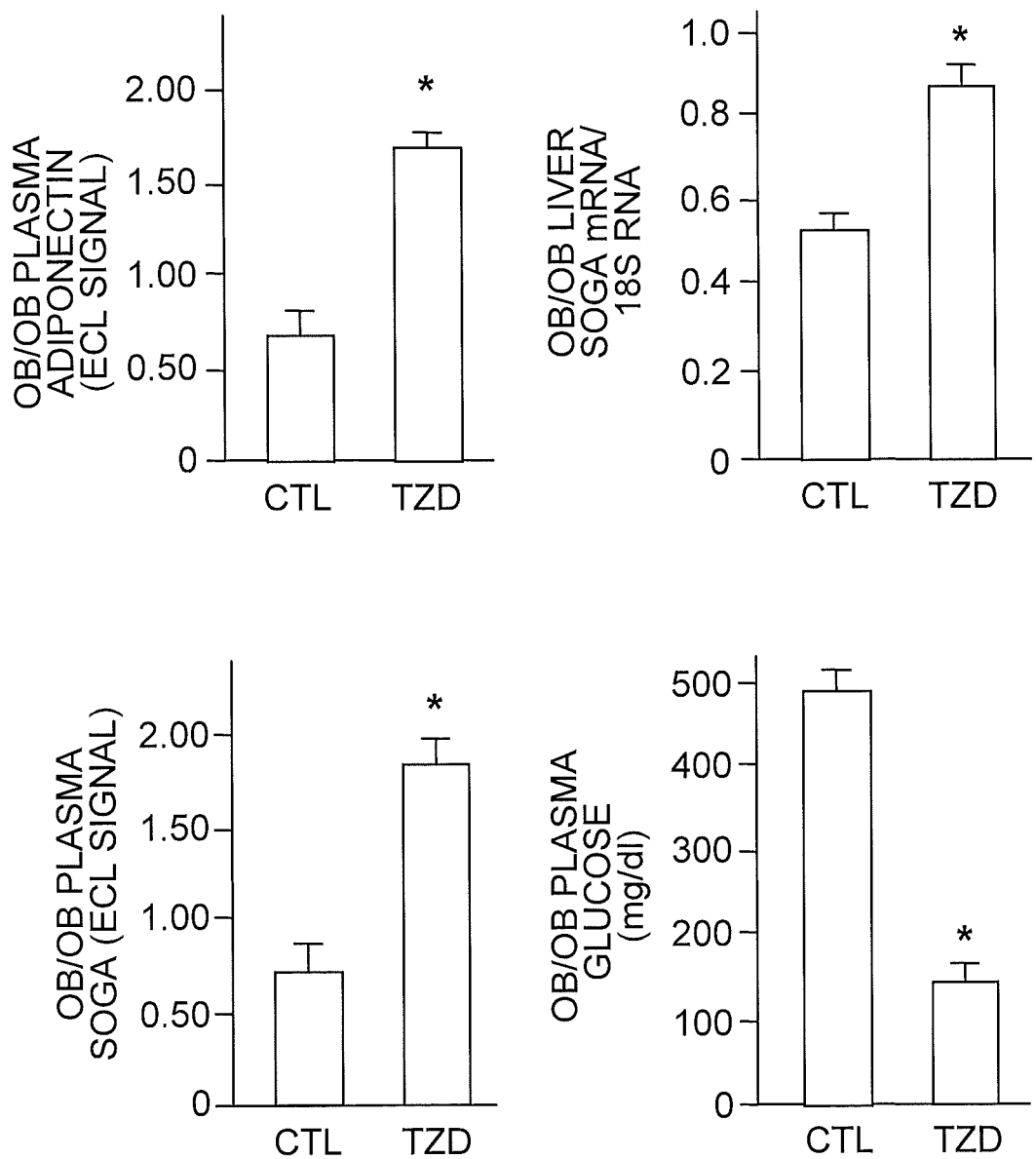

To further validate the link between adiponectin and SOGA in vivo, circulating levels of adiponectin and SOGA were measured in (a) healthy human volunteers, (b) wild-type mice after weight reduction by calorie restriction, and (c) pioglitazone treatment in ob/ob mice, a model of type II diabetes. FIG. 14A shows adiponectin and 25 kDa SOGA levels in human plasma from healthy female volunteers (ages 20-63; n=13). Plasma was collected after an overnight fast. Values represent averages from 2 plasma samples taken 10 minutes apart. A correlation coefficient ($R^2$) of 0.82 was found between SOGA and adiponectin. The analysis of human plasma from healthy fasting female volunteers (plasma insulin: 7.1±1.0 µU/ml) showed a positive correlation between circulating levels of adiponectin and SOGA ($R^2$=0.82) (FIG. 14A). FIG. 14B shows the effect of ad libitum (AL) versus 30% calorie restricted (CR) feeding on adiponectin, SOGA and glucose in wild-type mice. Bar graphs show levels of plasma adiponectin (top), 25 kDa SOGA (middle) and glucose (bottom). Calorie restriction, a nutritional intervention that doubled plasma adiponectin, resulted in a 2-fold elevation of circulating SOGA (FIG. 14B). The concentration of plasma glucose in calorie restricted mice compared to ad libitum fed mice was 80±7 mg/dl and 131±10 mg/dl, respectively (FIG. 14B). The complex oligomeric structure, high turnover rate and abundance of circulating adiponectin prevented us from using recombinant adiponectin to study the regulation of SOGA in vivo (Shetty et al., *Trends Pharmacol. Sci.* 30:234 (2009)). Therefore, oral pioglitazone treatment was used to elevate adiponectin in ob/ob mice, an obese model of type II diabetes. FIG. 14C shows the effect of pioglitazone treatment on liver SOGA mRNA and circulating adiponectin, SOGA and glucose in diabetic ob/ob mice. Mice received a daily dose of pioglitazone (TZD) or placebo (CTL) by oral gavage. Bar graphs show the levels of plasma adiponectin (top), liver SOGA mRNA/18S RNA (second), plasma 25 kDa SOGA (third) and plasma glucose (bottom) after 4 days of treatment. Pioglitazone treatment caused a 40% increase of SOGA mRNA in the liver and a 3-fold elevation of circulating adiponectin and SOGA (FIG. 14C). The concentration of plasma glucose was 155±8 mg/dl in pioglitazone treated ob/ob mice compared to 450±18 mg/dl in untreated ob/ob mice (p<0.05) (FIG. 14C). These results support the hypothesis that adiponectin elevation of SOGA increases insulin sensitivity. Both calorie restriction and pioglitazone treatment have pleiotropic effects beyond the elevation of circulating adiponectin making it difficult to draw any conclusions about the linkage between adiponectin and SOGA. Hence, circulating levels of SOGA between wild-type and adiponectin transgenic mice were compared. FIG. 14D shows circulating levels of adiponectin and SOGA in male adiponectin transgenic mice and their wild type litter mates on a high fat diet. Bars in panels B, C and D represent mean±SEM for n=4-5 per group where "*" indicates a significant difference (p<0.05) by nonparametric Student's t-test. Previous studies have shown that the 3-fold elevation of adiponectin in transgenic mice exerts a protective effect against diabetogenic high fat diet (Combs et a, *Endocrinology* 14.5:367 (2004); Brooks et al., *J. Biol. Chem.* 282: 35069 (2007)). Consistent with a stimulatory effect of adiponectin, circulating levels of SOGA were higher in adiponectin transgenic mice than their wild type litter mates on a high fat diet (FIG. 14D). These results support the hypothesis that the increase of SOGA in response to adiponectin contributes to the reduction of glucose production in vivo.

Example 8

Correlation between Circulating Insulin and SOGA

Figure 15A:
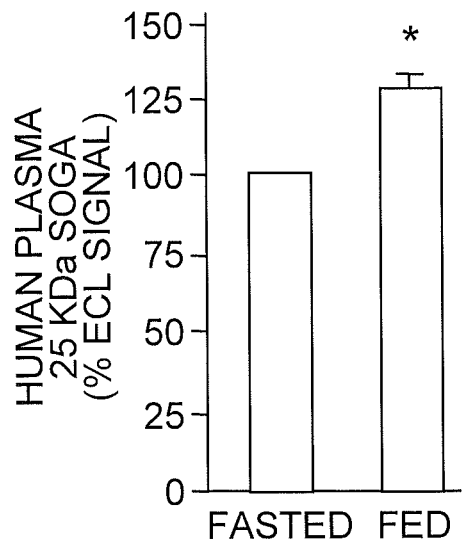
FIGS. 15A-15B show the circulating levels of SOGA in relation to insulin in humans and mice.
Figure 15B:
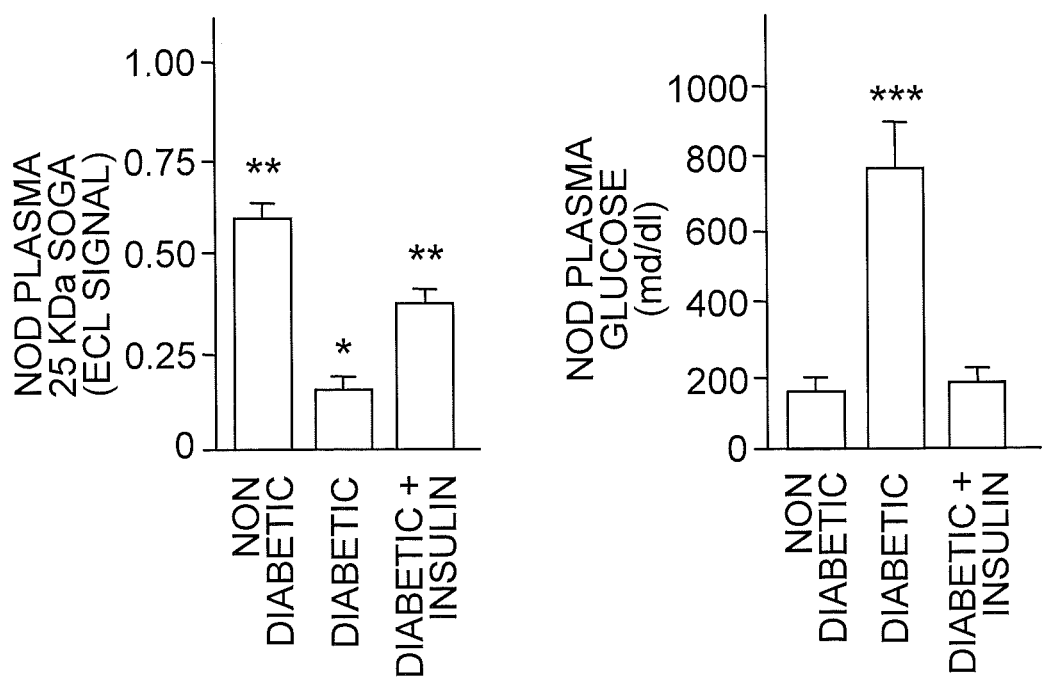

Because adiponectin is an insulin sensitizer and the inhibition of the insulin signaling intermediate PI3K blocked the induction of SOGA in isolated hepatocytes (FIG. 11D), we sought to determine whether there is a correlation between circulating insulin and SOGA during (a) feeding and fasting in humans and (b) insulin withdrawal in NOD mice, a model of type I diabetes. FIG. 15A shows the percent change in circulating levels of SOGA in healthy human volunteers (20-43 years old) measured at 8-11 AM, within 2 hours of feeding or following an overnight (10-12 hour) fast. Bars represent mean values±SEM for n=5 and "*" indicates a significant difference at p<0.05 by nonparametric Student's t-test. Consistent with the theory that insulin stimulates SOGA, a 12-hour fast in healthy human volunteers was associated with a 25% decrease in circulating SOGA (FIG. 15A). The reduction of SOGA in the fasted state is consistent with the induction of SOGA by insulin and the role of SOGA in the inhibition of autophagy and glucose production. FIG. 15B shows the effect of insulin withdrawal and insulin injection on SOGA and glucose in NOD mice. Circulating levels of 25 kDa SOGA and glucose in NOD mice without diabetes (Group I), NOD mice with diabetes (Group 2) and NOD mice with diabetes treated by a single injection of insulin 24 hours earlier (Group 3) were measured. Bar graphs show the levels of plasma SOGA (top) and glucose (bottom). Bars show mean±SEM for n=5 per group where "*" indicates significantly lower than Groups 1 and 3, "" indicates significantly greater than Group 2 and "*" indicates significantly greater than Groups 1 and 3. Statistical significance was determined by Student's t-test where p<0.05. A 3-fold reduction of circulating SOGA in hyperglycemic NOD mice, in comparison to euglycemic NOD mice, also suggests that insulin induces SOGA in vivo (FIG. 15B). In support of the theory that the increase of SOGA in response to insulin contributes to the reduction of plasma glucose, the treatment of type I diabetes by insulin injection was associated with a 2-fold induction of SOGA (FIG. 15B).

The results of this study suggest that the elevation of SOGA in response to adiponectin and insulin can lower liver glucose production through the inhibition of autophagy resulting in a decrease of plasma glucose. The observation that knockdown of SOGA elevated glucose production in primary hepatocytes suggested that SOGA is an inhibitor of glucose production. The elevation of glucose production during the reduction of SOGA was linked to changes in primary hepatocytes that suggested an increase in autophagy such as the reduction in protein content and the elevation of lysosome staining and the secretion of valine, a branched chain amino acid that cannot be synthesized or metabolized in hepatocytes.

The hypothesis that SOGA may interfere with autophagy is supported by the identification of conserved domains found in Atg16 and Rab5-binding proteins (Longatti et al., *Cell Death Differ.* 16:956 (2009)). Both Atg16 and the Rab5-binding proteins contribute to the early stages of autophagy. Although Atg16 is an essential component of the autophagic machinery, adenoviral overexpression of Atg16 inhibits autophagy in mammalian cells (Matsushita et al., *J. Biol. Chem.* 282:6763 (2007)); Fujita et al., *Mol. Biol. Cell* 19:2092 (2008)). The disruption of autophagy by overexpression of Atg16 provides a paradigm that may explain how elevated SOGA inhibits glucose production. Although the current study focuses on the role of SOGA in the liver, it is important to point out that SOGA is also expressed in the other gluconeogenic organs like the kidney and tissues that are rich sources of gluconeogenic substrates like skeletal and cardiac muscle. The elevation of SOGA in extrahepatic tissues may play a critical role in the reduction of glucose production and the amelioration of glucose homeostasis.

Intracellular levels of SOGA in isolated hepatocytes were proportional to the levels of SOGA in hepatocyte conditioned media leading us to propose that circulating levels of SOGA can be used as a biomarker of intracellular SOGA levels. This hypothesis was supported by the elevation of liver SOGA mRNA and circulating SOGA in pioglitazone treated ob/ob mice. Our in vitro experiments suggest that the elevation of circulating SOGA indicates a decrease in glucose production. This interpretation is consistent with the elevation of circulating SOGA after calorie restriction, oral pioglitazone, transgenic elevation of adiponectin, feeding and insulin injection. Although glucose production was not measured in the present study, previous reports in mice, rats and humans show that glucose production is reduced by the elevation of adiponectin in transgenic mice, the implementation of calorie restriction, the treatment of type II diabetes by oral insulin sensitizers and the treatment of type 1 diabetes by insulin (Wahren et al., *Annu. Rev. Nutr.* 27:329 (2007); Combs et al., *J. Clin. Invest.* 108:1875 (2001); Combs et al., *Endocrinology* 145:367 (2004); Barzilai et al., *J. Clin. Invest.* 101:1353 (2998); Miyazaki et al., *J. Clin. Endocrinol. Metab.* 89:4312 (2004)).

The elevation of SOGA in calorie restricted, pioglitazone and adiponectin transgenic mice supports the hypothesis that adiponectin induces SOGA. The elevation of SOGA in response to adiponectin was not impaired by pharmacologic inhibition of AMPK in isolated hepatocytes suggesting that the induction of SOGA is an insulin sensitizing effect of adiponectin that is mediated independent of AMPK. Adiponectin mediated increases in SOGA were impaired by pharmacologic inhibition of the insulin signaling intermediate PI3K suggesting that the expression of SOGA is regulated by the insulin signaling pathway. The reduction of circulating SOGA by a 12-hour fast in humans or hyperglycemic NOD mice and the elevation of circulating SOGA by insulin injection support the hypothesis that SOGA is induced by the insulin signaling pathway. Adiponectin could increase SOGA through the insulin signaling pathway via APPL1, an adaptor protein that binds to the intracellular domain of the adiponectin receptors and the catalytic subunit of PI3K (Mao et al., *Nat. Cell Biol.* 8:516 (2006); Mitsuuchi et al., *Oncogene* 18:4891 (1999); Yang et al., *J. Biol. Chem.* 278:16820 (2003)).

Antibodies recognizing the C-terminal region of murine SOGA show that cultured hepatocytes as well as liver samples incubated ex vivo secrete an 80 kDa SOGA fragment rather than a 161 kDa protein predicted by the 4.7 kb cDNA. The size discrepancy is explained by the location of an internal secretory signal peptide, also seen in chicken ovalbumin (Lingappa et al., *Nature* 281:117 (1979)). The presence of repeated LXXXXXL sequences in the amino terminal portion of the SOGA (amino acids 222-250 and 288-314) suggests a potential feedback mechanism through protein-protein interactions of leucine zipper motifs in SOGA and APPL1. The absence of 25 kDa SOGA in hepatocytes and liver conditioned media suggests that proteolytic cleavage of 80 kDa SOGA depends on an extracellular factor that is inactive or absent in vitro. The incubation of mouse hepatocyte conditioned media containing 80 kDa SOGA with endothelial cells (HUVECs) or human plasma did not yield a 25 kDa fragment. Circulating SOGA may play a physiologic role in glucose homeostasis.

The discovery that circulating levels of adiponectin and SOGA were highly correlated in humans suggests that the measurement of SOGA may be clinically relevant. For example, while TZD drug treatment is almost always effective in the induction of adiponectin, it is only effective in lowering glucose in 70% of type II diabetics (Snitlter et al., *Diabetes Care* 27:1365 (2004)). Insulin treatment in type I diabetics is also not completely effective 100% of the time. Based on the results presented here, it would not be surprising if specific cases of poor clinical outcomes were associated with poor induction of SOGA.

The foregoing is illustrative of the present invention, and is not to be construed as limiting thereof. The invention is defined by the following claims, with equivalents of the claims to be included therein.

That which is claimed is:

1. A method of identifying an agent that binds to or modulates the activity of a mammalian Suppressor of Glucose by Autophagy (SOGA) polypeptide or a functional fragment thereof, comprising:
    contacting the polypeptide or a functional fragment thereof with a test agent under conditions whereby binding between the polypeptide or a functional fragment thereof and the test agent can occur or modulation of the activity of the polypeptide or a functional fragment thereof can occur; and
    detecting binding between the polypeptide or a functional fragment thereof and the test agent or detecting modulation of the activity of the polypeptide or a functional fragment thereof upon contact with the test agent as compared to activity of the polypeptide or a functional fragment thereof in the absence of contact with the test agent.

2. The method of claim 1, wherein the method is carried out in a cell comprising the polypeptide or a functional fragment thereof.

3. The method of claim 2, wherein the cell comprises an isolated polynucleotide comprising a nucleotide sequence encoding the polypeptide or a functional fragment thereof.

4. The method of claim 3, wherein the cell is stably transformed with the isolated polynucleotide.

5. The method of claim 1, wherein the method is carried out as a cell-free assay.

6. The method of claim 1, wherein the method is carried out in a transgenic non-human mammal comprising an isolated polynucleotide comprising a nucleotide sequence encoding the polypeptide or a functional fragment thereof.

7. The method of claim 1, wherein the SOGA polypeptide or a functional fragment thereof is a human SOGA polypeptide or a functional fragment thereof.

8. The method of claim 1, wherein the SOGA polypeptide or a functional fragment thereof is a functional fragment of a SOGA polypeptide beginning immediately after an internal signal sequence.

9. The method of claim 1, wherein the SOGA polypeptide or a functional fragment thereof is a C-terminal functional fragment of a SOGA polypeptide of about 80 kDa.

10. The method of claim 1, wherein the SOGA polypeptide or a functional fragment thereof is a C-terminal functional fragment of a SOGA polypeptide of about 25 kDa.

* * * * *

UNITED STATES PATENT AND TRADEMARK OFFICE
CERTIFICATE OF CORRECTION

PATENT NO. : 8,530,174 B2  
APPLICATION NO. : 13/376239  
DATED : September 10, 2013  
INVENTOR(S) : Combs et al.

Page 1 of 4

It is certified that error appears in the above-identified patent and that said Letters Patent is hereby corrected as shown below:

On Title Page:
Item 56, References Cited, Other Publications, "RecName: Full=Uncharacterized protein C20orf117": Please correct "EBI accession No. UNIPORT:094964;"
to read -- EBI accession No. UNIPROT:094964; --

In the Specification:
Column 1, Line 7: Please correct "of PCT Application PCT/US2010/037,472,"
to read -- of PCT Application PCT/US2010/037472, --

Column 9, Line 6: Please correct "(Feigner et al., *Proc. Natl.*"
to read -- (Felgner et al., *Proc. Natl.* --

Column 9, Line 12: Please correct "(Feigner et al., *Science*"
to read -- (Felgner et al., *Science* --

Column 10, Lines 34-35: Please correct "Accession No. H977045 and"
to read -- Accession No. FJ977045 and --

Columns 9-10, SEQ ID NO: 1, Location 61-120: Please correct
"ggacccgcaccgggcagccgccccagccagcgcagtcggggcagcagcctccgcggcccc"
to read
-- ggacccgcaccgggcagccgccccagccagcgcagtcggggcagcagcctccgcggcctc --

Columns 13-14, SEQ ID NO: 1, Location 4021-4080: Please correct
"ctagcctctctagtgtggtggagcactctgggagcaccgagtctgtgtggaaactgggca"
to read
-- ctagcctctttagtgtggtggagcactctgggagcaccgagtctgtgtggaaactgggca --

Signed and Sealed this  
Thirtieth Day of September, 2014

Michelle K. Lee  
*Deputy Director of the United States Patent and Trademark Office*

CERTIFICATE OF CORRECTION (continued)
U.S. Pat. No. 8,530,174 B2

Columns 13-14, SEQ ID NO: 1, Location 4201-4260: Please correct
"aaccagagcccccttcgccagccagctaccatcaacccgagggtgtatccaggatcctga"
to read
-- aaccagagccccctttcgccagccagctaccatcaacccgagggtgtatccaggatcctga --

Columns 13-14, SEQ ID NO: 2, Location 661-720: Please correct
"RLEQKTOSOEKNILVQKSQQPKHNFLLLFMKLRWFLKRWRQGKVTPSKK
DDFLEVNSMKE"
to read
-- RLEQKTOSOEKNILVQESQQPKHNFLLLFMKLRWFLKRWRQGKVTPSEE
DDFLEVNSMKE --

Columns 15-16, SEQ ID NO: 3, Location 541-600: Please correct
"agcggctcatcgagactgagetggctaagcaggtgctgcagacggagctggagcgaccga"
to read
-- agcggctcatcgagactgagctggctaagcaggtgctgcagacggagctggagcgaccga --

Columns 19-20, SEQ ID NO: 4: Please correct

Human SOGA Polypeptide Sequence
(SEQ ID NO: 4)

```
MLDCGPSGLVRELEELRSENDYLKDEIEELRAEMLEMRDVYMKEDVYQLQYRLHKAERRS   60
LRAAQTGQVDGELIRGLEQDVKVSKDISMRLHKELEVVEKKRARLEEENEELRQRLIETE  120
IAKQVLQTELERPRKHSLKKRGTRSLGKADKKTLVQEDSADLKCQLHKAKEESALMCKKL  180
TKLAKENDSMKEELLKYRSLYGDLDSALSAEELADAPHSRETELKVHLKLVEEEANLLSR  240
RIVELEVENRQLRAEMDDMKDHGGGCGGPEARLAFSALGGGECGESLAELRRHLQFVEEE  300
AELLRRSSAKLEDQNKLLLNELAKPRSKHRLDVALSEDSCSVLSEPSQKKIAAAKLQIGE  360
LSGKVKKLQYENRVLLSNLQRCDIASCQSTRPMLETDAEAGDSAQCVPAPLGETHESHAV  420
RLCRAREAEVLPGLREQAALVSKAIDVLVADANGFTAGLRLCLDNECADFRLHEAPDNSE  480
GPRDTKLIHArLVRLSVLQQELNAFTRKADAVLGCSVKEQOESFSSLPPLGSQGLSKEIL  540
LAKDLGSDFQPPDFRDLPEWEPRIREAFRTGDLDSKPDPSRSPRPYRAEDNOSYASEIKE  600
LQLVLAKAHDSLRGLQEQLSQERQLRKKEADNFNQKHVQLKEDQQRALLRREPELQSLGL  660
QRRLEQKFWSQEKNMLVQESQQFKHNPLLLPMKLRWFLKRWRQGKVLPSEGDDFLEVNSM  720
KELYLLMEEEEINAQHSDNKACTGDSWTQNTPNEYIKTLADMKVTLKELCWLLRDERRGL  780
TELQQQPAKAKATWETERAELKGHTSQMELKTGKGAGERAGPDWKAALQREREEQQHLLA  840
KSYSAVMELTROLQISERNWSQKKLQLVERLQGEKQQVEQQVKELQNRLSQLQKAADPWV  900
LKHSELEKQDNSWKETRSEKIHDKEAVSEVELGGNGLKRTKSVSSMSEPESLLDCSPYIA  960
```

```
GGDARGKKLPNNPAPGPVSSEPGDPEKDTKEKPGLSSHUCNHLGALACODPPGRQMQRSY 1020
TAPDKTGIRVYYSPPVARRLGVPVVHDKEGKIIIEPGPLFTTAKPKESAKADGLAESSYG 1080
RWLCNFSRQRLDGGSAGSPSAAGPGPPAALHDFEMSGNMSDDMKEITNCVRQAMRSGSLE 1140
RKVKSTSSQTVGLASVGTQTIRTVSVGLQTDPPRSSLHGKAWSPRSSSLVSVRSKQTSSS 1200
LDKVHSRIERPCCSPKyGSPKLQRRSVSKLDSSKDRSLWNLHQGKQNGSAWARSTTTRDS 1250
PVLRNINDGLSSLFSVVEHSGSTESVWKLGMSKTRAKPEPPKYGIVQEPFRNVCGRAPSP 1320
TSSAGEEGTKKPEPLSPASYHQPEGVARILNKKAAKLGSSEKVRLTMLPQVGKDGVIRDG 1380
DGAVVLPNEDAVCDCSTQSLTSCPARSSRSAIRHSPSKCRLHPSESSWGGEERALPPSE 1439 ,,
``` to read

Human SOGA Polypeptide Sequence (SEQ ID NO:4)

```
MLDCGPSGLVRELEELRSENDYLKDEIEELRAEMLEMRDVYMEEDVYQLQYRLRKAERRS 60
LRAAQTGQVDGELIRGLEQDVKVSKDISMRLHKELEVVEKKRARLEEENEELRQRLIETE 120
LAKQVLQTELERPREHSLKKRGTRSLGKADKKTLVQEDSADLKCQLHFAKEESALMCKKL 180
TKLAKENDSMKEELLKYRSLYGDLDSALSAEELADAPHSRETELKVHLKLVEEEANLLSR 240
RIVELEVENRGLRAEMDDMKDHGGGCGGPEARLAFSALGGGECGESLAELRRHLQFVEEE 300
AELLRRSSAELEDQNKLLINELARFRSEHELDVALSEDSCSVLSEPSQEELAAAKLQIGE 360
LSGKVKKLQYENRVLLSNLQRCOLASCQSTRPMLETDABAGDSAQCVPAPLGRTHESHAV 420
RLCRAREAEVLPGLREQAALVSKAIDVLVADANGFTAGLRLCLDNECADFRLHEAPDNSE 480
GPRDTKLIHAILVRLSVLQQELNAFTRKADAVLGCSVKEQQESFSSLPPLGSQGLSKEIL 540
LAKDLGSDFQPPDFRDLPEWEPRIREAFRTGDLDSKPDPSRSFRPYRAEDNDSYASEIKE 600
LQLVLABAHDSLRGLQEQLSQERQLRKBEADNFNQKMVQLEBDQQRALLRREFELQSLBL 660
QRRLEQKFWSQEKNMLVQRSQQFKHNFLLLFMKLRWPLKRWRQQGKVLPSEGDDFLEVNSM 720
KELYLIMBEEERINAQHSDNKACTGDSWTQNTPNEYIKTLADMKVTLKELCWLLRDSRRGL 780
TELQQQPFAKAKATWETERAELKGHTSQMELKTGKGAGERAGDWKAALQREREEQQHLLA 840
ESYSAVMELTRQLQISERNWSQEKLQLVSRLQGEKQQVECQVKELQNRLSQLQKAADPWV 900
LKHSSLBKQDNSWKETRSEKIHDKEAVSEVELGGNGLKRTKSVSSMSEFESLLDCSPYLA 960
GGDARGKKLPNNPAFGFVSSEPGDPSKDTKEKPGLSSRDCNHLGALACQDPPGRQMQRSY 1020
TAPDKTGIRVYYSPPVARRLGVPVVHDKEGKIIIEPGPLFTTAKPKESAEADGLABSSYG 1080
RWLCNFSRQRLDGGSAGSPSAAGPGFPAALHDFEMSGNMSDDMKEITNCVRQAMRSGSLE 1140
RKVKSTSSQTVGLASVGTQTIRTVSVGLQTDPPRSSLHGKAWSPRSSSLVSVRSKQISSS 1200
LDKVHSRIERPCCSPKYGSPKLQRRSVSKLDSSKDRSLWNLHQGKQNGSAWARSTTTRDS 1260
PVLRNINDGLSSLFSVVEHSGSTESVWKLGMSHTRAKPEPPKYGIVQRPFRNVCGRAPSP 1320
TSSAGEEGTKKPEPLSPASYHQPEGVARILNKKAAKLGSSEEVRLTMLPQVGKDGVLRDG 1380
DGAVVLPNEDAVCDCSTQSLTSCPARSSRSAIRHSPSKCRLHPSESSWGGEERALPPSE 1439
```
--                                                              --

Column 23, Line 42: Please correct "lysine (+3.0);"
to read -- lysine (±3.0); --

Column 24, Lines 54-55: Please correct "blastmustl/edu/blast/README.html."
to read -- blast.wustl/edu/blast/README.html. --

Column 26, Line 52: Please correct "include CYC1, E1TS3,"
to read -- include CYC1, HIS3, --

Column 26, Line 53: Please correct "P1105, GAPDH,"
to read -- PHO5, GAPDH, --

Column 26, Line 60: Please correct "virus $^{35}$S, CMV $^{35}$S minimal,"
to read -- virus 35S, CMV 35S minimal, --

Column 28, Line 26: Please correct "in culture (Feigner and Ringold,"
to read -- in culture (Felgner and Ringold, --

Column 28, Line 57: Please correct "in vitro (Feigner et al.,"
to read -- in vitro (Felgner et al., --

Column 28, Line 59: Please correct "(1993); Feigner et al., *J. Biol. Chem.* 269:2550 (1.994))."
to read -- (1993); Felgner et al., *J. Biol. Chem.* 269:2550 (1994)). --

Column 36, Line 10: Please correct "activity of SAGA polypeptides is"
to read -- activity of SOGA polypeptides is --

Column 39, Line 47: Please correct "and reglitazar (ITT-501);"
to read -- and reglitazar (JTT-501); --

Column 40, Line 4: Please correct "and/or in a subject,"
to read -- and/or in a subject. --

Column 52, Lines 51-52: Please correct "cholines and lecithin,"
to read -- cholines and lecithin. --

Column 53, Line 5: Please correct "are about 1 mal/kg to"
to read -- are about 1 μmol/kg to --

Column 56, Line 37: Please correct "with Krebs-Ringer-HEPES $Ca^{2+}$"
to read -- with Krebs-Ringer-HEPES+ $Ca^{2+}$ --

Column 58, Line 47: Please correct "(GENBANK ID: H977045)."
to read -- (GENBANK ID: FJ977045). --

Column 59, Line 29: Please correct "of SOGA (11.2 E 0.6 μg/well"
to read -- of SOGA (11.2 ± 0.6 μg/well --

Column 60, Lines 30-31: Please correct
"antisera, SAQSLASCFIRPSRNPIRFISPSKC (SEQ ID NO:7)"
to read
-- antisera, SAQSLASCFIRPSRNPIRHSPSKC (SEQ ID NO:7) --